(12) United States Patent
Okumura et al.

(10) Patent No.: US 10,428,273 B2
(45) Date of Patent: Oct. 1, 2019

(54) LIQUID CRYSTAL COMPOUND HAVING BENZOPYRAN SKELETON, LIQUID CRYSTAL COMPOSITION, AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Kazuo Okumura, Chiba (JP); Tokifumi Masukawa, Chiba (JP); Keiji Kimura, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 56 days.

(21) Appl. No.: 15/655,918

(22) Filed: Jul. 21, 2017

(65) Prior Publication Data
US 2018/0022998 A1    Jan. 25, 2018

(30) Foreign Application Priority Data

Jul. 22, 2016 (JP) ................. 2016-144239

(51) Int. Cl.

| | |
|---|---|
| G02F 1/1333 | (2006.01) |
| C09K 19/34 | (2006.01) |
| C07D 311/76 | (2006.01) |
| C07D 405/08 | (2006.01) |
| C07D 405/12 | (2006.01) |
| C07D 407/10 | (2006.01) |
| C07D 407/12 | (2006.01) |
| C09K 19/18 | (2006.01) |
| C09K 19/30 | (2006.01) |

(52) U.S. Cl.
CPC ........ *C09K 19/3402* (2013.01); *C07D 311/76* (2013.01); *C07D 405/08* (2013.01); *C07D 405/12* (2013.01); *C07D 407/10* (2013.01); *C07D 407/12* (2013.01); *C09K 19/3466* (2013.01); *C09K 2019/181* (2013.01); *C09K 2019/301* (2013.01); *C09K 2019/304* (2013.01); *C09K 2019/3009* (2013.01); *C09K 2019/3016* (2013.01); *C09K 2019/3019* (2013.01); *C09K 2019/3021* (2013.01); *C09K 2019/3042* (2013.01); *C09K 2019/3077* (2013.01); *C09K 2019/3422* (2013.01); *C09K 2019/3425* (2013.01)

(58) Field of Classification Search
CPC ............ C09K 19/3402; C09K 19/3466; C09K 2019/181; C09K 2019/3009; C09K 2019/301; C09K 2019/3016; C09K 2019/3019; C09K 2019/3021; C09K 2019/304; C09K 2019/3042; C09K 2019/3077; C09K 2019/3422; C09K 2019/3425; G02F 1/1333; C07D 311/76; C07D 405/08; C07D 405/12; C07D 407/10; C07D 407/12
USPC .................................................... 252/299.61
See application file for complete search history.

(56) References Cited

U.S. PATENT DOCUMENTS

| | | | |
|---|---|---|---|
| 8,366,963 B2 * | 2/2013 | Goto ................. | C07D 311/20 252/299.01 |
| 2006/0177603 A1 | 8/2006 | Taugerbeck et al. | |
| 2009/0267026 A1 | 10/2009 | Goto et al. | |

FOREIGN PATENT DOCUMENTS

| | | |
|---|---|---|
| JP | 2006-520327 | 9/2006 |
| WO | 2007066755 | 6/2007 |

OTHER PUBLICATIONS

Shangjun Cai, et al., "Assembly of 3-Substituted Isocoumarins via a CuI-Catalyzed Domino Coupling/Addition/Deacylation Process," The Journal of Organic Chemistry, vol. 77, No. 5, Feb. 2, 2012, pp. 2331-2336.
Veerababurao Kavala, et al., "Synthesis of Isocoumarin Derivatives via the Copper-Catalyzed Tandem Sequential Cyclization of 2-Halo-N-phenyl Benzamides and Acyclic 1,3-Diketones," The Journal of Organic Chemistry, vol. 77, No. 11, Apr. 18, 2012, pp. 5022-5029.

* cited by examiner

*Primary Examiner* — Geraldina Visconti
(74) *Attorney, Agent, or Firm* — JCIPRNET

(57) ABSTRACT

Shown are a liquid crystal compound satisfying at least one of physical properties such as high stability to heat and light, a high clearing point (or high maximum temperature), low minimum temperature of a liquid crystal phase, small viscosity, suitable optical anisotropy, large negative dielectric anisotropy, a suitable elastic constant and satisfactory compatibility with other liquid crystal compounds, a liquid crystal composition containing the compound and a liquid crystal display device including the composition. A compound is represented by formula (1), a liquid crystal composition contains the compound, or the like

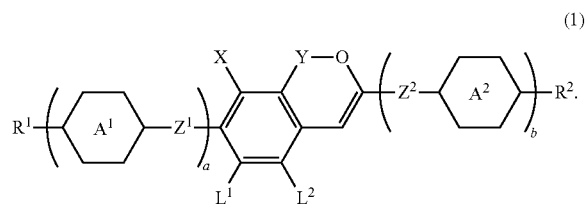

(1)

17 Claims, No Drawings

LIQUID CRYSTAL COMPOUND HAVING BENZOPYRAN SKELETON, LIQUID CRYSTAL COMPOSITION, AND LIQUID CRYSTAL DISPLAY DEVICE

CROSS-REFERENCE TO RELATED APPLICATION

This application claims the priority benefit of Japan application serial no. 2016-144239, filed on Jul. 22, 2016. The entirety of the above-mentioned patent application is hereby incorporated by reference herein and made a part of this specification.

TECHNICAL FIELD

The invention relates to a liquid crystal compound, a liquid crystal composition and a liquid crystal display device. More specifically, the invention relates to a liquid crystal compound that has a benzopyran skeleton, and has negative dielectric anisotropy, a liquid crystal composition containing the compound, and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth.

A liquid crystal composition is sealed into the device. Physical properties of the composition are associated with characteristics of the device. Specific examples of the physical properties in the composition include stability to heat and light, a temperature range of a nematic phase, viscosity, optical anisotropy, dielectric anisotropy, specific resistance and an elastic constant. The composition is prepared by mixing a large number of liquid crystal compounds. The physical properties required for the compound include high stability to an environment such as water, air, heat and light, a wide temperature range of a liquid crystal phase, small viscosity, suitable optical anisotropy, large dielectric anisotropy, a suitable elastic constant, satisfactory compatibility with other liquid crystal compounds. A compound having high maximum temperature of a nematic phase is preferred. A compound having low minimum temperature in the liquid crystal phase such as the nematic phase and a smectic phase is preferred. A compound having small viscosity contributes to a short response time in the device. A suitable value of optical anisotropy is different depending on a mode of the device. In order to drive the device at a low voltage, a compound having large positive or negative dielectric anisotropy is preferred. In order to prepare the composition, a compound having satisfactory compatibility with other liquid crystal compounds is preferred. The device may be occasionally used at a temperature below a freezing point, and therefore a compound having satisfactory compatibility at a low temperature is preferred.

A great number of liquid crystal compounds have been so far prepared. Development of a new liquid crystal compound is still continued. The reason is that satisfactory physical properties that are not found in a conventional compound are expected in a new compound. The reason is also that the new compound provides at least two physical properties in the composition with a suitable balance in several cases. Only a limited number of reports has been found on a compound having divalent group (pr-I) described below.

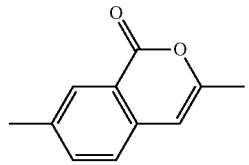

(pr-1)

WO 2007/066755 A (Patent literature No. 1) discloses a compound represented by No. 298 on page 42. The compound is abbreviated as comparative compound (298). See Comparative Example 1.

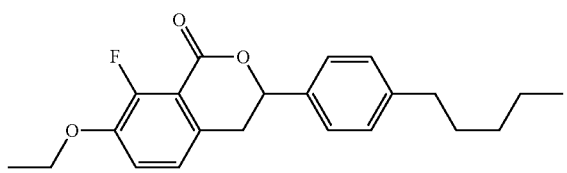

(298)

JP 2006-520327 A (Patent literature No. 2) discloses a compound represented by No. 121 on page 87. The compound is abbreviated as comparative compound (121). See Comparative Example 1.

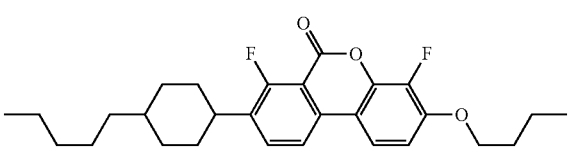

(121)

The Journal Organic Chemistry, 2012, 77, 2331-2336 (Non-patent literature No. 1) and The Journal Organic Chemistry, 2012, 77, 5022-5029 (Non-patent literature No. 2) disclose a compound having an isocoumarin skeleton (for example, the compound described below).

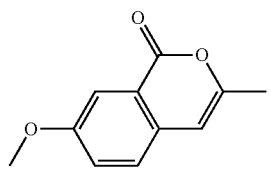

CITATION LIST

Patent Literature

Patent literature No. 1: WO 2007/066755 A
Patent literature No. 2: JP 2006-520327 A

Non-Patent Literature

Non-patent literature No. 1: The Journal Organic Chemistry, 2012, 77, 2331-2336.
Non-patent literature No. 2: The Journal Organic Chemistry, 2012, 77, 5022-5029.

SUMMARY OF INVENTION

Technical Problem

The invention provides a liquid crystal compound satisfying at least one of physical properties such as high stability to heat and light, a high clearing point (or high maximum temperature of a nematic phase), low minimum temperature of a liquid crystal phase, small viscosity, suitable optical anisotropy, large negative dielectric anisotropy, a suitable elastic constant and satisfactory compatibility with other liquid crystal compounds. The invention provides a compound having smaller viscosity and superb compatibility with other liquid crystal compounds in comparison with a similar compound. The invention also provides a liquid crystal composition that contains the compound and satisfies at least one of physical properties such as high stability to heat and light, high maximum temperature of the nematic phase, low minimum temperature of the nematic phase, small viscosity, suitable optical anisotropy, large negative dielectric anisotropy, large specific resistance and the suitable elastic constant. The invention provides a liquid crystal composition having a suitable balance regarding at least two of the physical properties. The invention further provides a liquid crystal display device including the composition and having a wide temperature range in which the device can be used, a short response time, a large voltage holding ratio, low threshold voltage, a large contrast ratio, a small flicker rate and a long service life.

Solution to Problem

The invention concerns a composition containing a compound represented by formula (1), a liquid crystal display device including the composition, and so forth:

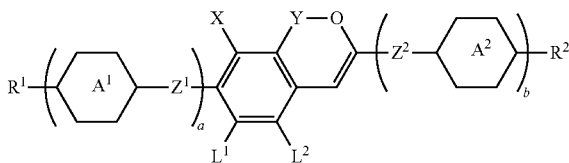

wherein, in formula (1),

R$^1$ and R$^2$ are independently hydrogen, alkyl having 1 to 16 carbons, alkenyl having 2 to 16 carbons, cyclopropyl, cyclobutyl or cyclopentyl, and in the alkyl and the alkenyl, at least one piece of —CH$_2$— may be replaced by —O—, —S—, —CO—, —COO—, —OCO—, —OCOO—, —C≡C—, cyclopropane-1,2-diyl or —Si(CH$_3$)$_2$—, and in the groups, at least one hydrogen may be replaced by fluorine or chlorine, and in the groups, at least one piece of —CH$_3$ may be replaced by any one of monovalent groups (G1) to (G4) described below:

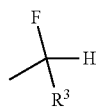

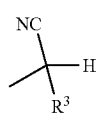

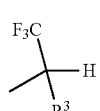

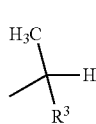

wherein, in groups (G1) to (G4),

R$^3$ is alkyl having 1 to 12 carbons or alkenyl having 2 to 12 carbons, and in the alkyl and the alkenyl, at least one piece of —CH$_2$— may be replaced by —O—, and in the groups, at least one hydrogen may be replaced by fluorine or chlorine; and in formula (1), ring A$^1$ and ring A$^2$ are independently 1,4-cyclohexylene, 1,4-cyclohexenylene, 1,4-phenylene, decahydronaphthalene-2,6-diyl, tetrahydronaphthalene-2,6-diyl or naphthalene-2,6-diyl, and in the groups, one or two pieces of —CH$_2$— may be replaced by —O—, —S—, —CO—, —CF$_2$—, —SiH$_2$— or —Si(CH$_3$)$_2$—, and one or two pieces of —CH$_2$CH$_2$— may be replaced by —CH═CH— or —CH═N—, and in the groups, at least one hydrogen on an aromatic ring may be replaced by halogen, —CF$_3$, —CHF$_2$, —CH$_2$F, —OCF$_3$, —OCHF$_2$, —OCH$_2$F or —C≡N;

Z$^1$ and Z$^2$ are independently a single bond or alkylene having 1 to 4 carbons, and one piece of —CH$_2$— may be replaced by —O— or —CO—, and at least one piece of —CH$_2$CH$_2$— may be replaced by —CH═CH— or —C≡C—, and in the groups, at least one hydrogen may be replaced by fluorine or chlorine;

X, L$^1$ and L$^2$ are independently hydrogen or halogen;

Y is —CO— or —CF$_2$—; and a and b are independently 0, 1 or 2.

Advantageous Effects of Invention

A first advantage is to provide a liquid crystal compound satisfying at least one of physical properties such as high stability to heat and light, a high clearing point (or high maximum temperature of a nematic phase), low minimum temperature of a liquid crystal phase, small viscosity, suitable optical anisotropy, large negative dielectric anisotropy, a suitable elastic constant and satisfactory compatibility with other liquid crystal compounds. The advantage is to provide a compound having smaller viscosity and superb compatibility with other liquid crystal compounds in comparison with a similar compound (see Comparative Example 1). A second advantage is to provide a liquid crystal composition that contains the compound and satisfies at least one of physical properties such as high stability to heat and light, high maximum temperature of the nematic phase, low minimum temperature of the nematic phase, small viscosity, suitable optical anisotropy, large negative dielectric anisotropy, large specific resistance and the suitable elastic constant. The advantage is to provide a liquid crystal composition having a suitable balance regarding at least two of the physical properties. A third advantage is to provide a liquid crystal display device including the composition and having a wide temperature range in which the device can be used, a short response time, a large voltage holding ratio, low threshold voltage, a large contrast ratio, a small flicker rate and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase and a smectic phase, and a compound having no liquid crystal phase but to be added for the purpose of adjusting physical properties of a composition, such as maximum temperature, minimum temperature, viscosity and dielectric anisotropy. The compound has a six-membered ring such as 1,4-cyclohexylene and 1,4-phenylene, and has rod-like molecular structure. "Liquid crystal display device" is a generic term for a liquid crystal display panel and a liquid crystal display module. "Polymerizable compound" is a compound to be added for the purpose of forming a polymer in the composition.

The liquid crystal composition is prepared by mixing a plurality of liquid crystal compounds. An additive is added to the composition for the purpose of further adjusting the physical properties. The additive such as a polymerizable compound, a polymerization initiator, a polymerization inhibitor, an optically active compound, an antioxidant, an ultraviolet light absorber, a light stabilizer, a heat stabilizer, a dye and an antifoaming agent is added thereto when necessary. The liquid crystal compound and the additive are mixed in such a procedure. Even when such an additive is added thereto, a proportion of the liquid crystal compounds is expressed in terms of weight percent (% by weight) based on the weight of the liquid crystal composition containing no additive. A proportion of the additive is expressed in terms of weight percent (% by weight) based on the weight of the liquid crystal composition containing no additive. More specifically, the proportion of the liquid crystal compound or the additive is calculated based on the total weight of the liquid crystal compound. Weight parts per million (ppm) may be occasionally used. A proportion of the polymerization initiator and the polymerization inhibitor is exceptionally expressed based on the weight of the polymerizable compound.

"Clearing point" is a transition temperature between the liquid crystal phase and an isotropic phase in the liquid crystal compound. "Minimum temperature of the liquid crystal phase" is a transition temperature between a solid and the liquid crystal phase (the smectic phase, the nematic phase or the like) in the liquid crystal compound. "Maximum temperature of the nematic phase" is a transition temperature between the nematic phase and the isotropic phase in a mixture of the liquid crystal compound and a base liquid crystal or in the liquid crystal composition, and may be occasionally abbreviated as "maximum temperature." "Minimum temperature of the nematic phase" may be occasionally abbreviated as "minimum temperature." An expression "increase the dielectric anisotropy" means that a value of dielectric anisotropy positively increases in a composition having positive dielectric anisotropy, and the value of dielectric anisotropy negatively increases in a composition having negative dielectric anisotropy. An expression "having a large voltage holding ratio" means that the device has a large voltage holding ratio at room temperature and also at a temperature close to the maximum temperature in the initial stage, and the device has the large voltage holding ratio at room temperature and also at a temperature close to the maximum temperature even after the device has been used for a long period of time. In the composition and the device, the characteristics are examined before and after an aging test (including an accelerated deterioration test), in several cases.

A compound represented by formula (1) may be occasionally abbreviated as compound (1). At least one compound selected from the group of compounds represented by formula (1) may be occasionally abbreviated as compound (1). "Compound (1)" means one compound, a mixture of two compounds or a mixture of three or more compounds each represented by formula (1). A same rule applies also to any other compound represented by any other formula. In formulas (1) to (15), a symbol such as $A^1$, $B^1$ and $C^1$ surrounded by a hexagonal shape corresponds to ring $A^1$, ring $B^1$ and ring $C^1$, respectively. The hexagonal shape represents a six-membered ring such as cyclohexane or benzene. The hexagonal shape may occasionally represent a fused ring such as naphthalene or a bridged ring such as adamantane.

A symbol of terminal group $R^{11}$ is used in a plurality of compounds in chemical formulas of component compounds. In the compounds, two groups represented by two pieces of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule applies also to a symbol such as $R^{12}$, $R^{13}$ and $Z^{11}$. In compound (15), when i is 2, two of ring $E^1$ exists. In the compound, two groups represented by two of ring $E^1$ may be identical or different. A same rule applies also to two of arbitrary ring $E^1$ when i is larger than 2. A same rule applies also to other symbols.

An expression "at least one piece of 'A'" means that the number of 'A' is arbitrary. An expression "at least one piece of 'A' may be replaced by 'B'" means that, when the number of 'A' is 1, a position of 'A' is arbitrary, and also when the number of 'A' is 2 or more, positions thereof can be selected without restriction. A same rule applies also to an expression "at least one piece of 'A' is replaced by 'B'." An expression "at least one piece of 'A' may be replaced by 'B', 'C' or 'D'" includes a case where arbitrary 'A' is replaced by 'B', a case where arbitrary 'A' is replaced by 'C', and a case where arbitrary 'A' is replaced by 'D', and also a case where a plurality of pieces of 'A' are replaced by at least two pieces of 'B', 'C' and/or 'D'. For example, "alkyl in which at least one piece of —$CH_2$— may be replaced by —O— or —CH=CH—" includes alkyl, alkoxy, alkoxyalkyl, alkenyl, alkoxyalkenyl and alkenyloxyalkyl. In addition, a case where two pieces of consecutive —$CH_2$— are replaced by —O— to form —O—O— is not preferred. In alkyl or the like, a case where —$CH_2$— of a methyl part (—$CH_2$—H) is replaced by —O— to form —O—H is not preferred, either.

An expression "$R^{11}$ and $R^{12}$ are independently alkyl having 1 to 10 carbons or alkenyl having 2 to 10 carbons, and in the alkyl and the alkenyl, at least one piece of —CH$_2$— may be replaced by —O—, and in the groups, at least one hydrogen may be replaced by fluorine" is used in several cases. In the expression, an expression "in the groups" may be understood as was. In the expression, "the groups" mean alkyl, alkenyl, alkoxy, alkenyloxy or the like. More specifically, "the groups" represent all groups described prior to the term "in the groups." A common interpretation is applied also to terms of "in the monovalent groups" and "in the divalent groups." For example, "the monovalent groups" represent all of the groups described prior to the term "in the monovalent groups."

Halogen means fluorine, chlorine, bromine and iodine. Preferred halogen is fluorine and chlorine. Further preferred halogen is fluorine. Alkyl of the liquid crystal compound is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature. Then, 2-fluoro-1,4-phenylene means two divalent groups described below. In a chemical formula, fluorine may be leftward (L) or rightward (R). A same rule applies also to an asymmetrical divalent group formed by removing two pieces of hydrogen from a ring, such as tetrahydropyran-2,5-diyl.

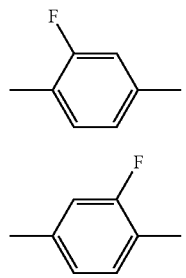

(L)

(R)

The invention includes items described below.

Item 1. A liquid crystal composition containing at least one compound represented by formula (1) as component (a):

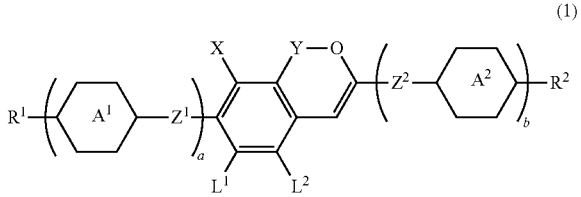

(1)

wherein, in formula (1),
R$^1$ and R$^2$ are independently hydrogen, alkyl having 1 to 16 carbons, alkenyl having 2 to 16 carbons, cyclopropyl, cyclobutyl or cyclopentyl, and in the alkyl and the alkenyl, at least one piece of —CH$_2$— may be replaced by —O—, —S—, —CO—, —COO—, —OCO—, —OCOO—, —C≡C—, cyclopropane-1,2-diyl or —Si(CH$_3$)$_2$—, and in the groups, at least one hydrogen may be replaced by fluorine or chlorine, and in the groups, at least one piece of —CH$_3$ may be replaced by any one of monovalent groups (G1) to (G4) below;

(G1)

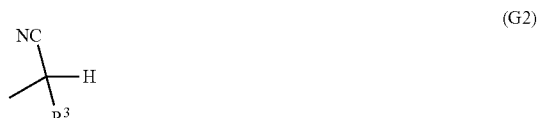

(G2)

(G3)

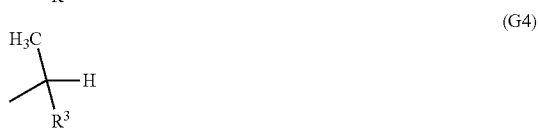

(G4)

wherein, in groups (G1) to (G4),
R$^3$ is alkyl having 1 to 12 carbons or alkenyl having 2 to 12 carbons, and in the alkyl and the alkenyl, at least one piece of —CH$_2$— may be replaced by —O—, and in the groups, at least one hydrogen may be replaced by fluorine or chlorine; and in formula (1), ring A$^1$ and ring A$^2$ are independently 1,4-cyclohexylene, 1,4-cyclohexenylene, 1,4-phenylene, decahydronaphthalene-2,6-diyl, tetrahydronaphthalene-2,6-diyl or naphthalene-2,6-diyl, and in the groups, one or two pieces of —CH$_2$— may be replaced by —O—, —S—, —CO—, —CF$_2$—, —SiH$_2$— or —Si(CH$_3$)$_2$—, and one or two pieces of —CH$_2$CH$_2$— may be replaced by —CH=CH— or —CH=N—, and in the groups, at least one hydrogen on an aromatic ring may be replaced by halogen, —CF$_3$, —CHF$_2$, —CH$_2$F, —OCF$_3$, —OCHF$_2$, —OCH$_2$F or —C≡N;

Z$^1$ and Z$^2$ are independently a single bond or alkylene having 1 to 4 carbons, and one piece of —CH$_2$— may be replaced by —O— or —CO—, and at least one piece of —CH$_2$CH$_2$— may be replaced by —CH=CH— or —C≡C—, and in the groups, at least one hydrogen may be replaced by fluorine or chlorine;

X, L$^1$ and L$^2$ are independently hydrogen or halogen;
Y is —CO— or —CF$_2$—; and
a and b are independently 0, 1 or 2.

Item 2. The liquid crystal composition according to item 1, further containing at least one compound selected from the group of compounds represented by formulas (2) to (4) as component (b):

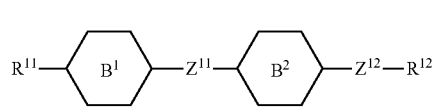

(2)

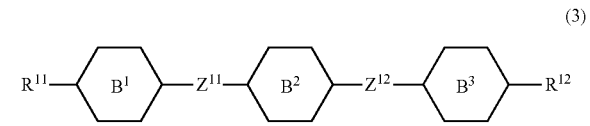

(3)

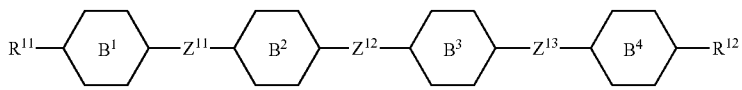

wherein, in formulas (2) to (4), $R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —COO—, —$CH_2CH_2$—, —CH=CH— or —C≡C—.

Item 3. The liquid crystal composition according to item 1 or 2, wherein component (a) is at least one compound represented by formula (1-1):

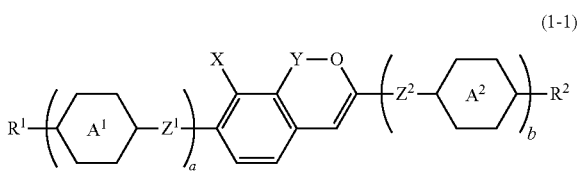

wherein, in formula (1-1), $R^1$ and $R^2$ are independently hydrogen, alkyl having 1 to 14 carbons or alkenyl having 2 to 14 carbons, and in the alkyl and the alkenyl, one or two pieces of —$CH_2$— may be replaced by —O—, and in the groups, at least one hydrogen may be replaced by fluorine, and in the groups, at least one piece of —$CH_3$ may be replaced by any one of monovalent groups (G1) to (G4) below;

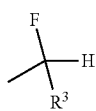

(G1)

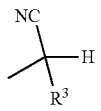

(G2)

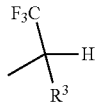

(G3)

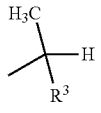

(G4)

wherein, in groups (G1) to (G4), $R^3$ is alkyl having 1 to 10 carbons, and in the alkyl, at least one piece of —$CH_2$— may be replaced by —O—; and in formula (1-1), ring $A^1$ and ring $A^2$ are independently 1,4-cyclohexylene, 1,4-cyclohexenylene, 1,4-phenylene, decahydronaphthalene-2,6-diyl, tetrahydronaphthalene-2,6-diyl or naphthalene-2,6-diyl, and in the groups, one or two pieces of —$CH_2$— may be replaced by —O—, and one or two pieces of —$CH_2CH_2$— may be replaced by —CH=CH—, and in the groups, at least one hydrogen on an aromatic ring may be replaced by fluorine;

$Z^1$ and $Z^2$ are independently a single bond, —O—, —COO—, —OCO—, —$CH_2O$—, —$OCH_2$—, —$CF_2O$—, —$OCF_2$—, —$CH_2CH_2$—, —$CF_2CF_2$—, —CH=CH—, —CF=CF—, —C≡C—, —$(CH_2)_4$— or —$CH_2CH$=$CHCH_2$—;

X is hydrogen, fluorine or chlorine;

Y is —CO— or —$CF_2$—; and a and b are independently 0, 1 or 2.

Item 4. The liquid crystal composition according to item 3, wherein, in formula (1-1), $R^1$ and $R^2$ are independently hydrogen, alkyl having 1 to 14 carbons or alkenyl having 2 to 14 carbons, and in the alkyl and the alkenyl, one or two pieces of —$CH_2$— may be replaced by —O—, and in the groups, at least one hydrogen may be replaced by fluorine;

ring $A^1$ and ring $A^2$ are independently 1,4-cyclohexylene, 1,4-cyclohexenylene, 1,3-dioxane-2,5-diyl, tetrahydropyran-2,5-diyl, 1,4-phenylene, 3-fluoro-1,4-phenylene, 3,5-difluoro-1,4-phenylene, pyridine-2,5-diyl or pyrimidine-2,5-diyl;

$Z^1$ and $Z^2$ are independently a single bond, —O—, —COO—, —OCO—, —$CH_2O$—, —$OCH_2$—, —$CF_2O$—, —$OCF_2$—, —$CH_2CH_2$— or —CH=CH—;

X is hydrogen or fluorine;

Y is —CO— or —$CF_2$—; and a and b are independently 0, 1 or 2, and a sum of a and b is 0, 1 or 2.

Item 5. The liquid crystal composition according to item 3, wherein, in formula (1-1), $R^1$ and $R^2$ are independently alkyl having 1 to 8 carbons, alkoxy having 1 to 8 carbons or alkenyl having 2 to 8 carbons;

ring $A^1$ and ring $A^2$ are independently 1,4-cyclohexylene, 1,4-phenylene or 1,4-phenylene in which at least one hydrogen is replaced by fluorine;

$Z^1$ and $Z^2$ are independently a single bond, —O—, —COO—, —OCO—, —$CH_2O$—, —$OCH_2$— or —$CH_2CH_2$—;

X is hydrogen or fluorine;

Y is —CO— or —$CF_2$—; and a and b are independently 0, 1 or 2, and a sum of a and b is 0, 1 or 2.

Item 6. The liquid crystal composition according to any one of items 1 to 5, wherein component (a) is at least one compound selected from the group of compounds represented by formulas (1a) to (1t):

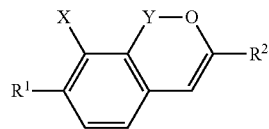

(1a)

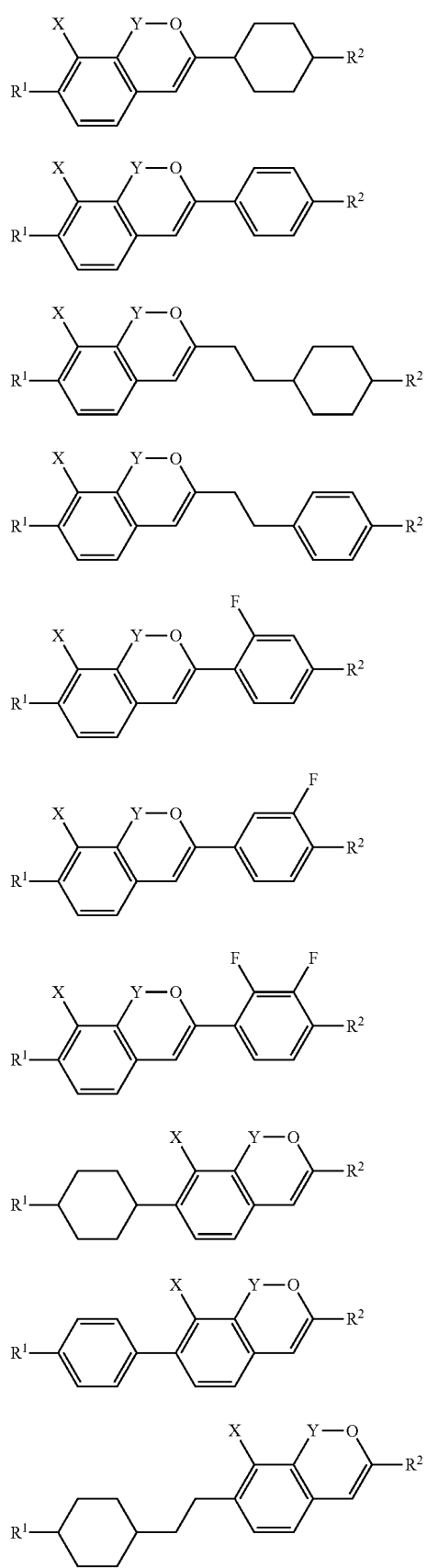
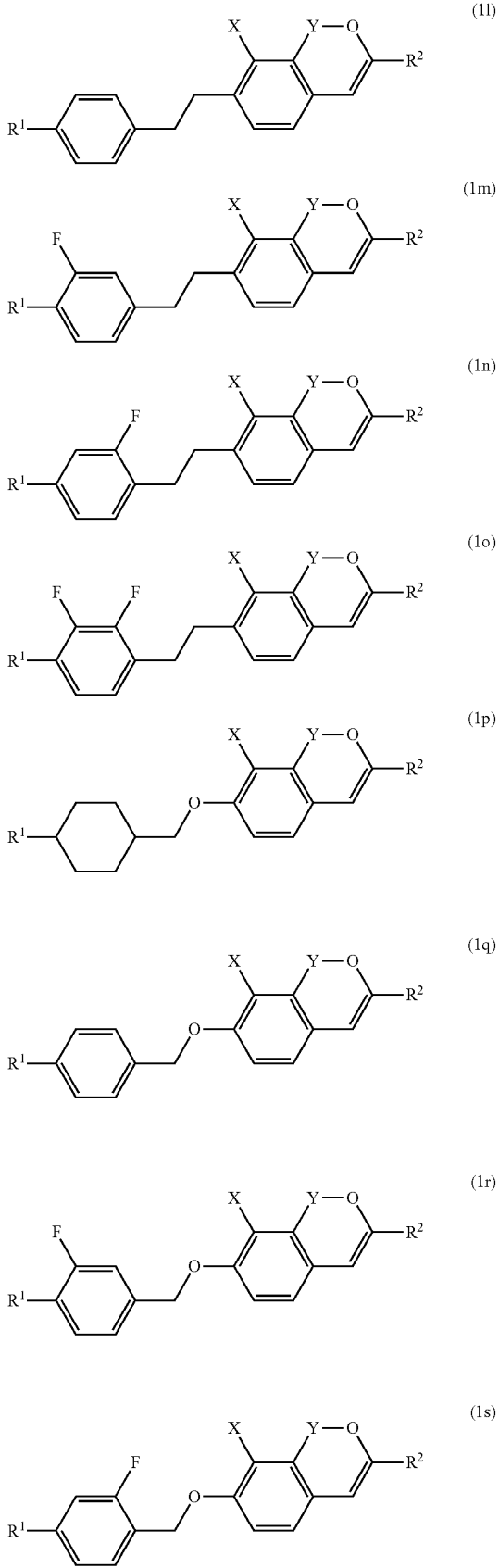

(1t) 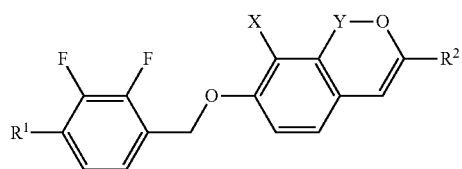

wherein, in formulas (1a) to (1t), $R^1$ and $R^2$ are independently alkyl having 1 to 12 carbons, alkoxy having 1 to 12 carbons or alkenyl having 2 to 12 carbons;

X is hydrogen, fluorine or chlorine; and

Y is —CO— or —CF$_2$—.

Item 7. The liquid crystal composition according to any one of items 1 to 6, wherein component (a) is at least one compound selected from the group of compounds represented by formulas (1a-1) to (1t-1):

(1a-1) 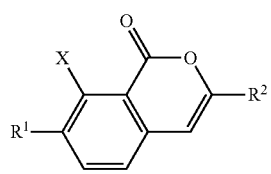

(1b-1) 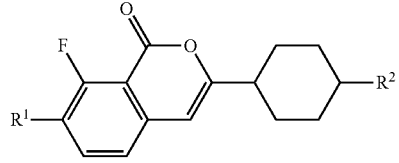

(1c-1) 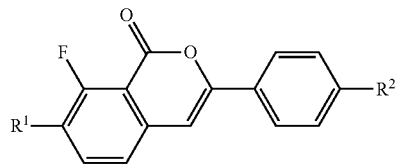

(1d-1) 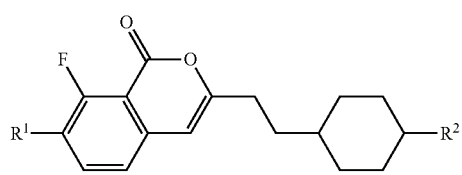

(1e-1) 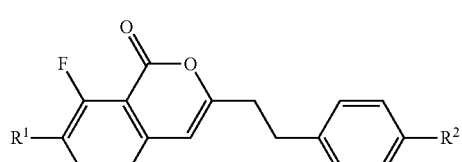

(1f-1) 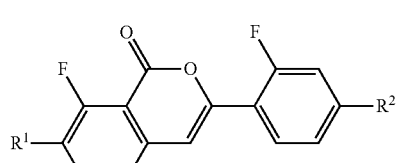

(1g-1) 

(1h-1)

(1i-1)

(1i-1)

(1k-1)

(1l-1) 

(1m-1)

(1n-1) 

-continued

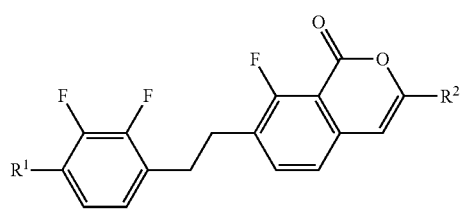
(1o-1)

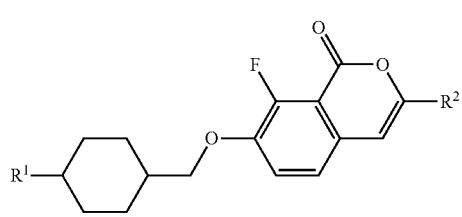
(1p-1)

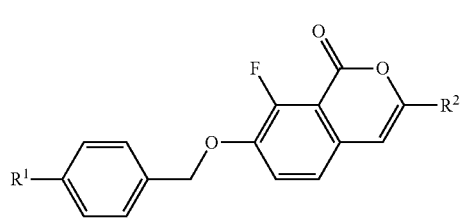
(1q-1)

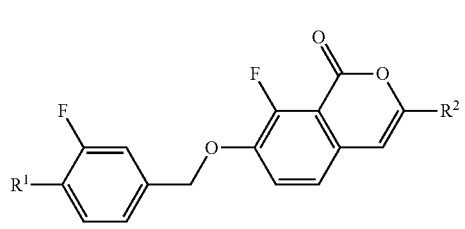
(1r-1)

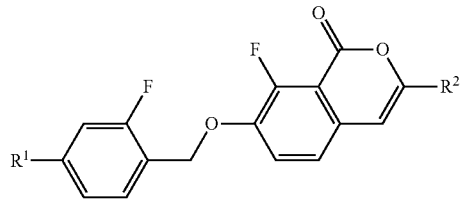
(1s-1)

-continued

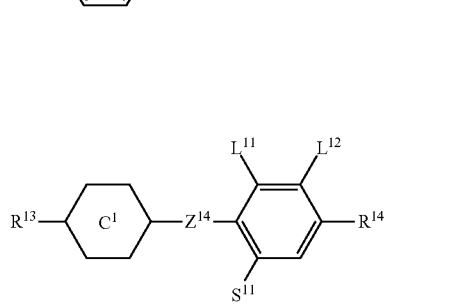
(1t-1)

wherein, in formulas (1a-1) to (1t-1), $R^1$ and $R^2$ are independently alkyl having 1 to 12 carbons, alkoxy having 1 to 12 carbons or alkenyl having 2 to 12 carbons; and X is hydrogen or fluorine.

Item 8. The liquid crystal composition according to any one of items 1 to 7, wherein component (a) is at least one compound selected from the group of compounds represented by formulas (1a-11) and (1a-12):

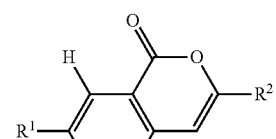
(1a-11)

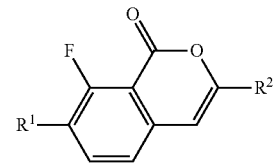
(1a-12)

wherein, in formulas (1a-11) and (1a-12), $R^1$ and $R^2$ are independently alkyl having 1 to 12 carbons, alkoxy having 1 to 12 carbons or alkenyl having 2 to 12 carbons.

Item 9. The liquid crystal composition according to any one of items 1 to 8, further containing at least one compound selected from the group of compounds represented by formulas (5) to (11) as component (c):

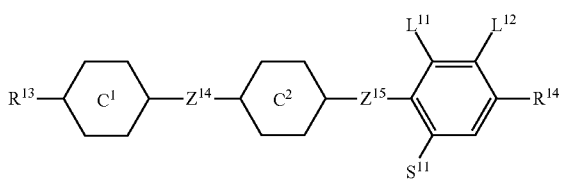
(5)

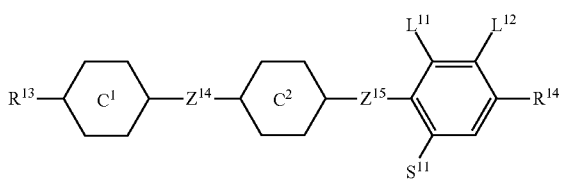
(6)

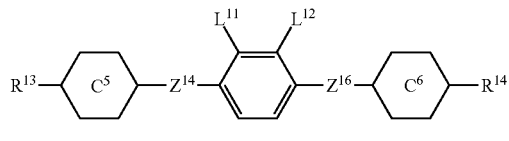
(7)

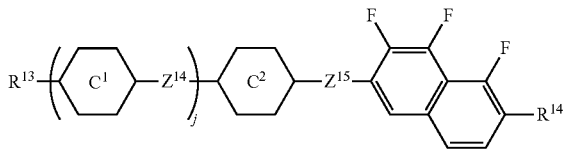
(8)

-continued

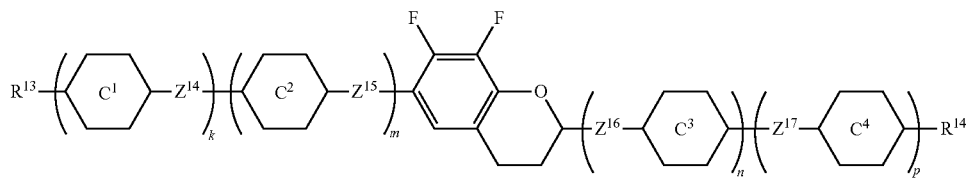
(9)

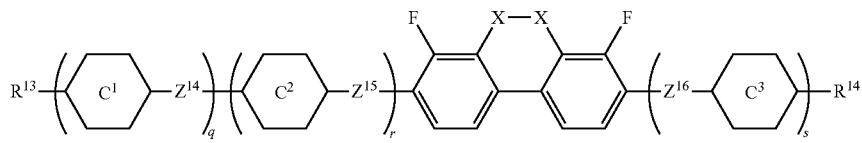
(10)

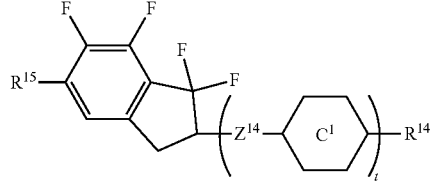
(11)

wherein, in formulas (5) to (11), $R^{13}$, $R^{14}$ and $R^{15}$ are independently alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine, and $R^{15}$ may be hydrogen or fluorine;

ring $C^1$, ring $C^2$, ring $C^3$ and ring $C^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;

ring $C^5$ and ring $C^6$ are independently 1,4-cyclohexylene, 1,4-cyclohexenylene, 1,4-phenylene, tetrahydropyran-2,5-diyl or decahydronaphthalene-2,6-diyl;

$Z^{14}$, $Z^{15}$, $Z^{16}$ and $Z^{17}$ are independently a single bond, —COO—, —$CH_2O$—, —$OCF_2$—, —$CH_2CH_2$— or —$OCF_2CH_2CH_2$—;

$L^{11}$ and $L^{12}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 10. The liquid crystal composition according to any one of items 1 to 9, further containing at least one compound selected from the group of compounds represented by formulas (12) to (14) as component (d):

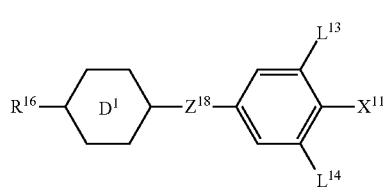
(12)

-continued

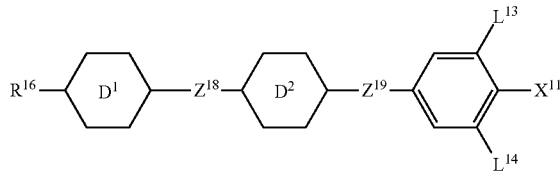
(13)

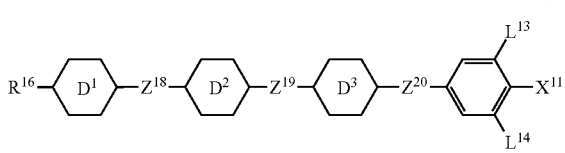
(14)

wherein, in formulas (12) to (14), $R^{16}$ is alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine;

$X^{11}$ is fluorine, chlorine, —$CF_3$, —$CHF_2$, —$CH_2F$, —$OCF_3$, —$OCHF_2$, —$OCF_2CHF_2$ or —$OCF_2CHFCF_3$;

ring $D^1$, ring $D^2$ and ring $D^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{18}$, $Z^{19}$ and $Z^{20}$ are independently a single bond, —COO—, —$CH_2O$—, —$CF_2O$—, —$OCF_2$—, —$CH_2CH_2$—, —CH=CH—, —C≡C— or —$(CH_2)_4$—; and $L^{13}$ and $L^{14}$ are independently hydrogen or fluorine.

Item 11. The liquid crystal composition according to any one of items 1 to 10, further containing at least one compound selected from the group of compounds represented by formula (15) as component (e):

(15)

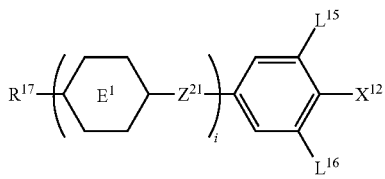

wherein, in formula (15), $R^{17}$ is alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine;

$X^{12}$ is —C≡N or —C≡C—C≡N;

ring $E^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{21}$ is a single bond, —COO—, —$CH_2O$—, —$CF_2O$—, —$OCF_2$—, —$CH_2CH_2$— or —C≡C—;

$L^{15}$ and $L^{16}$ are independently hydrogen or fluorine; and i is 1, 2, 3 or 4.

Item 12. A compound, represented by formula (1-2):

(1-2)

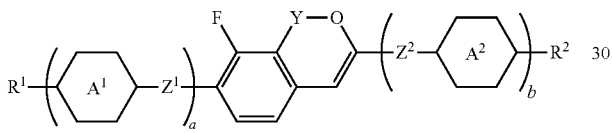

wherein, in formula (1-2), $R^1$ and $R^2$ are independently hydrogen, alkyl having 1 to 14 carbons or alkenyl having 2 to 14 carbons, and in the alkyl and the alkenyl, one or two pieces of —$CH_2$— may be replaced by —O—, and in the groups, at least one hydrogen may be replaced by fluorine;

ring $A^1$ and ring $A^2$ are independently 1,4-cyclohexylene, 1,4-cyclohexenylene, 1,3-dioxane-2,5-diyl, tetrahydropyran-2,5-diyl, 1,4-phenylene, 3-fluoro-1,4-phenylene, 3,5-difluoro-1,4-phenylene, pyridine-2,5-diyl or pyrimidine-2,5-diyl;

$Z^1$ and $Z^2$ are independently a single bond, —O—, —COO—, —OCO—, —$CH_2O$—, —$OCH_2$—, —$CF_2O$—, —$OCF_2$—, —$CH_2CH_2$— or —CH=CH—;

Y is —CO— or —$CF_2$—; and a and b are independently 0, 1 or 2, and a sum of a and b is 0, 1 or 2.

Item 13. The compound according to item 12, represented by any one of formulas (1a-2) to (1t-2):

(1a-2)

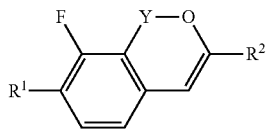

(1b-2)

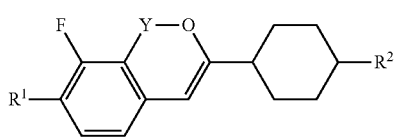

(1c-2)

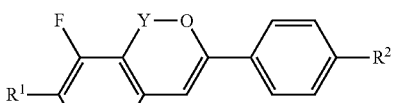

(1d-2)

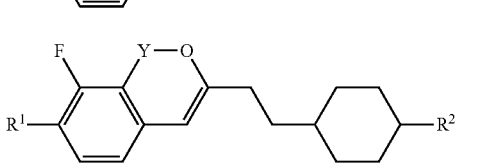

(1e-2)

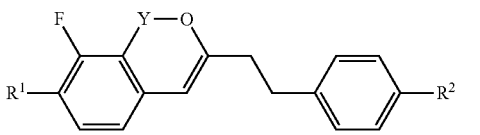

(1f-2)

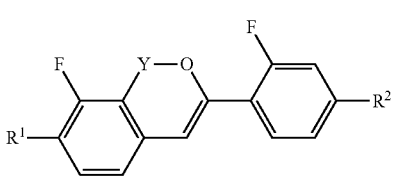

(1g-2)

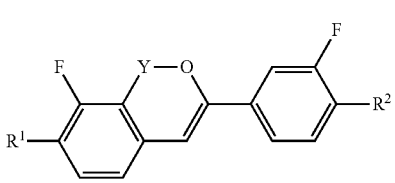

(1h-2)

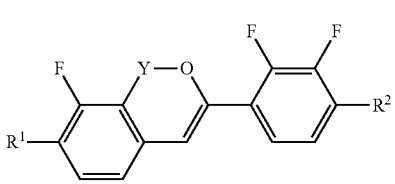

(1i-2)

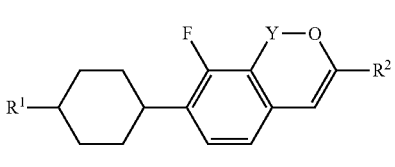

(1j-2)

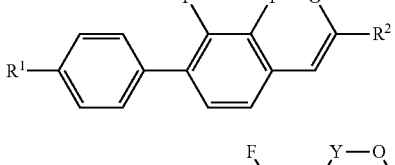

(1k-2)

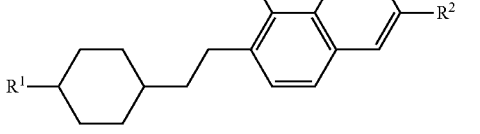

(1l-2)

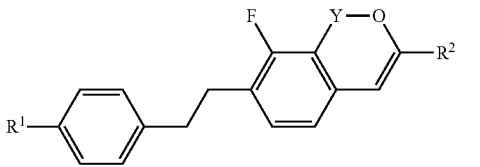

-continued
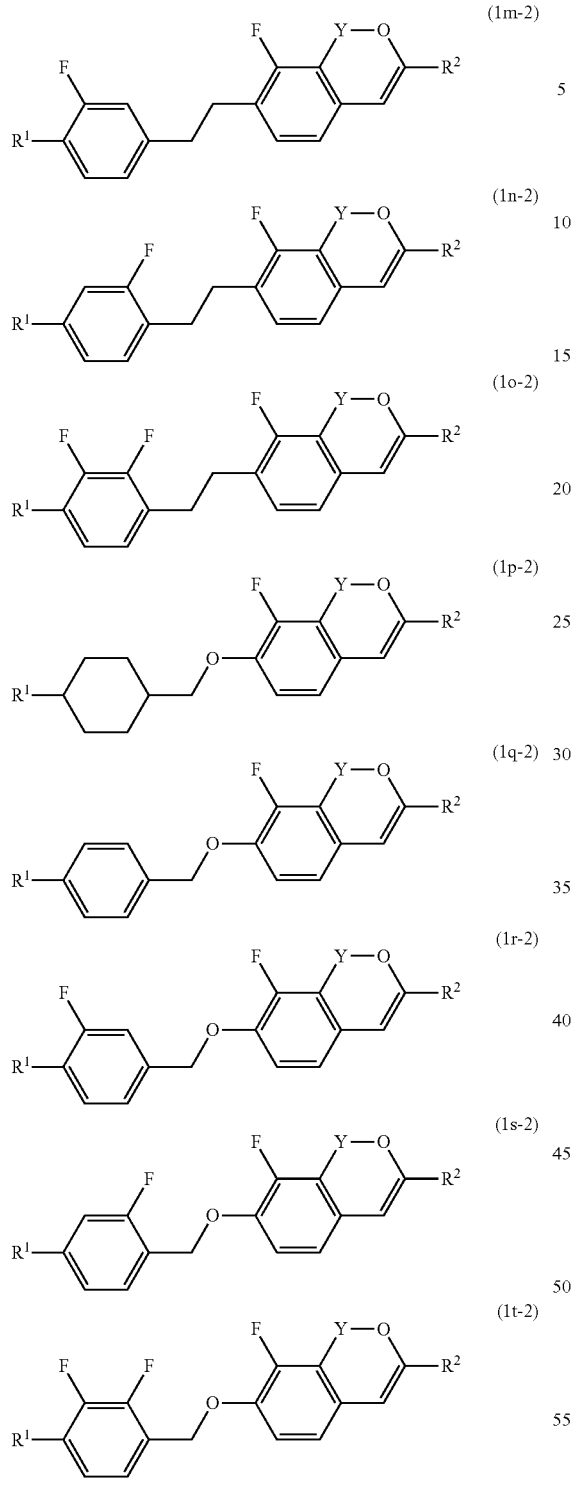
wherein, in formulas (1a-2) to (1t-2),
R¹ and R² are independently alkyl having 1 to 12 carbons, alkoxy having 1 to 12 carbons or alkenyl having 2 to 12 carbons; and
Y is —CO— or —CF$_2$—.
Item 14. The compound according to item 12 or 13, represented by any one of formulas (1a-3) to (1t-3):
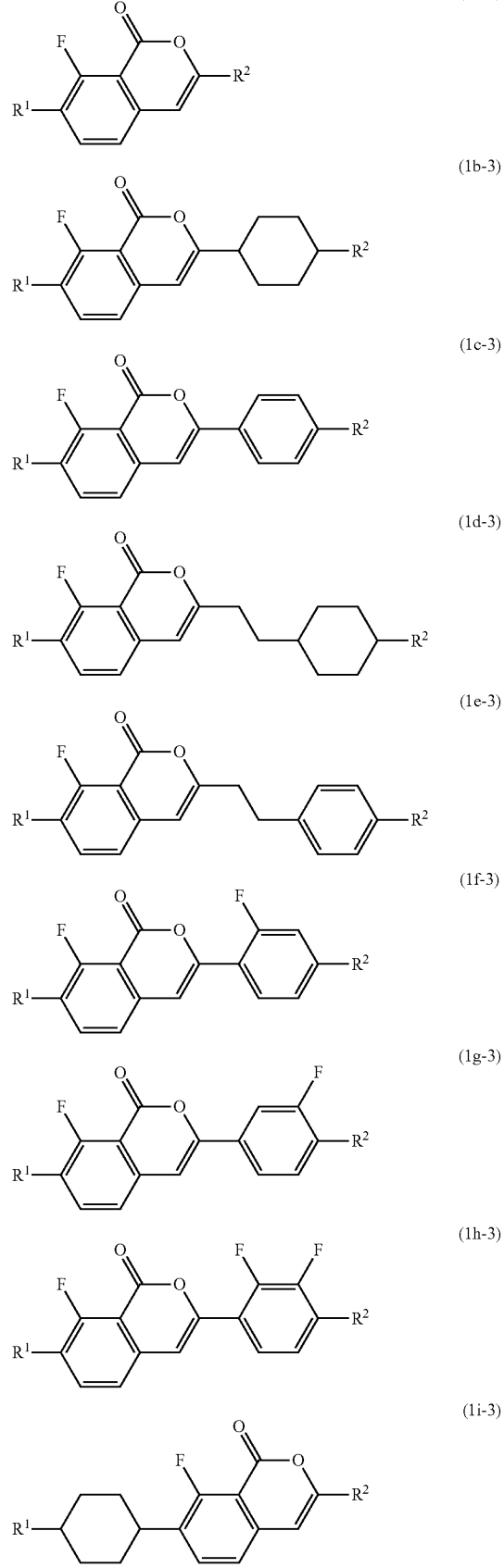

(1j-3)
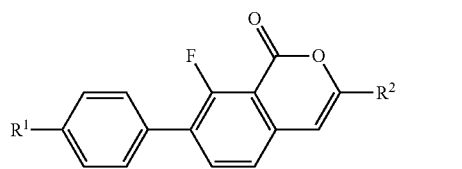

(1k-3)
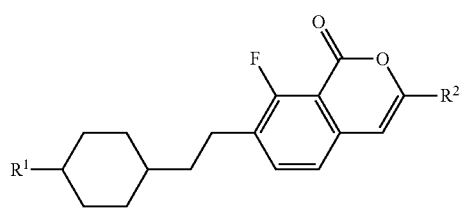

(1l-3)
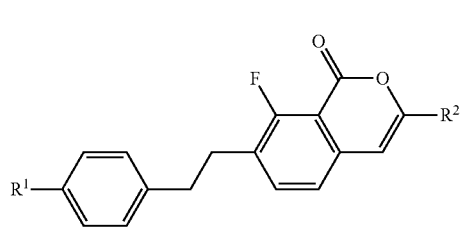

(1m-3)
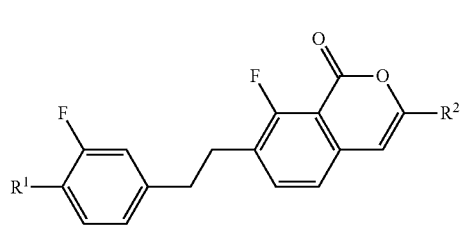

(1n-3)
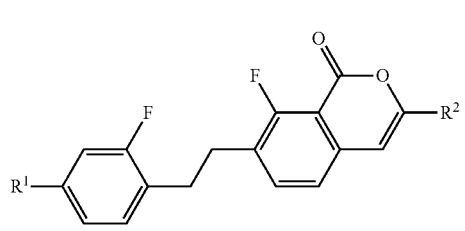

(1o-3)
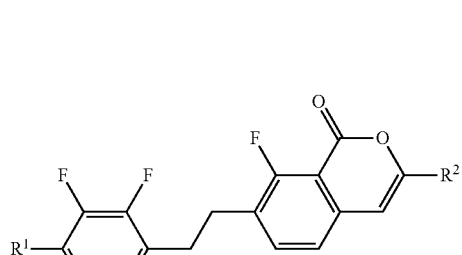

(1p-3)
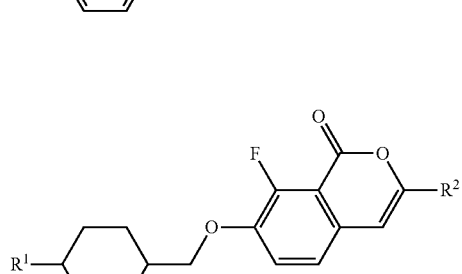

(1q-3)
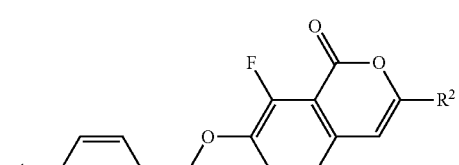

(1r-3)
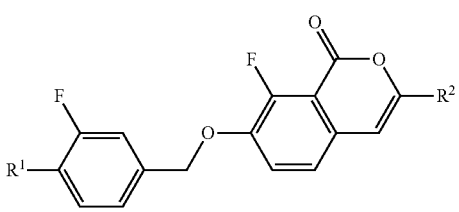

(1s-3)
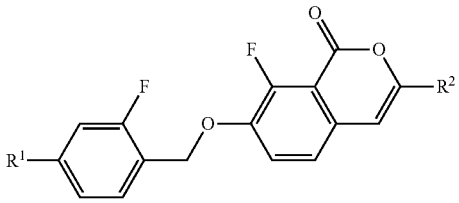

(1t-3)
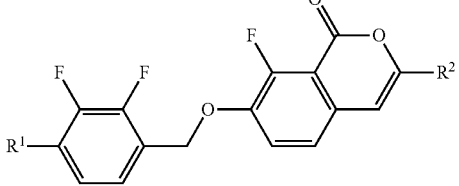

wherein, in formulas (1a-3) to (1t-3), $R^1$ and $R^2$ are independently alkyl having 1 to 12 carbons, alkoxy having 1 to 12 carbons or alkenyl having 2 to 12 carbons.

Item 15. The compound according to any one of items 12 to 14, represented by formula (1a-12):

(1a-12)
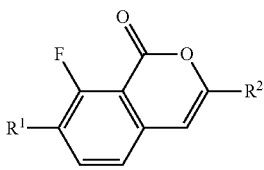

wherein, in formula (1a-12), $R^1$ and $R^2$ are independently alkyl having 1 to 12 carbons, alkoxy having 1 to 12 carbons or alkenyl having 2 to 12 carbons.

Item 16. The compound according to item 15, wherein, in formula (1a-12), $R^1$ is alkoxy having 1 to 12 carbons, $R^2$ is alkyl having 1 to 12 carbons, alkoxy having 1 to 12 carbons or alkenyl having 2 to 12 carbons.

Item 17. A liquid crystal display device, including the liquid crystal composition according to any one of items 1 to 11.

The invention further includes the following items: (a) the composition, further containing at least one of an optically active compound and/or a polymerizable compound, and (b) the composition, further containing at least one of an antioxidant and/or an ultraviolet light absorber.

The invention further includes the following items: (c) the composition, further containing one, two or at least three additives selected from the group of a polymerizable compound, a polymerization initiator, a polymerization inhibitor, an optically active compound, an antioxidant, an ultraviolet light absorber, a light stabilizer, a heat stabilizer, a dye and an antifoaming agent; (d) the composition, wherein a maximum temperature of a nematic phase is 70° C. or more, an optical anisotropy (measured at 25° C.) at a wavelength of 589 nanometers is 0.08 or more, and a dielectric anisotropy (measured at 25° C.) at a frequency of 1 kHz is −2 or less.

The invention further includes the following items: (e) a device including the composition and having the PC mode, the TN mode, the STN mode, the ECB mode, the OCB mode, the IPS mode, the VA mode, the FFS mode, the FPA or the PSA mode; (f) an AM device including the composition; (g) a transmissive device including the composition; (h) use of the composition as the composition having the nematic phase; and (i) use as an optically active composition by adding the optically active compound to the composition.

An aspect of compound (1), synthesis of compound (1), the liquid crystal composition and the liquid crystal display device will be described in the order.

1. Aspect of Compound (1)

Compound (1) has a feature of having a benzopyran skeleton in which benzene and pyran are fused. When Y is carbonyl, the skeleton is isocoumarin (1H-2-benzopyrane-1-one). When Y is difluoromethylene, the skeleton is 1H-isochromene (1H-2-benzopyran).

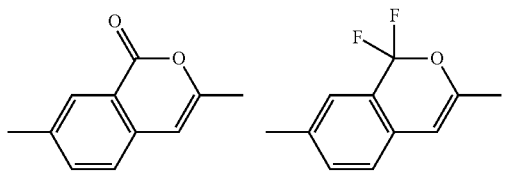

The compound has negative dielectric anisotropy. The compound is physically and chemically significantly stable under a condition at which the device is ordinarily used, and is excellent in compatibility with other liquid crystal compounds. A composition containing the compound is stable under a condition at which the device is ordinarily used. When the composition is kept at low temperature, the compound has small tendency of precipitation as crystals (or smectic phase). The compound has general physical properties required for the component of the composition, suitable optical anisotropy and suitable dielectric anisotropy.

Preferred examples of terminal groups ($R^1$ and $R^2$), rings ($A^1$ and $A^2$), bonding groups ($Z^1$ and $Z^2$) and substitutional groups (X, $L^1$ and $L^2$) in compound (1) are as described below. The examples are applied also in a subordinate formula of compound (1). In compound (1), physical properties can be arbitrarily adjusted by suitably combining the groups. Compound (1) may contain a larger amount of isotope such as $^2H$ (deuterium) and $^{13}C$ than the amount of natural abundance because no significant difference exists in the physical properties of the compound. In addition, symbols in compound (1) are defined according to item 1.

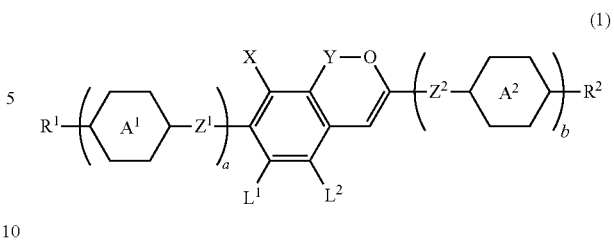

In formula (1), $R^1$ and $R^2$ are independently hydrogen, alkyl having 1 to 16 carbons, alkenyl having 1 to 16 carbons, cyclopropyl, cyclobutyl or cyclopentyl, and in the alkyl and the alkenyl, at least one piece of —$CH_2$— may be replaced by —O—, —S—, —CO—, —COO—, —OCO—, —OCOO—, —C≡C—, cyclopropane-1,2-diyl or —Si(CH_3)_2—, and in the groups, at least one hydrogen may be replaced by fluorine or chlorine.

Preferred $R^1$ or $R^2$ is hydrogen, alkyl, alkoxy, alkoxyalkyl, alkoxyalkoxy, alkylthio, alkylthioalkoxy, acyl, acylalkyl, acyloxy, acyloxyalkyl, alkoxycarbonyl, alkoxycarbonylalkyl, alkenyl, alkenyloxy, alkenyloxyalkyl, alkoxyalkenyl, alkynyl, alkynyloxy, silaalkyl or disilaalkyl. In the groups, at least one hydrogen may be replaced by fluorine or chlorine. The example includes a group in which at least two pieces of hydrogen are replaced by both fluorine and chlorine. A group in which at least one hydrogen is replaced by only fluorine is further preferred. In the groups, a straight chain is preferred to a branched chain. However, if $R^1$ or $R^2$ has a branched chain, the group is preferred when the group has optical activity.

Further preferred $R^1$ or $R^2$ is alkyl, alkoxy, alkoxyalkyl, alkenyl, monofluoroalkyl, polyfluoroalkyl, monofluoroalkoxy or polyfluoroalkoxy. In addition, polyfluoroalkyl and polyfluoroalkoxy include perfluoroalkyl and perfluoroalkoxy. Particularly preferred $R^1$ or $R^2$ is alkyl, alkoxy or alkenyl.

A preferred configuration of —CH═CH— in the alkenyl depends on a position of a double bond. A trans configuration is preferred in the alkenyl such as 1-propenyl, 1-butenyl, 1-pentenyl, 1-hexenyl, 3-pentenyl and 3-hexenyl. A cis configuration is preferred in the alkenyl such as 2-butenyl, 2-pentenyl and 2-hexenyl.

Specific $R^1$ or $R^2$ is methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 1-propynyl or 1-pentenyl.

Specific $R^1$ or $R^2$ is also 2-fluoroethyl, 3-fluoropropyl, 2,2,2-trifluoroethyl, 2-fluorovinyl, 2,2-difluorovinyl, 2-fluoro-2-vinyl, 3-fluoro-1-propenyl, 3,3,3-trifluoro-1-propenyl, 4-fluoro-1-propenyl or 4,4-difluoro-3-butenyl.

Further preferred $R^1$ or $R^2$ is methyl, ethyl, propyl, butyl, pentyl, methoxy, ethoxy, propoxy, butoxy, pentyloxy, methoxymethyl, ethoxymethyl, propoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy or 2-pentenyloxy. Most preferred $R^1$ or $R^2$ is methyl, ethyl, propyl, butyl, pentyl, methoxy, ethoxy, propoxy, methoxymethyl, vinyl, 1-propenyl, 3-butenyl or 3-pentenyl.

In formula (1), $R^1$ or $R^2$ is alkyl or the like. In the groups, at least one piece of —$CH_3$ may be replaced by any one of monovalent groups (G1) to (G4) described below.

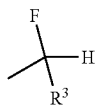 (G1)

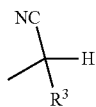 (G2)

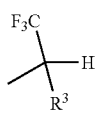 (G3)

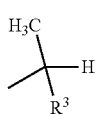 (G4)

In which, in groups (G1) to (G4), $R^3$ is alkyl having 1 to 12 carbons or alkenyl having 2 to 12 carbons, and in the alkyl and the alkenyl, at least one piece of —$CH_2$— may be replaced by —O—, and in the groups, at least one hydrogen may be replaced by fluorine or chlorine.

Preferred $R^3$ is alkyl. Specific $R^3$ is methyl or ethyl. Compounds each having monovalent groups (G1) to (G4) may have optical activity or may be a racemic form.

In formula (1), ring $A^1$ and ring $A^2$ are independently 1,4-cyclohexylene, 1,4-cyclohexenylene, 1,4-phenylene, decahydronaphthalene-2,6-diyl, tetrahydronaphthalene-2,6-diyl or naphthalene-2,6-diyl, and in the groups, one or two pieces of —$CH_2$— may be replaced by —O—, —S—, —CO—, —$CF_2$—, —$SiH_2$— or —$Si(CH_3)_2$—, and one or two pieces of —$CH_2CH_2$— may be replaced by —CH=CH— or —CH=N—, and in the groups, at least one hydrogen on an aromatic ring may be replaced by halogen, —$CF_3$, —$CHF_2$, —$CH_2F$, —$OCF_3$, —$OCHF_2$, —$OCH_2F$ or —C≡N.

Preferred examples of the group under an expression "in the groups, one or two pieces of —$CH_2$— may be replaced by —O—, —S—, —CO—, —$CF_2$—, —$SiH_2$— or —$Si(CH_3)_2$—, and one or two pieces of —$CH_2CH_2$— may be replaced by —CH=CH— or —CH=N—" include a divalent group represented by formulas (16-1) to (16-50) described below. Further preferred examples include a divalent group represented by formulas (16-1) to (16-4), formula (16-15), formula (16-23), formulas (16-27) to (16-29), formula (16-36), formula (16-39) or formula (16-45).

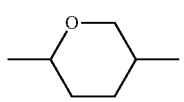 (16-1)

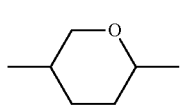 (16-2)

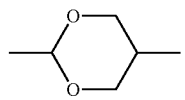 (16-3)

 (16-4)

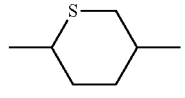 (16-5)

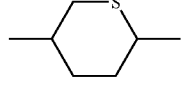 (16-6)

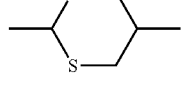 (16-7)

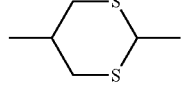 (16-8)

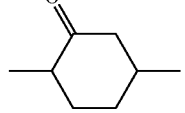 (16-9)

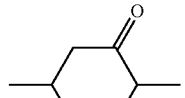 (16-10)

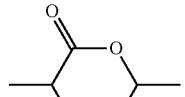 (16-11)

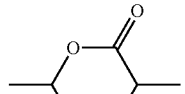 (16-12)

 (16-13)

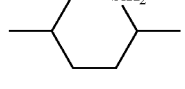 (16-14)

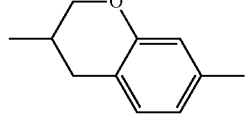 (16-15)

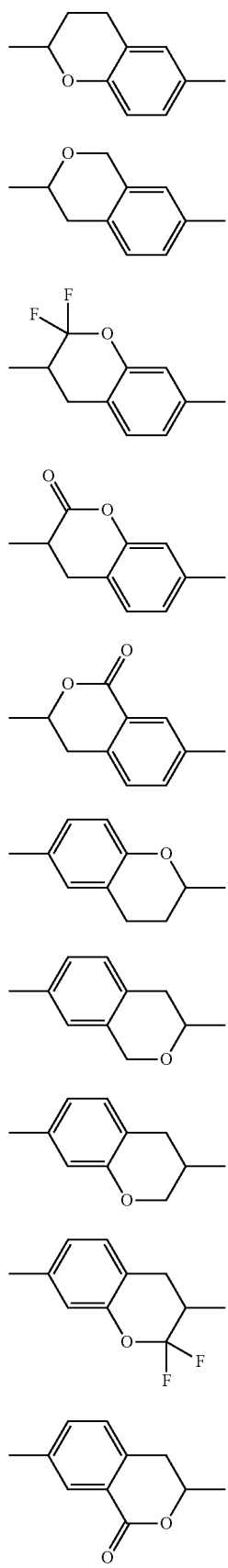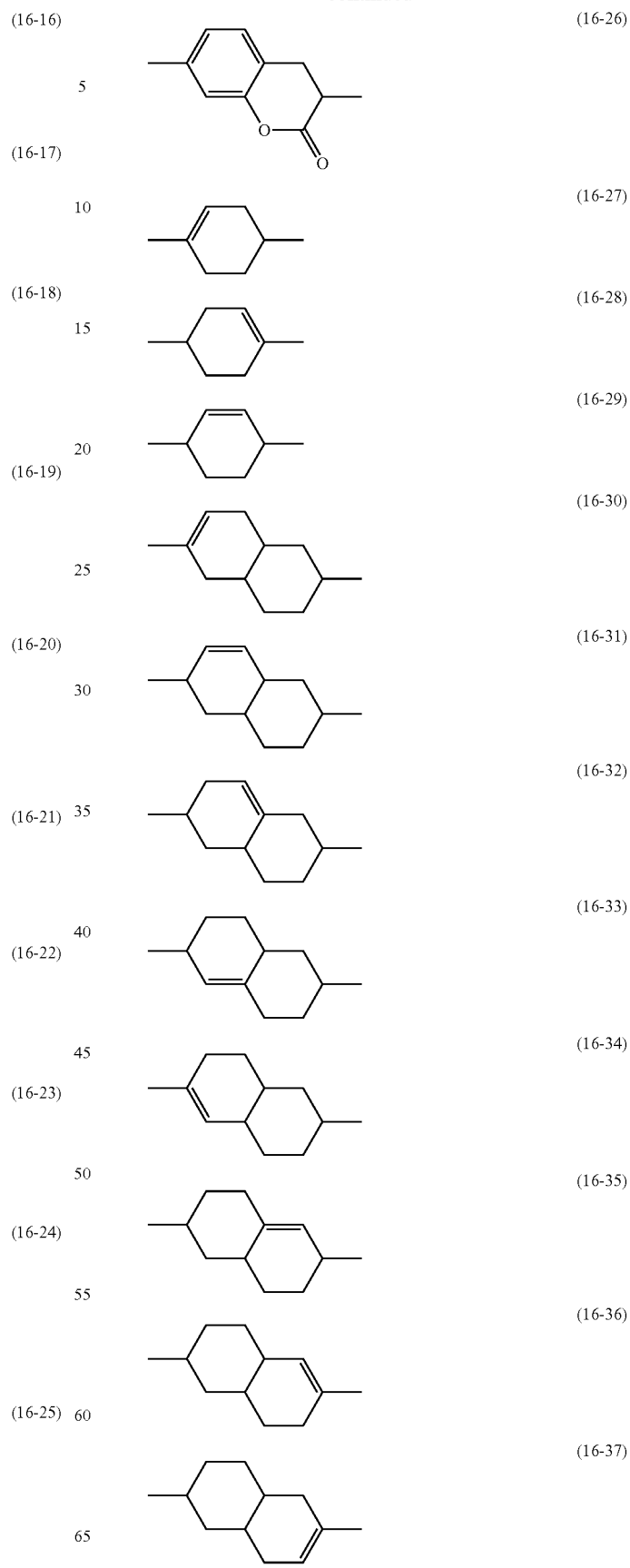

(16-38)
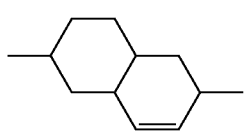
(16-39)
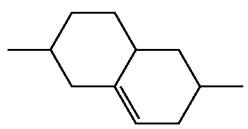
(16-40)
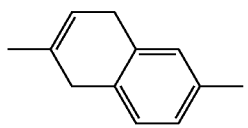
(16-41)
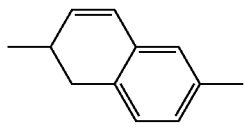
(16-42)
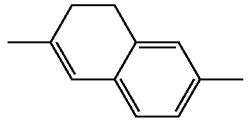
(16-43)
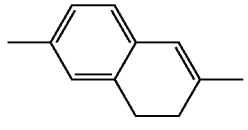
(16-44)
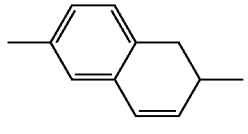
(16-45)
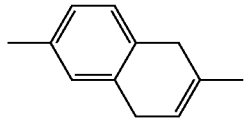
(16-46)
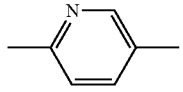
(16-47)
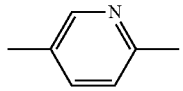
(16-48)
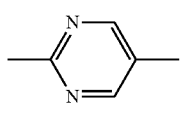
(16-49)
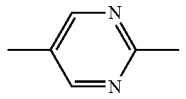
(16-50)
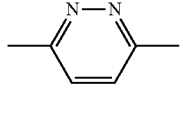
Preferred examples of the group under an expression "in the divalent groups, at least one hydrogen may be replaced by fluorine, chlorine, —C≡N, —CF$_3$, —CHF$_2$, —CH$_2$F, —OCF$_3$, —OCHF$_2$ or —OCH$_2$F" include a divalent group represented by formulas (17-1) to (17-71). Further preferred examples include a divalent group represented by formulas (17-1) to (17-4), formula (17-6), formulas (17-10) to (17-15) or formulas (17-54) to (17-59).
(17-1)
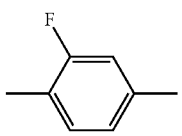
(17-2)
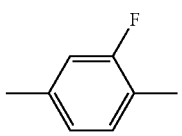
(17-3)
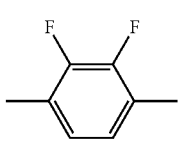
(17-4)
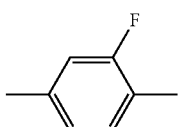
(17-5)
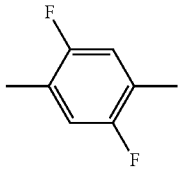
(17-6)
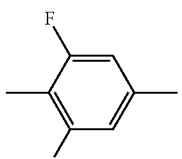
(17-7)
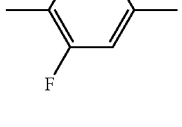
(17-8)
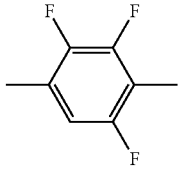

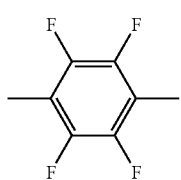 (17-9)
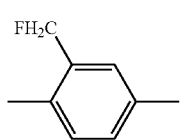 (17-10)
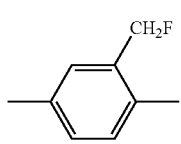 (17-11)
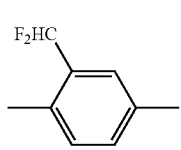 (17-12)
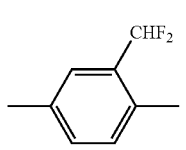 (17-13)
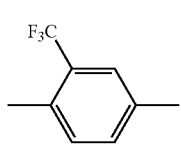 (17-14)
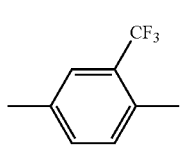 (17-15)
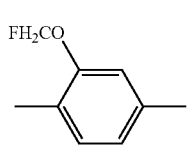 (17-16)
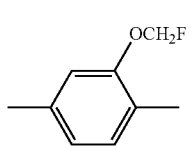 (17-17)
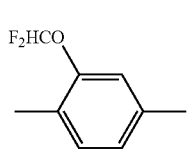 (17-18)
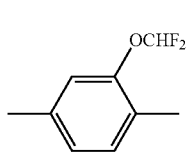 (17-19)
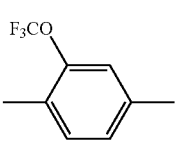 (17-20)
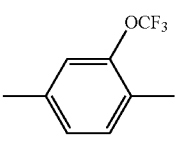 (17-21)
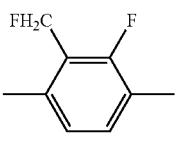 (17-22)
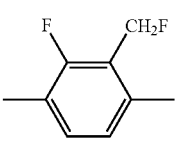 (17-23)
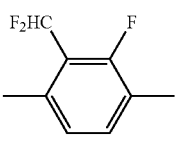 (17-24)
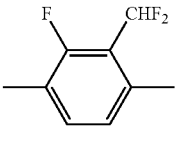 (17-25)
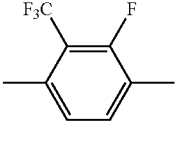 (17-26)
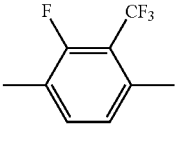 (17-27)
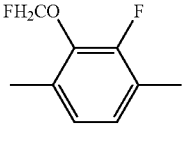 (17-28)
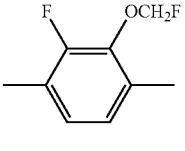 (17-29)
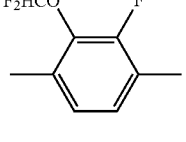 (17-30)

(17-31) 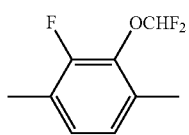
(17-32) 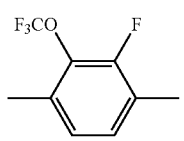
(17-33) 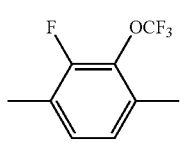
(17-34) 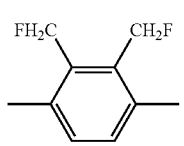
(17-35) 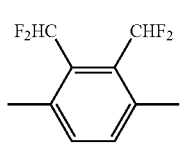
(17-36) 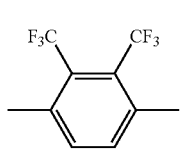
(17-37) 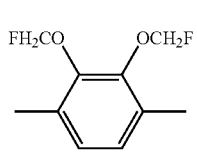
(17-38) 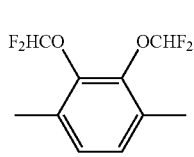
(17-39) 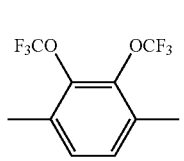
(17-40) 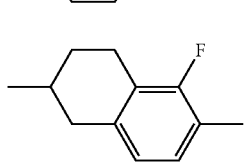
(17-41) 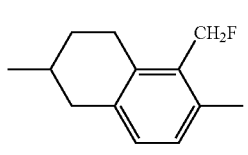
(17-42) 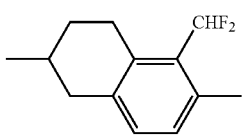
(17-43) 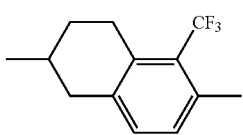
(17-44) 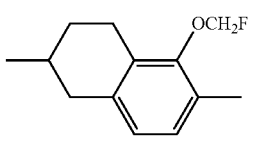
(17-45) 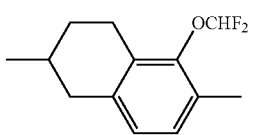
(17-46) 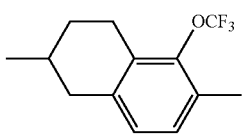
(17-47) 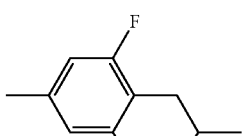
(17-48) 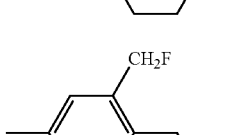
(17-49) 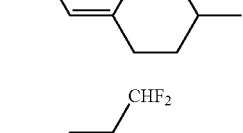
(17-50) 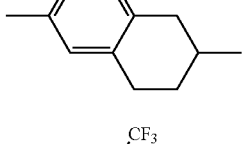
(17-51) 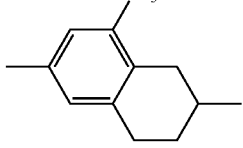
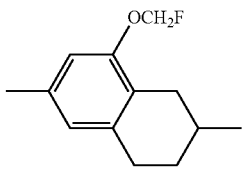

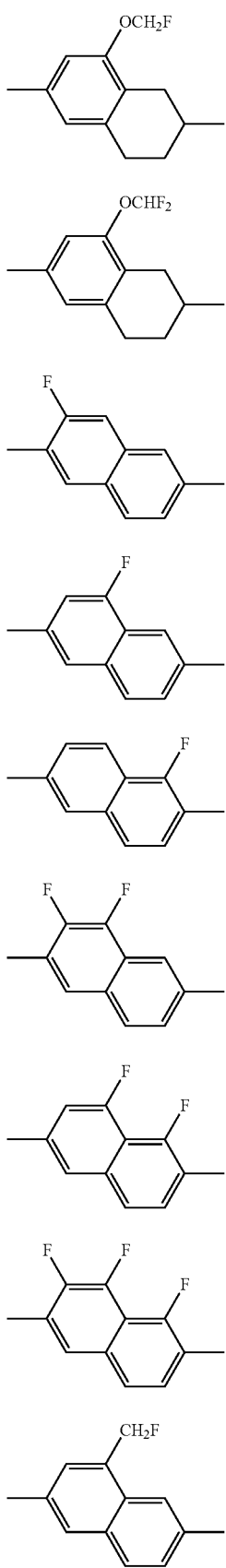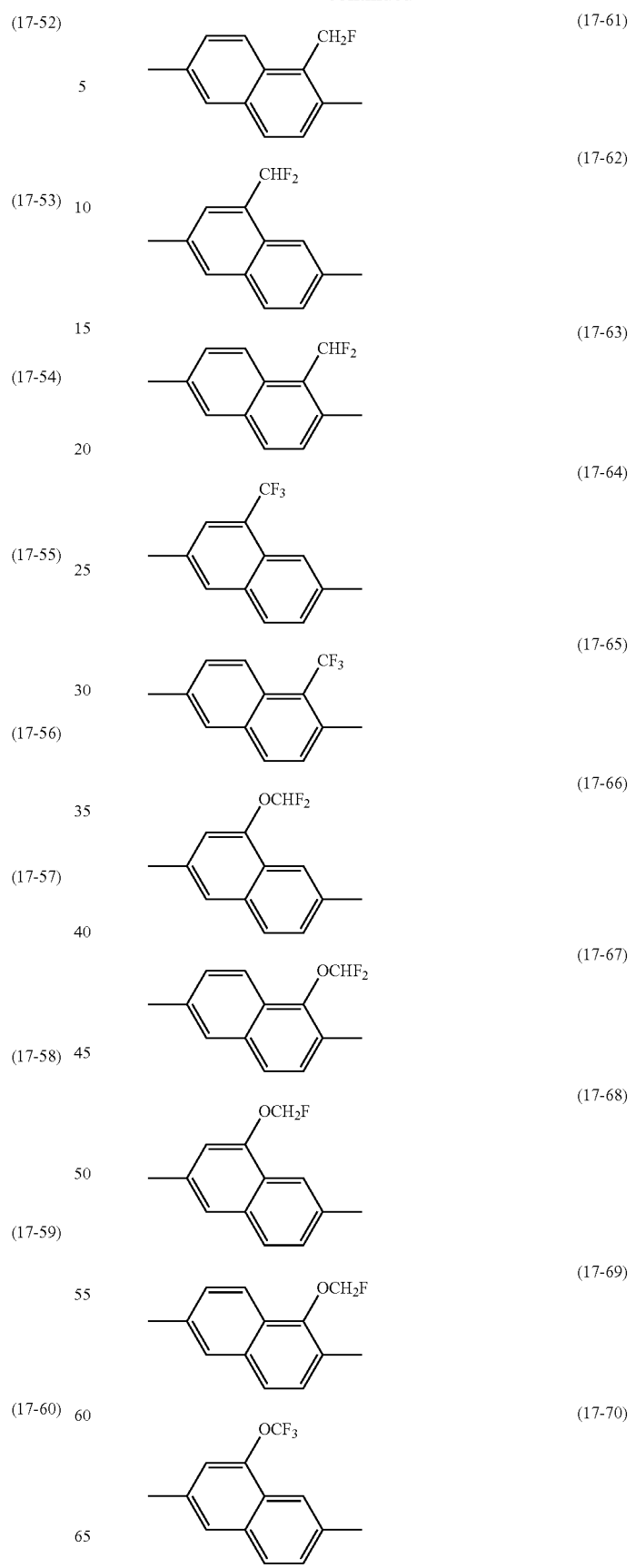

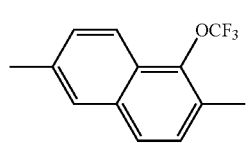

(17-71)

Further preferred ring $A^1$ or ring $A^2$ is 1,4-cyclohexylene, 1,4-cyclohexenylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5-trifluoro-1,4-phenylene, pyridine-2,5-diyl, 3-fluoropyridine-2,5-diyl, pyrimidine-2,5-diyl, pyridazine-2,5-diyl, decahydronaphthalene-2,6-diyl, 1,2,3,4-tetrahydronaphthalene-2,6-diyl or naphthalene-2,6-diyl. In a configuration of 1,4-cyclohexylene and 1,3-dioxane-2,5-diyl, trans is preferred to cis.

Particularly preferred ring $A^1$ or ring $A^2$ is 1,4-cyclohexylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, pyridine-2,5-diyl or pyrimidine-2,5-diyl. Most preferred ring $A^1$ or ring $A^2$ is 1,4-cyclohexylene or 1,4-phenylene.

In formula (1), $Z^1$ and $Z^2$ are independently a single bond or alkylene having 1 to 4 carbons, and one piece of —CH$_2$— may be replaced by —O— or —CO—, and at least one piece of —CH$_2$CH$_2$— may be replaced by —CH=CH— or —C≡C—, and in the groups, at least one hydrogen may be replaced by fluorine or chlorine.

Specific examples of $Z^1$ or $Z^2$ include a single bond, —O—, —COO—, —OCO—, —CH$_2$O—, —OCH$_2$—, —CF$_2$O—, —OCF$_2$—, —CH$_2$CH$_2$—, —CH=CH—, —CF=CH—, —CH=CF—, —CF=CF—, —C≡C—, —CH$_2$CO—, —COCH$_2$—, —(CH$_2$)$_4$—, —(CH$_2$)$_2$COO—, —(CH$_2$)$_2$CO—, —OCO(CH$_2$)$_2$—, —COO(CH$_2$)$_2$—, —(CH$_2$)$_2$CF$_2$O—, —(CH$_2$)$_2$OCF$_2$—, —OCF$_2$(CH$_2$)$_2$—, —CF$_2$O(CH$_2$)$_2$—, —(CH$_2$)$_3$O— or —O(CH$_2$)$_3$—. With regard to a configuration of a double bond in the bonding group such as —CH=CH—, —CF=CF—, —CH=CH—CH$_2$O— and —OCH$_2$—CH=CH—, trans is preferred to cis.

Preferred $Z^1$ or $Z^2$ is a single bond, —O—, —COO—, —OCO—, —CH$_2$O—, —OCH$_2$—, —CF$_2$O—, —OCF$_2$—, —CH$_2$CH$_2$—, —CH=CH—, —CF=CF—, —C≡C— or —(CH$_2$)$_4$—. Further preferred $Z^1$ or $Z^2$ is a single bond, —COO—, —OCO—, —CF$_2$O—, —OCF$_2$—, —CH=CH—, —CH$_2$CH$_2$— or —C≡C—. Most preferred $Z^1$ or $Z^2$ is a single bond.

In formula (1), X, $L^1$ and $L^2$ are hydrogen or halogen. Preferred X, L or $L^2$ is hydrogen, fluorine or chlorine. Further preferred X, L or $L^2$ is hydrogen or fluorine. Particularly preferred X is fluorine. Particularly preferred $L^1$ or $L^2$ is hydrogen.

In formula (1), Y is —CO— or —CF$_2$—. When Y is —CO—, the skeleton is isocoumarin. When Y is —CO—, preferred X is fluorine for negatively increasing dielectric anisotropy. When Y is —CF$_2$—, the skeleton is 1H-isochromene. Preferred Y is —CO—. When Y is —CF$_2$—, preferred X is fluorine.

In formula (1), a and b are independently 0, 1 or 2. When the benzopyran skeleton is understood as one ring, the compound includes one ring to five rings. In compound (1), when a and b are 0, the compatibility with other liquid crystal compounds is satisfactory, and the viscosity is small. In formula (1), when a and b are 1 or 2, the maximum temperature is high and a temperature range of a liquid crystal phase is wide.

In compound (1), physical properties such as optical anisotropy and dielectric anisotropy can be arbitrarily adjusted by suitably selecting a terminal group, ring, bonding group and substitutional group. Effects of kinds of the groups on the physical properties of compound (1) will be described.

In compound (1), when $R^1$ or $R^2$ has a straight chain, the temperature range of the liquid crystal phase is wide and the viscosity is small. When $R^1$ or $R^2$ has a branched chain, the compatibility with other liquid crystal compounds is satisfactory. A compound in which $R^1$ or $R^2$ is an optically active group is useful as a chiral dopant. A reverse twisted domain to be generated in the device can be prevented by adding the compound to the composition. A compound in which $R^1$ or $R^2$ is not an optically active group is useful as a component of the composition. When $R^1$ or $R^2$ is alkenyl, a preferred configuration depends on a position of a double bond. An alkenyl compound having a preferred configuration has high maximum temperature or wide temperature range of the liquid crystal phase. A detailed description is found in Mol. Cryst. Liq. Cryst., 1985, 131, 109 and Mol. Cryst. Liq. Cryst., 1985, 131, 327.

When ring $A^1$ or ring $A^2$ is 1,4-phenylene in which at least one hydrogen may be replaced by fluorine or chlorine, pyridine-2,5-diyl, pyrimidine-2,5-diyl or pyridazine-3,6-diyl, the optical anisotropy is large. When the ring is 1,4-cyclohexylene, 1,4-cyclohexenylene or 1,3-dioxane-2,5-diyl, the optical anisotropy is small.

When at least one of the rings is 1,4-cyclohexylene, the maximum temperature is high and the optical anisotropy is small. When at least one of the rings is 1,4-phenylene, the optical anisotropy is comparatively large and an orientational order parameter is large. When at least two of the rings are 1,4-phenylene, the optical anisotropy is large, the temperature range of the liquid crystal phase is wide and the maximum temperature is high.

When bonding group $Z^1$ or $Z^2$ is a single bond, —O—, —CH$_2$O—, —CF$_2$O—, —OCF$_2$—, —CH$_2$CH$_2$—, —CH=CH—, —CF=CF— or —(CH$_2$)$_4$—, the viscosity is small. When the bonding group is a single bond, —OCF$_2$—, —CF$_2$O—, —CH$_2$CH$_2$— or —CH=CH—, the viscosity is further small. When the bonding group is —CH=CH—, the temperature range of the liquid crystal phase is large and a ratio $K_{33}/K_{11}$ ($K_{33}$: bend elastic constant, $K_{11}$: splay elastic constant) of the elastic constant is large. When the bonding group is —C≡C—, the optical anisotropy is large.

When compound (1) has one ring or two rings, the viscosity is small. When compound (1) has four rings or five rings, the maximum temperature is high. Thus, a compound having required physical properties can be obtained by suitably selecting a terminal group, ring, kinds of the bonding group and numbers of the ring. Accordingly, compound (1) is useful as a component of the composition to be used for the device having a mode such as PC, TN, STN, ECB, OCB, IPS and VA. Compound (1) is suitable for the device having the mode such as VA, IPS and PSA.

2. Synthesis of Compound (1)

A synthesis method of compound (1) will be described. Compound (1) can be prepared by suitably combining methods in synthetic organic chemistry. Methods for introducing a required terminal group, ring and bonding group into a starting material are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course" (Shin Jikken Kagaku Koza in Japanese) (Maruzen Co., Ltd.).

2-1. Formation of Bonding Group Z

First, a scheme is shown with regard to a method for forming bonding groups $Z^1$ and $Z^2$. Next, reactions described in the scheme in methods (1) to (11) are described. In the scheme, $MSG^1$ (or $MSG^2$) is a monovalent organic group. The monovalent organic groups represented by a plurality of $MSG^1$ (or $MSG^2$) used in the scheme may be identical or different. Compounds (1A) to (1J) correspond to compound (1).

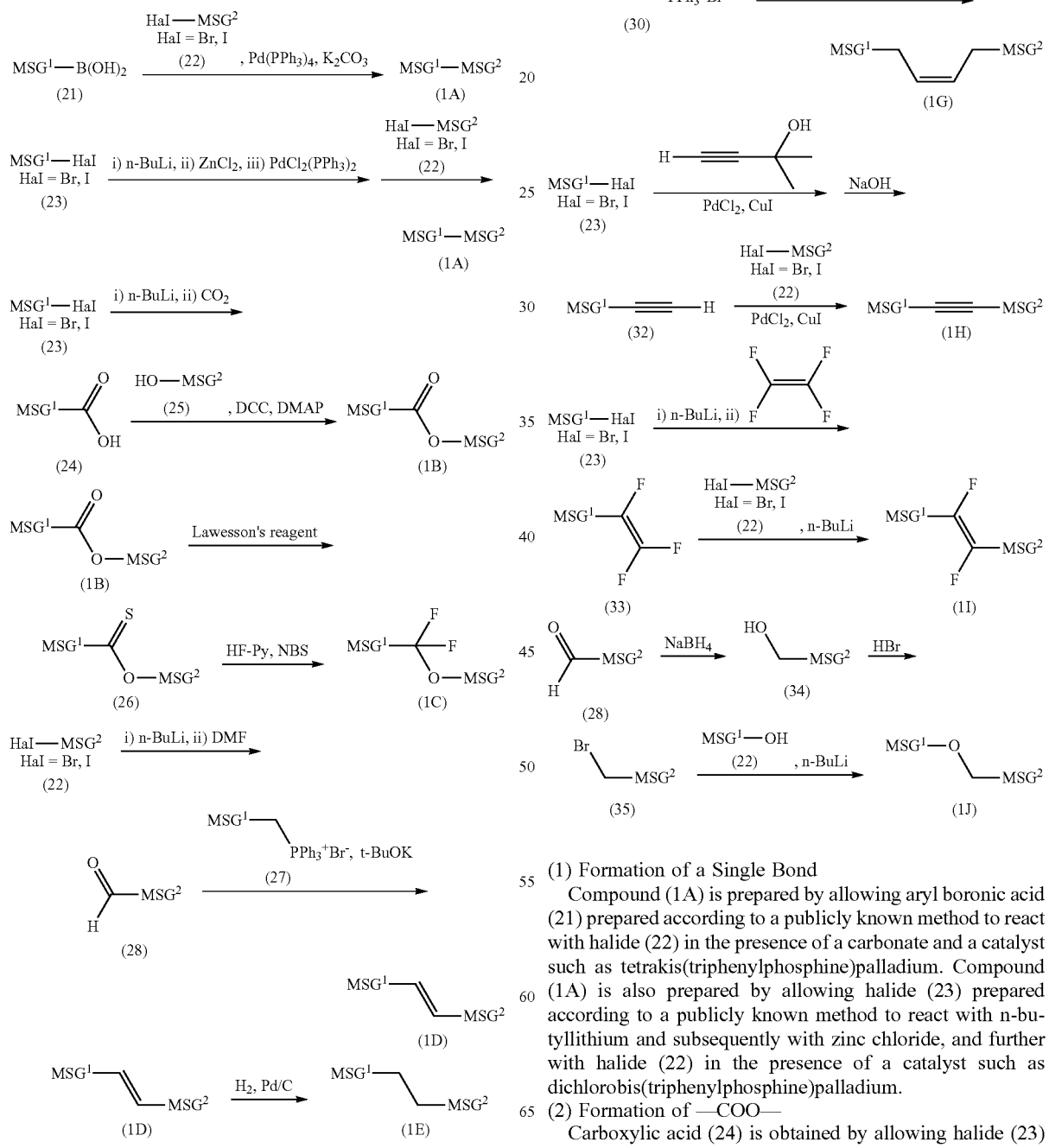

(1) Formation of a Single Bond

Compound (1A) is prepared by allowing aryl boronic acid (21) prepared according to a publicly known method to react with halide (22) in the presence of a carbonate and a catalyst such as tetrakis(triphenylphosphine)palladium. Compound (1A) is also prepared by allowing halide (23) prepared according to a publicly known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and subsequently with carbon dioxide. Compound (1B) is prepared by dehydration of compound (25) prepared according to a publicly known method and carboxylic acid (24) in the presence of 1,3-dicyclohexylcarbodiimide (DCC) and 4-dimethylaminopyridine (DMAP).

(3) Formation of —$CF_2O$—

Thionoester (26) is obtained by treating compound (1B) with a thiation reagent such as Lawesson's reagent. Compound (1C) is prepared by fluorinating thionoester (26) with a hydrogen fluoride-pyridine complex and N-bromosuccinimide (NBS). Refer to M. Kuroboshi et al., Chem. Lett., 1992, 827. Compound (1C) is also prepared by fluorinating thionoester (26) with (diethylamino) sulfur trifluoride (DAST). Refer to W. H. Bunnelle et al., J. Org. Chem. 1990, 55, 768. The bonding group can also be formed according to the method described in Peer. Kirsch et al., Angew. Chem. Int. Ed. 2001, 40, 1480.

(4) Formation of —CH=CH—

Aldehyde (28) is obtained by treating halide (22) with n-butyllithium and then allowing the treated halide to react with N,N-dimethylformamide (DMF). Phosphorus ylide is generated by treating phosphonium salt (27) prepared according to a publicly known method with a base such as potassium t-butoxide. Compound (1D) is prepared by allowing the phosphorus ylide to react with aldehyde (28). A cis isomer may be generated depending on reaction conditions, and therefore the cis isomer is isomerized into a trans isomer according to a publicly known method when necessary.

(5) Formation of —$CH_2CH_2$—

Compound (1E) is prepared by hydrogenating compound (1D) in the presence of a catalyst such as palladium on carbon.

(6) Formation of —$(CH_2)_4$—

A compound having —$(CH_2)_2$—CH=CH— is obtained by using phosphonium salt (29) in place of phosphonium salt (27) according to the method in method (4). Compound (1F) is prepared by performing catalytic hydrogenation of the compound obtained.

(7) Formation of —$CH_2CH$=$CHCH_2$—

Compound (1G) is prepared by using phosphonium salt (30) in place of phosphonium salt (27) and aldehyde (31) in place of aldehyde (28) according to the method in method (4). A trans isomer may be generated depending on reaction conditions, and therefore the trans isomer is isomerized into a cis isomer according to a publicly known method when necessary.

(8) Formation of —C≡C—

Compound (32) is obtained by allowing halide (23) to react with 2-methyl-3-butyn-2-ol in the presence of a catalyst including dichloropalladium and copper halide, and then performing deprotection under basic conditions. Compound (1H) is prepared by allowing compound (32) to react with halide (22) in the presence of the catalyst including dichloropalladium and copper halide.

(9) Formation of —CF=CF—

Compound (33) is obtained by treating halide (23) with n-butyllithium and then allowing the treated halide to react with tetrafluoroethylene. Compound (1I) is prepared by treating halide (22) with n-butyllithium and then allowing the treated halide to react with compound (33).

(10) Formation of —$OCH_2$—

Compound (34) is obtained by reducing aldehyde (28) with a reducing agent such as sodium borohydride. Bromide (35) is obtained by brominating compound (34) with hydrobromic acid or the like. Compound (1J) is prepared by allowing bromide (35) to react with compound (36) in the presence of a base such as potassium carbonate.

(11) Formation of —$(CF_2)_2$—

A compound having —(CF2)2- is obtained by fluorinating diketone (—COCO—) with sulfur tetrafluoride, in the presence of a hydrogen fluoride catalyst, according to the method described in J. Am. Chem. Soc., 2001, 123, 5414.

2-2. Formation of Rings $A^1$ to $A^3$ and Ring $N^1$

Next, a synthesis method regarding to rings $A^1$ to $A^3$ and ring $N^1$ will be described. With regard to a ring such as 1,4-cyclohexylene, 1,3-dioxane-2,5-diyl, 1,4-phenylene, 2-fluoro-1,4-phenylene, 2, 3-difluoro-1,4-phenylene, pyridine-2,5-diyl or pyrimidine-2,5-diyl, a starting material is commercially available or a synthesis method is well known. Thus, a synthesis method of compounds (64), (67) and (71) described below will be described.

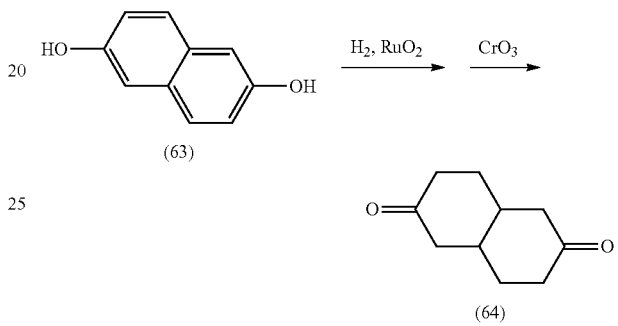

Decahydronaphthalene-2,6-dione (64) is a starting material of a compound containing decahydronaphthalene-2,6-diyl. The compound (64) is obtained by performing catalytic hydrogenation with diol (63) in the presence of ruthenium oxide according to a method described in JP 2000-239564 A, and subsequently oxidizing the resulting material with chromium oxide. The compound obtained is converted into compound (1) according to a conventional method.

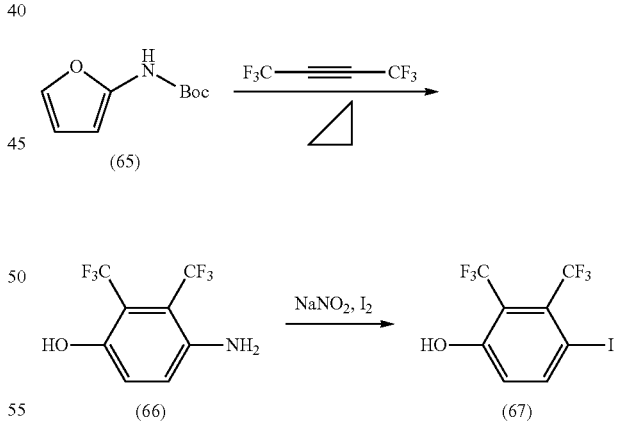

A structural unit of 2,3-(bistrifluoromethyl)phenylene is prepared according to a method described in Org. Lett., 2000, 2(21), 3345. Aniline (66) is prepared by allowing furan (65) to perform Diels Alder reaction with 1,1,1,4,4,4-hexafluoro-2-butyne at high temperature. Iodide (67) is obtained by performing a Sandmeyer reaction to the compound obtained according to a method described in Org. Synth. Coll., Vol. 2, 1943, 355. The compound obtained is converted to compound (1) according to a conventional method.

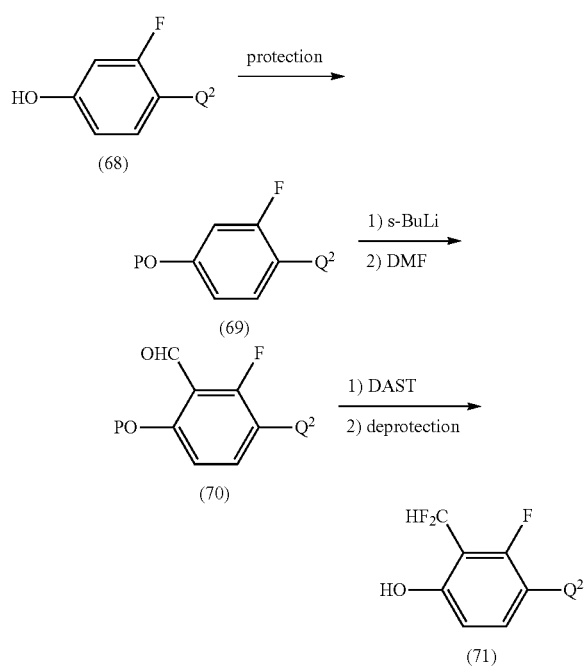

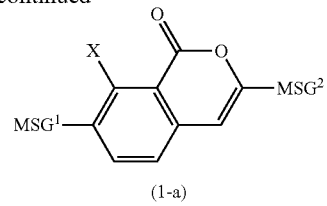

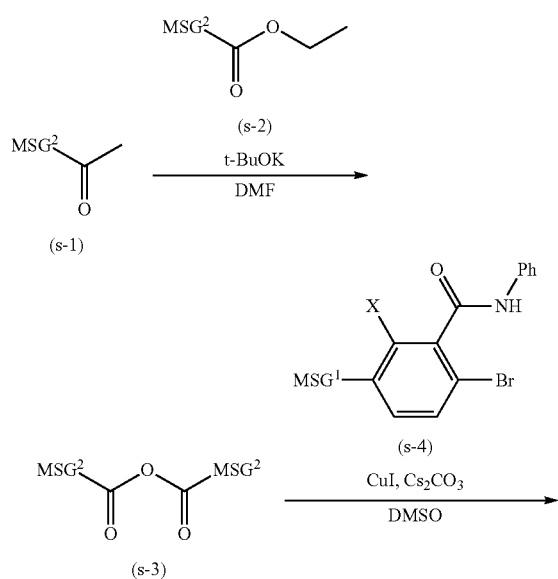

A structural unit of 2-difluoromethyl-3-fluorophenylene is prepared by a method as described below. A hydroxyl group of compound (68) is protected with a suitable protective group to obtain compound (69). P represents the protective group. Aldehyde (70) is obtained by acting compound (69) with s-butyllithium and subsequently allowing the obtained material to react with N,N-dimethylformamide (DMF). Phenol (71) is obtained by fluorinating the compound obtained with diethylaminosulfur trifluoride (DAST), and subsequently deprotecting the resulting material. The compound obtained is converted into compound (1) according to a conventional method.

2-3. Formation of Isocoumarin Skeleton

A synthesis scheme of compound (1-a) is as described below.

Diketone (s-3) is prepared by condensing commercially available ketone (s-1) with commercially available ester (s-2) according to an ordinary method. Compound (1-a) is obtained by acting compound (s-4) on the compound obtained in the presence of cesium carbonate and copper iodide in dimethyl sulfoxide. See The Journal Organic Chemistry, 2012, 77, 5022-5029.

3. Liquid Crystal Composition 3-1. Component Compound

A liquid crystal composition of the invention will be described. The composition contains at least one compound (1) as component (a) The composition may contain two, three or more compounds (1). A component in the composition may be only compound (1). In order to develop satisfactory physical properties, the composition preferably contains at least one of compounds (1) in the range of about 1% by weight to about 99% by weight. In a composition having negative dielectric anisotropy, a preferred proportion of compound (1) is in the range of about 5% by weight to about 60% by weight. In a composition having positive dielectric anisotropy, a preferred proportion of compound (1) is about 30% by weight or less.

TABLE 1

Component compounds of composition

| Component | Component compound | Dielectric anisotropy |
| --- | --- | --- |
| Component (a) | Compound (1) | Negatively large |
| Component (b) | Compound (2) to Compound (4) | Small |
| Component (c) | Compound (5) to Compound (11) | Negatively large |
| Component (d) | Compound (12) to Compound (14) | Positively large |
| Component (e) | Compound (15) | Positively large |

The composition contains compound (1) as component (a). The composition further preferably contains a liquid crystal compound selected from components (b) to (e) described in Table 1. When the composition is prepared, components (b) to (e) are preferably selected by taking into account the positive or negative dielectric anisotropy and magnitude of the dielectric anisotropy. The composition may contain a liquid crystal compound different from compounds (1) to (15). The composition may not contain such a liquid crystal compound.

Component (b) includes a compound in which two terminal groups are alkyl or the like. Preferred examples of component (b) include compounds (2-1) to (2-11), compounds (3-1) to (3-19) and compounds (4-1) to (4-7). In the compounds, $R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine.

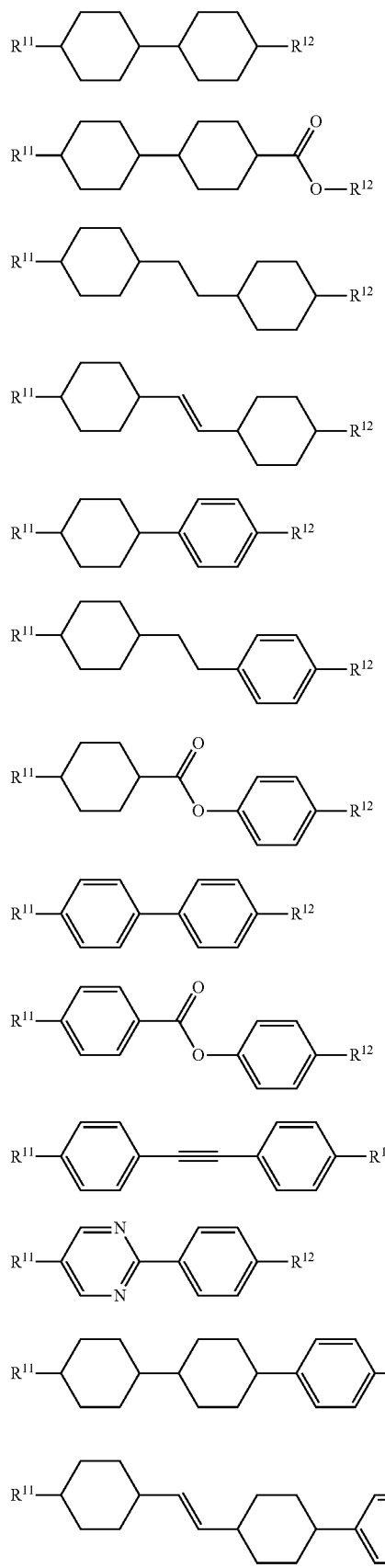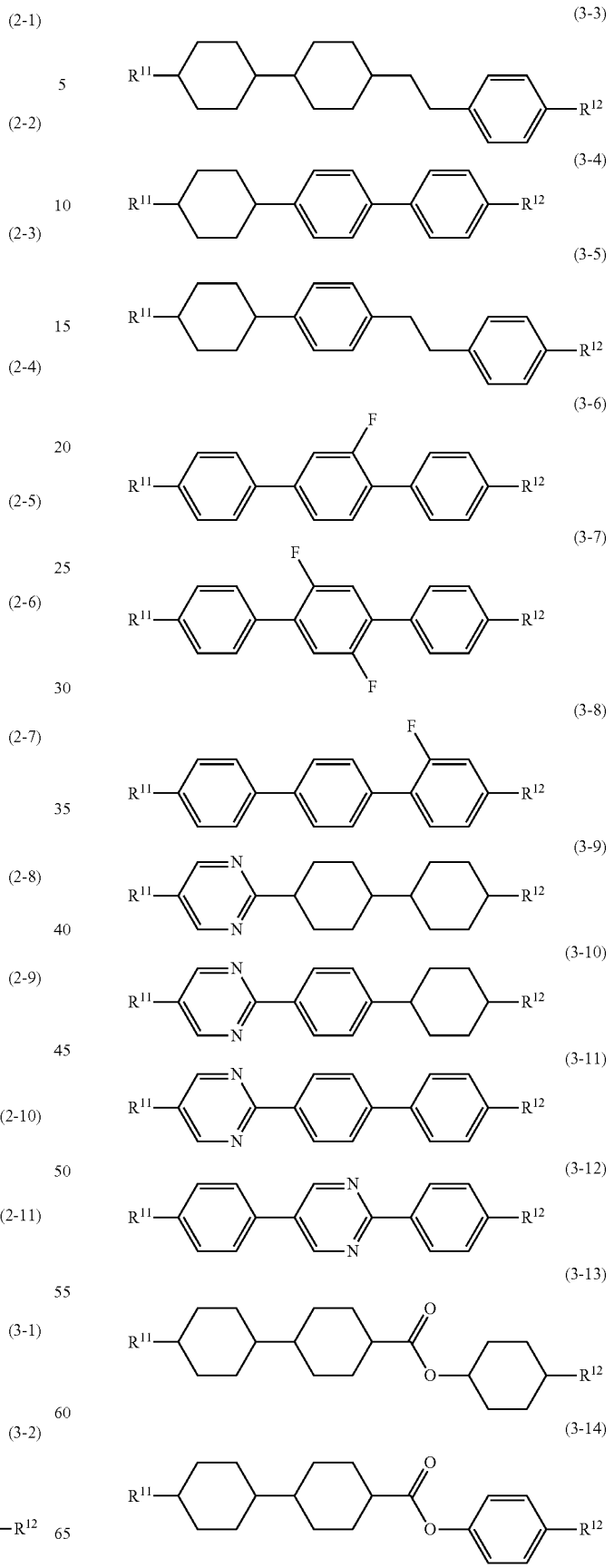

(3-15)
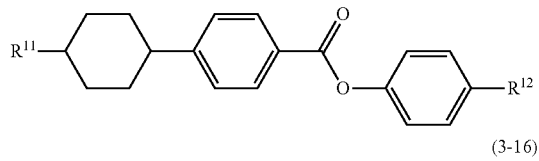

(3-16)
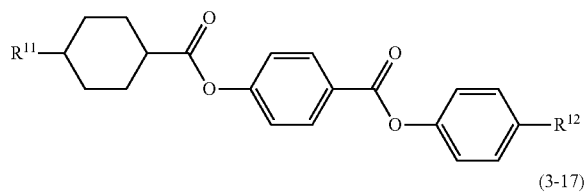

(3-17)
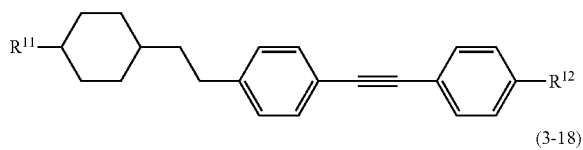

(3-18)
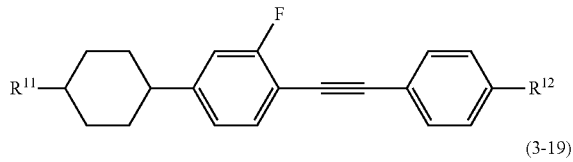

(3-19)
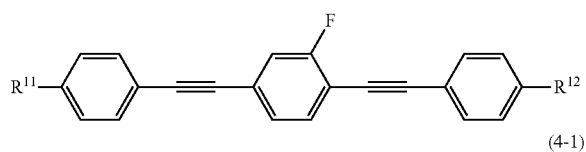

(4-1)
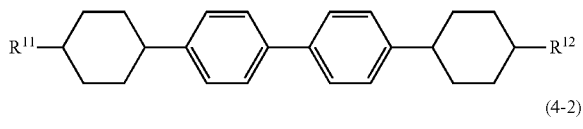

(4-2)
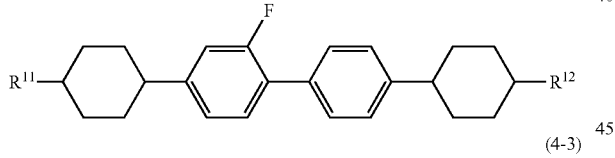

(4-3)
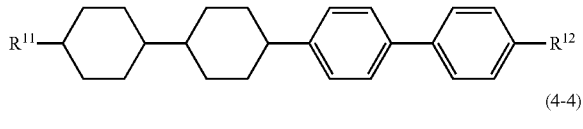

(4-4)
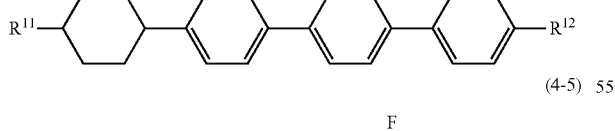

(4-5)
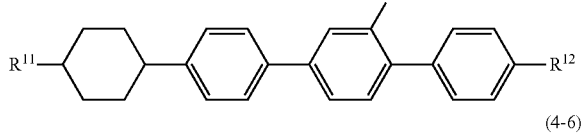

(4-6)
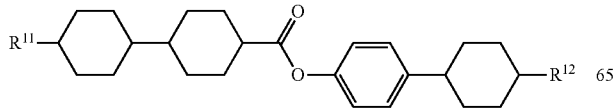

(4-7)
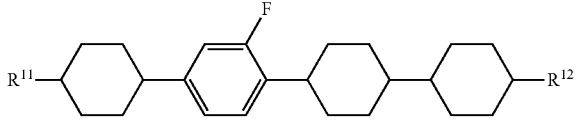

Component (b) has small dielectric anisotropy. Component (b) is close to neutrality. Compound (2) is effective in decreasing viscosity or adjusting optical anisotropy. Compounds (3) and (4) are effective in extending a temperature range of a nematic phase by increasing maximum temperature, or adjusting the optical anisotropy.

As a proportion of component (b) is increased, the viscosity of the composition is decreased, and the dielectric anisotropy is decreased. Thus, as long as a desired value of a threshold voltage of the device is met, the content is preferably as large as possible. When a composition for the IPS mode, the VA mode or the like is prepared, a proportion of component (b) is preferably about 30% by weight or more, and further preferably about 40% by weight or more.

Component (c) includes compounds (5) to (11). The compounds have phenylene in which hydrogen in lateral positions are replaced by two halogens, such as 2,3-difluoro-1,4-phenylene. Preferred examples of component (c) include compounds (5-1) to (5-8), compounds (6-1) to (6-17), compound (7-1), compounds (8-1) to (8-3), compounds (9-1) to (9-11), compounds (10-1) to (10-3) and compounds (11-1) to (11-3). In the compounds, $R^{13}$, $R^{14}$ and $R^{15}$ are independently alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine, and $R^{15}$ may be hydrogen or fluorine.

(5-1)
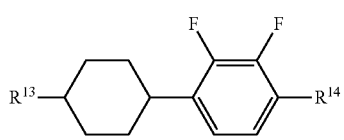

(5-2)
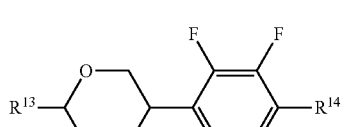

(5-3)
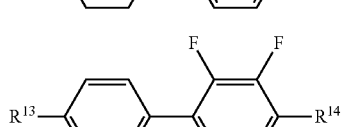

(5-4)
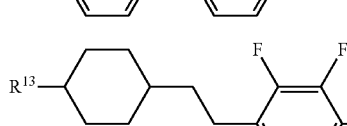

(5-5)
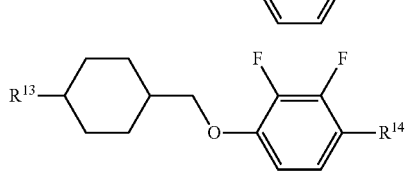

(5-6) 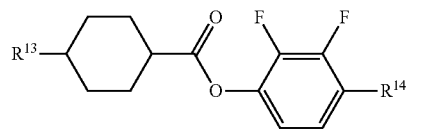
(5-7) 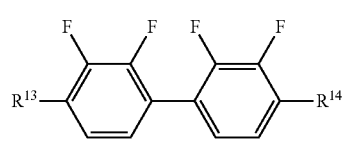
(5-8) 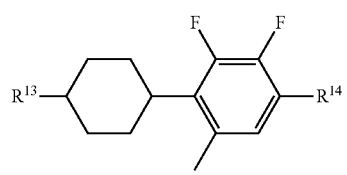
(6-1) 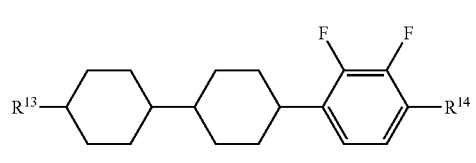
(6-2) 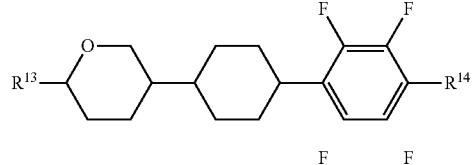
(6-3) 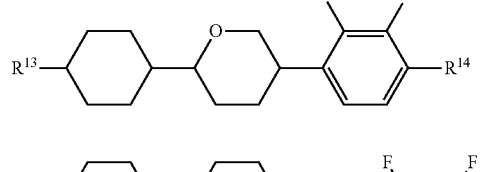
(6-4) 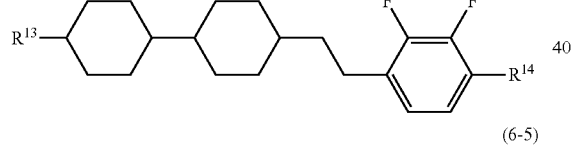
(6-5) 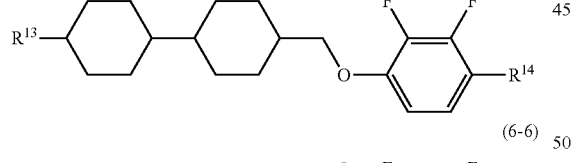
(6-6) 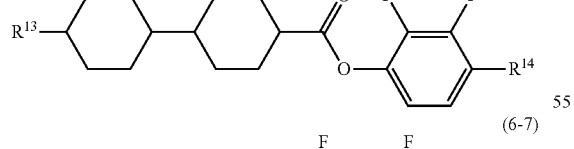
(6-7) 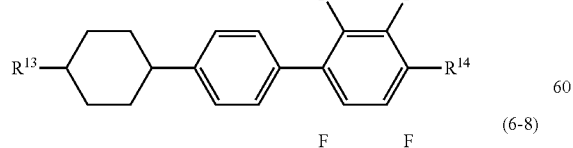
(6-8) 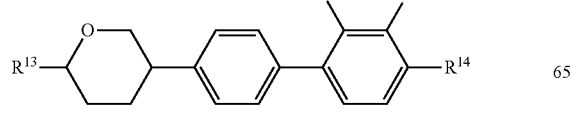
(6-9) 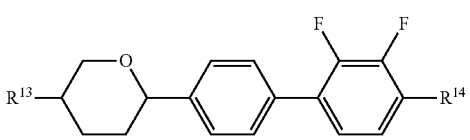
(6-10) 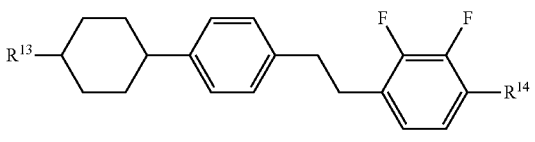
(6-11) 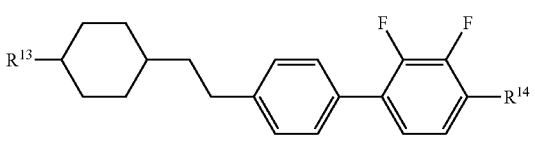
(6-12) 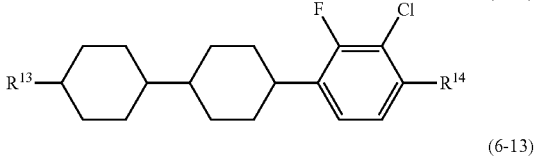
(6-13) 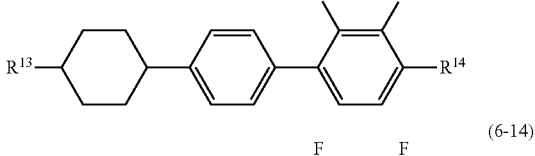
(6-14) 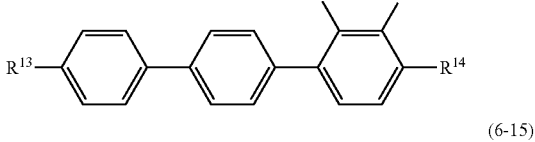
(6-15) 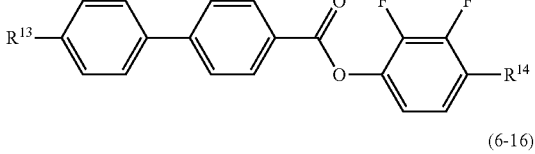
(6-16) 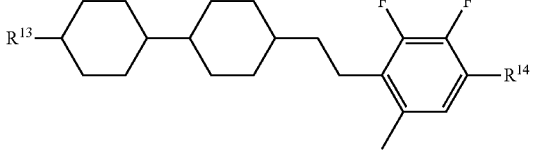
(6-17) 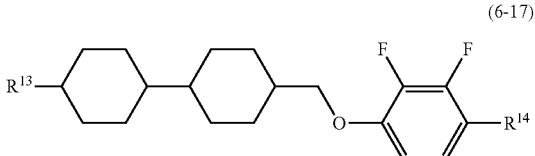
(7-1) 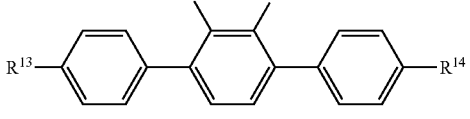

-continued (8-1), (8-2), (8-3), (9-1), (9-2), (9-3), (9-4), (9-5), (9-6), (9-7), (9-8), (9-9), (9-10), (9-11), (10-1), (10-2)

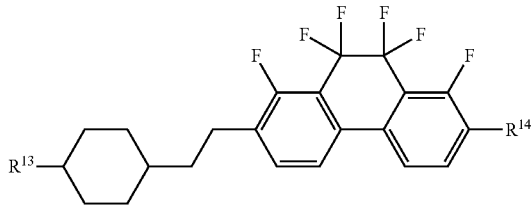
(10-3)

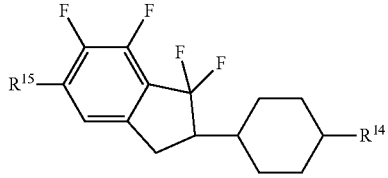
(11-1)

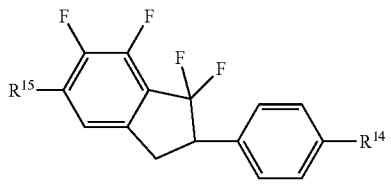
(11-2)

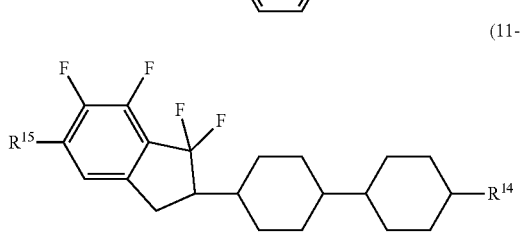
(11-3)

Component (c) has negatively large dielectric anisotropy. Component (c) is used when a composition for the IPS mode, the VA mode, the PSA mode or the like is prepared. As a proportion of component (c) is increased, the dielectric anisotropy of the composition is negatively increased, but the viscosity is increased. Thus, as long as a desired value of a threshold voltage of the device is met, the content is preferably as small as possible. When taking into account the dielectric anisotropy being at a degree of −5, a proportion is preferably about 40% by weight or more in order to allow sufficient voltage driving.

Among types of component (c), compound (5) is a bicyclic compound, and therefore is effective in decreasing the viscosity, adjusting the optical anisotropy or increasing the dielectric anisotropy. Compounds (5) and (6) are a tricyclic compound, and therefore are effective in increasing the maximum temperature, the optical anisotropy or the dielectric anisotropy. Compounds (8) to (11) are effective in increasing the dielectric anisotropy.

When a composition for the IPS mode, the VA mode, the PSA mode or the like is prepared, a content of component (c) is preferably about 40% by weight or more, and further preferably in the range of about 50% by weight to about 95% by weight. When component (c) is added to the composition having positive dielectric anisotropy, a proportion of component (c) is preferably about 30% by weight or less. The elastic constant of the composition can be adjusted, and a voltage-transmittance curve of the device can be adjusted by adding component (c) thereto.

Component (d) is a compound having a halogen-containing group or a fluorine-containing group at a right terminal. Preferred examples of component (d) include compounds (12-1) to (12-16), compounds (13-1) to (13-113) and compounds (14-1) to (14-57). In the compounds, $R^{16}$ is alkyl having 1 to 10 carbons or alkenyl having 2 to 10 carbons, and in the alkyl and the alkenyl, at least one piece of —$CH_2$— may be replaced by —O—, and in the groups, at least one hydrogen may be replaced by fluorine. $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

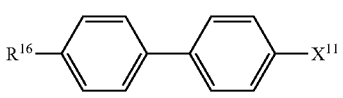
(12-1)

(12-2)

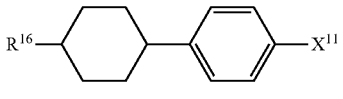
(12-3)

(12-4)

(12-5)

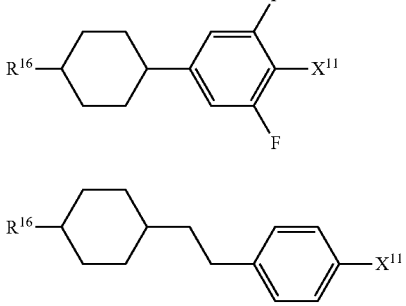
(12-6)

(12-7)

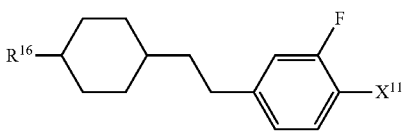
(12-8)

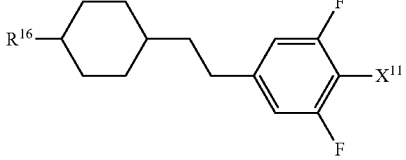
(12-9)

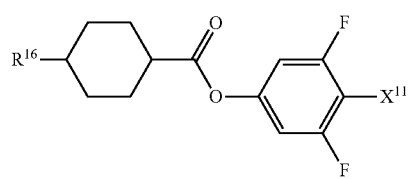 (12-10)
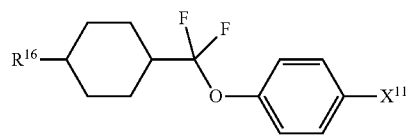 (12-11)
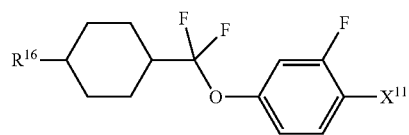 (12-12)
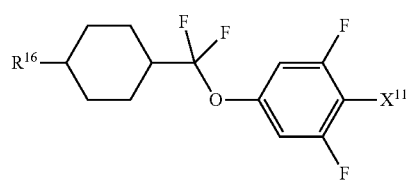 (12-13)
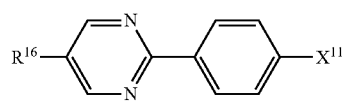 (12-14)
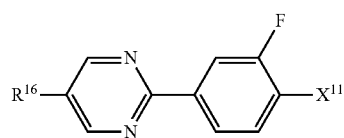 (12-15)
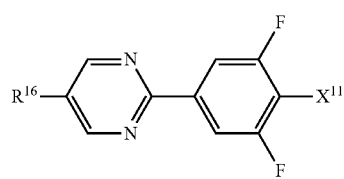 (12-16)
 (13-1)
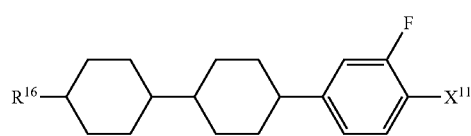 (13-2)
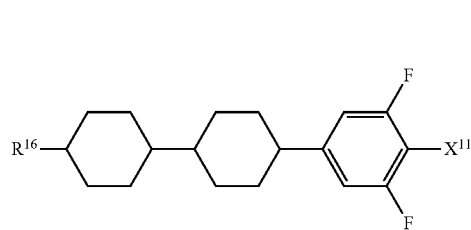 (13-3)
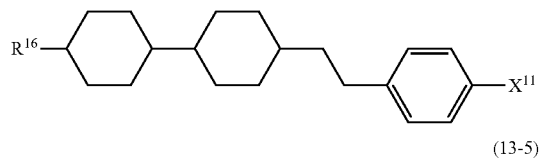 (13-4)
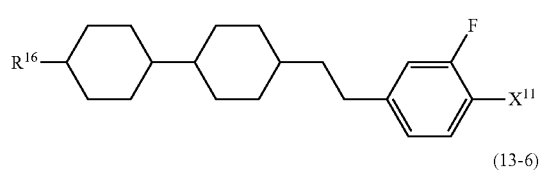 (13-5)
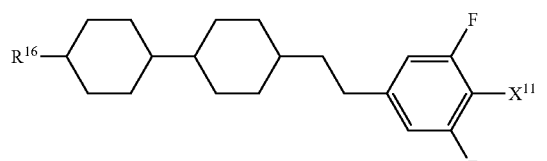 (13-6)
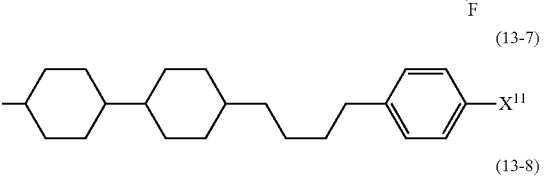 (13-7)
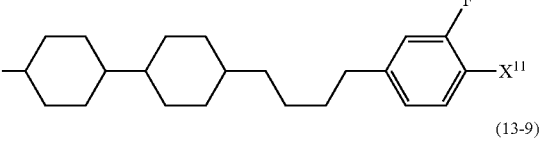 (13-8)
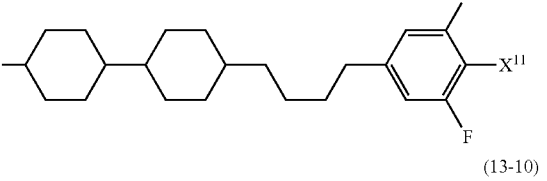 (13-9)
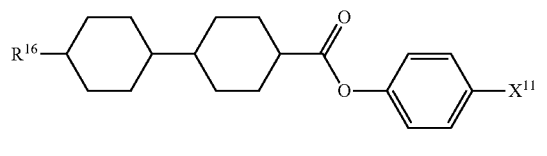 (13-10)
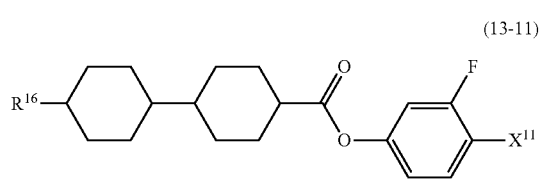 (13-11)
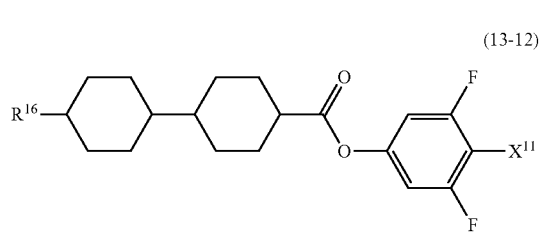 (13-12)

(13-13) 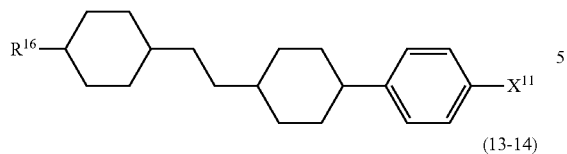
(13-14) 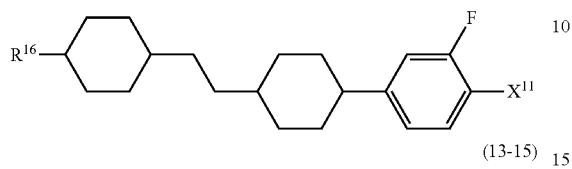
(13-15) 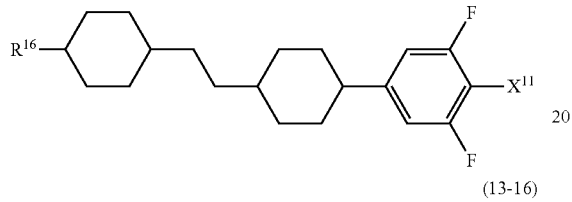
(13-16) 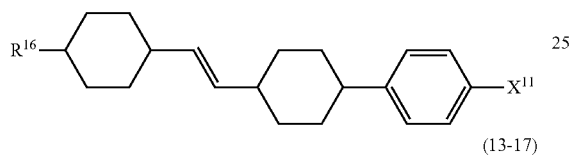
(13-17) 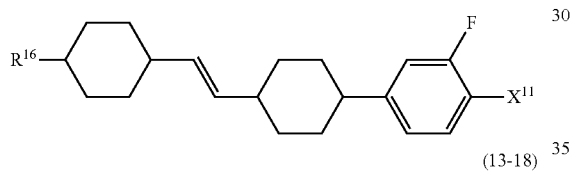
(13-18) 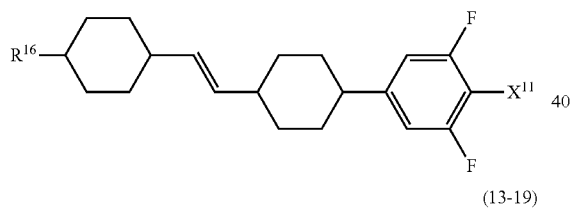
(13-19) 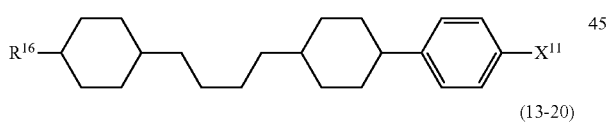
(13-20) 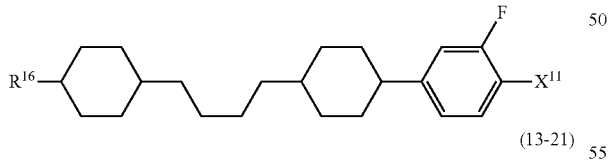
(13-21) 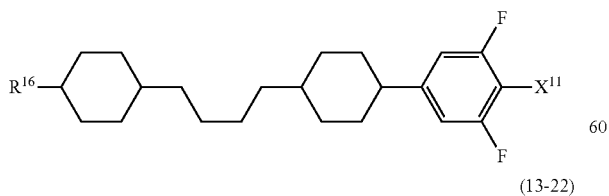
(13-22) 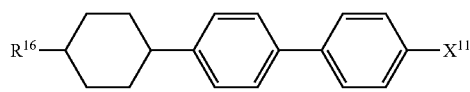
(13-23) 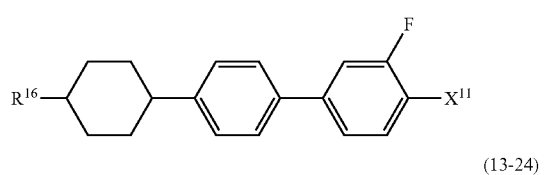
(13-24) 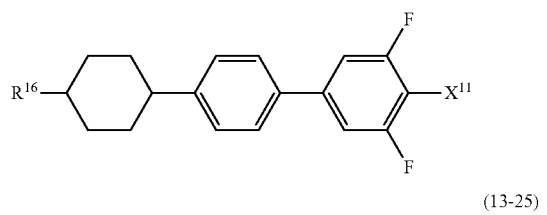
(13-25) 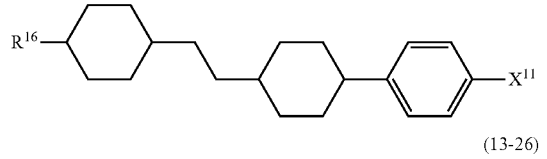
(13-26) 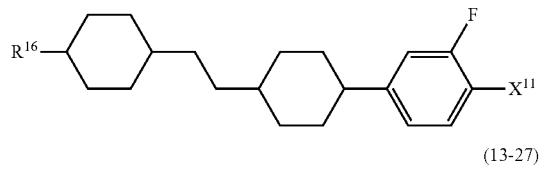
(13-27) 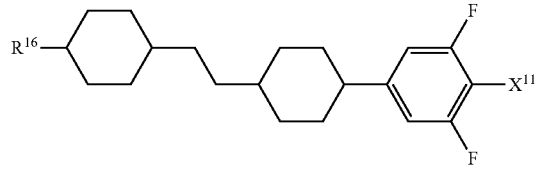
(13-28) 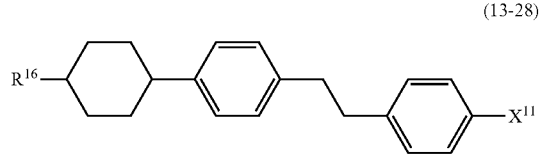
(13-29) 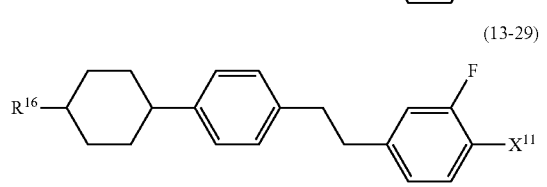
(13-30) 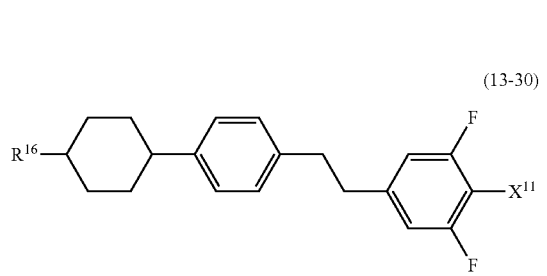
(13-31) 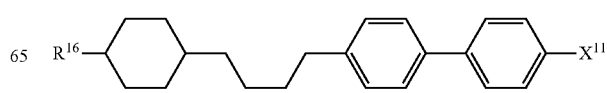

(13-32) 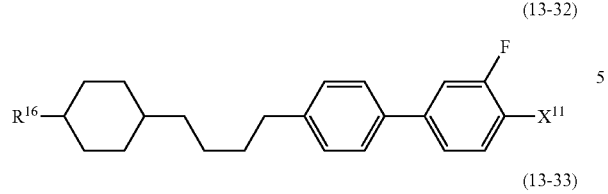
(13-33) 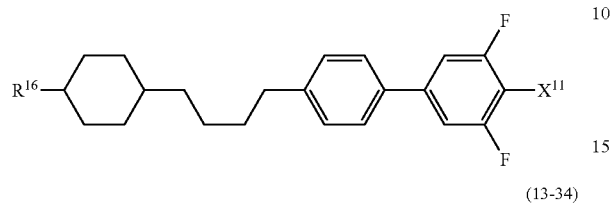
(13-34) 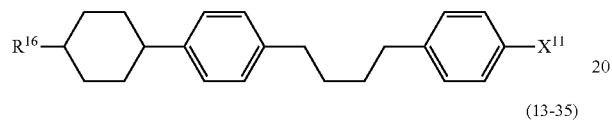
(13-35) 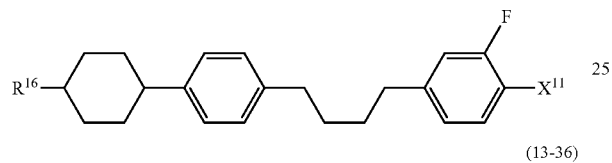
(13-36) 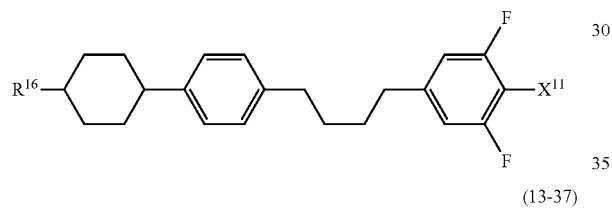
(13-37) 
(13-38) 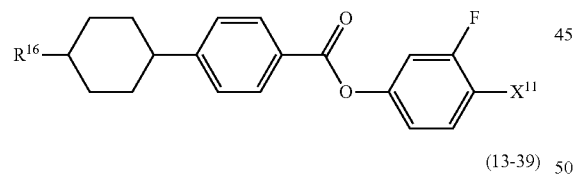
(13-39) 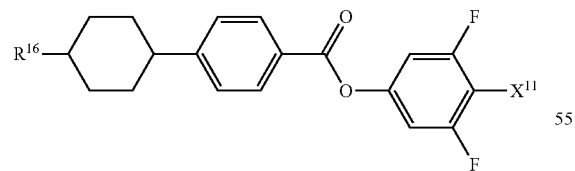
(13-40) 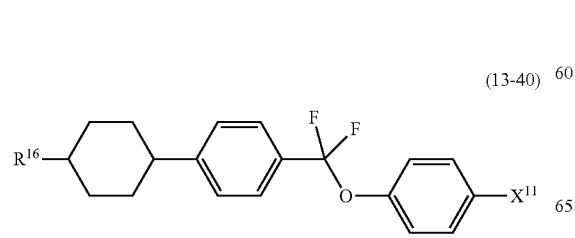
(13-41) 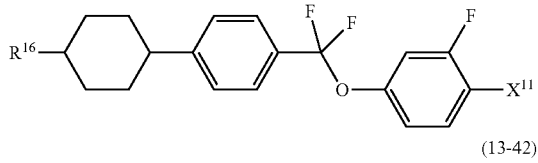
(13-42) 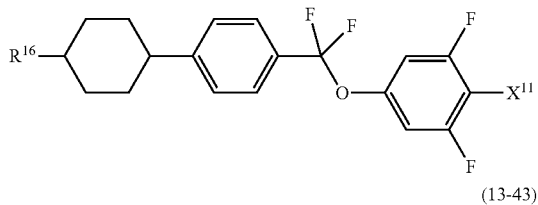
(13-43) 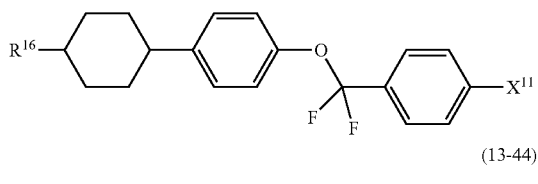
(13-44) 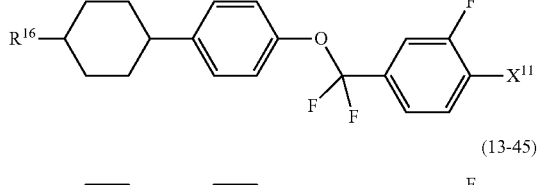
(13-45) 
(13-46) 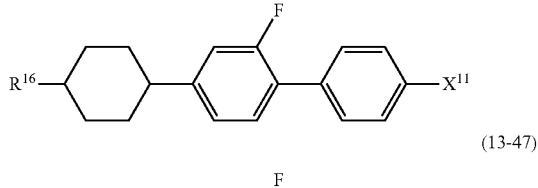
(13-47) 
(13-48) 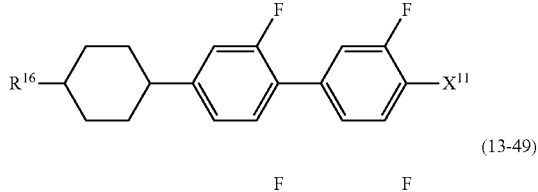
(13-49) 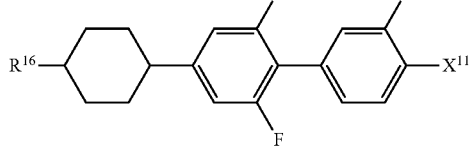

(13-50)
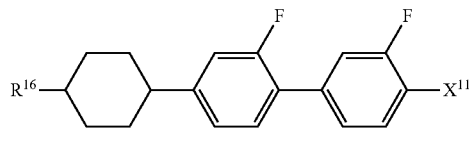
(13-51)
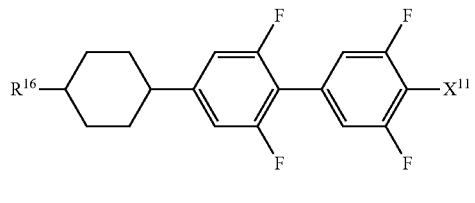
(13-52)
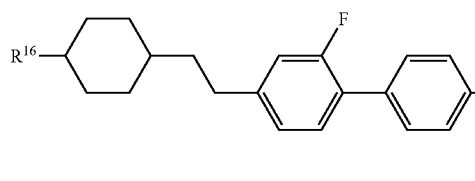
(13-53)
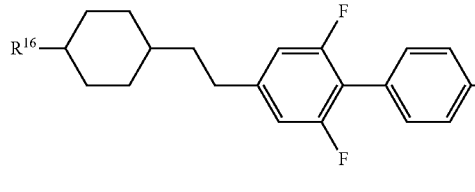
(13-54)
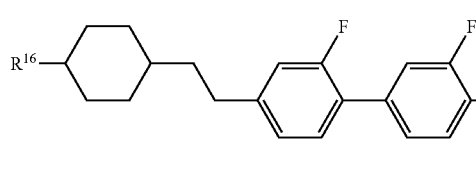
(13-55)
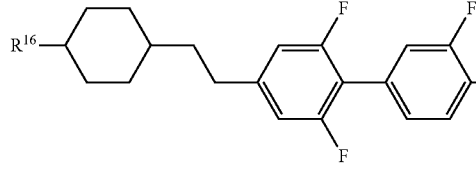
(13-56)
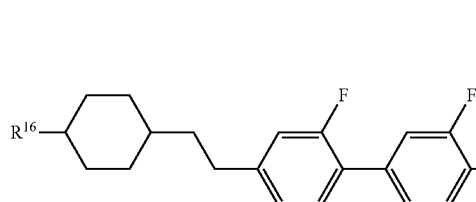
(13-57)
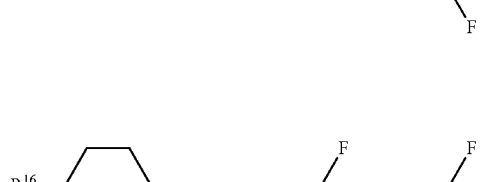
(13-58)
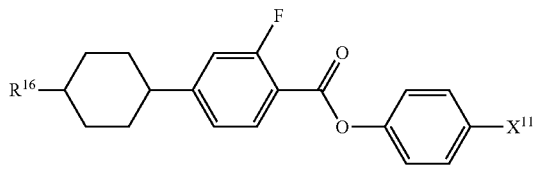
(13-59)
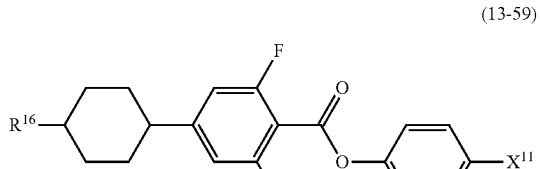
(13-60)
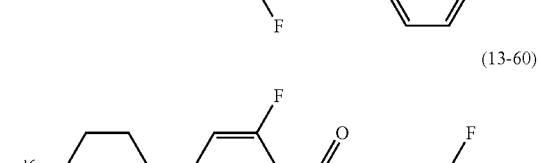
(13-61)
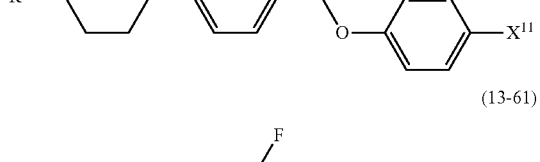
(13-62)
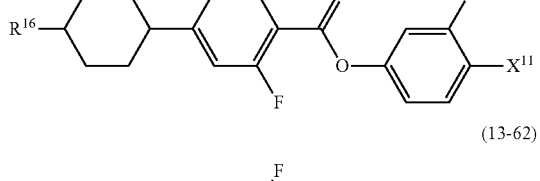
(13-63)
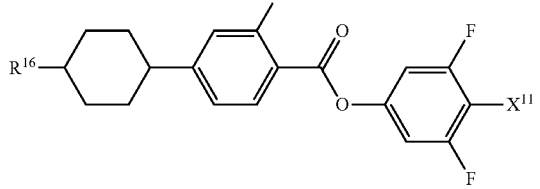
(13-64)
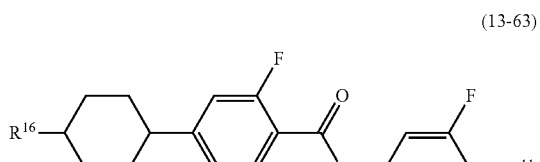
(13-65)
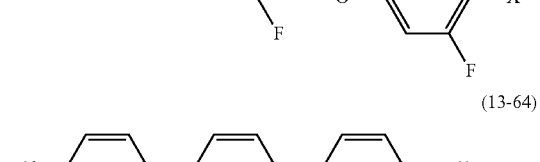

(13-66) 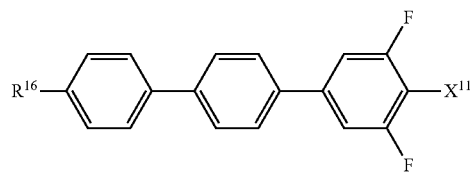
(13-67) 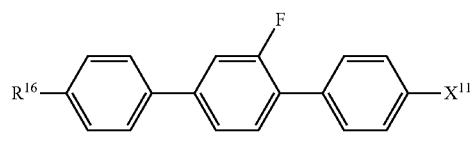
(13-68) 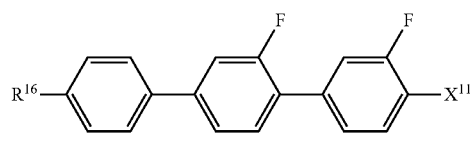
(13-69) 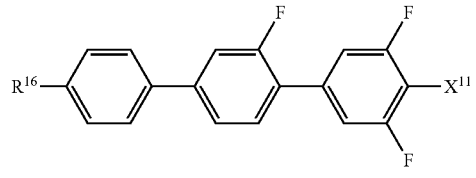
(13-70) 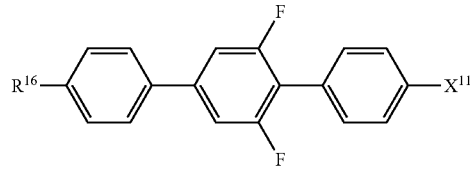
(13-71) 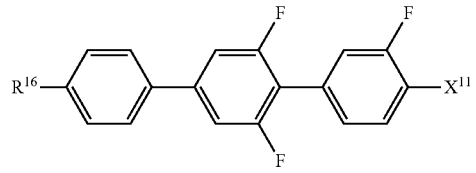
(13-72) 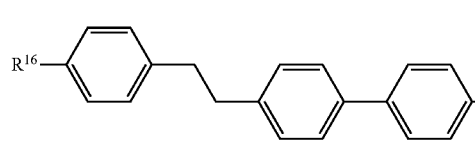
(13-73) 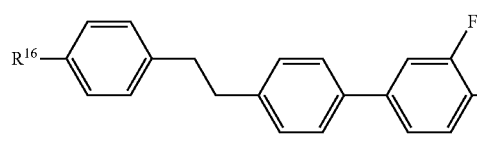
(13-84) 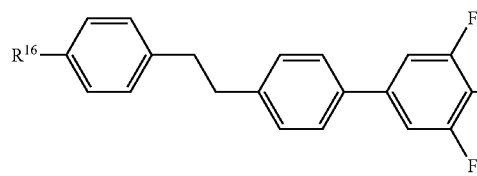
(13-75) 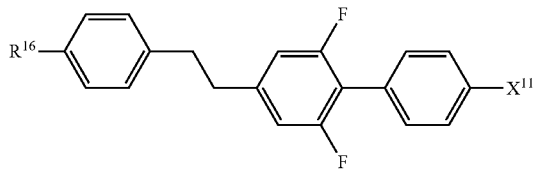
(13-76) 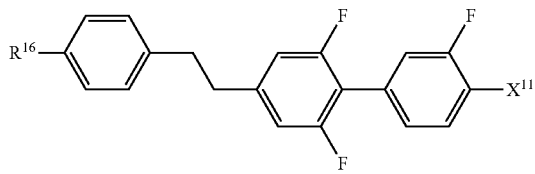
(13-77) 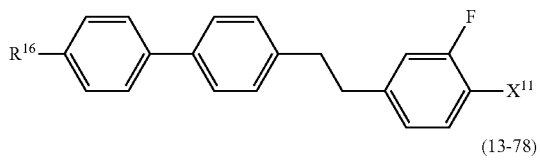
(13-78) 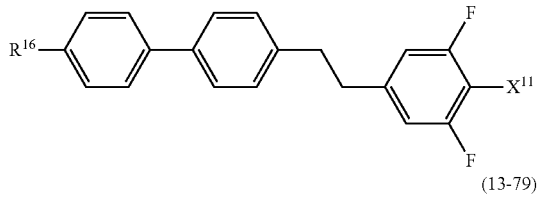
(13-79) 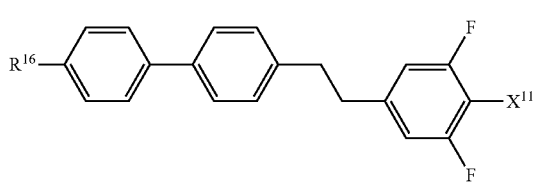
(13-80) 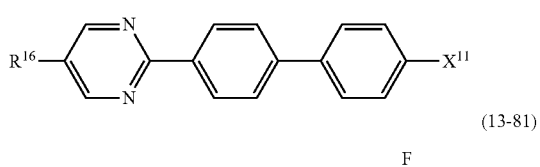
(13-81) 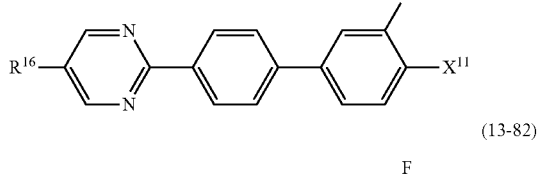
(13-82) 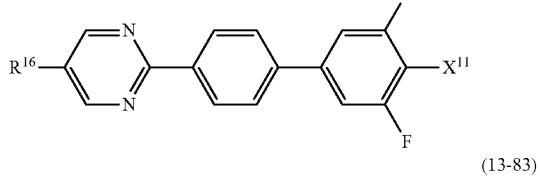
(13-83) 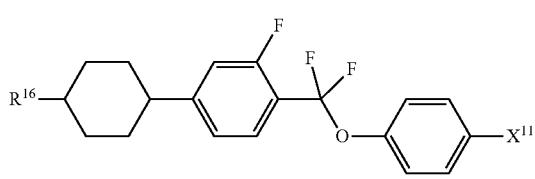

(13-84)
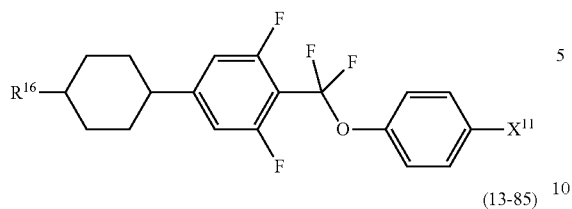
(13-85)
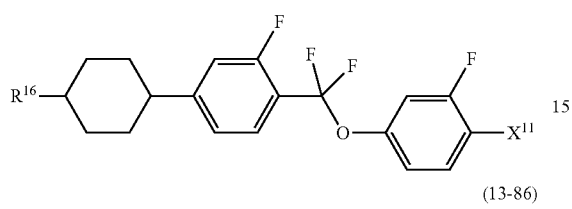
(13-86)
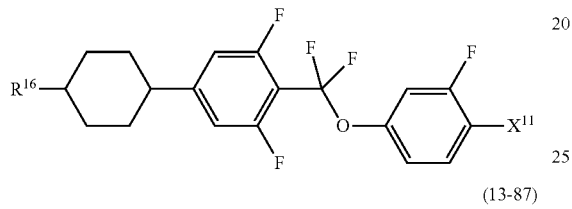
(13-87)

(13-88)
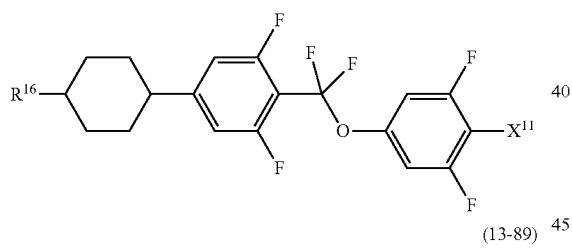
(13-89)
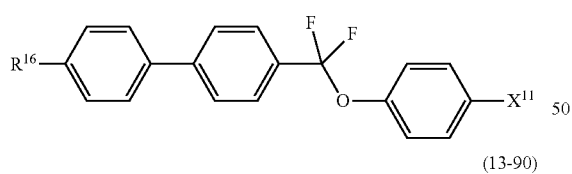
(13-90)
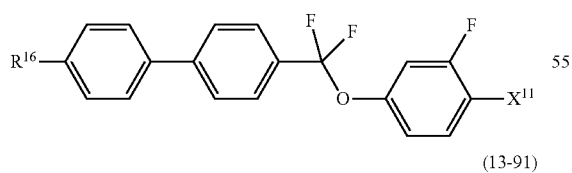
(13-91)
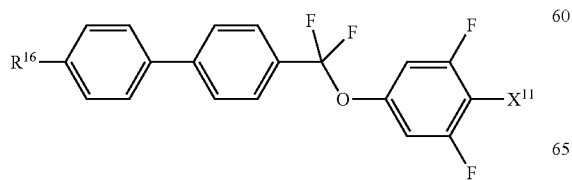
(13-92)
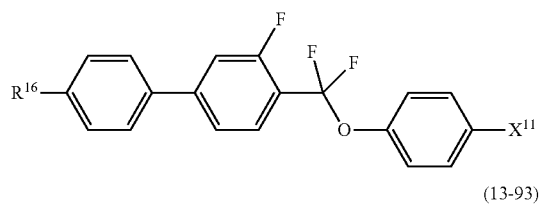
(13-93)

(13-94)
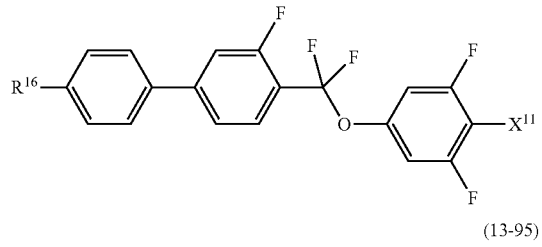
(13-95)
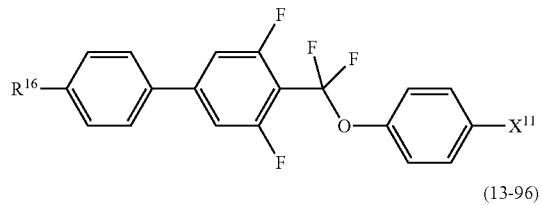
(13-96)
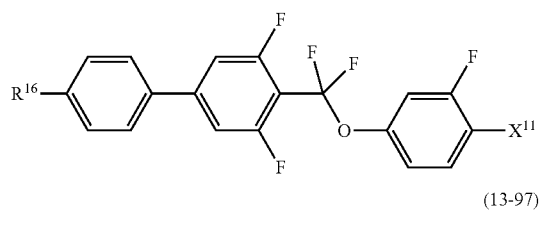
(13-97)
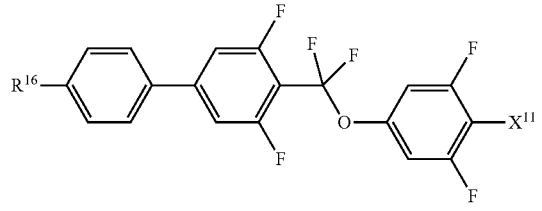
(13-98)
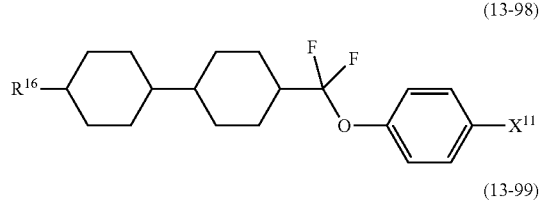
(13-99)
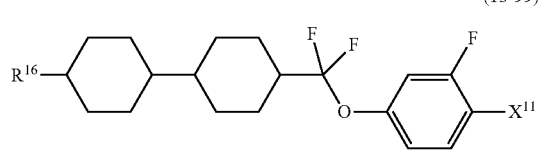

(13-100) 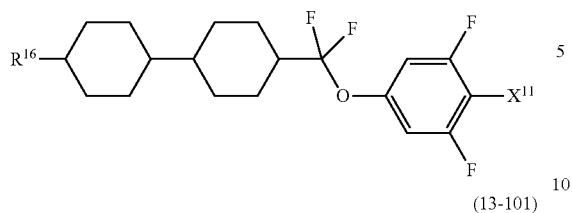
(13-101) 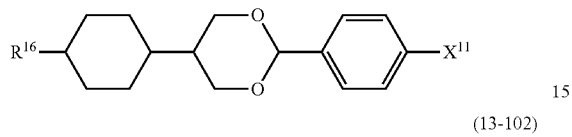
(13-102) 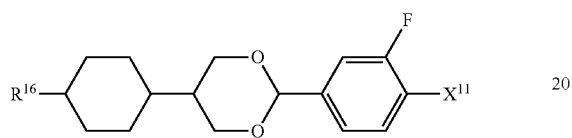
(13-103) 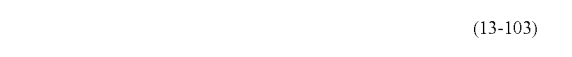
(13-104) 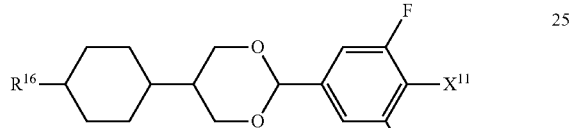
(13-105) 
(13-106) 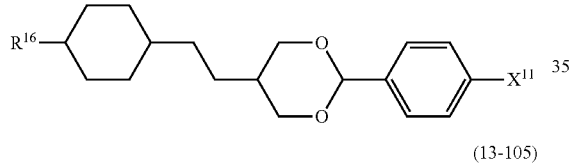
(13-107) 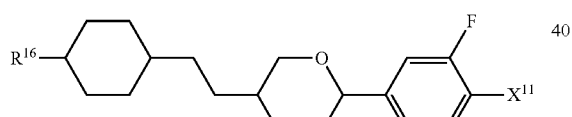
(13-108) 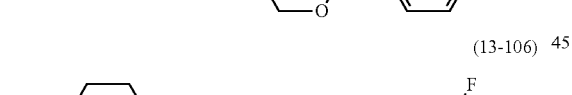
(13-109) 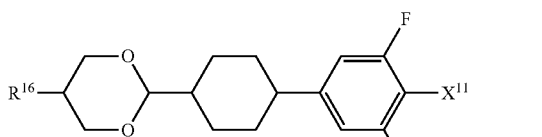
(13-110) 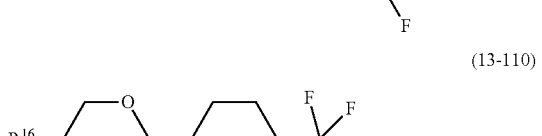
(13-111) 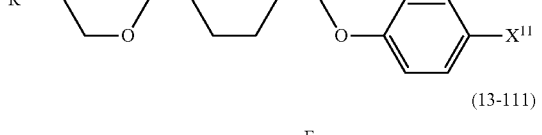
(13-112) 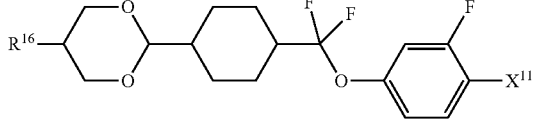
(13-113) 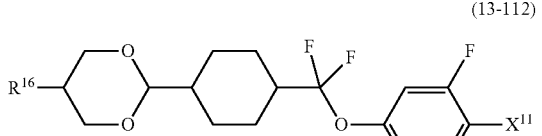
(14-1) 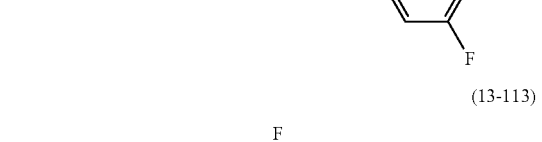
(14-2) 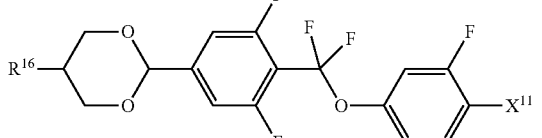
(14-3) 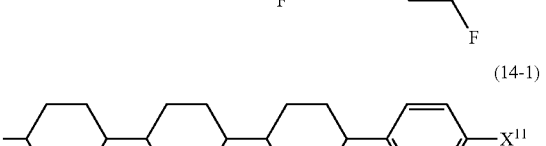
(14-4) 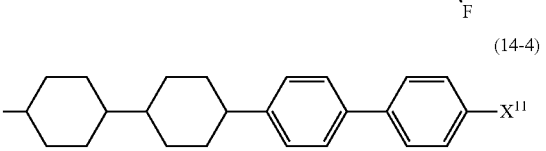

(14-5) (14-6) (14-7) (14-8) (14-9) (14-10) (14-11) (14-12) (14-13) (14-14) (14-15) (14-16) (14-17) (14-18) (14-19) (14-20) (14-21) (14-22) (14-23)

(14-24) 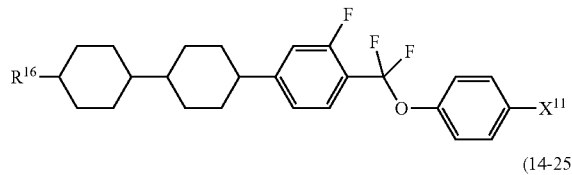
(14-25) 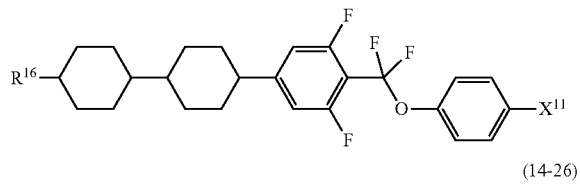
(14-26) 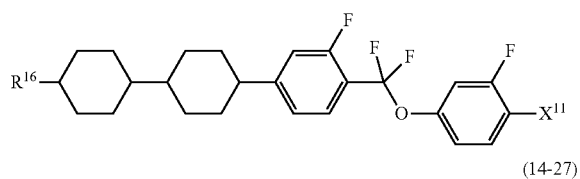
(14-27) 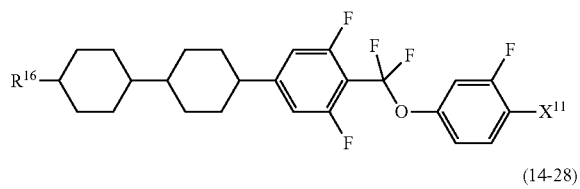
(14-28) 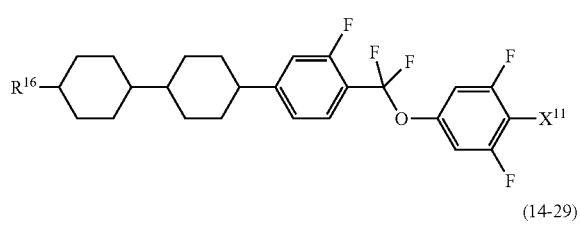
(14-29) 
(14-30) 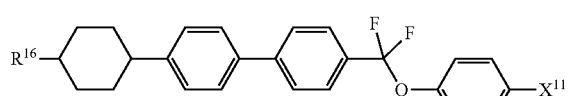
(14-31) 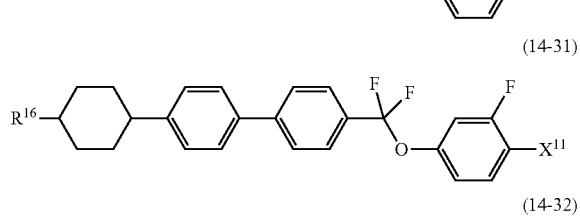
(14-32) 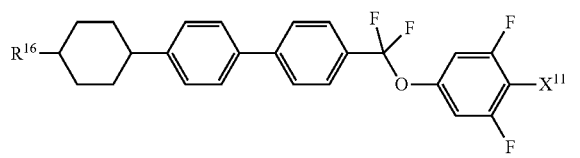
(14-33) 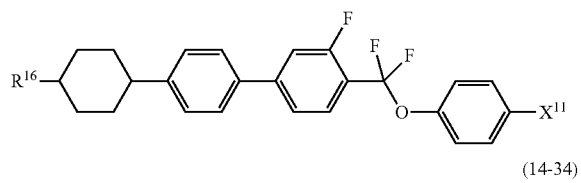
(14-34) 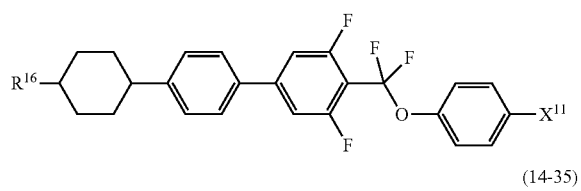
(14-35) 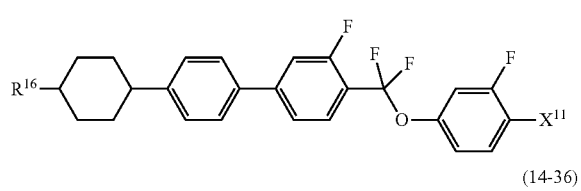
(14-36) 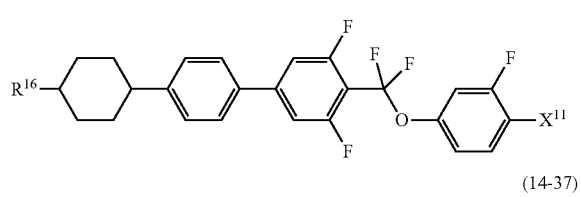
(14-37) 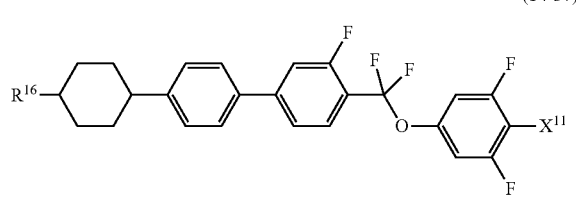
(14-38) 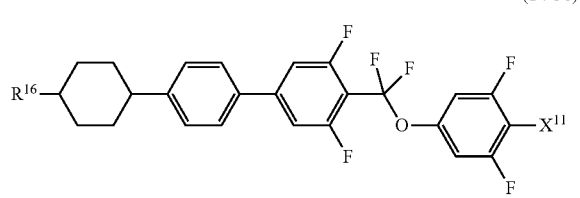
(14-39) 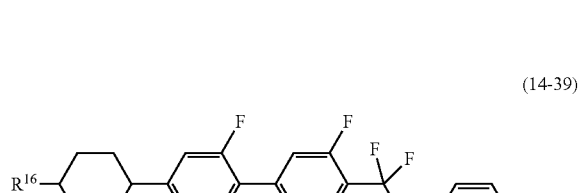
(14-40) 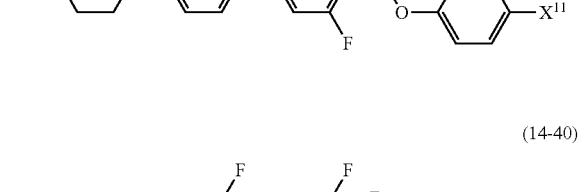
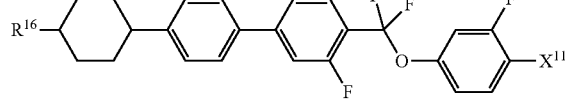

(14-41)
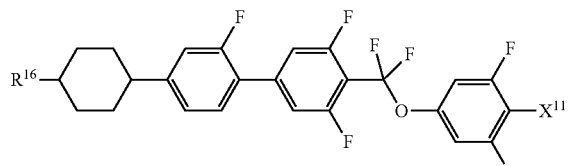
(14-42)
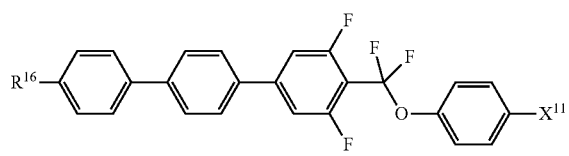
(14-43)
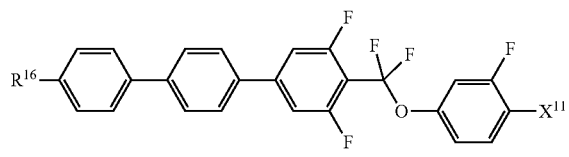
(14-44)
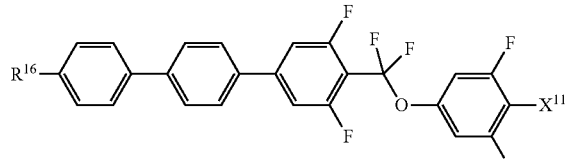
(14-45)
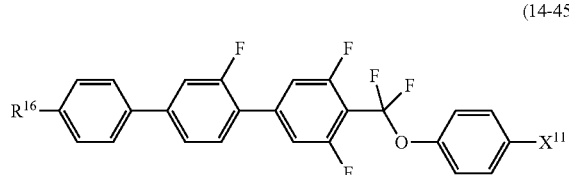
(14-46)
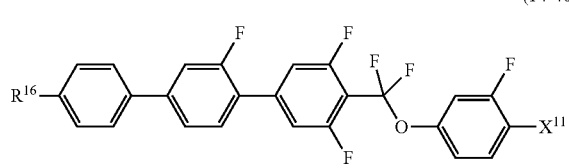
(14-47)
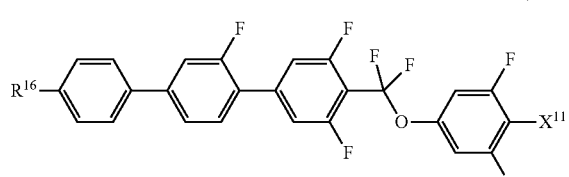
(14-48)
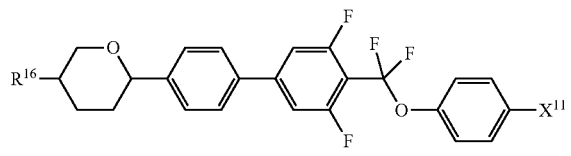
(14-49)
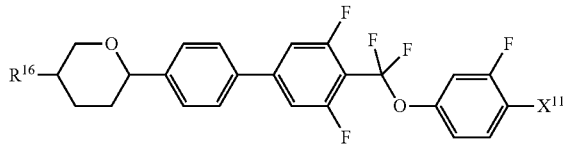
(14-49)
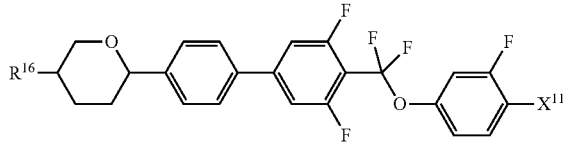
(14-50)
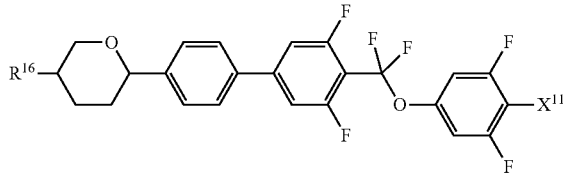
(14-51)
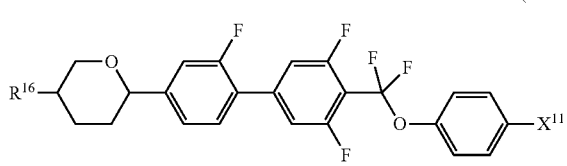
(14-52)
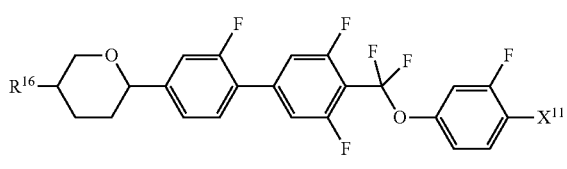
(14-53)
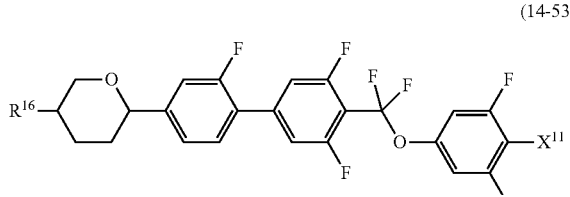
(14-54)
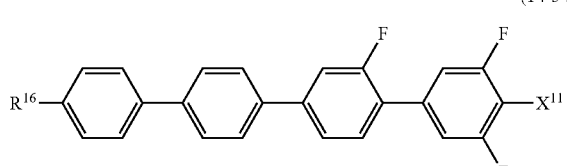
(14-55)

-continued

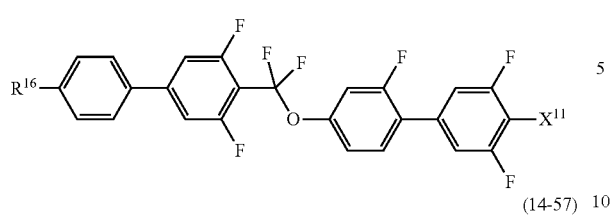
(14-56)

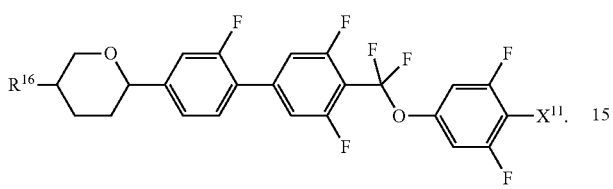
(14-57)

Component (d) has positive dielectric anisotropy and satisfactory stability to heat and light, and therefore is used when a composition for the IPS mode, the FFS mode, the CB mode or the like is prepared. A proportion of component (d) is suitably in the range of about 1% by weight to about 99% by weight, preferably in the range of about 10% by weight to about 97% by weight, and further preferably in the range of about 40% by weight to about 95% by weight. When component (d) is added to a composition having negative dielectric anisotropy, a proportion of component (d) is preferably about 30% by weight or less. The elastic constant of the composition can be adjusted, and the voltage-transmittance curve of the device can be adjusted by adding component (d) thereto.

Component (e) is compound (15) in which a right-terminal group is —C≡N or —C≡C—C≡N. Preferred examples of component (e) include compounds (15-1) to (15-64). In the compounds, $R^{17}$ is alkyl having 1 to 10 carbons or alkenyl having 2 to 10 carbons, and in the alkyl and the alkenyl, at least one piece of —CH$_2$— may be replaced by —O—, and in the groups, at least one hydrogen may be replaced by fluorine. $X^{12}$ is —C≡N or —C≡C—C≡N.

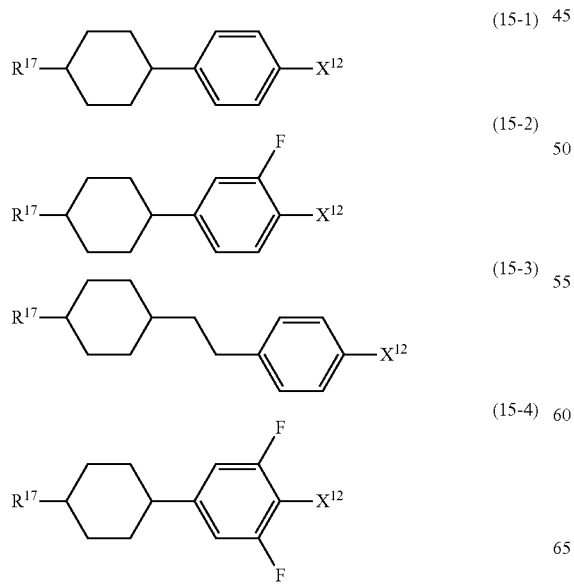

(15-1)

(15-2)

(15-3)

(15-4)

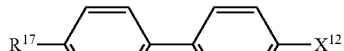
(15-5)

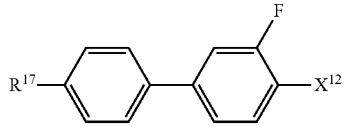
(15-6)

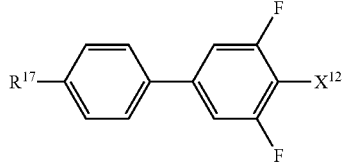
(15-7)

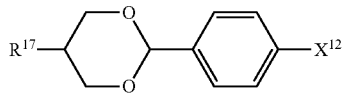
(15-8)

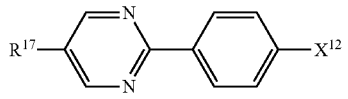
(15-9)

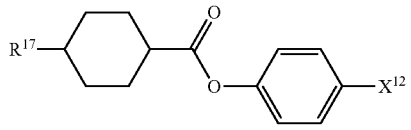
(15-10)

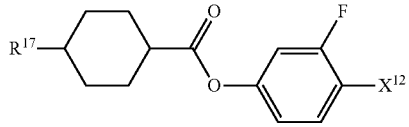
(15-11)

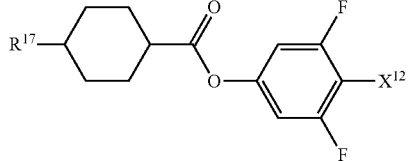
(15-12)

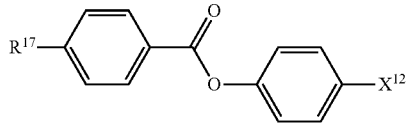
(15-13)

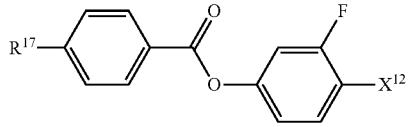
(15-14)

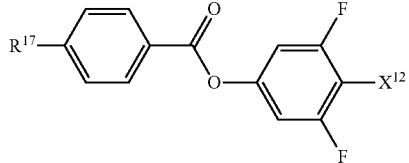
(15-15)

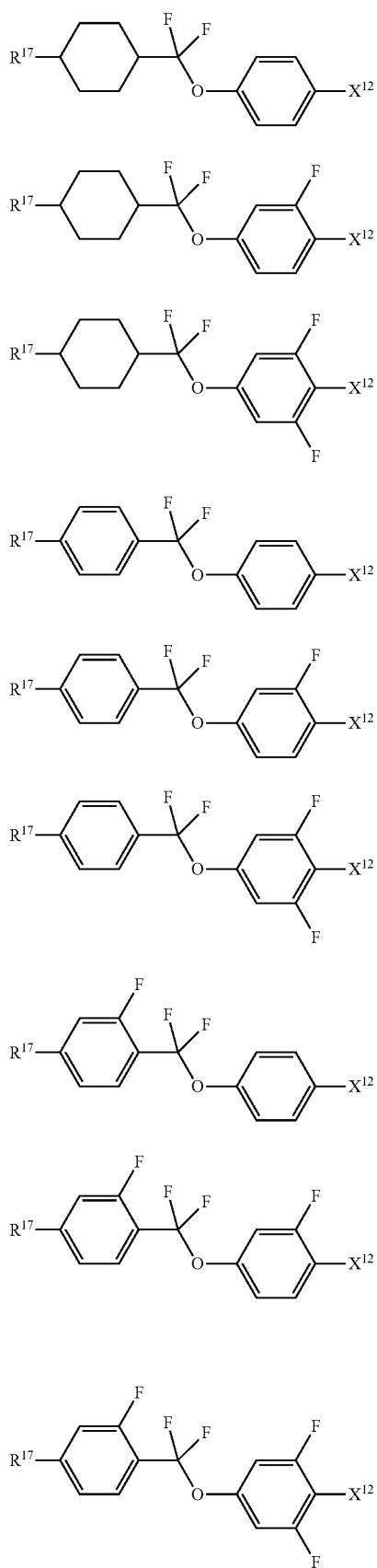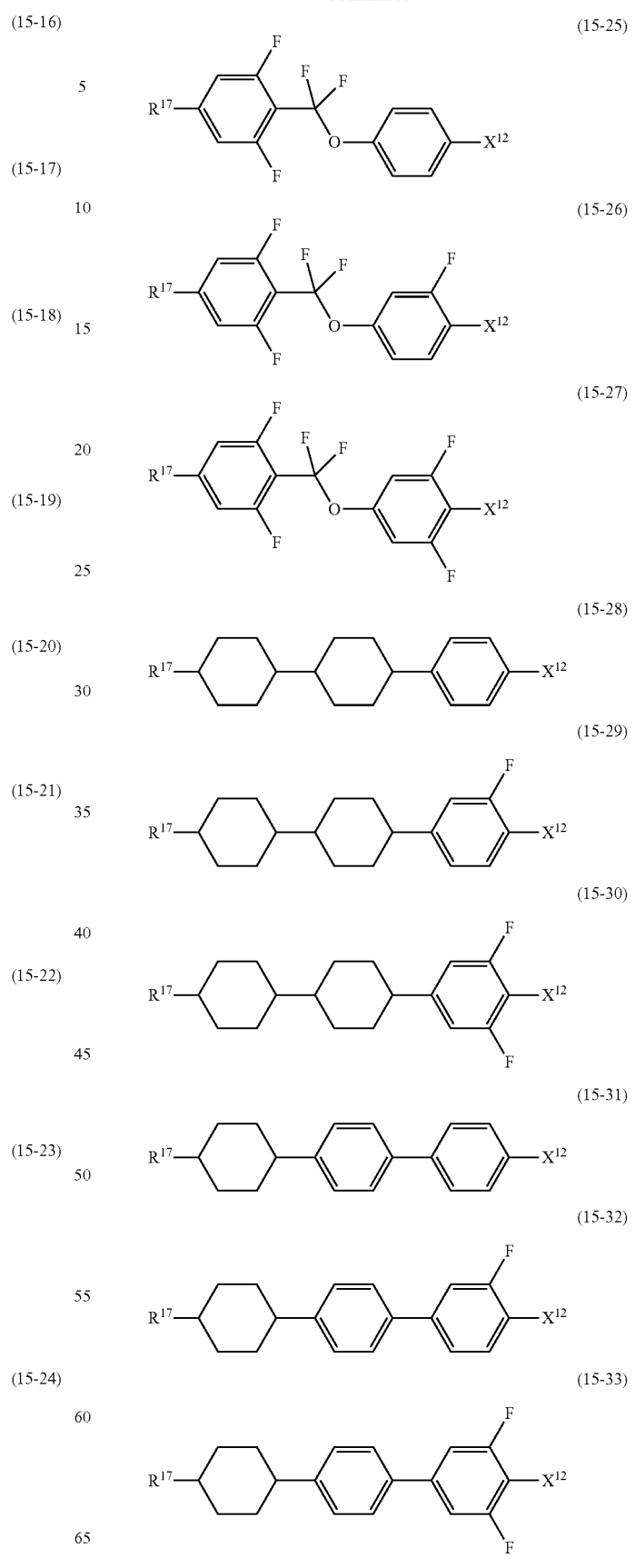

(15-34) 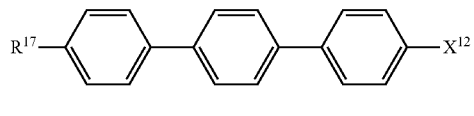
(15-35) 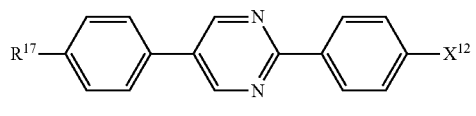
(15-36) 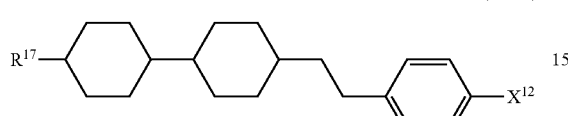
(15-37) 
(15-38) 
(15-39) 
(15-40) 
(15-41) 
(15-42) 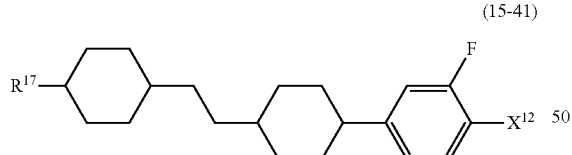
(15-43) 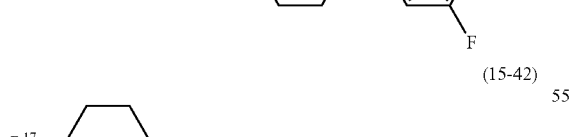
(15-44) 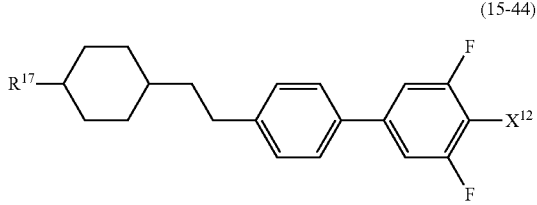
(15-45) 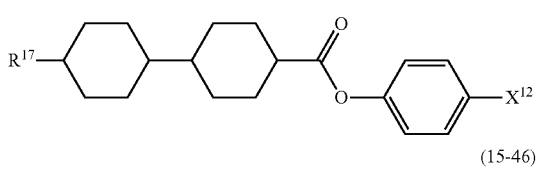
(15-46) 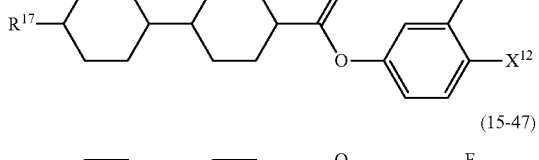
(15-47) 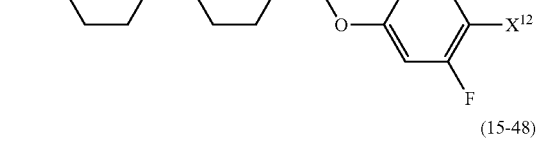
(15-48) 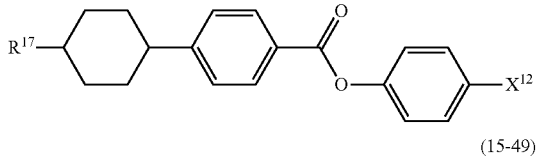
(15-49) 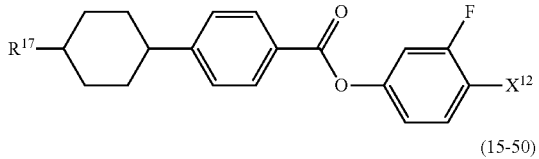
(15-50) 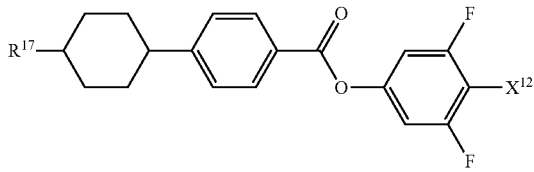
(15-51) 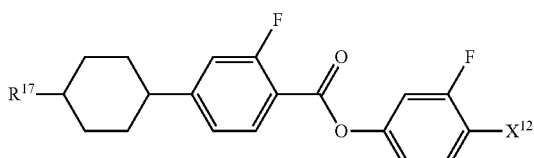
(15-52) 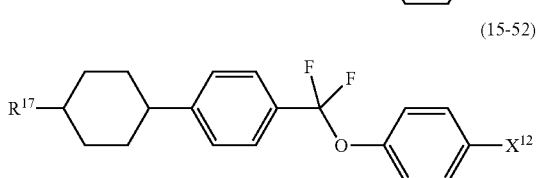

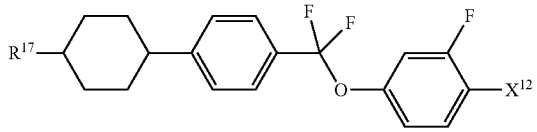
(15-53)

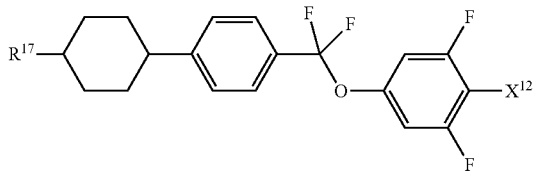
(15-54)

(15-55)

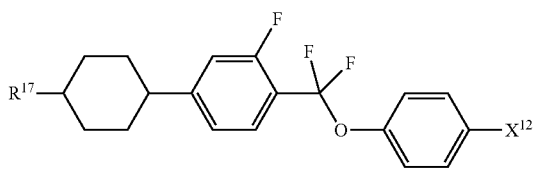
(15-56)

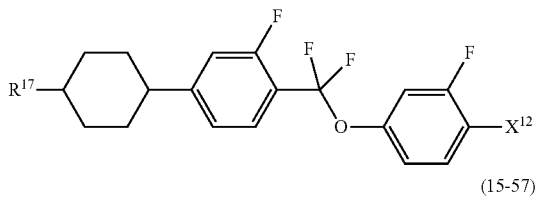
(15-57)

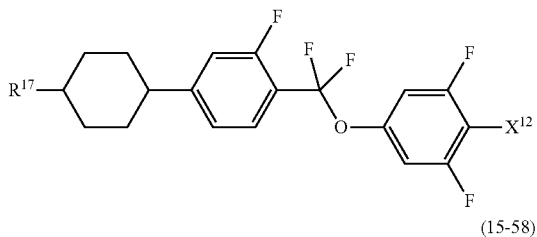
(15-58)

(15-59)

(15-60)


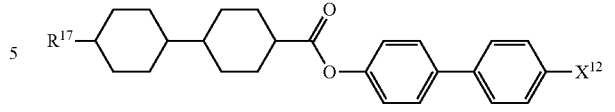
(15-61)

(15-62)

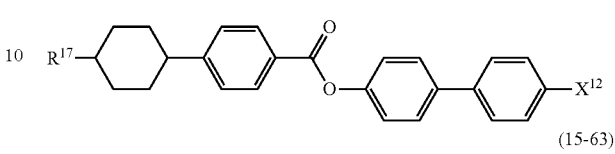
(15-63)

(15-64)

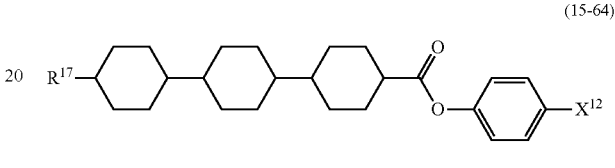

Component (e) has positive dielectric anisotropy and a value thereof is large, and therefore is used when a composition for the TN mode or the like is prepared. The dielectric anisotropy of the composition can be increased by adding the component (e). Component (e) is effective in extending the temperature range of the liquid crystal phase, adjusting the viscosity or adjusting the optical anisotropy. Component (e) is also useful for adjustment of the voltage-transmittance curve of the device.

When a composition for the TN mode or the like is prepared, a proportion of component (e) is suitably in the range of about 1% by weight to about 99% by weight, preferably in the range of about 10% by weight to about 97% by weight, and further preferably in the range of about 40% by weight to about 95% by weight. When component (e) is added to the composition having negative dielectric anisotropy, a proportion of component (e) is preferably about 30% by weight or less. The elastic constant of the composition can be adjusted, and the voltage-transmittance curve of the device can be adjusted by adding component (e) thereto.

A liquid crystal composition satisfying at least one of physical properties such as high stability to heat and light, high maximum temperature, low minimum temperature, small viscosity, suitable optical anisotropy (more specifically, large optical anisotropy or small optical anisotropy), large positive or negative dielectric anisotropy, large specific resistance and a suitable elastic constant (more specifically, a large elastic constant or a small elastic constant) can be prepared by combining a compound appropriately selected from components (b) to (e) described above with compound (1). The device including such a composition has a wide temperature range in which the device can be used, a short response time, a large voltage holding ratio, low threshold voltage, a large contrast ratio, a small flicker rate and a long service life.

If the device is used for a long period of time, a flicker may be occasionally generated on a display screen. The flicker rate (%) can be represented by a formula (|luminance when applying positive voltage−luminance when applying negative voltage|)/(average luminance)×100. In a device having the flicker rate in the range of about 0% to about 1%, a flicker is hardly generated on the display screen even if the device is used for a long period of time. The flicker is associated with image persistence, and is presumed to be generated according to a difference in electric potential between a positive frame and a negative frame in driving at alternating current. The composition containing compound (1) is also useful for a decrease in generation of the flicker.

3-2. Additive

The liquid crystal composition is prepared according to a publicly known method. For example, the component compounds are mixed and dissolved in each other by heating. According to an application, an additive may be added to the composition. Examples of the additive include a polymerizable compound, a polymerization initiator, a polymerization inhibitor, an optically active compound, an antioxidant, an ultraviolet light absorber, a light stabilizer, a heat stabilizer, a dye and an antifoaming agent. Such additives are well known to those skilled in the art, and described in literature.

In a liquid crystal display device having the polymer sustained alignment (PSA) mode, the composition contains a polymer. The polymerizable compound is added for the purpose of forming the polymer in the composition. The polymerizable compound is polymerized by irradiation with ultraviolet light while voltage is applied between electrodes, and thus the polymer is formed in the composition. A suitable pretilt is achieved by the method, and therefore the device in which a response time is shortened and the image persistence is improved is prepared.

Specific examples of a preferred polymerizable compound include acrylate, methacrylate, a vinyl compound, a vinyloxy compound, propenyl ether, an epoxy compound (oxirane, oxetane) and vinyl ketone. Further preferred examples include a compound having at least one piece of acryloyloxy, and a compound having at least one piece of methacryloyloxy. Still further preferred examples also include a compound having both acryloyloxy and methacryloyloxy.

Still further preferred examples include compounds (M-1) to (M-18). In the compounds, $R^{25}$ to $R^{31}$ are independently hydrogen or methyl; $R^{32}$, $R^{33}$ and $R^{34}$ are independently hydrogen or alkyl having 1 to 5 carbons, and at least one piece of $R^{32}$, $R^{33}$ and $R^{34}$ is alkyl having 1 to 5 carbons; v, w and x are independently 0 or 1; and u and y are independently an integer from 1 to 10. $L^{21}$ to $L^{26}$ are independently hydrogen or fluorine; and $L^{27}$ and $L^{28}$ are independently hydrogen, fluorine or methyl.

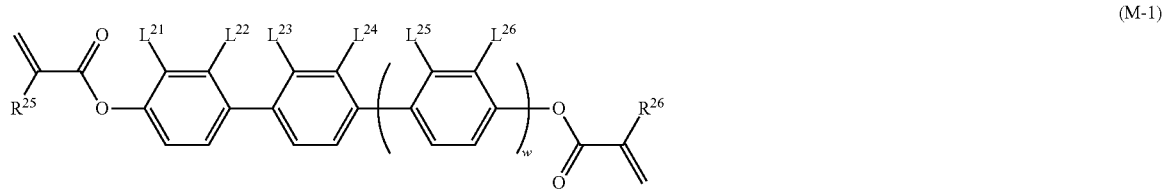

(M-1)

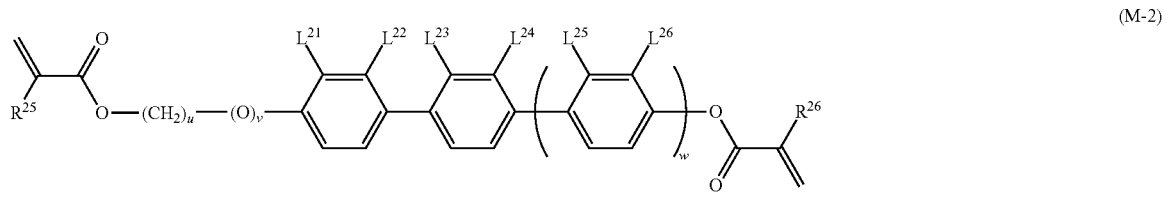

(M-2)

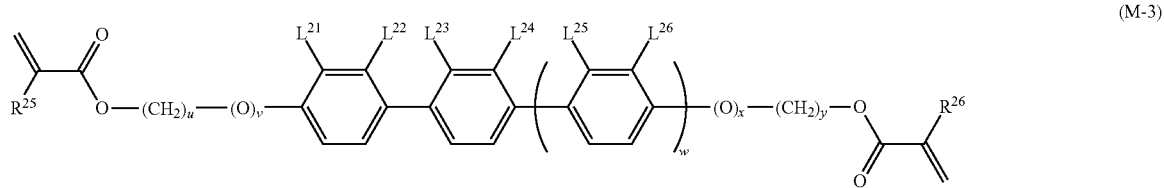

(M-3)

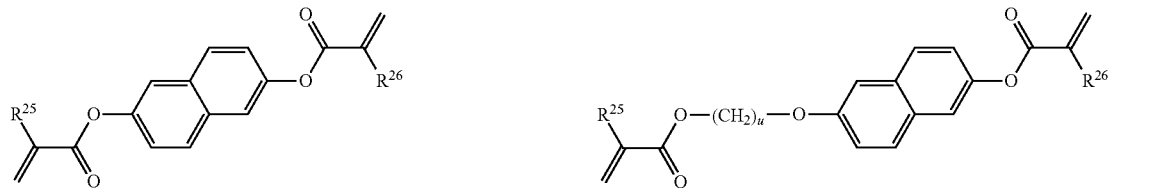

(M-4)         (M-5)

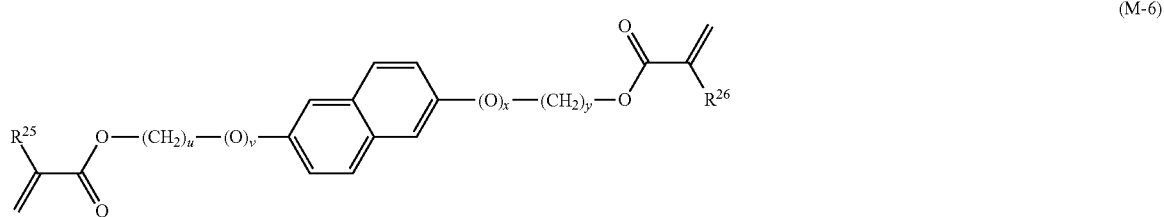

(M-6)

-continued
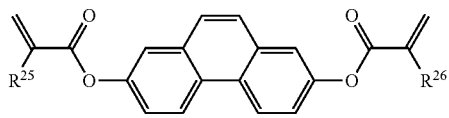 (M-7)
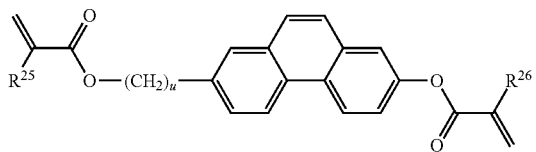 (M-8)
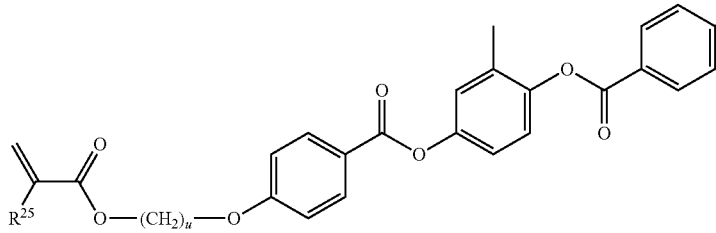 (M-9)
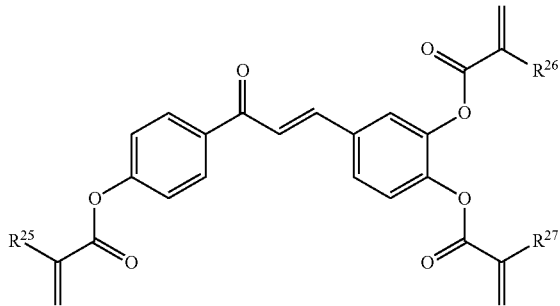 (M-10)
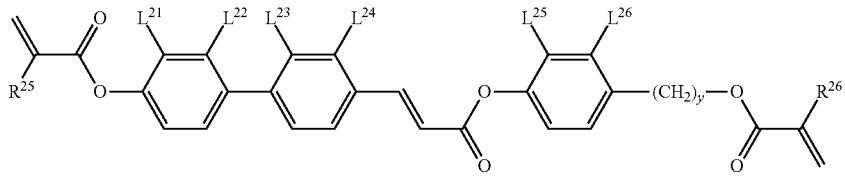 (M-11)
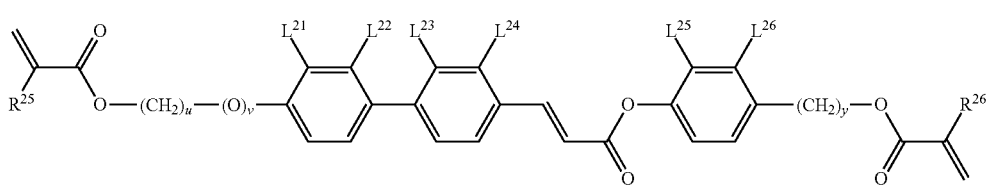 (M-12)
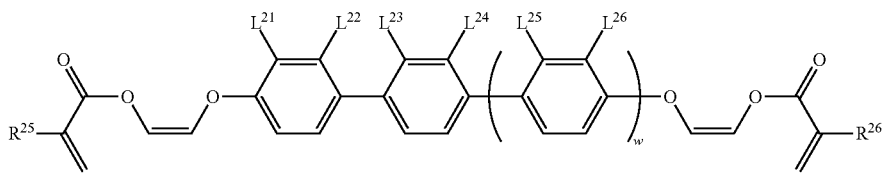 (M-13)
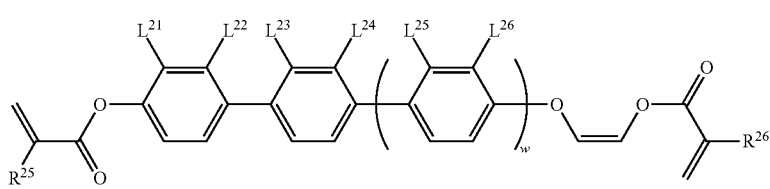 (M-14)

(M-15) 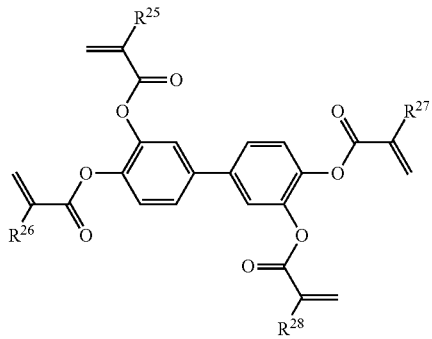

(M-16) 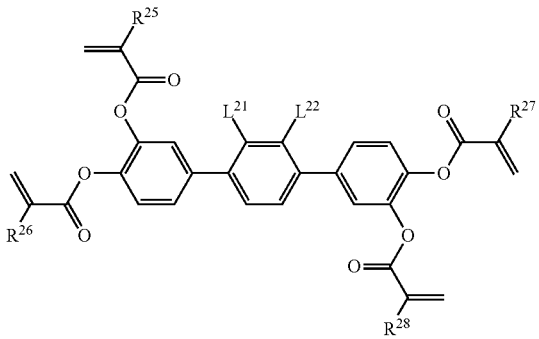

(M-17) 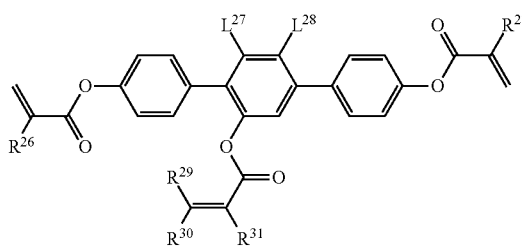

(M-18) 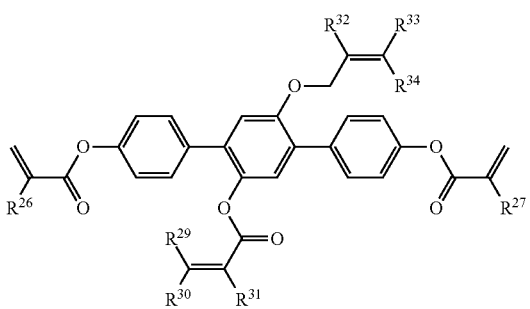

The polymerizable compound can be rapidly polymerized by adding the polymerization initiator thereto. An amount of a remaining polymerizable compound can be reduced by optimizing reaction conditions. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate and a mixture of benzophenone and methyltriethanolamine.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause poor display such as the image persistence in the device. In order to prevent such an event, photopolymerization may be performed with no addition of the polymerization initiator. A preferred wavelength of irradiation light is in the range of about 150 nanometers to about 500 nanometers. A further preferred wavelength is in the range of about 250 nanometers to about 450 nanometers, and a most preferred wavelength is in the range of about 300 nanometers to about 400 nanometers.

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include hydroquinone, a hydroquinone derivative such as methylhydroquinone, 4-t-butylcatechol, 4-methoxyphenol and phenothiazine.

The optically active compound is effective in inducing a helical structure in liquid crystal molecules to give a required twist angle, and thereby preventing a reverse twist. A helical pitch can be adjusted by adding the optically active compound thereto. Two or more optically active compounds may be added for the purpose of adjusting temperature dependence of the helical pitch. Specific examples of a preferred optically active compound include compounds (Op-1) to (Op-18) described below. In compound (Op-18), ring J is 1,4-cyclohexylene or 1,4-phenylene, and $R^{28}$ is alkyl having 1 to 10 carbons. Asterisk mark * represents asymmetrical carbon.

(Op-1) 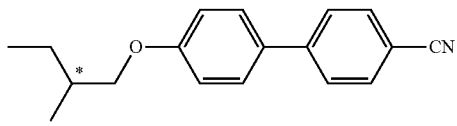

(Op-2) 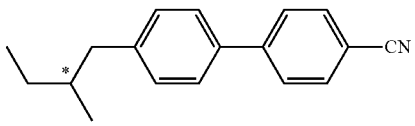

-continued
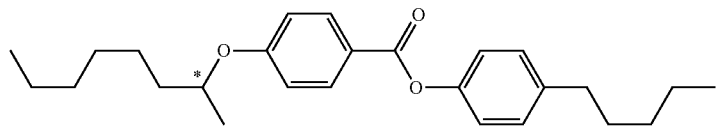
(Op-3)
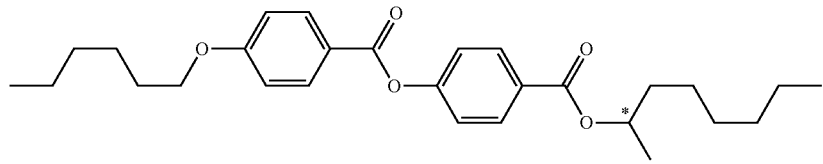
(Op-4)
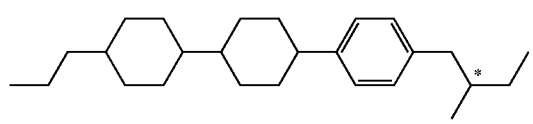
(Op-5)
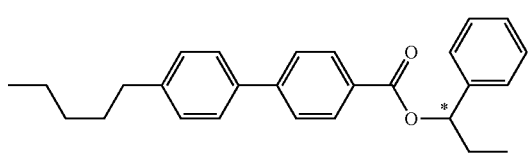
(Op-6)
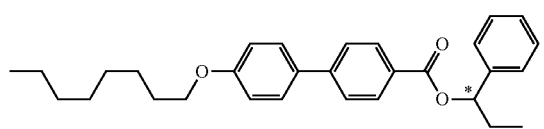
(Op-7)
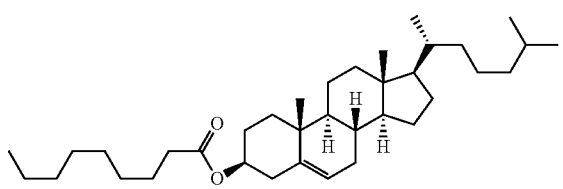
(Op-8)
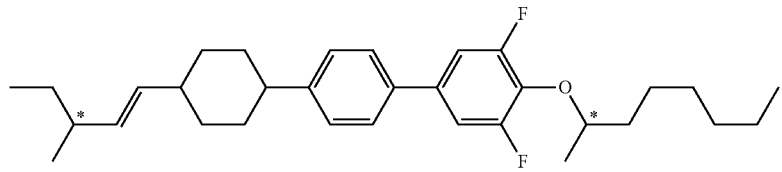
(Op-9)
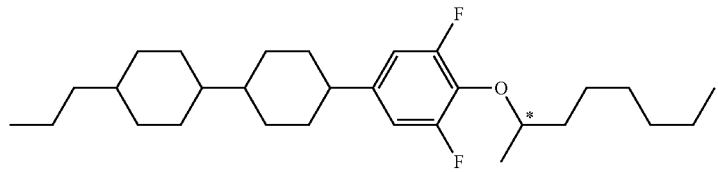
(Op-10)
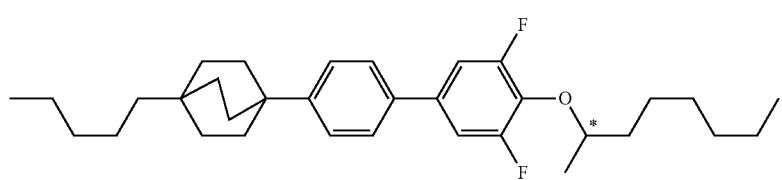
(Op-11)
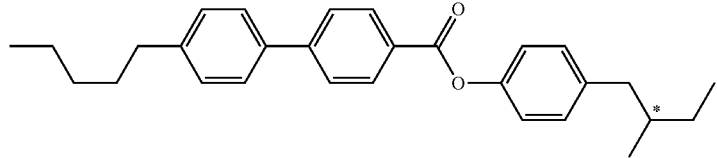
(Op-12)

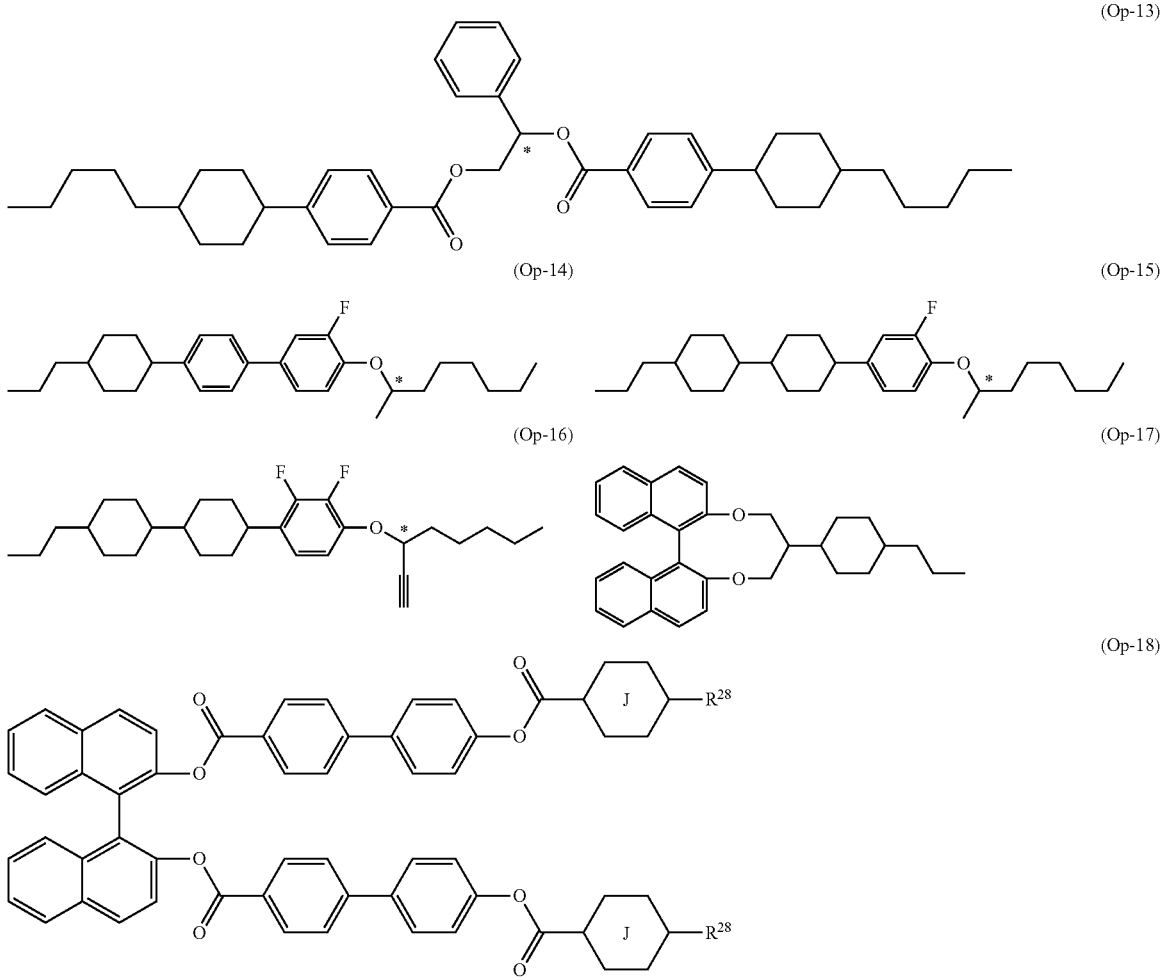

The antioxidant is effective for maintaining a large voltage holding ratio. Specific examples of a preferred antioxidant include compounds (AO-1) and (AO-2) described below; and Irganox 415, Irganox 565, Irganox 1010, Irganox 1035, Irganox 3114 and Irganox 1098 (trade names; BASF SE). The ultraviolet light absorber is effective for preventing reduction of the maximum temperature. Specific examples of a preferred ultraviolet light absorber include a benzophenone derivative, a benzoate derivative and a triazole derivative, and specific examples include compounds (AO-3) and (AO-4) described below; and Tinuvin 329, Tinuvin P, Tinuvin 326, Tinuvin 234, Tinuvin 213, Tinuvin 400, Tinuvin 328 and Tinuvin 99-2 (trade names; BASF SE); and 1,4-diazabicyclo[2.2.2]octane (DABCO).

The light stabilizer such as an amine having steric hindrance is preferred for maintaining the large voltage holding ratio. Specific examples of a preferred light stabilizer include compounds (AO-5), (AO-6) and (AO-7) described below; and Tinuvin 144, Tinuvin 765 and Tinuvin 770DF (trade names; BASF SE); and LA-77Y and LA-77G (trade names; ADEKA Corporation). The heat stabilizer is also effective for maintaining the large voltage holding ratio, and specific preferred examples thereof include Irgafos 168 (trade name; BASF SE). A dichroic dye such as an azo dye or an anthraquinone dye is added to the composition to be adapted for a device having a guest host (GH) mode. The antifoaming agent is effective for preventing foam formation. Specific examples of a preferred antifoaming agent include dimethyl silicone oil and methylphenyl silicone oil.

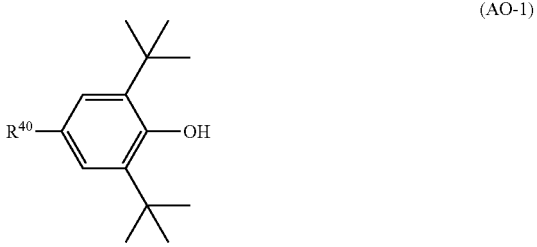

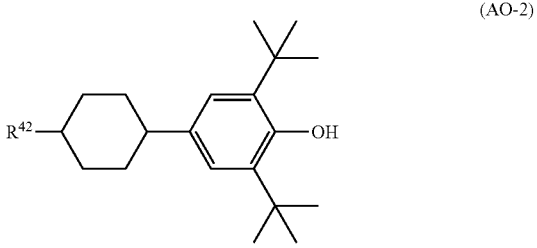

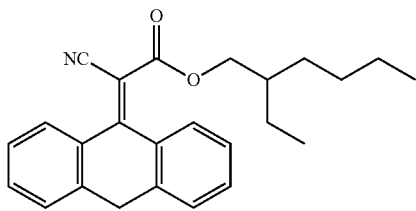
(AO-3)

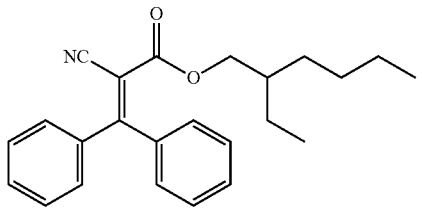
(AO-4)

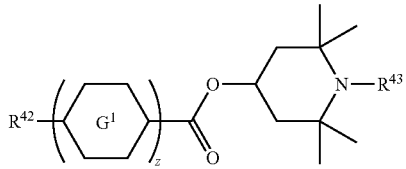
(AO-5)

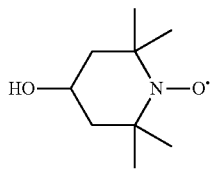
(AO-6)

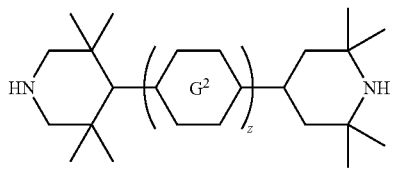
(AO-7)

In compound (AO-1), $R^{40}$ is alkyl having 1 to 20 carbons, alkoxy having 1 to 20 carbons, —COOR$^{41}$ or —CH$_2$CH$_2$COOR$^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O$^-$ (oxygen radical); and ring $G^1$ is 1,4-cyclohexylene or 1,4-phenylene; and in compound (AO-7), ring $G^2$ is 1,4-cyclohexylene, 1,4-phenylene or 1,4-phenylene in which at least one hydrogen is replaced by fluorine; and in compounds (AO-5) and (AO-7), z is 1, 2 or 3.

4. Liquid Crystal Display Device

The liquid crystal composition can be used for the liquid crystal display device having an operating mode such as the PC mode, the TN mode, the STN mode, the OCB mode and the PSA mode, and driven by an active matrix mode. The composition can also be used for the liquid crystal display device having an operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition is also suitable for a nematic curvilinear aligned phase (NCAP) device, and the composition is microencapsulated herein. The composition can also be used for a polymer dispersed liquid crystal display device (PDLCD) and a polymer network liquid crystal display device (PNLCD). In the compositions, a lot of polymerizable compounds are added. On the other hand, when a proportion of the polymerizable compound is about 10% by weight or less based on the weight of the liquid crystal composition, the liquid crystal display device having the PSA mode can be prepared. A preferred proportion is in the range of about 0.1% by weight to about 2% by weight. A further preferred proportion is in the range of about 0.2% by weight to about 1.0% by weight. The device having the PSA mode can be driven with a drive mode such as an active matrix mode and a passive matrix mode. Such a device can be applied to any of a reflective type, a transmissive type and a transflective type.

EXAMPLES

1. Example of Compound (1)

The invention will be described in greater detail by way of Examples. However, Examples each are described as a typical example, and therefore the invention is not limited by the Examples. Compound (1) was prepared according to procedures described below. The thus prepared compound was identified by methods such as an NMR analysis. Physical properties of the compound and the composition and characteristics of a device were measured by methods described below.

NMR analysis: For measurement, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, CFCl$_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Mass analysis: For measurement, GCMS-QP-2010 Ultra Gas Chromatograph Mass Spectrometer made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporization chamber, a temperature of an ion source, an ionizing voltage and an emission current were set to 300° C., 200° C., 70 eV and 150 uA, respectively. A sample was dissolved in acetone and prepared to be a 1 weight % solution, and then 1 microliter of the solution was injected into the sample vaporizing chamber. As a recorder, GC Solution System made by Shimadzu Corporation was used.

Gas chromatographic analysis: For measurement, GC-2010 Gas Chromatograph made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber and a temperature of a detector (FID) were set to 300° C. and 300° C., respectively. A sample was dissolved in acetone and prepared to be a 1 weight % solution, and then 1 microliter of the solution obtained was injected into the sample vaporizing chamber. As a recorder, GC Solution System made by Shimadzu Corporation or the like was used.

HPLC Analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set at 254 nanometers. A sample was dissolved in acetonitrile and prepared to be a 0.1 weight % solution, and then 1 microliter of the solution was injected into a sample chamber. As a recorder, C-R7Aplus made by Shimadzu Corporation was used.

Ultraviolet-Visible Spectrophotometry: For measurement, PharmaSpec UV-1700 made by Shimadzu Corporation was used. A detection wavelength was adjusted in the range of 190 nanometers to 700 nanometers. A sample was dissolved in acetonitrile and prepared to be a 0.01 mmol/L solution, and measurement was carried out by putting the solution in a quartz cell (optical path length: 1 cm).

Sample for measurement: Upon measuring phase structure and a transition temperature (a clearing point, a melting point, a polymerization start temperature or the like), a compound itself was used as a sample. Upon measuring physical properties such as maximum temperature of a nematic phase, viscosity, optical anisotropy and dielectric anisotropy, a mixture of a compound and a base liquid crystal was used as a sample.

When the sample prepared by mixing the compound with the base liquid crystal was used, measurement was performed as described below. The sample was prepared by mixing 15% by weight of the compound and 85% by weight of the base liquid crystal. From the measured value of the sample, an extrapolated value was calculated according to the following equation, and the calculated value was described: [extrapolated value]=(100×[measured value of a sample]−[% by weight of a base liquid crystal]×[measured value of the base liquid crystal])/[% by weight of a compound].

When crystals (or a smectic phase) precipitated at 25° C. at the ratio, a ratio of the compound to base liquid crystal was changed in the order of (10% by weight:90% by weight), (5% by weight:95% by weight) and (1% by weight: 99% by weight), and the physical properties of the sample were measured at a ratio at which no crystal (or no smectic phase) precipitated at 25° C. In addition, unless otherwise noted, the ratio of the compound to base liquid crystal was (15% by weight:85% by weight).

When the dielectric anisotropy of the compound was zero or positive, base liquid crystal (A) described below was used. A proportion of each component was expressed in terms of weight percent (% by weight).

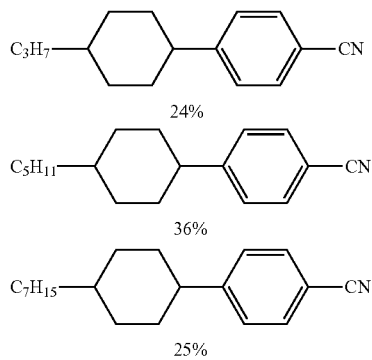

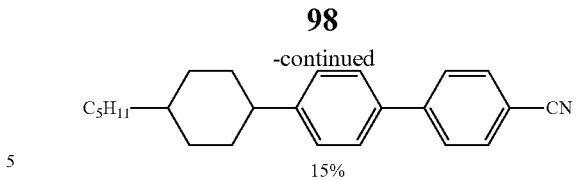

When the dielectric anisotropy of the compound was zero or negative, base liquid crystal (B) described below was used. A proportion of each component was expressed in terms of weight percent (% by weight).

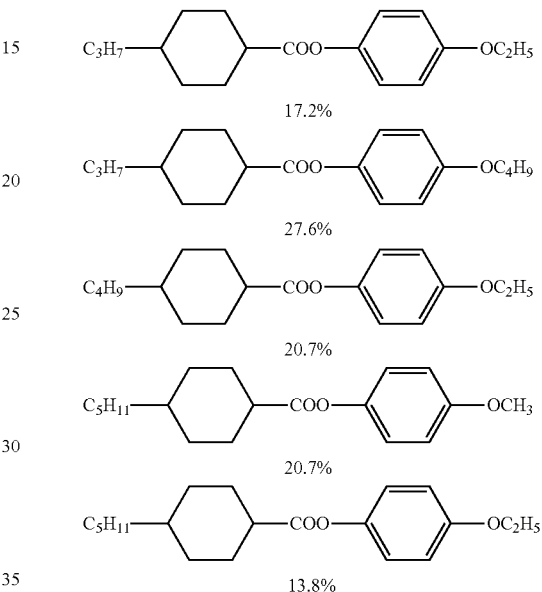

Measuring method: Physical properties were measured according to methods described below. Most of the methods are described in the Standard of Japan Electronics and Information Technology Industries Association (JEITA) discussed and established in JEITA (JEITA ED-2521B). A modified method was also applied. No thin film transistor (TFT) was attached to a TN device used for measurement.

(1) Phase structure: A sample was placed on a hot plate in a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition temperature (° C.): For measurement, a differential scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A melting point and a polymerization starting temperature of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When the crystals were distinguishable into two kinds, each of the crystals was expressed as $C_1$ or $C_2$. The smectic phase or the nematic phase was expressed as S or N. When the phases such as smectic A phase, smectic B phase, smectic C phase and smectic F phase were distinguishable, the phases were expressed as $S_A$, $S_B$, $S_C$ and $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility of compound: Samples in which the base liquid crystal and the compound were mixed for proportions of the compounds to be 20% by weight, 15% by weight, 10% by weight, 5% by weight, 3% by weight or 1% by weight were prepared. The samples each was put in a glass vial and kept in freezers at −10° C. or −20° C. for a fixed period of time. Observation was performed whether the nematic phase of the sample was maintained or crystals (or smectic phase) precipitated. The conditions on which the nematic phase was maintained were used as a scale of compatibility. Ratio of the compound or temperature of the freezer were changed when necessary.

(4) Maximum temperature of nematic phase ($T_{NI}$ or NI; ° C.): A sample was placed on a hot plate in a melting point apparatus equipped with a polarizing microscope, and heated at a rate of 1° C. per minute. Temperature when part of the sample began to change from a nematic phase to an isotropic liquid was measured. When the sample was a mixture of compound (1) and the base liquid crystal, the maximum temperature was expressed in terms of a symbol $T_{NI}$. When the sample was a mixture of compound (1) and a compound selected from compounds (2) to (15), the maximum temperature was expressed in terms of a symbol NI. A maximum temperature of the nematic phase may be occasionally abbreviated as "maximum temperature."

(5) Minimum temperature of nematic phase ($T_C$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_C$ was expressed as $T_C$<−20° C. A minimum temperature of the nematic phase may be occasionally abbreviated as "minimum temperature."

(6) Viscosity (bulk viscosity; η; measured at 20° C.; mPa·s): For measurement, a cone-plate (E type) rotational viscometer made by Tokyo Keiki Inc. was used.

(7) Optical anisotropy (refractive index anisotropy; measured at 25° C.; Δn): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n∥−n⊥.

(8) Specific resistance (ρ; measured at 25° C.; Ωcm): Into a vessel equipped with electrodes, 1.0 milliliter of sample was injected. A direct current voltage (10 V) was applied to the vessel, and a direct current after 10 seconds was measured. Specific resistance was calculated from the following equation: (specific resistance)={(voltage)×(electric capacity of a vessel)}/{(direct current)×(dielectric constant of vacuum)}.

(9) Voltage holding ratio (VHR-1; measured at 25° C.; %): A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the device and the device was charged. A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(10) Voltage holding ratio (VHR-2; measured at 80° C.; %): A voltage holding ratio was measured according to methods described above except that measurement was carried out at 80° C. in place of 25° C. The results obtained were expressed in terms of a symbol VHR-2.

(11) Flicker rate (measured at 25° C.; %): For measurement, 3298F Multimedia Display Tester made by Yokogawa Electric Corporation was used. A light source was LED. A sample was put in a normally black mode FFS device in which a distance (cell gap) between two glass substrates was 3.5 micrometers and a rubbing direction was anti-parallel. The device was sealed with an ultraviolet-curable adhesive. Voltage was applied to the device, and a voltage having a maximum amount of light transmitted through the device was measured. A flicker rate displayed thereon was read by bringing a sensor unit close to the device while voltage was applied to the device.

Measuring methods of physical properties for samples each having positive or negative dielectric anisotropy may be occasionally different. The measuring methods when dielectric anisotropy was positive were described in measurement (12a) to measurement (16a) The measuring methods when dielectric anisotropy was negative were described in measurement (12b) to measurement (16b).

(12a) Viscosity (rotational viscosity; γ1; measured at 25° C.; mPa·s; for a sample having positive dielectric anisotropy): Measurement was carried out according to a method described in M. Imai et al., Molecular Crystals and Liquid Crystals, Vol. 259, p. 37 (1995). A sample was put in a TN device in which a twist angle was 0 degree and a distance (cell gap) between two glass substrates was 5 micrometers. Voltage was applied stepwise to the device from 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and equation (8) described on page 40 of the paper presented by M. Imai et al. A value of dielectric anisotropy required for the calculation was determined using the device by which the rotational viscosity was measured and by the method described below.

(12b) Viscosity (rotational viscosity; γ1; measured at 25° C.; mPa·s; for a sample having negative dielectric anisotropy): Measurement was carried out according to a method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device from 39 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and equation (8) described on page 40 of the paper presented by M. Imai et al. A dielectric anisotropy required for the calculation was measured in the section of dielectric anisotropy described below.

(13a) Dielectric anisotropy ($\Delta\varepsilon$; measured at 25° C.; for a sample having positive dielectric anisotropy): A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant ($\varepsilon\|$) of liquid crystal molecules in a major axis direction was measured. Sine waves (0.5 V, 1 kHz) were applied to the device, and after 2 seconds, a dielectric constant ($\varepsilon\bot$) of liquid crystal molecules in a minor axis direction was measured. A value of dielectric anisotropy was calculated from an equation: $\Delta\varepsilon=\varepsilon\|-\varepsilon\bot$.

(13b) Dielectric anisotropy ($\Delta\varepsilon$; measured at 25° C.; for a sample having negative dielectric anisotropy): A value of dielectric anisotropy was calculated from an equation: $\Delta\varepsilon=\varepsilon\|-\varepsilon\bot$. A dielectric constant ($\varepsilon\|$ and $\varepsilon\bot$) was measured as described below.

(1) Measurement of a dielectric constant ($\varepsilon\|$): An ethanol (20 mL) solution of octadecyltriethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant ($\varepsilon\|$) of the liquid crystal molecules in a major axis direction was measured.

(2) Measurement of a dielectric constant ($\varepsilon\bot$): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant ($\varepsilon\|$) of liquid crystal molecules in a minor axis direction was measured.

(14a) Elastic constant (K; measured at 25° C.; pN; for a sample having positive dielectric anisotropy): For measurement, HP4284A LCR Meter made by Yokogawa-Hewlett-Packard Co. was used. A sample was put in a horizontal alignment device in which a distance (cell gap) between two glass substrates was 20 micrometers. An electric charge from 0 V to 20 V was applied to the device, and electrostatic capacity (C) and applied voltage (V) were measured. The values obtained were fitted to equation (2.98) and equation (2.101) on page 75 of "Liquid Crystal Device Handbook" (Ekisho Debaisu Handobukku in Japanese) (Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed in terms of a mean value of the thus determined $K_{11}$, $K_{22}$ and $K_{33}$.

(14b) Elastic constant ($K_{11}$ and $K_{33}$; measured at 25° C.; pN; for a sample having negative dielectric anisotropy): For measurement, Elastic Constant Measurement System Model EC-1 made by TOYO Corporation was used. A sample was put in a vertical alignment device in which a distance (cell gap) between two glass substrates was 20 micrometers. An electric charge from 20 V to 0 V was applied to the device, and electrostatic capacity (C) and applied voltage (V) were measured. The values obtained were fitted to equation (2.98) and equation (2.101) on page 75 of "Liquid Crystal Device Handbook" (Ekisho Debaisu Handobukku in Japanese; Nikkan Kogyo Shimbun, Ltd.) and values of elastic constant were obtained from equation (2.100)

(15a) Threshold voltage (Vth; measured at 25° C.; V); for a sample having positive dielectric anisotropy): For measurement, an LCD-5100 luminance meter made by Otsuka Electronics Co., Ltd. was used. A light source was a halogen lamp. A sample was put in a normally white mode TN device in which a distance (cell gap) between two glass substrates was 0.45/$\Delta$n ($\mu$m) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of a voltage at 90% transmittance.

(15b) Threshold voltage (Vth; measured at 25° C.; V; for a sample having negative dielectric anisotropy): For measurement, an LCD-5100 luminance meter made by Otsuka Electronics Co., Ltd. was used. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 10% transmittance.

(16a) Response Time ($\tau$; measured at 25° C.; ms; for a sample having positive dielectric anisotropy): For measurement, an LCD-5100 luminance meter made by Otsuka Electronics Co., Ltd. was used. A light source was a halogen lamp. A low-pass filter was set to 5 kHz. A sample was put in a normally white mode TN device in which a distance (cell gap) between two glass substrates was 5.0 micrometers and a twist angle was 80 degrees. A voltage of rectangular waves (60 Hz, 5 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time ($\tau$r; millisecond) was expressed in terms of time required for a change from 90% transmittance to 10% transmittance. A fall time ($\tau$f; millisecond) was expressed in terms of time required for a change from 10% transmittance to 90% transmittance. A response time was expressed by a sum of the rise time and the fall time thus determined.

(16b) Response Time (τ; measured at 25° C.; ms; for a sample having negative dielectric anisotropy): For measurement, an LCD-5100 luminance meter made by Otsuka Electronics Co., Ltd. was used. A light source was a halogen lamp. A low-pass filter was set to 5 kHz. A sample was put in a normally black mode PVA device in which a distance (cell gap) between two glass substrates was 3.2 micrometers and a rubbing direction was anti-parallel. The device was sealed with an ultraviolet-curable adhesive. A voltage in a degree of a little over of the threshold voltage was applied to the device for 1 minute, and subsequently the device was irradiated with ultraviolet light of 23.5 mW/cm$^2$ for 8 minutes while applying a voltage of 5.6V to the device. A voltage (rectangular waves; 60 Hz, 10 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time was expressed in terms of time required for a change from 90% transmittance to 10% transmittance (fall time; millisecond).

Synthesis Example 1

Synthesis of Compound (No. 39)

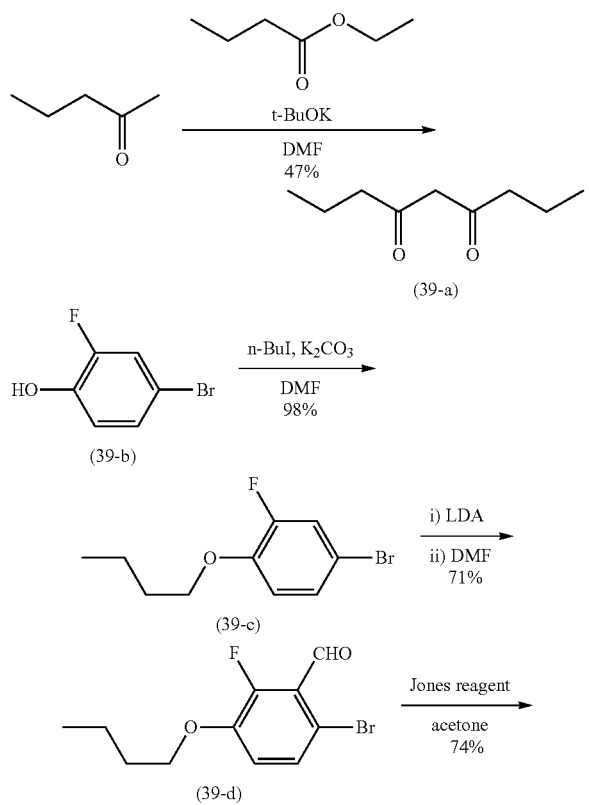

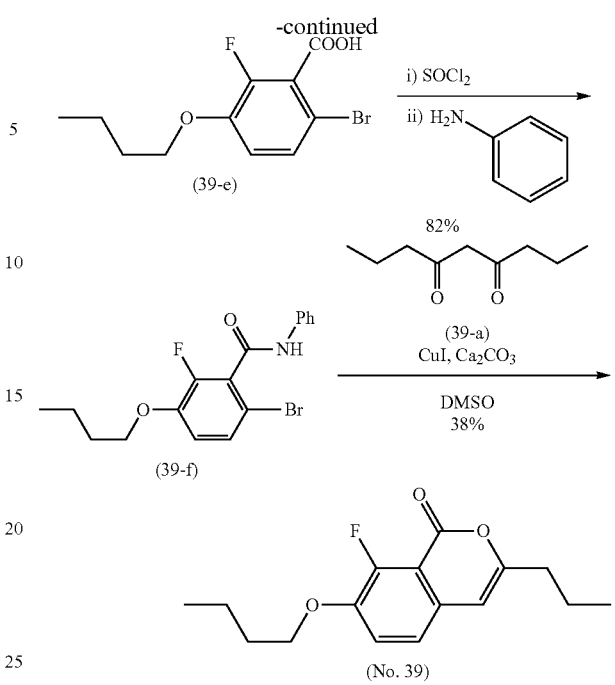

First Step: Synthesis of Compound (39-a)

To DMF (75 mL), potassium tert-butoxide (50.50 g, 450 mmol) was added, and the resulting mixture was heated and stirred at 50° C. for 30 minutes. To the mixture obtained, a mixture of propylmethylketone (31.9 g, 300 mmol) and ethylbutylate (108.0 g, 930 mmol) was added dropwise, and the resulting mixture was heated and stirred. After 5 hours, the mixture was returned to room temperature, and stirred for 14 hours. The resulting reaction mixture was poured into 1 N hydrochloric acid (250 mL) and subjected to extraction with heptane (4 times, using 100 mL for each). A combined organic layer was washed with water, dried over anhydrous magnesium sulfate, and concentrated under reduced pressure. The residue was purified by a vacuum distillation to obtain compound (39-a) (22.2 g, 142 mmol) as a colorless liquid.

Second Step: Synthesis of Compound (39-c)

Commercially available compound (39-b) (40 g, 209.4 mmol) was dissolved in DMF (200 mL). Into the resulting solution, potassium carbonate (57.9 g, 418.9 mmol) and 1-Iodobutane (42.4 g, 230.4 mmol) were added, and the resulting mixture was heated and stirred at 80° C. After 3 hours, the resulting mixture was returned to room temperature, and the reaction mixture was poured into water, and subjected to extraction with toluene (3 times, using 100 mL for each). A combined organic layer was washed with water, dried over anhydrous magnesium sulfate, and concentrated under reduced pressure. The residue was purified by silica gel chromatography (heptane) to obtain compound (39-c) (50.7 g, 205 mmol) as a colorless liquid.

Third Step: Synthesis of Compound (39-d)

N,N-isopropylethylamine (4.5 g, 44.5 mmol) was dissolved in THF (15 mL), and then n-butyllithium (1.60 mol/L; 27.8 mL, 44.5 mmol) was added dropwise thereto at −70° C. or lower. After 1 hour, a THF (30 mL) solution of compound (39-c) (10.0 g, 40.5 mmol) was added dropwise thereto at −70° C. or lower. After 3 hours, a THF (20 mL) solution of N,N-dimethylformamide (DMF; 5.9 g, 80.9 mmol) was added dropwise thereto. After 30 minutes, the resulting mixture was returned to room temperature, and stirred overnight. The resulting reaction mixture was poured into a saturated aqueous solution of ammonium chloride (100 mL), and subjected to extraction with ethyl acetate (3 times, using 80 mL for each). A combined organic layer was washed with a saturated aqueous solution of sodium chloride and water, dried over anhydrous magnesium sulfate, and concentrated under reduced pressure. The residue was purified by silica gel chromatography (heptane:ethyl acetate=9:1) and by recrystallization (heptane-ethyl acetate) to obtain compound (39-d) (7.9 g, 28.8 mmol) as colorless crystals.

Fourth Step: Synthesis of Compound (39-e)

A Jones reagent was prepared according to the description in "New Experimental Chemistry Course" (Shin Jikken Kagaku Koza in Japanese) (Maruzen Co., Ltd.). The reagent obtained (16.2 mL, 43.2 mmol) was added dropwise to an acetone solution (100 mL) of compound (39-d) (7.9 g, 28.8 mmol) at 10° C. or lower. After 30 minutes, the resulting mixture was returned to room temperature, and further stirred overnight. Celite (5 g) was added to the reaction mixture, and the resulting mixture was stirred for 5 minutes, and then IPA (20 mL) was added thereto under ice cooling, and the resulting mixture was further stirred for 30 minutes. The reaction mixture was filtered, and water (100 mL) was added to the filtrate, and the resulting mixture was concentrated under reduced pressure, and acetone and IPA were removed. The resulting aqueous solution was subjected to extraction with ethyl acetate (3 times, using 50 mL for each). A combined organic layer was washed with a saturated aqueous solution of sodium chloride (500 mL) and water, dried over anhydrous magnesium sulfate, and concentrated under reduced pressure. The residue was washed with heptane to obtain compound (39-e) (6.2 g, 21.4 mmol) as colorless crystals.

Fifth Step: Synthesis of Compound (39-f)

Compound (39-e) (5.0 g, 17.2 mmol) was dissolved in toluene (50 mL), and then pyridine (4 mg, 0.05 mmol) was added thereto, and the resulting mixture was heated at 50° C. Thionyl chloride (2.2 g, 18.1 mmol) was added thereto, and the resulting mixture was further heated and stirred. After 3 hours, the resulting reaction mixture was concentrated under reduced pressure. The residue was dissolved in methylene chloride (10 mL), and then the resulting solution was added dropwise to a methylene chloride (50 mL) solution of aniline (3.2 g, 34.4 mmol) under ice cooling. After 30 minutes, the resulting mixture was returned to room temperature, and further stirred overnight. The resulting reaction mixture was poured into water, and subjected to extraction with methylene chloride (2 times, using 50 mL for each). A combined organic layer was washed with a saturated aqueous solution of sodium chloride (50 mL), dried over anhydrous magnesium sulfate, and concentrated under reduced pressure. The residue was purified by recrystallization (heptane-ethyl acetate) to obtain compound (39-f) (5.2 g, 14.1 mmol) as colorless crystals.

Sixth Step: Synthesis of Compound (No. 39)

Compound (39-f) (5.1 g, 14.0 mmol) was dissolved in dimethyl sulfoxide (50 mL), and then compound (39-a) prepared in the first step (4.4 g, 28.0 mmol), cesium carbonate (9.1 g, 28.0 mmol) and copper iodide (0.27 g, 1.4 mmol) were added thereto, and the resulting mixture was stirred at 100° C. After 3 hours, the reaction mixture was poured into water (500 mL), and subjected to extraction with heptane (2 times, using 30 mL for each). A combined organic layer was washed with a saturated aqueous solution of sodium chloride (50 mL), dried over anhydrous magnesium sulfate, and concentrated under reduced pressure. The residue was purified by silica gel chromatography (20% ethyl acetate-heptane) to obtain compound (No. 39) (1.5 g, 5.4 mmol) as colorless crystals.

$^1$H-NMR (CDCl$_3$; δ ppm): 7.34 (dd, J=8.0 Hz, 8.1 Hz, 1H), 7.05 (dd, J=1.6 Hz, 8.0 Hz, 1H), 6.16 (d, J=2.1 Hz, 1H), 4.09 (t, J=6.5 Hz, 2H), 2.46 (t, J=7.5 Hz, 2H), 1.83-1.77 (m, 2H), 1.75-1.68 (m, 2H), 1.55-1.47 (m, 2H), 0.98 (t, J=7.5 Hz, 3H×2). 19F-NMR (6 ppm; CDCl$_3$): −129.8 (d, J=8.1 Hz, 1F).

Phase transition temperature: C 38.9 I. Maximum temperature (NI)=−53.7C; dielectric anisotropy (Δε)=−18.23; optical anisotropy (Δn)=0.094; viscosity (η)=86.5 mPa·s.

Comparative Example 1

Viscosity of compound (No. 39) was compared with viscosity of comparative compound (298) and comparative compound (121) each having structure similar thereto. Samples for measurement were prepared by adding the compounds to base liquid crystal (B). The results were summarized in Table 2.

TABLE 2

Comparison of viscosity

| Sample for measurement | Components of sample | | Viscosity (η) |
|---|---|---|---|
| Sample 1 | 15% by weight of compound (No. 39) | 85% by weight of base liquid crystal (B) | 86.5 mPa·s |
| Comparative sample 2 | 15% by weight of compound (298) | 85% by weight of base liquid crystal (B) | 182.5 mPa·s |
| Comparative sample 3 | 1% by weight of compound (121) | 99% by weight of base liquid crystal (B) | Unmeasurable |

As is obvious from Table 2, the viscosity of compound (No. 39) was smaller than the viscosity of comparative compound (298). The compatibility of comparative compound (121) and base liquid crystal (B) was low. The mixture of 1% by weight of comparative compound (121) and 99% by weight of base liquid crystal (B) was uniformized by heating, but when the temperature was returned to room temperature, crystals precipitated. Accordingly, the viscosity was unable to be measured.

Compounds (No. 1) to (No. 984) described below can be prepared with reference to the method described in Synthesis Examples and the section "2. Synthesis of compound (1)."

| No. |
|---|
| 1 |

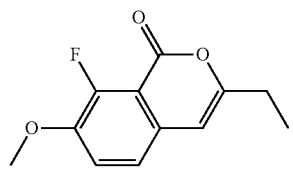 [SMILES: CCc1cc2ccc(OC)c(F)c2c(=O)o1]

-continued
| No. | |
|---|---|
| 2 | 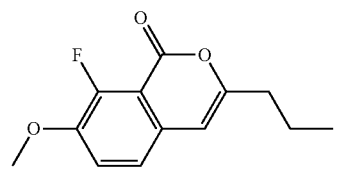 [SMILES: CCCc1cc2ccc(OC)c(F)c2c(=O)o1] |
| 3 | 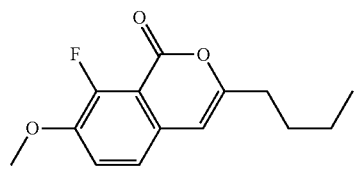 |
| 4 | 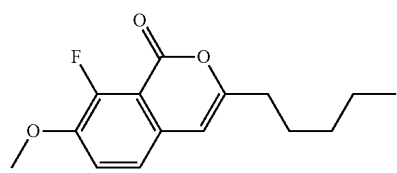 [SMILES: CCCCCc1cc2ccc(OC)c(F)c2c(=O)o1] |
| 5 | 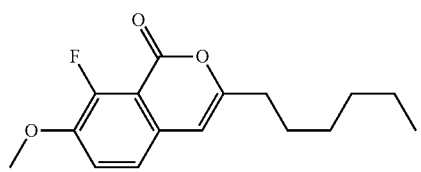 [SMILES: CCCCCCc1cc2ccc(OC)c(F)c2c(=O)o1] |
| 6 | 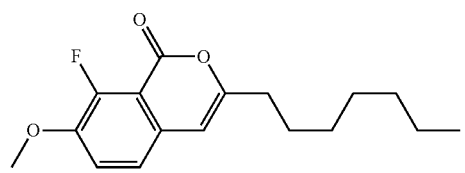 |
| 7 | 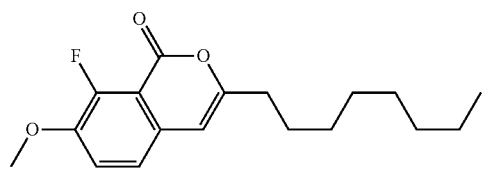 |
| 8 | 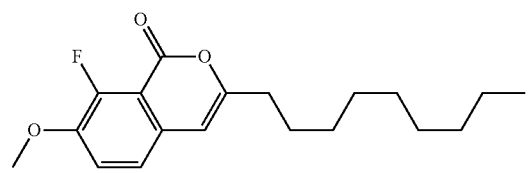 [SMILES: CCCCCCCCCc1cc2ccc(OC)c(F)c2c(=O)o1] |
| 9 | 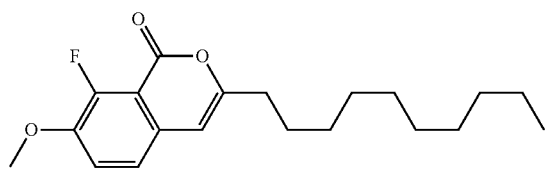 [SMILES: CCCCCCCCCCc1cc2ccc(OC)c(F)c2c(=O)o1] |
| 10 | 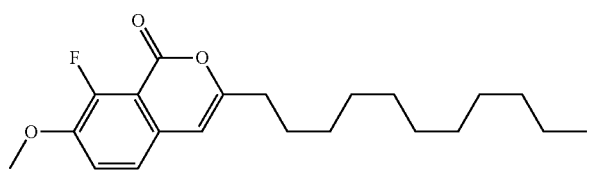 |

-continued
| No. | |
|---|---|
| 11 | 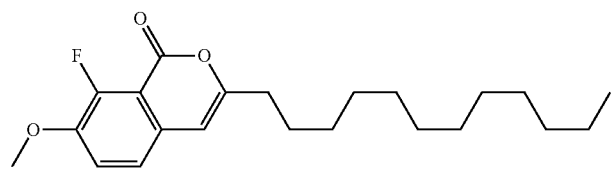 |
| 12 | 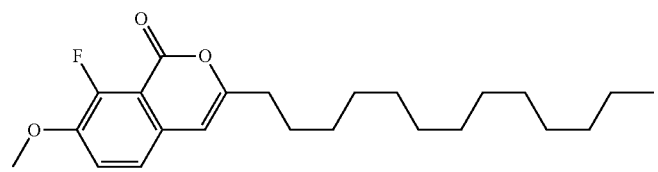 [SMILES: CCCCCCCCCCCCCc1cc2ccc(OC)c(F)c2c(=O)o1] |
| 13 | 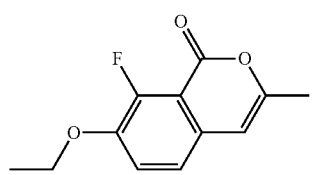 [SMILES: CCOc1ccc2cc(C)oc(=O)c2c1F] |
| 14 | 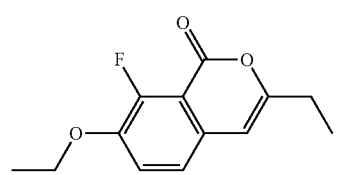 [SMILES: CCOc1ccc2cc(CC)oc(=O)c2c1F] |
| 15 | 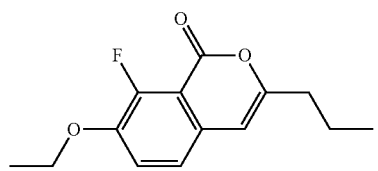 |
| 16 | 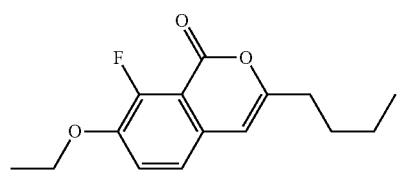 |
| 17 | 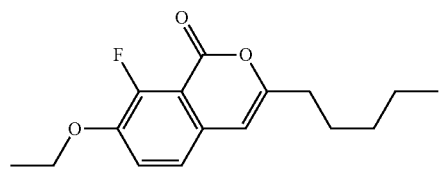 |
| 18 | 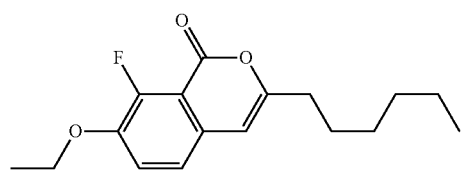 [SMILES: CCCCCCc1cc2ccc(OCC)c(F)c2c(=O)o1] |
| 19 | 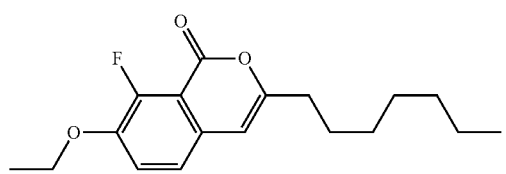 [SMILES: CCCCCCCc1cc2ccc(OCC)c(F)c2c(=O)o1] |

-continued
| No. | |
|---|---|
| 20 | 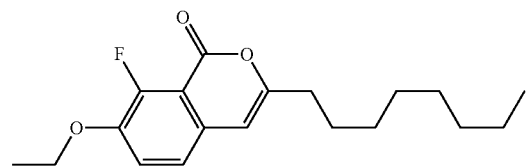 [SMILES: CCCCCCCCc1cc2ccc(OCC)c(F)c2c(=O)o1] |
| 21 | 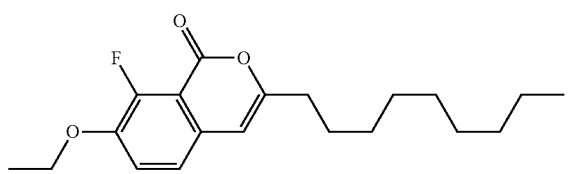 [SMILES: CCCCCCCCCc1cc2ccc(OCC)c(F)c2c(=O)o1] |
| 22 | 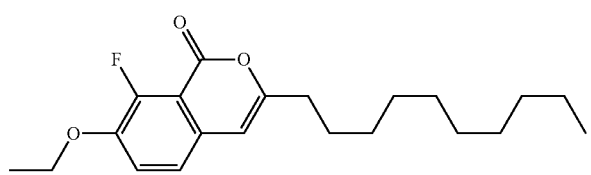 [SMILES: CCCCCCCCCCc1cc2ccc(OCC)c(F)c2c(=O)o1] |
| 23 | 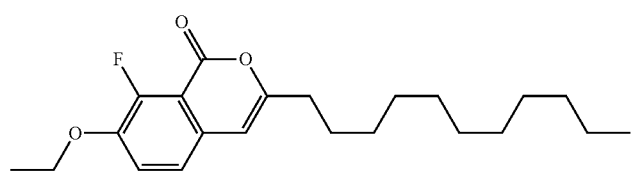 [SMILES: CCCCCCCCCCCc1cc2ccc(OCC)c(F)c2c(=O)o1] |
| 24 | 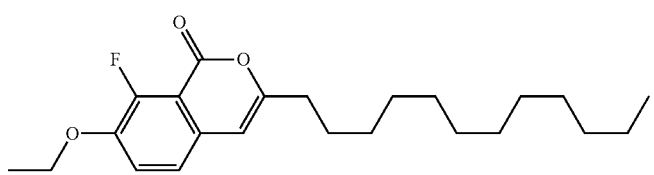 [SMILES: CCCCCCCCCCCCc1cc2ccc(OCC)c(F)c2c(=O)o1] |
| 25 | 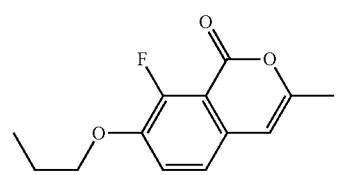 [SMILES: CCCOc1ccc2cc(C)oc(=O)c2c1F] |
| 26 | 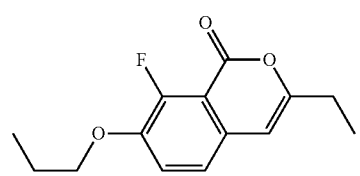 [SMILES: CCCOc1ccc2cc(CC)oc(=O)c2c1F] |
| 27 | 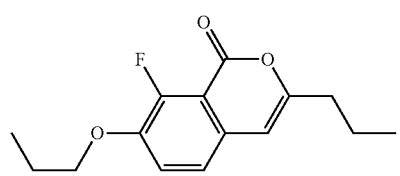 [SMILES: CCCOc1ccc2cc(CCC)oc(=O)c2c1F] |
| 28 | 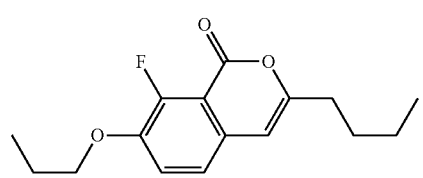 |

-continued
| No. | |
|---|---|
| 29 | 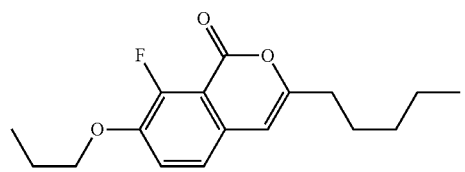 [SMILES: CCCCCc1cc2ccc(OCCC)c(F)c2c(=O)o1] |
| 30 | 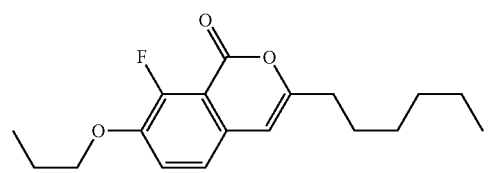 [SMILES: CCCCCCc1cc2ccc(OCCC)c(F)c2c(=O)o1] |
| 31 | 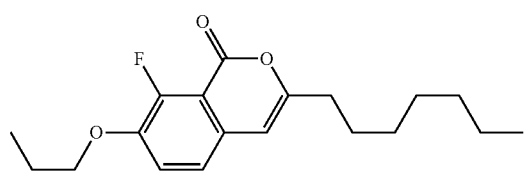 [SMILES: CCCCCCCc1cc2ccc(OCCC)c(F)c2c(=O)o1] |
| 32 | 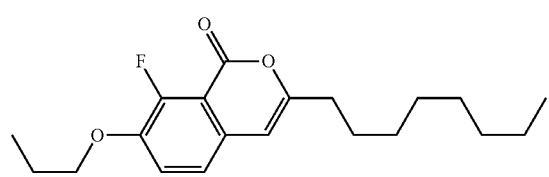 [SMILES: CCCCCCCCc1cc2ccc(OCCC)c(F)c2c(=O)o1] |
| 33 | 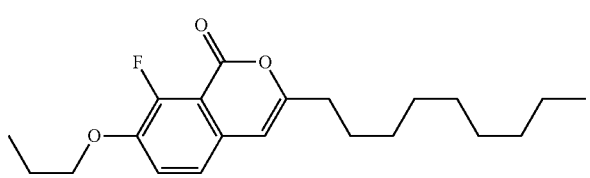 [SMILES: CCCCCCCCCc1cc2ccc(OCCC)c(F)c2c(=O)o1] |
| 34 | 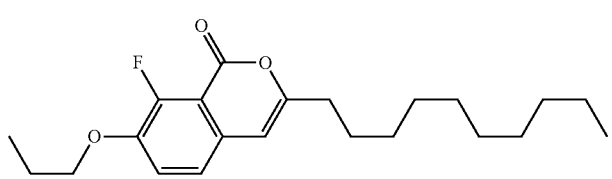 |
| 35 | 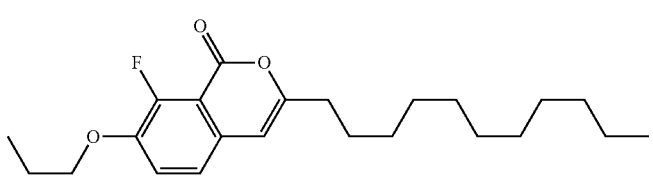 |
| 36 | 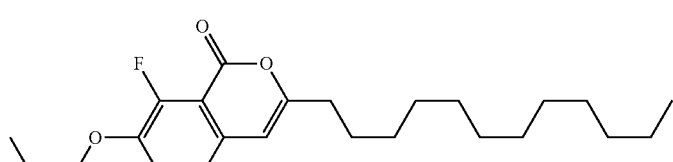 |
| 37 | 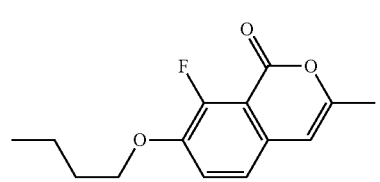 [SMILES: CCCCOc1ccc2cc(C)oc(=O)c2c1F] |

-continued
| No. | |
|---|---|
| 38 | 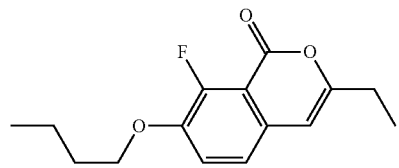 [SMILES: CCCCOc1ccc2cc(CC)oc(=O)c2c1F] |
| 39 | 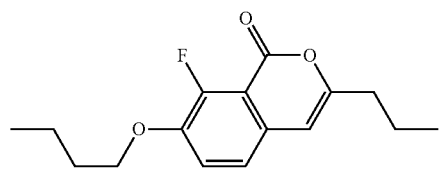 [SMILES: CCCCOc1ccc2cc(CCC)oc(=O)c2c1F] |
| 40 | 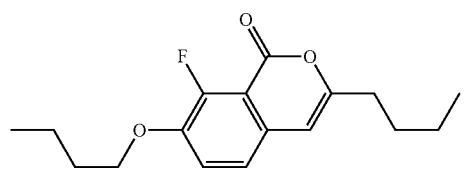 [SMILES: CCCCOc1ccc2cc(CCCC)oc(=O)c2c1F] |
| 41 | 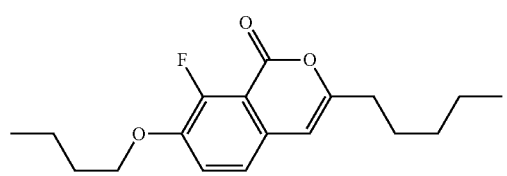 |
| 42 | 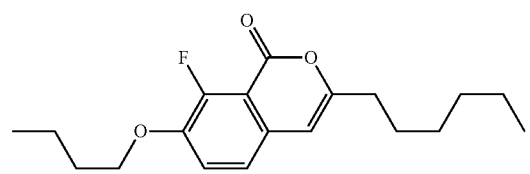 [SMILES: CCCCCCc1cc2ccc(OCCCC)c(F)c2c(=O)o1] |
| 43 | 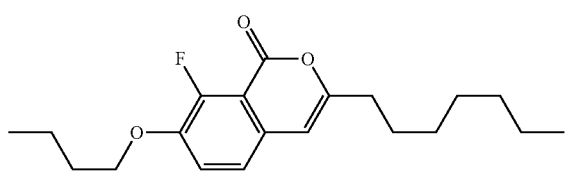 |
| 44 | 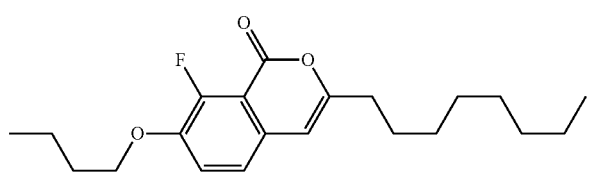 [SMILES: CCCCCCCCc1cc2ccc(OCCCC)c(F)c2c(=O)o1] |
| 45 | 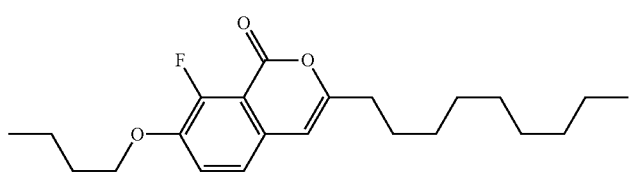 [SMILES: CCCCCCCCCc1cc2ccc(OCCCC)c(F)c2c(=O)o1] |
| 46 | 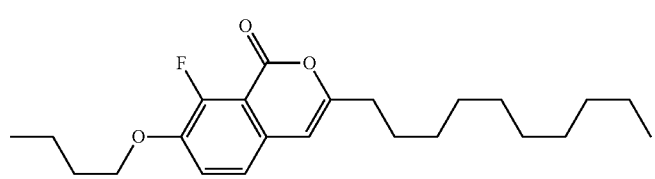 |

| No. | |
|---|---|
| 47 | 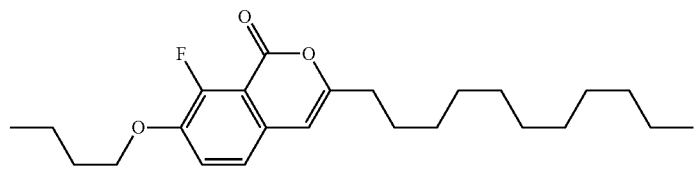 [SMILES: CCCCCCCCCCCc1cc2ccc(OCCCC)c(F)c2c(=O)o1] |
| 48 | 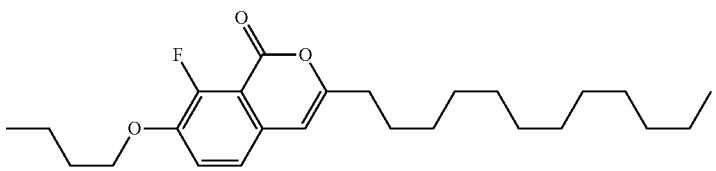 [SMILES: CCCCCCCCCCCCc1cc2ccc(OCCCC)c(F)c2c(=O)o1] |
| 49 | 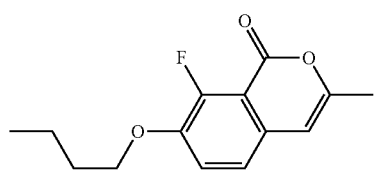 |
| 50 | 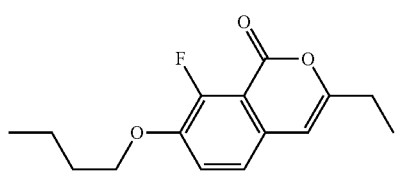 |
| 51 | 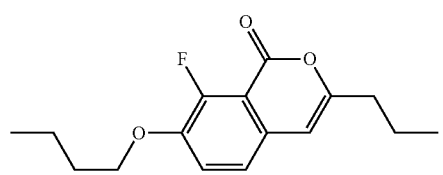 [SMILES: CCCCOc1ccc2cc(CCC)oc(=O)c2c1F] |
| 52 | 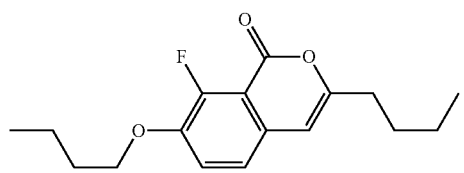 [SMILES: CCCCOc1ccc2cc(CCCC)oc(=O)c2c1F] |
| 53 | 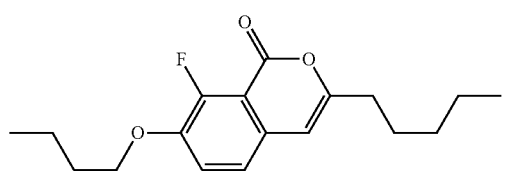 [SMILES: CCCCCc1cc2ccc(OCCCC)c(F)c2c(=O)o1] |
| 54 | 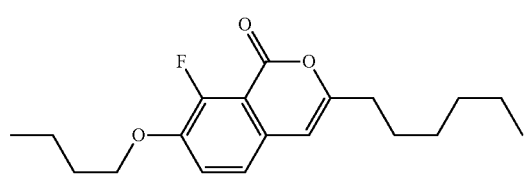 [SMILES: CCCCCCc1cc2ccc(OCCCC)c(F)c2c(=O)o1] |
| 55 | 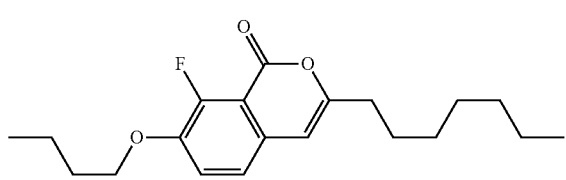 |

| No. | |
|---|---|
| 56 | 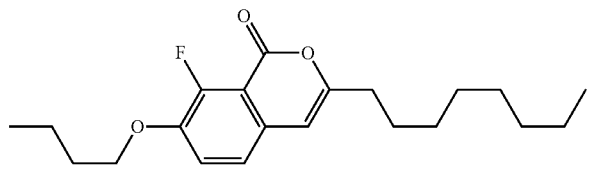 [SMILES: CCCCCCCCc1cc2ccc(OCCCC)c(F)c2c(=O)o1] |
| 57 | 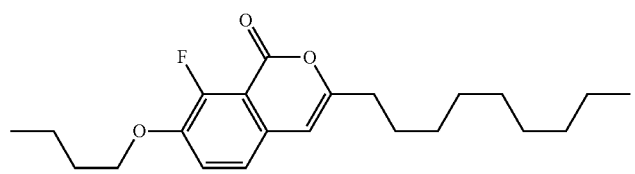 [SMILES: CCCCCCCCCc1cc2ccc(OCCCC)c(F)c2c(=O)o1] |
| 58 | 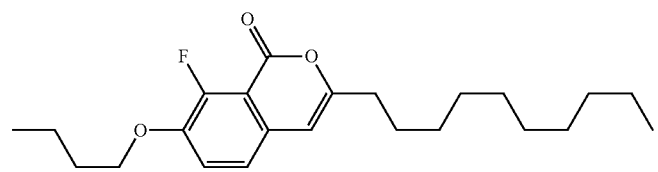 |
| 59 | 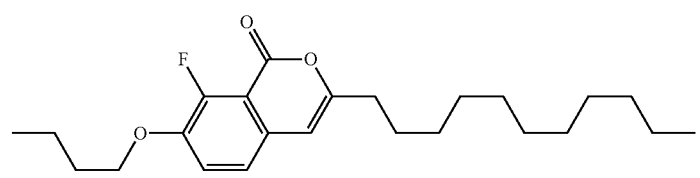 |
| 60 | 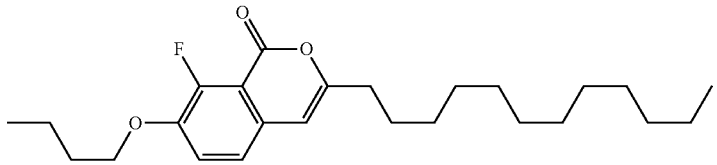 [SMILES: CCCCCCCCCCCCc1cc2ccc(OCCCC)c(F)c2c(=O)o1] |
| 61 | 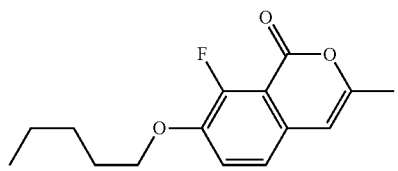 [SMILES: CCCCCOc1ccc2cc(C)oc(=O)c2c1F] |
| 62 | 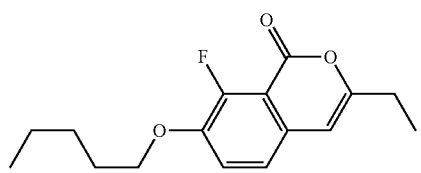 [SMILES: CCCCCOc1ccc2cc(CC)oc(=O)c2c1F] |
| 63 | 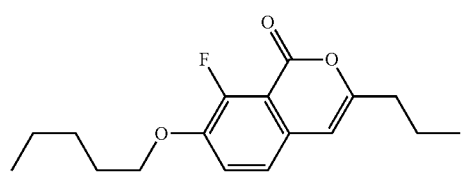 [SMILES: CCCCCOc1ccc2cc(CCC)oc(=O)c2c1F] |
| 64 | 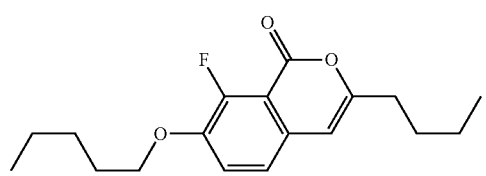 |

| No. | |
|---|---|
| 65 | 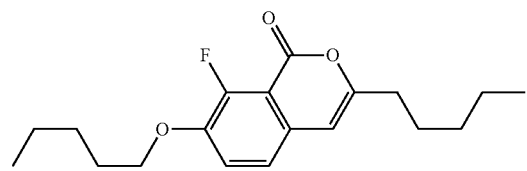 [SMILES: CCCCCOc1ccc2cc(CCCCC)oc(=O)c2c1F] |
| 66 | 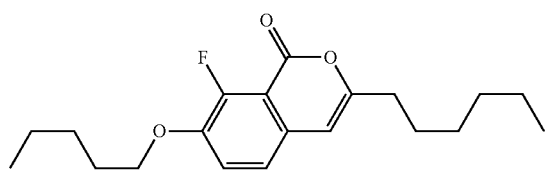 [SMILES: CCCCCCc1cc2ccc(OCCCCC)c(F)c2c(=O)o1] |
| 67 | 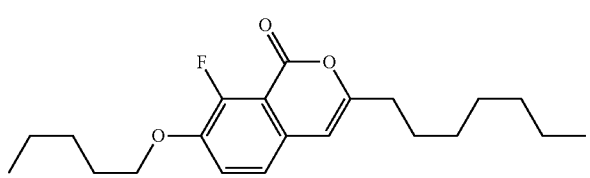 [SMILES: CCCCCCCc1cc2ccc(OCCCCC)c(F)c2c(=O)o1] |
| 68 | 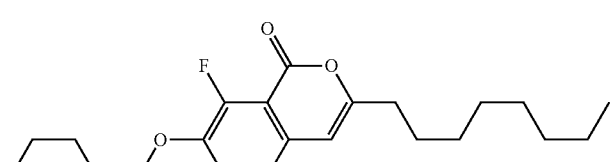 |
| 69 | 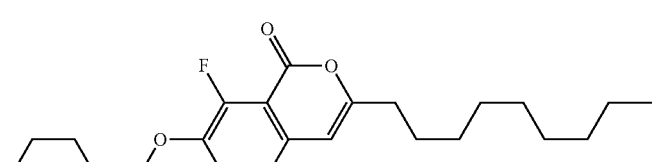 |
| 70 | 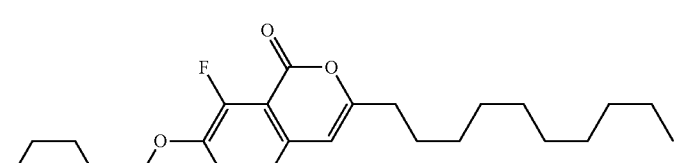 |
| 71 | 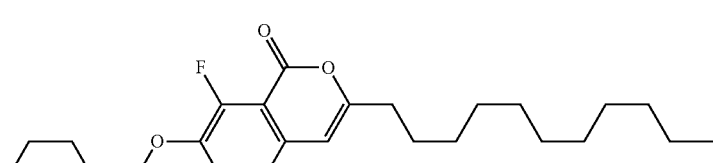 |
| 72 | 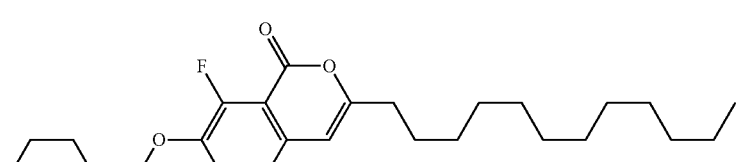 |
| 73 | 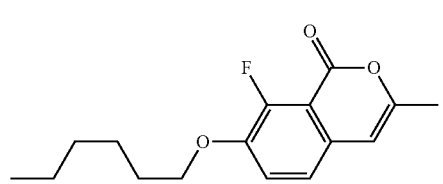 |

-continued
No.
74
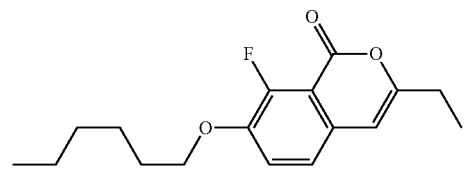 [SMILES: CCCCCCOc1ccc2cc(CC)oc(=O)c2c1F]
75
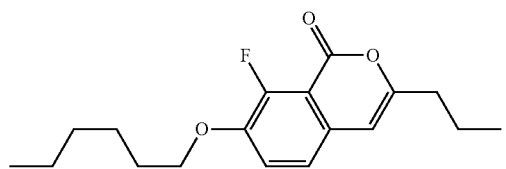 [SMILES: CCCCCCOc1ccc2cc(CCC)oc(=O)c2c1F]
76
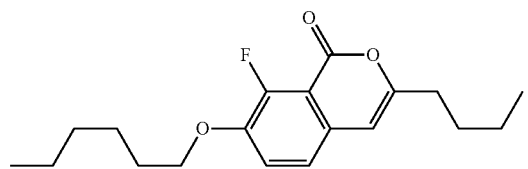 [SMILES: CCCCCCOc1ccc2cc(CCCC)oc(=O)c2c1F]
77
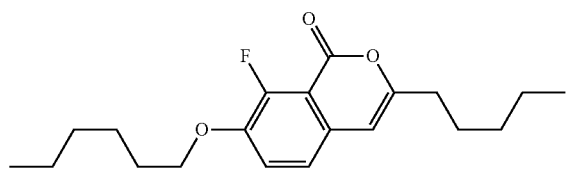
78
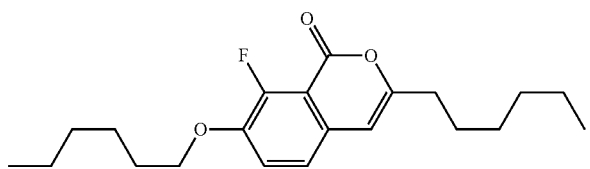
79
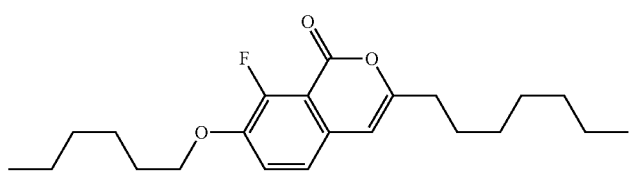 [SMILES: CCCCCCCc1cc2ccc(OCCCCCC)c(F)c2c(=O)o1]
80
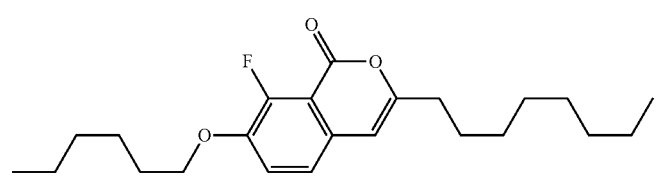
81
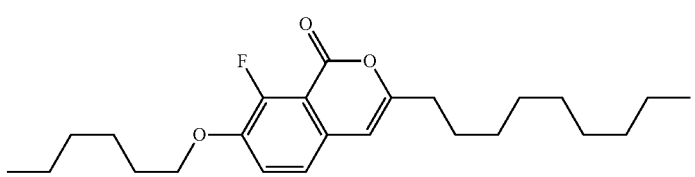 [SMILES: CCCCCCCCCc1cc2ccc(OCCCCCC)c(F)c2c(=O)o1]

-continued
| No. | |
|---|---|
| 82 | 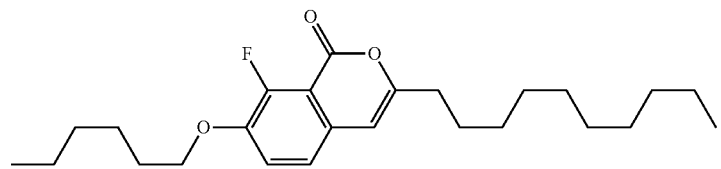 |
| 83 | 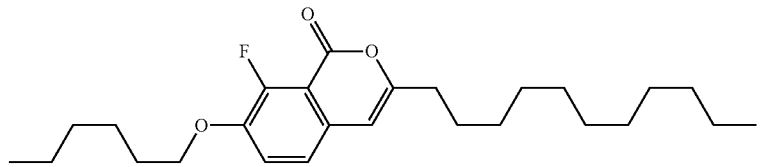 [SMILES: CCCCCCCCCCCc1cc2ccc(OCCCCCC)c(F)c2c(=O)o1] |
| 84 | 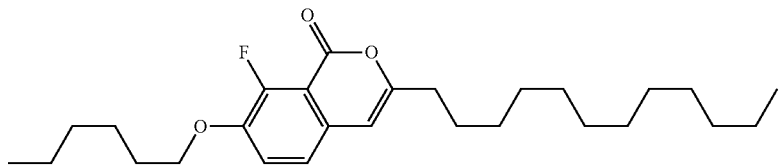 [SMILES: CCCCCCCCCCCCc1cc2ccc(OCCCCCC)c(F)c2c(=O)o1] |
| 85 | 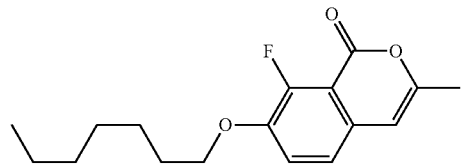 [SMILES: CCCCCCCOc1ccc2cc(C)oc(=O)c2c1F] |
| 86 | 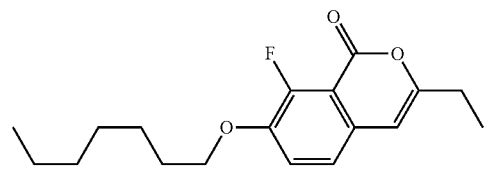 [SMILES: CCCCCCCOc1ccc2cc(CC)oc(=O)c2c1F] |
| 87 | 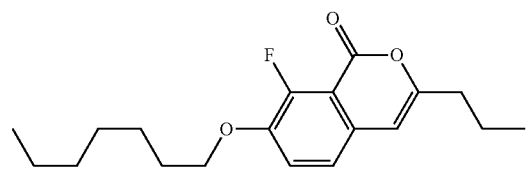 [SMILES: CCCCCCCOc1ccc2cc(CCC)oc(=O)c2c1F] |
| 88 | 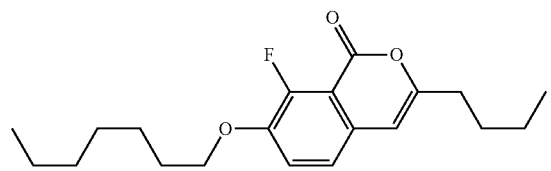 |
| 89 | 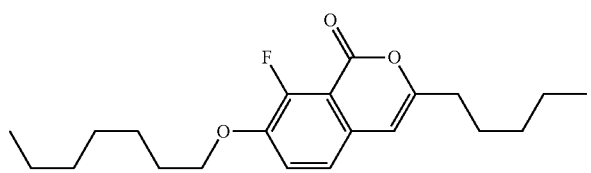 [SMILES: CCCCCCCOc1ccc2cc(CCCCC)oc(=O)c2c1F] |
| 90 | 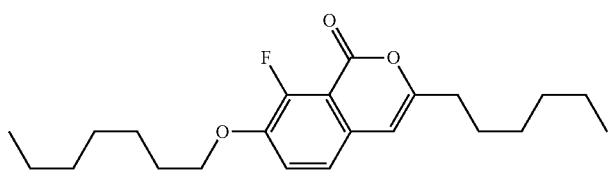 |

-continued
| No. |
|---|
| 91 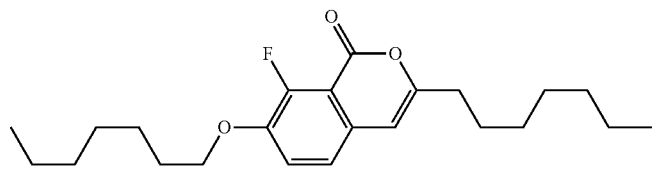 |
| 92 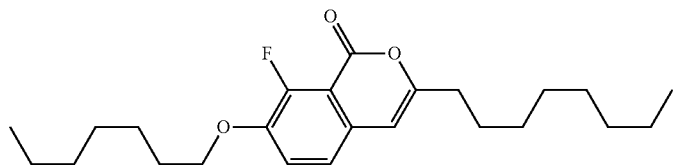 [SMILES: CCCCCCCCc1cc2ccc(OCCCCCCC)c(F)c2c(=O)o1] |
| 93 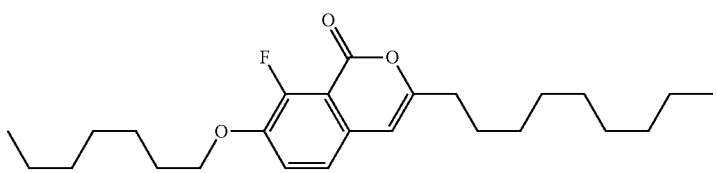 [SMILES: CCCCCCCCCc1cc2ccc(OCCCCCCC)c(F)c2c(=O)o1] |
| 94 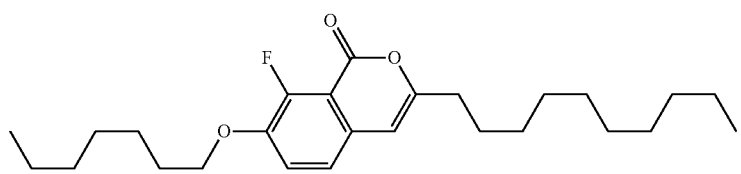 [SMILES: CCCCCCCCCCc1cc2ccc(OCCCCCCC)c(F)c2c(=O)o1] |
| 95 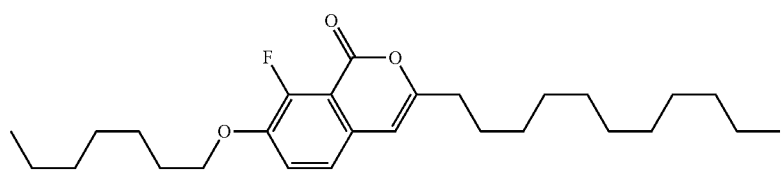 [SMILES: CCCCCCCCCCCc1cc2ccc(OCCCCCCC)c(F)c2c(=O)o1] |
| 96 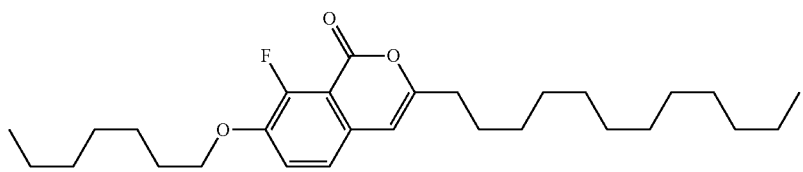 |
| 97 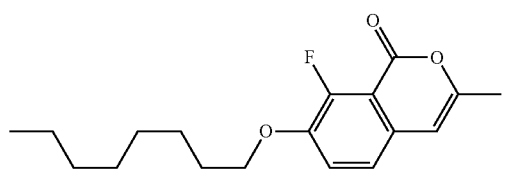 [SMILES: CCCCCCCCOc1ccc2cc(C)oc(=O)c2c1F] |
| 98 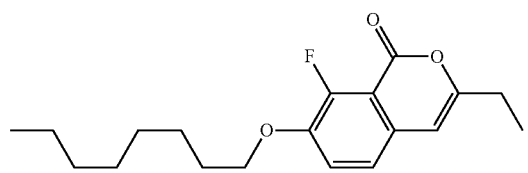 |
| 99 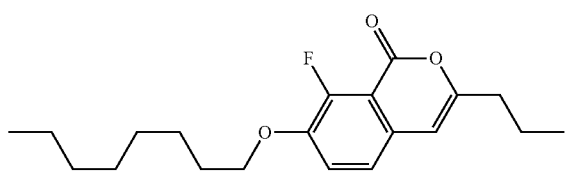 [SMILES: CCCCCCCCOc1ccc2cc(CCC)oc(=O)c2c1F] |

| No. |
|---|
| 100 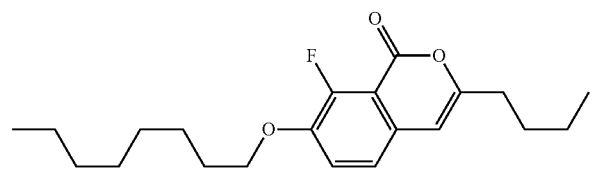 |
| 101 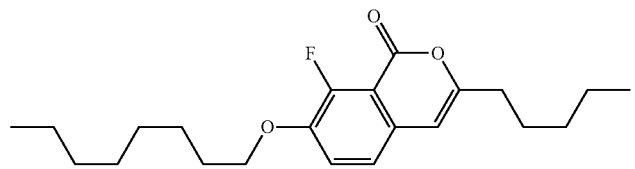 [SMILES: CCCCCCCCOc1ccc2cc(CCCCC)oc(=O)c2c1F] |
| 102 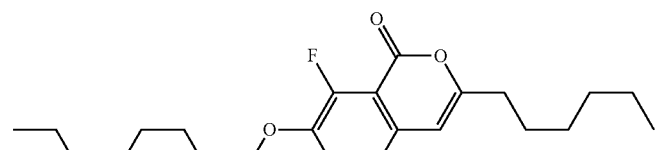 |
| 103 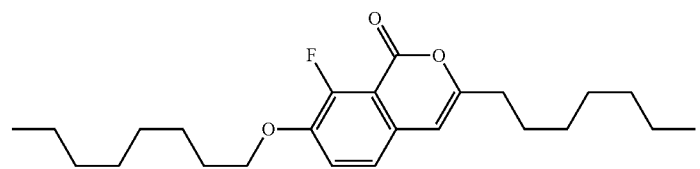 [SMILES: CCCCCCCCOc1ccc2cc(CCCCCCC)oc(=O)c2c1F] |
| 104 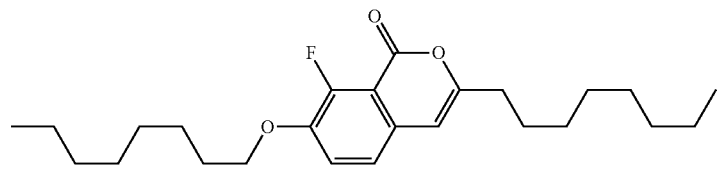 |
| 105 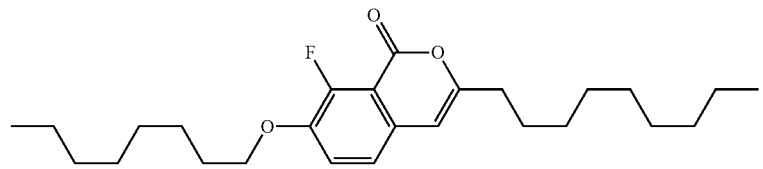 |
| 106 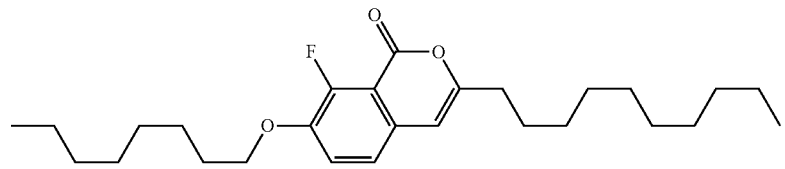 |
| 107 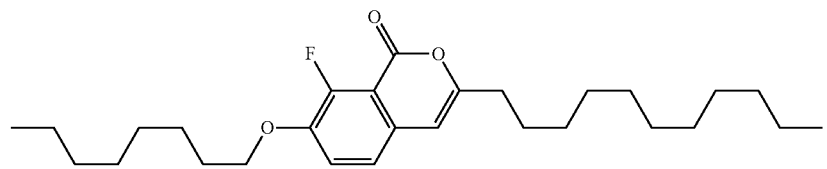 |
| 108 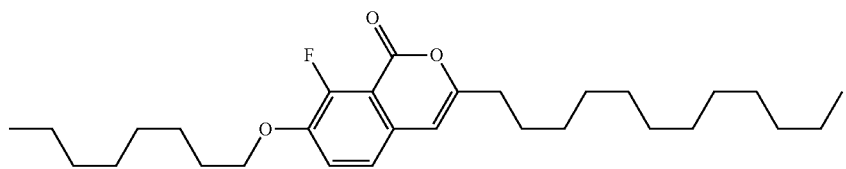 [SMILES: CCCCCCCCCCCCc1cc2ccc(OCCCCCCCC)c(F)c2c(=O)o1] |

| No. |  |
|---|---|
| 109 | 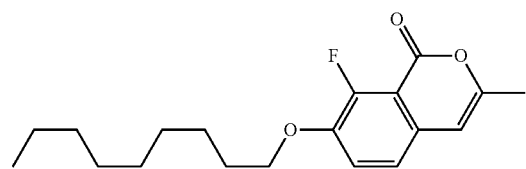 |
| 110 | 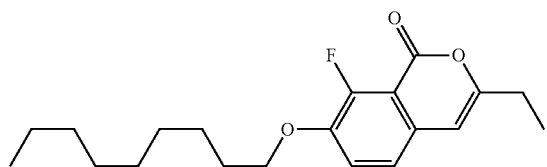 [SMILES: CCCCCCCCCOc1ccc2cc(CC)oc(=O)c2c1F] |
| 111 | 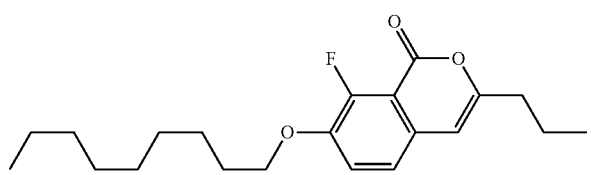 |
| 112 | 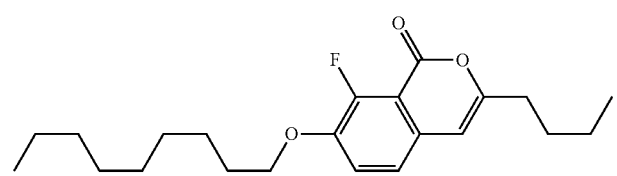 [SMILES: CCCCCCCCCOc1ccc2cc(CCCC)oc(=O)c2c1F] |
| 113 | 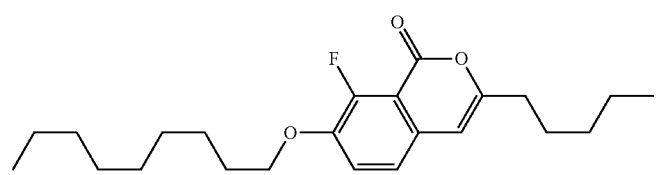 |
| 114 | 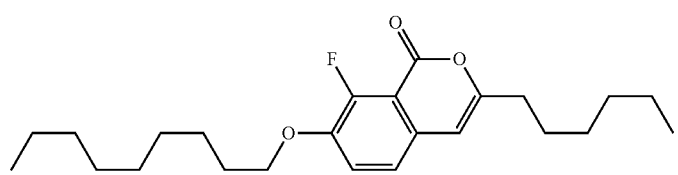 [SMILES: CCCCCCCCCOc1ccc2cc(CCCCCC)oc(=O)c2c1F] |
| 115 | 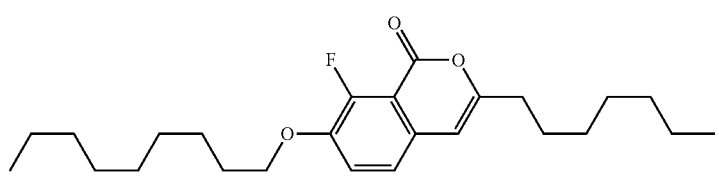 |
| 116 | 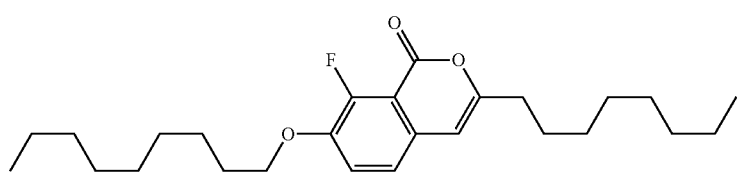 [SMILES: CCCCCCCCCOc1ccc2cc(CCCCCCCC)oc(=O)c2c1F] |
| 117 | 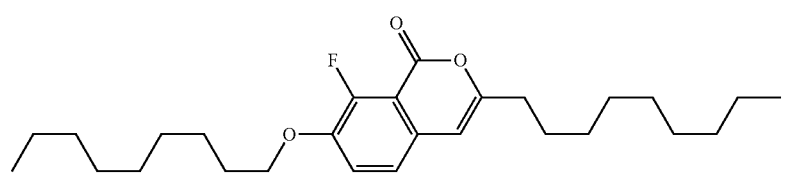 |

-continued
| No. | |
|---|---|
| 118 | 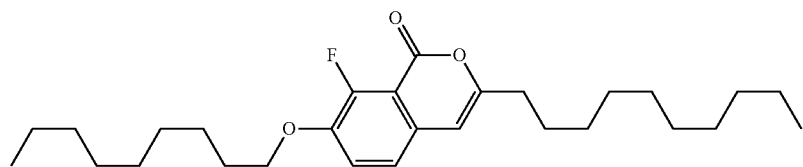 [SMILES: CCCCCCCCCCc1cc2ccc(OCCCCCCCCC)c(F)c2c(=O)o1] |
| 119 | 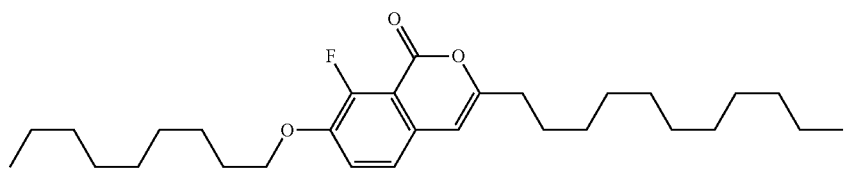 [SMILES: CCCCCCCCCCCc1cc2ccc(OCCCCCCCCC)c(F)c2c(=O)o1] |
| 120 | 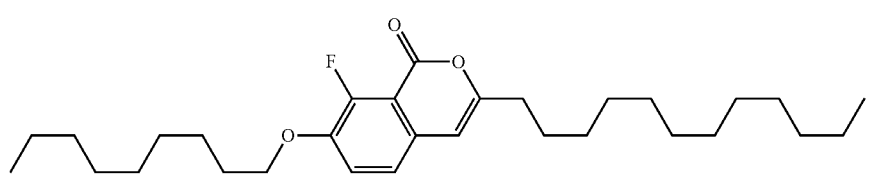 [SMILES: CCCCCCCCCCCCc1cc2ccc(OCCCCCCCCC)c(F)c2c(=O)o1] |
| 121 | 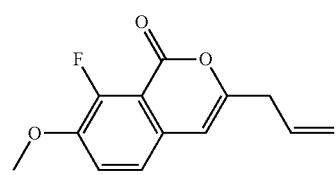 [SMILES: C=CCc1cc2ccc(OC)c(F)c2c(=O)o1] |
| 122 | 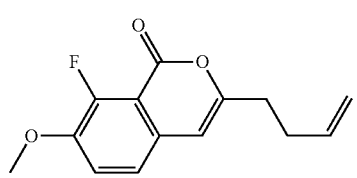 [SMILES: C=CCCc1cc2ccc(OC)c(F)c2c(=O)o1] |
| 123 | 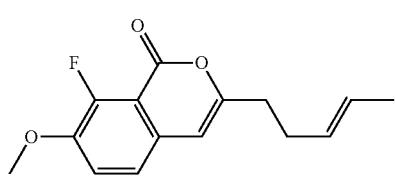 [SMILES: C/C=C/CCc1cc2ccc(OC)c(F)c2c(=O)o1] |
| 124 | 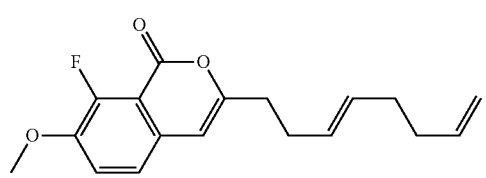 [SMILES: C=CCC/C=C/CCc1cc2ccc(OC)c(F)c2c(=O)o1] |
| 126 | 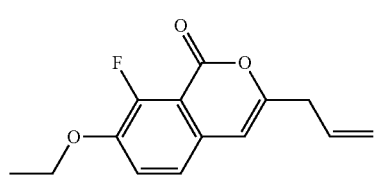 [SMILES: C=CCc1cc2ccc(OCC)c(F)c2c(=O)o1] |
| 127 | 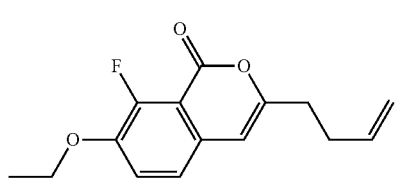 [SMILES: C=CCCc1cc2ccc(OCC)c(F)c2c(=O)o1] |

-continued
| No. | |
|---|---|
| 128 | 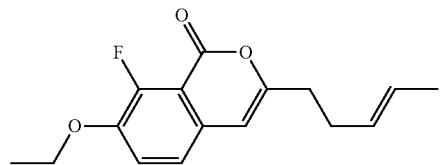 [SMILES: C/C=C/CCc1cc2ccc(OCC)c(F)c2c(=O)o1] |
| 129 | 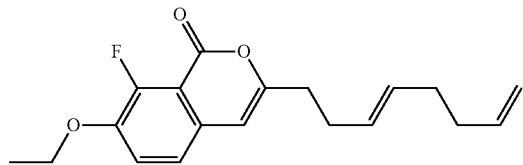 |
| 130 | 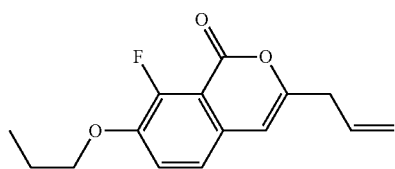 |
| 131 | 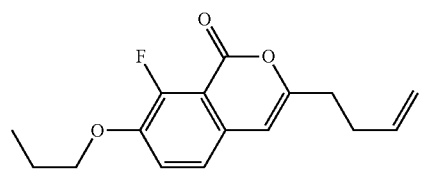 [SMILES: C=CCCc1cc2ccc(OCCC)c(F)c2c(=O)o1] |
| 132 | 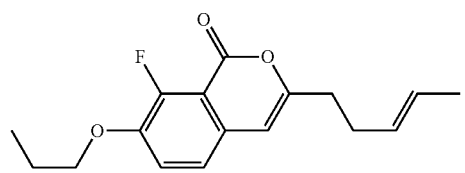 |
| 133 | 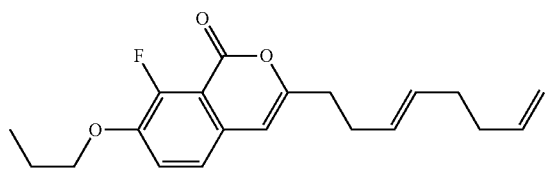 [SMILES: C=CCC/C=C/CCc1cc2ccc(OCCC)c(F)c2c(=O)o1] |
| 133 | 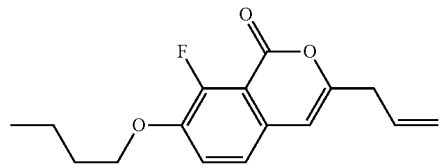 [SMILES: C=CCc1cc2ccc(OCCCC)c(F)c2c(=O)o1] |
| 134 | 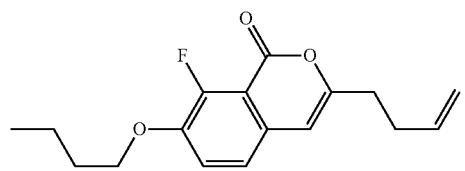 |
| 135 |  |

-continued
| No. | |
|---|---|
| 136 | 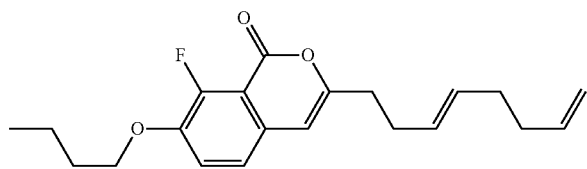 [SMILES: C=CCC/C=C/CCc1cc2ccc(OCCCC)c(F)c2c(=O)o1] |
| 137 | 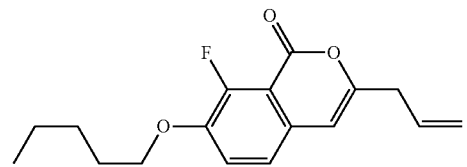 |
| 138 | 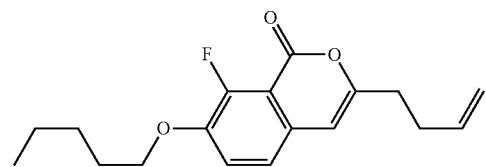 |
| 139 | 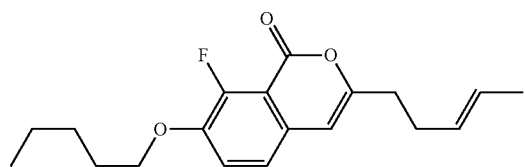 [SMILES: C/C=C/CCc1cc2ccc(OCCCCC)c(F)c2c(=O)o1] |
| 140 | 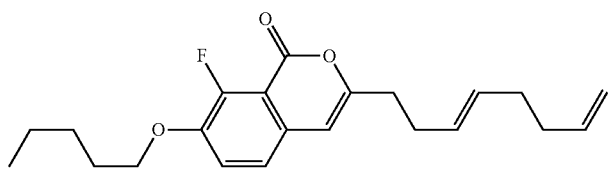 |
| 141 | 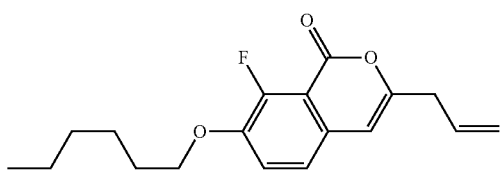 [SMILES: C=CCc1cc2ccc(OCCCCCC)c(F)c2c(=O)o1] |
| 142 | 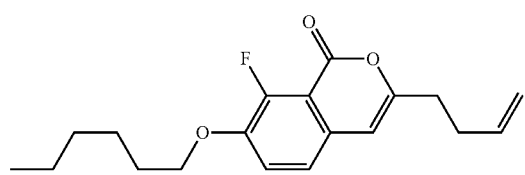 |
| 143 | 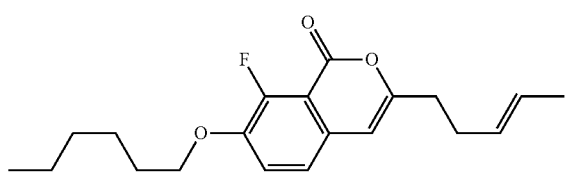 [SMILES: C/C=C/CCc1cc2ccc(OCCCCCC)c(F)c2c(=O)o1] |
| 144 | 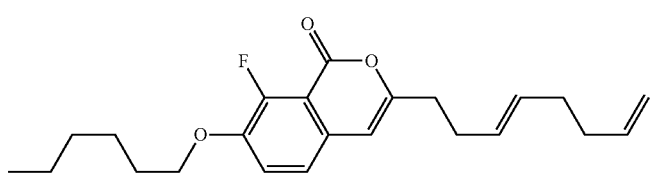 |

| No. | |
|---|---|
| 145 | 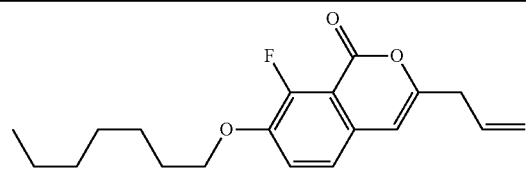 |
| 146 | 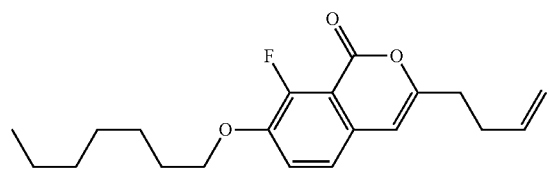 [SMILES: C=CCCc1cc2ccc(OCCCCCCC)c(F)c2c(=O)o1] |
| 147 | 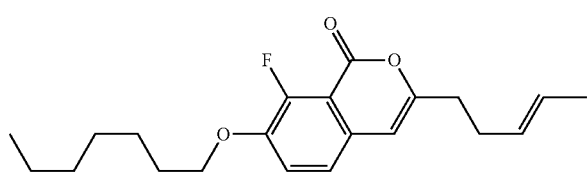 [SMILES: C/C=C/CCc1cc2ccc(OCCCCCCC)c(F)c2c(=O)o1] |
| 148 | 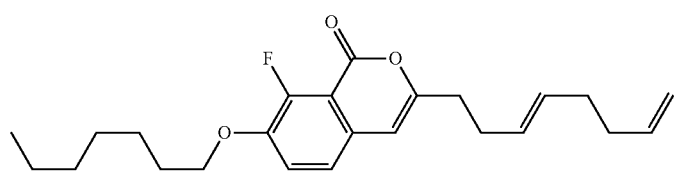 |
| 149 | 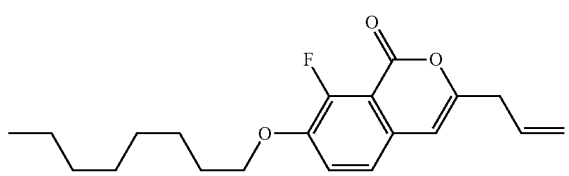 [SMILES: C=CCc1cc2ccc(OCCCCCCCC)c(F)c2c(=O)o1] |
| 150 | 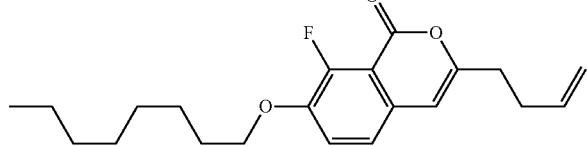 |
| 151 | 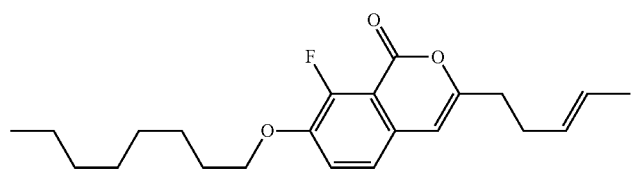 |
| 152 | 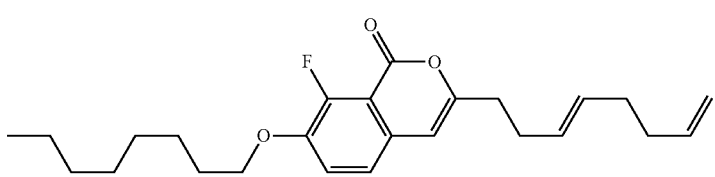 [SMILES: C=CCC/C=C/CCc1cc2ccc(OCCCCCCCC)c(F)c2c(=O)o1] |
| 153 | 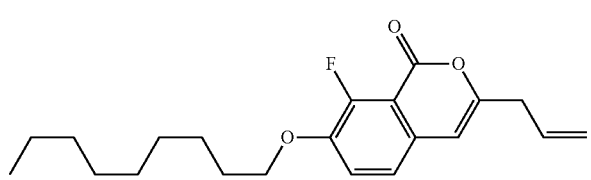 |

-continued
| No. | |
|---|---|
| 154 | 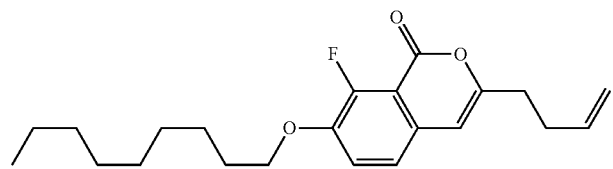 [SMILES: C=CCCc1cc2ccc(OCCCCCCCCC)c(F)c2c(=O)o1] |
| 155 | 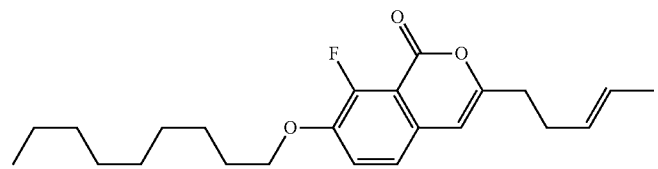 |
| 156 | 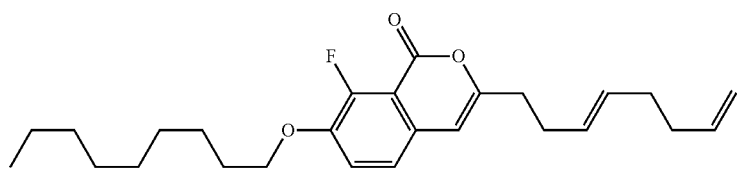 |
| 157 | 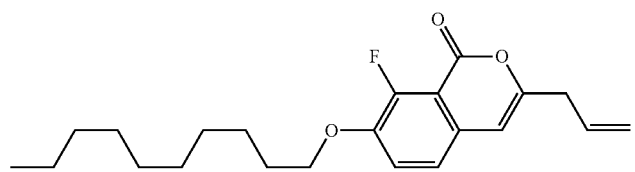 [SMILES: C=CCc1cc2ccc(OCCCCCCCCCC)c(F)c2c(=O)o1] |
| 158 | 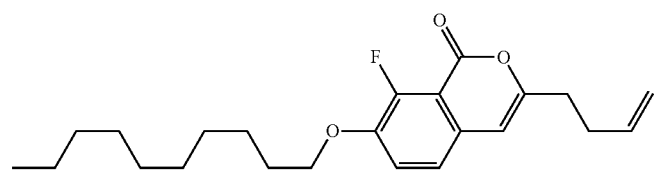 [SMILES: C=CCCc1cc2ccc(OCCCCCCCCCC)c(F)c2c(=O)o1] |
| 159 | 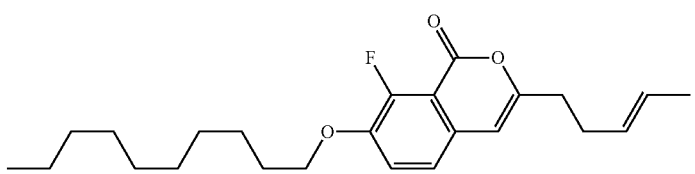 |
| 160 | 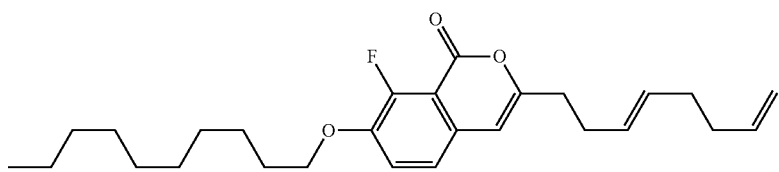 [SMILES: C=CCC/C=C/CCc1cc2ccc(OCCCCCCCCCC)c(F)c2c(=O)o1] |
| 161 | 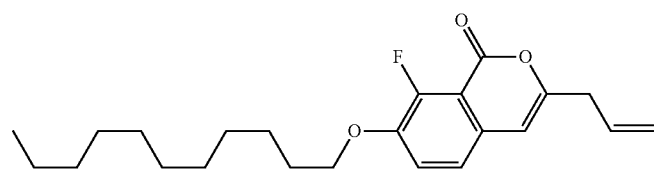 |
| 162 | 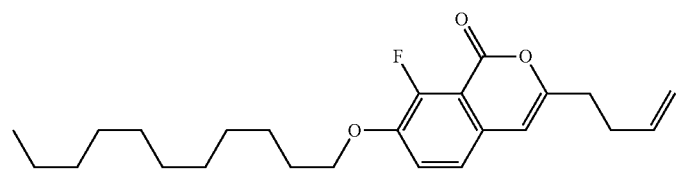 [SMILES: C=CCCc1cc2ccc(OCCCCCCCCCCC)c(F)c2c(=O)o1] |

-continued
| No. | |
|---|---|
| 163 | 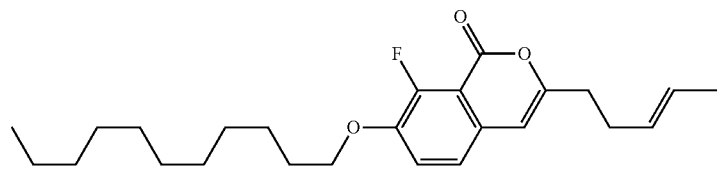 [SMILES: C/C=C/CCc1cc2ccc(OCCCCCCCCCCC)c(F)c2c(=O)o1] |
| 164 | 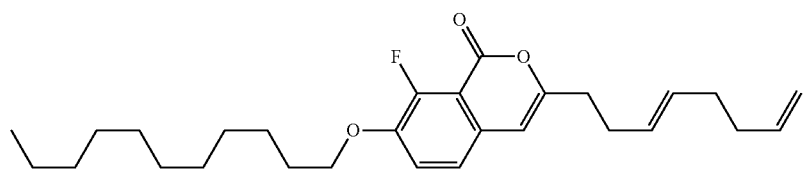 |
| 165 | 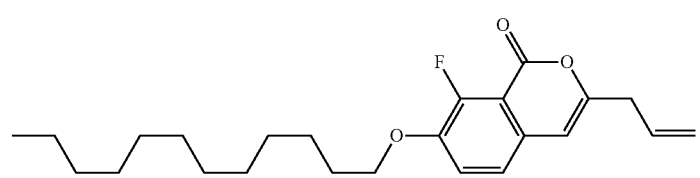 [SMILES: C=CCc1cc2ccc(OCCCCCCCCCCCC)c(F)c2c(=O)o1] |
| 166 | 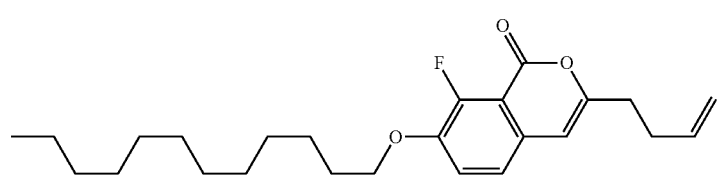 [SMILES: C=CCCc1cc2ccc(OCCCCCCCCCCCC)c(F)c2c(=O)o1] |
| 167 | 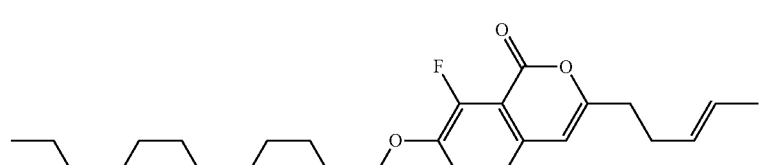 |
| 168 | 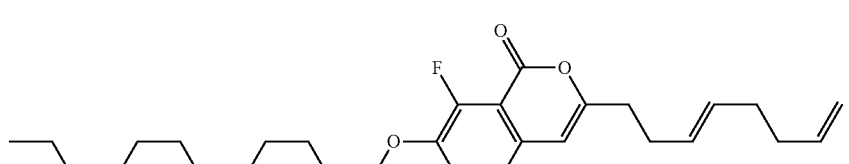 |
| 169 | 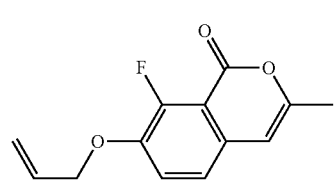 [SMILES: C=CCOc1ccc2cc(C)oc(=O)c2c1F] |
| 170 | 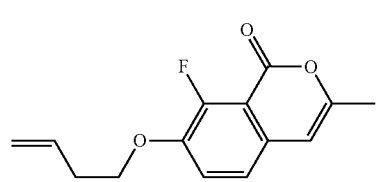 |
| 171 | 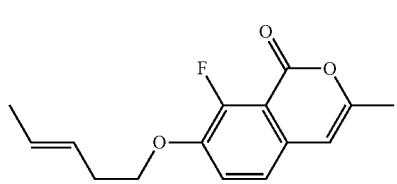 [SMILES: C/C=C/CCOc1ccc2cc(C)oc(=O)c2c1F] |

-continued
| No. | |
|---|---|
| 172 | 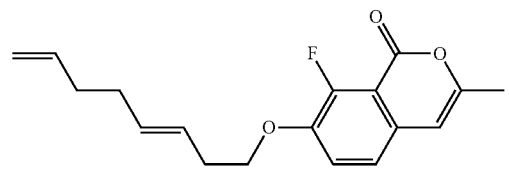 [SMILES: C=CCC/C=C/CCOc1ccc2cc(C)oc(=O)c2c1F] |
| 173 | 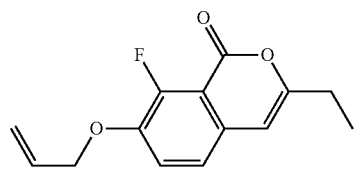 [SMILES: C=CCOc1ccc2cc(CC)oc(=O)c2c1F] |
| 174 | 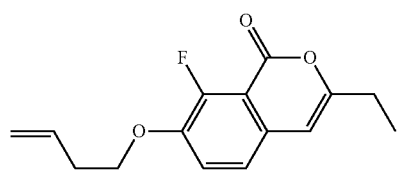 [SMILES: C=CCCOc1ccc2cc(CC)oc(=O)c2c1F] |
| 175 | 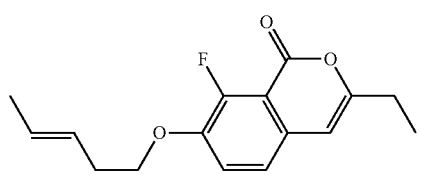 [SMILES: C/C=C/CCOc1ccc2cc(CC)oc(=O)c2c1F] |
| 176 | 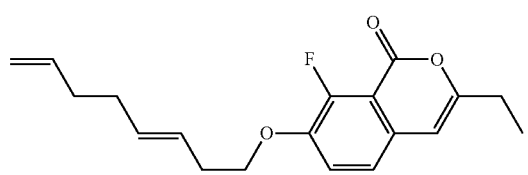 [SMILES: C=CCC/C=C/CCOc1ccc2cc(CC)oc(=O)c2c1F] |
| 177 | 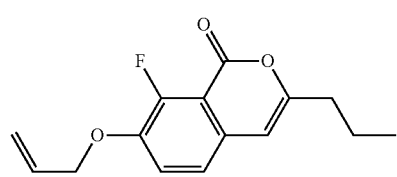 |
| 178 | 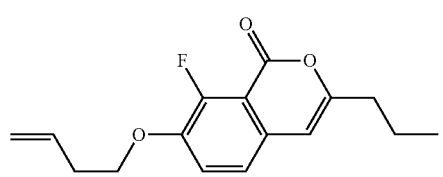 [SMILES: C=CCCOc1ccc2cc(CCC)oc(=O)c2c1F] |
| 179 | 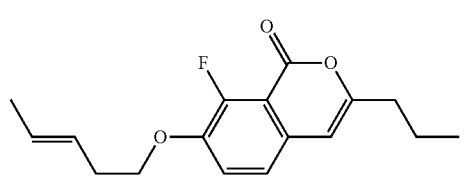 |
| 180 | 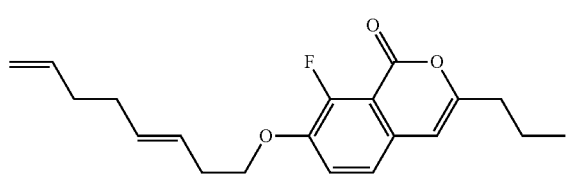 [SMILES: C=CCC/C=C/CCOc1ccc2cc(CCC)oc(=O)c2c1F] |

| No. |
|---|
| 181 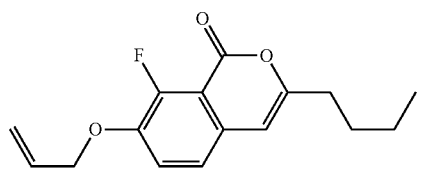 [SMILES: C=CCOc1ccc2cc(CCCC)oc(=O)c2c1F] |
| 182 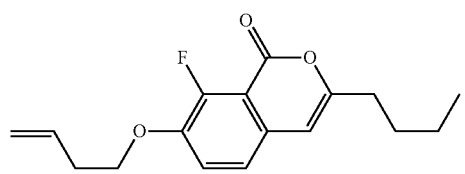 [SMILES: C=CCCOc1ccc2cc(CCCC)oc(=O)c2c1F] |
| 183 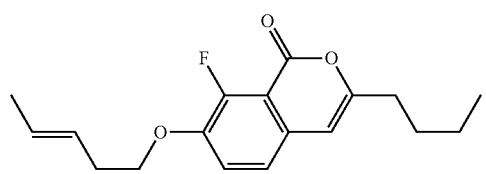 [SMILES: C/C=C/CCOc1ccc2cc(CCCC)oc(=O)c2c1F] |
| 184 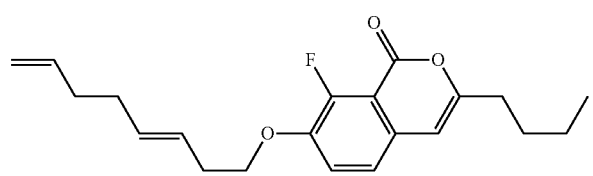 [SMILES: C=CCC/C=C/CCOc1ccc2cc(CCCC)oc(=O)c2c1F] |
| 185 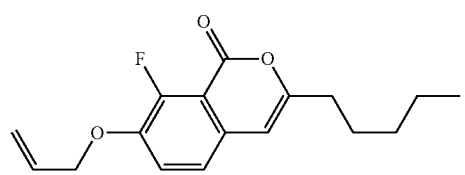 |
| 186 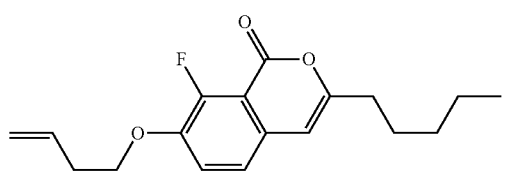 [SMILES: C=CCCOc1ccc2cc(CCCCC)oc(=O)c2c1F] |
| 187 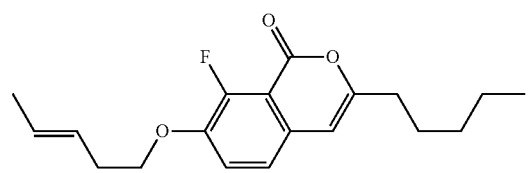 [SMILES: C/C=C/CCOc1ccc2cc(CCCCC)oc(=O)c2c1F] |
| 188 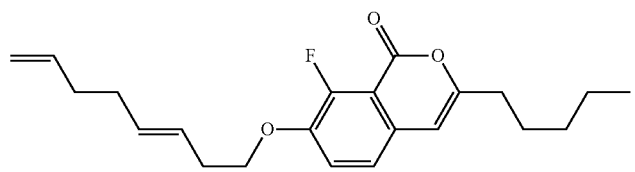 [SMILES: C=CCC/C=C/CCOc1ccc2cc(CCCCC)oc(=O)c2c1F] |
| 189 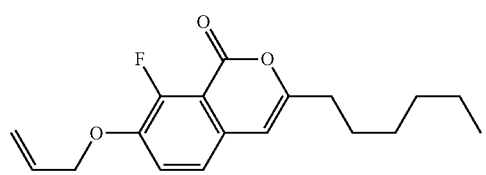 [SMILES: C=CCOc1ccc2cc(CCCCCC)oc(=O)c2c1F] |

| No. | |
|---|---|
| 190 | 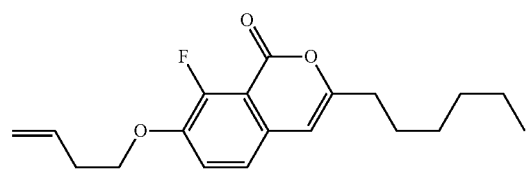 |
| 191 | 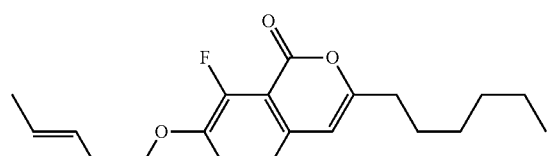 |
| 192 | 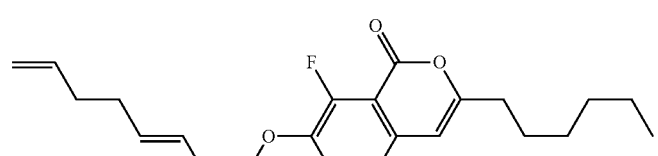 |
| 193 | 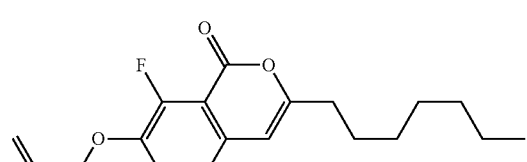 |
| 194 | 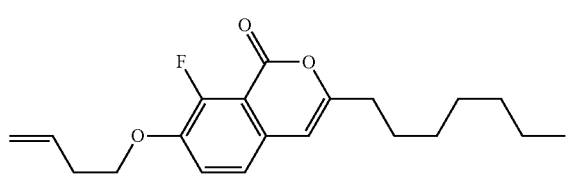 |
| 195 | 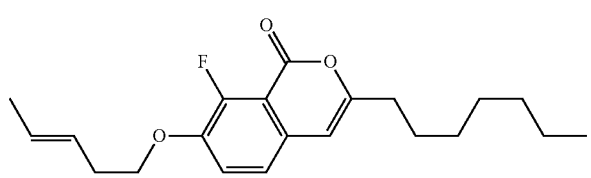 [SMILES: C/C=C/CCOc1ccc2cc(CCCCCCC)oc(=O)c2c1F] |
| 196 | 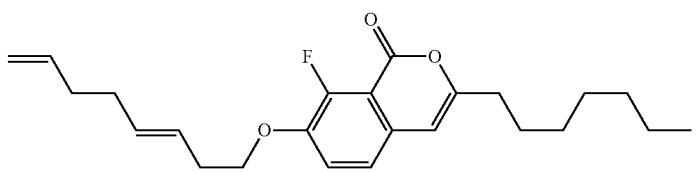 [SMILES: C=CCC/C=C/CCOc1ccc2cc(CCCCCCC)oc(=O)c2c1F] |
| 197 | 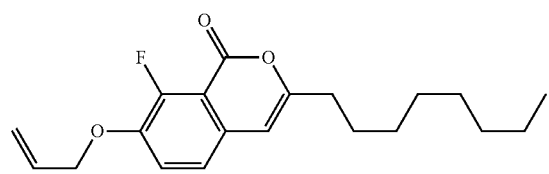 |
| 198 | 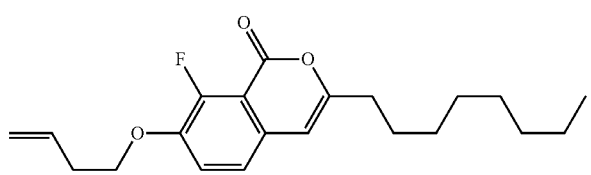 |

-continued
| No. | |
|---|---|
| 199 | 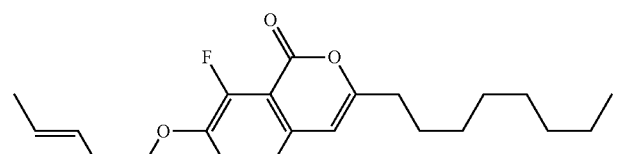 |
| 200 | 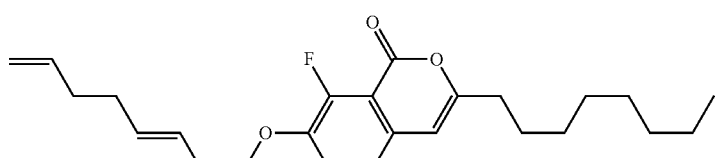 |
| 201 | 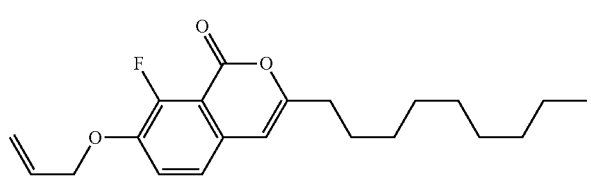 |
| 202 | 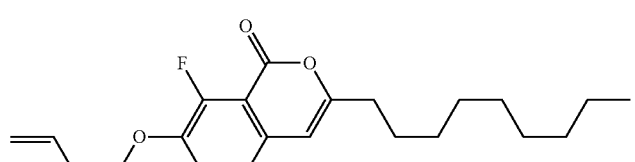 |
| 203 | 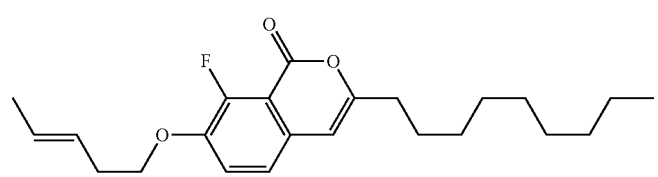 [SMILES: C/C=C/CCOc1ccc2cc(CCCCCCCCC)oc(=O)c2c1F] |
| 204 | 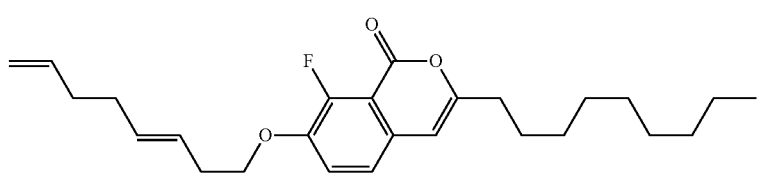 [SMILES: C=CCC/C=C/CCOc1ccc2cc(CCCCCCCCC)oc(=O)c2c1F] |
| 205 | 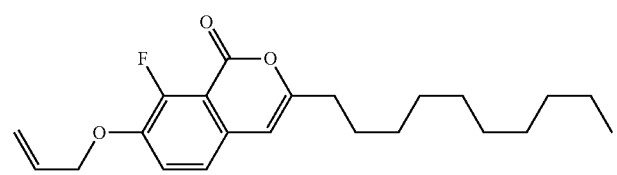 [SMILES: C=CCOc1ccc2cc(CCCCCCCCCC)oc(=O)c2c1F] |
| 206 | 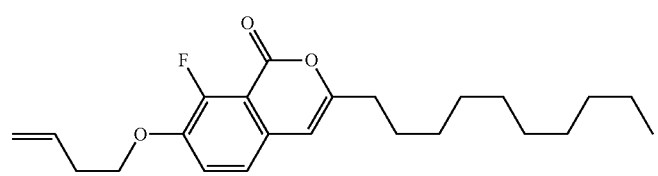 [SMILES: C=CCCOc1ccc2cc(CCCCCCCCCC)oc(=O)c2c1F] |
| 207 | 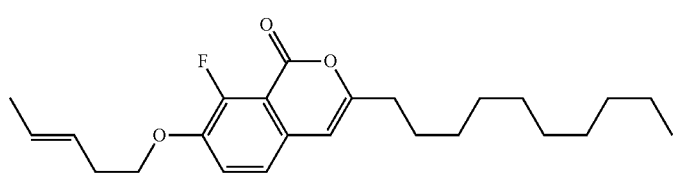 [SMILES: C/C=C/CCOc1ccc2cc(CCCCCCCCCC)oc(=O)c2c1F] |

| No. |  |
|---|---|
| 208 | 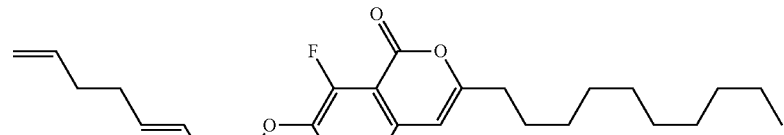 |
| 209 | 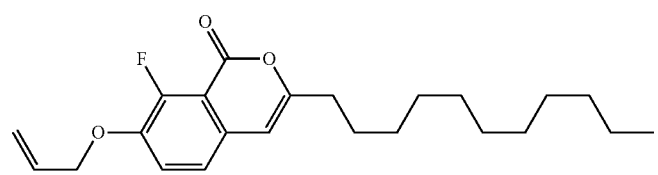 [SMILES: C=CCOc1ccc2cc(CCCCCCCCCCC)oc(=O)c2c1F] |
| 210 | 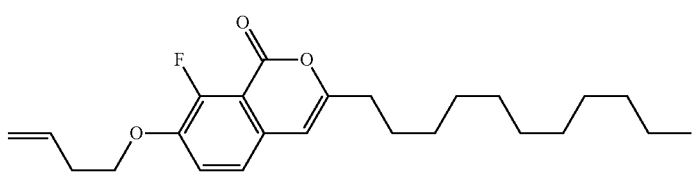 |
| 211 | 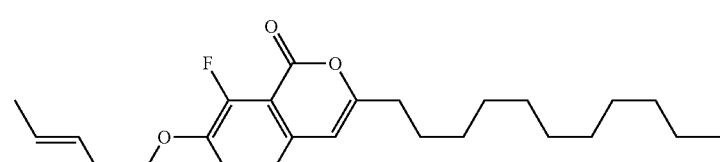 |
| 212 | 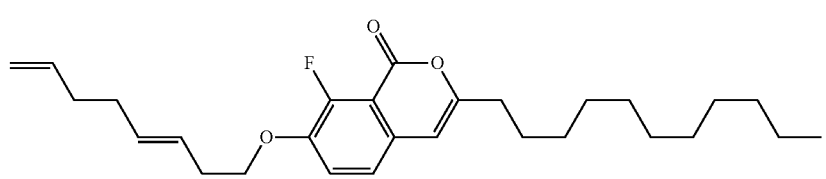 [SMILES: C=CCC/C=C/CCOc1ccc2cc(CCCCCCCCCCC)oc(=O)c2c1F] |
| 213 | 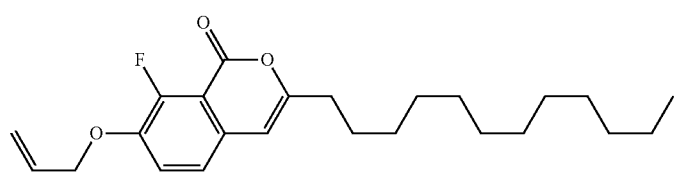 [SMILES: C=CCOc1ccc2cc(CCCCCCCCCCCC)oc(=O)c2c1F] |
| 214 | 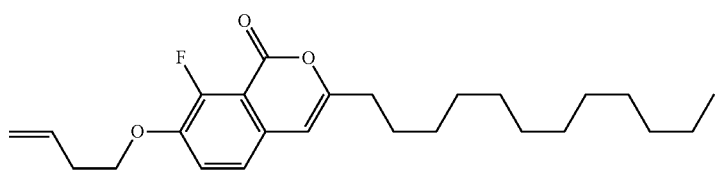 [SMILES: C=CCCOc1ccc2cc(CCCCCCCCCCCC)oc(=O)c2c1F] |
| 215 | 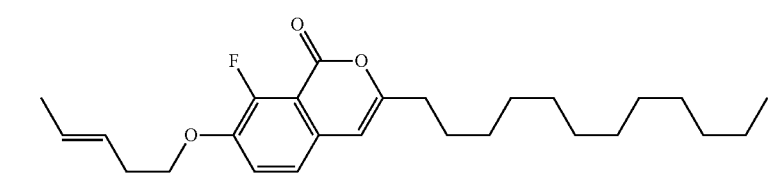 |
| 216 | 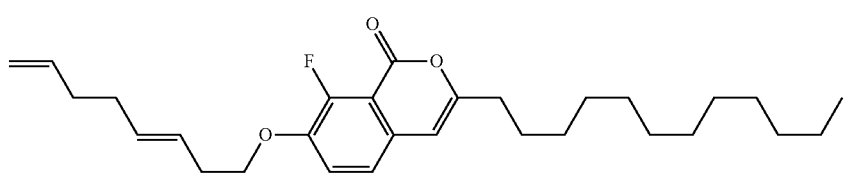 [SMILES: C=CCC/C=C/CCOc1ccc2cc(CCCCCCCCCCCC)oc(=O)c2c1F] |

-continued
| No. | |
|---|---|
| 217 | 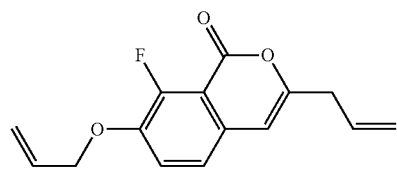 [SMILES: C=CCOc1ccc2cc(CC=C)oc(=O)c2c1F] |
| 218 | 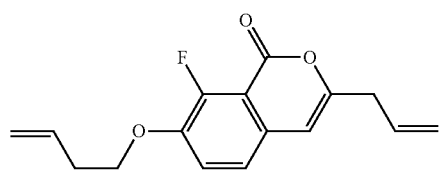 [SMILES: C=CCCOc1ccc2cc(CC=C)oc(=O)c2c1F] |
| 219 | 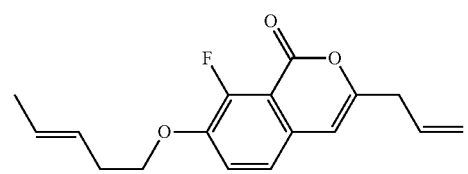 [SMILES: C=CCc1cc2ccc(OCC/C=C/C)c(F)c2c(=O)o1] |
| 220 | 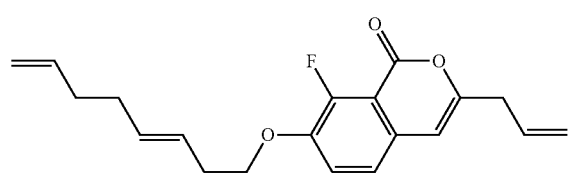 [SMILES: C=CCC/C=C/CCOc1ccc2cc(CC=C)oc(=O)c2c1F] |
| 221 | 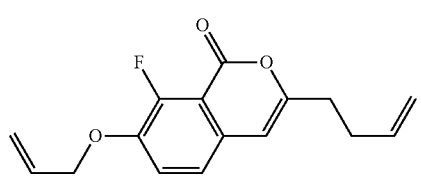 [SMILES: C=CCCc1cc2ccc(OCC=C)c(F)c2c(=O)o1] |
| 222 | 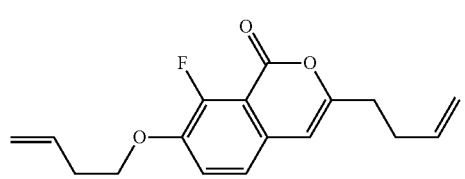 |
| 223 | 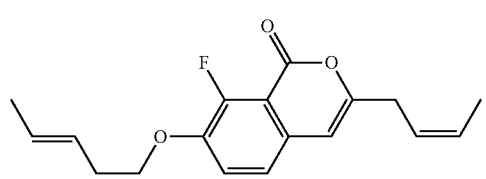 [SMILES: C/C=C\Cc1cc2ccc(OCC/C=C/C)c(F)c2c(=O)o1] |
| 224 | 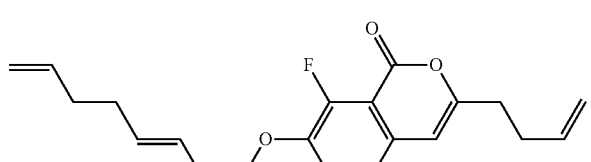 |
| 225 | 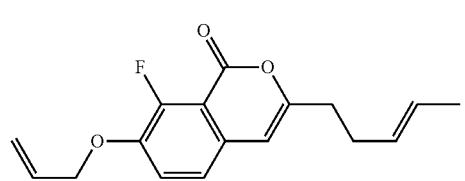 |

-continued
| No. |
|---|
| 226 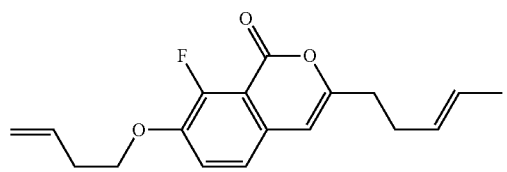 [SMILES: C=CCCOc1ccc2cc(CC/C=C/C)oc(=O)c2c1F] |
| 227 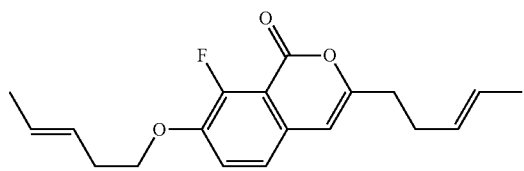 [SMILES: C/C=C/CCOc1ccc2cc(CC/C=C/C)oc(=O)c2c1F] |
| 228 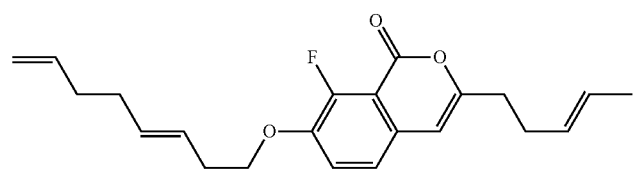 |
| 229 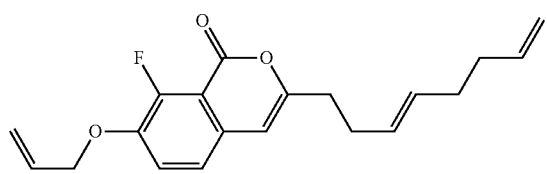 [SMILES: C=CCC/C=C/CCc1cc2ccc(OCC=C)c(F)c2c(=O)o1] |
| 230 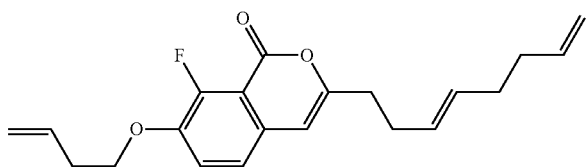 |
| 231 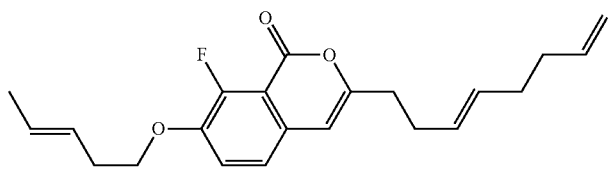 [SMILES: C=CCC/C=C/CCc1cc2ccc(OCC/C=C/C)c(F)c2c(=O)o1] |
| 232 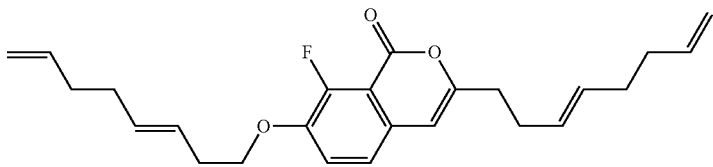 [SMILES: C=CCC/C=C/CCOc1ccc2cc(CC/C=C/CCC=C)oc(=O)c2c1F] |
| 233 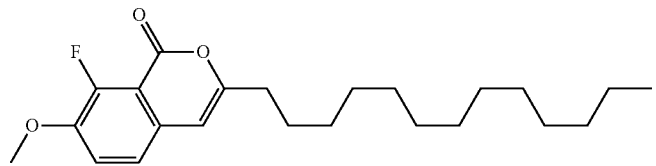 |
| 234 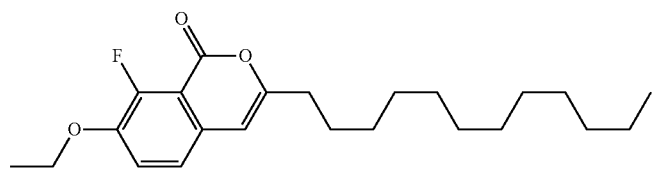 |

| No. | |
|---|---|
| 235 | 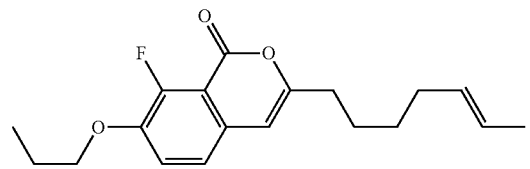 [SMILES: C/C=C/CCCCc1cc2ccc(OCCC)c(F)c2c(=O)o1] |
| 236 | 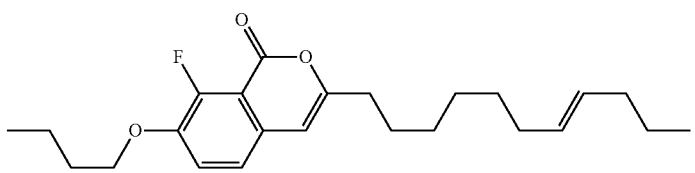 |
| 237 | 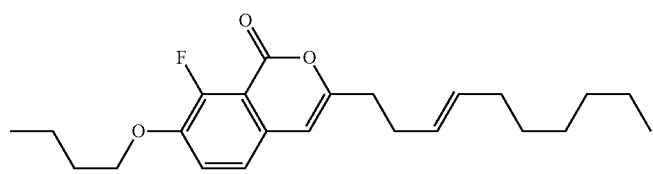 |
| 238 | 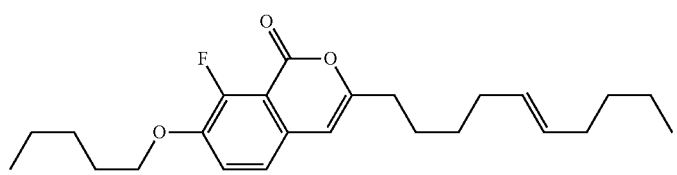 [SMILES: CCCC/C=C/CCCCc1cc2ccc(OCCCCC)c(F)c2c(=O)o1] |
| 239 | 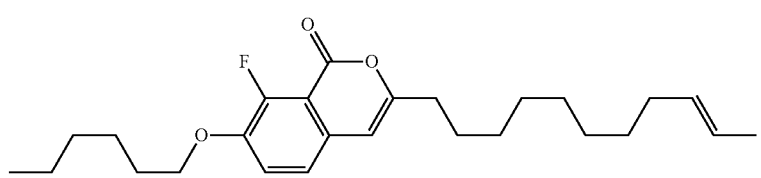 |
| 240 | 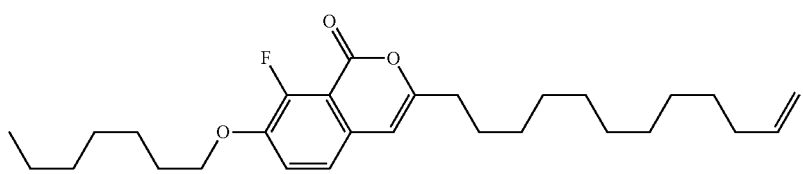 [SMILES: C=CCCCCCCCCCCc1cc2ccc(OCCCCCCC)c(F)c2c(=O)o1] |
| 241 | 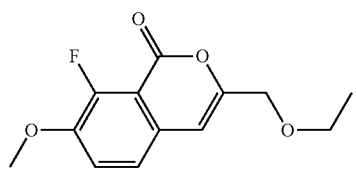 [SMILES: CCOCc1cc2ccc(OC)c(F)c2c(=O)o1] |
| 242 | 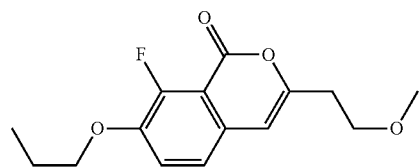 |
| 243 | 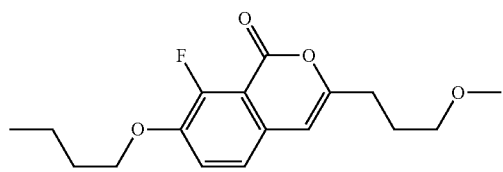 |

| No. | |
|---|---|
| 244 | 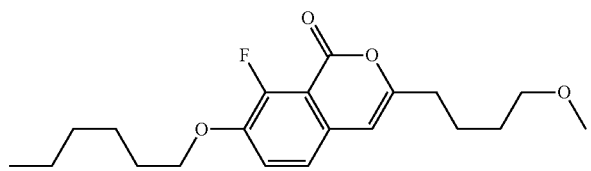 [SMILES: CCCCCCOc1ccc2cc(CCCCOC)oc(=O)c2c1F] |
| 245 | 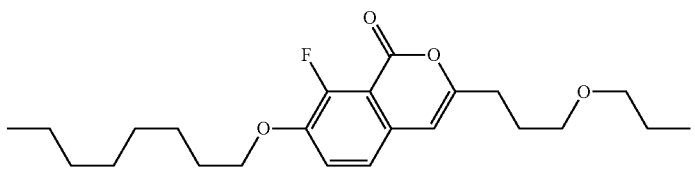 |
| 246 | 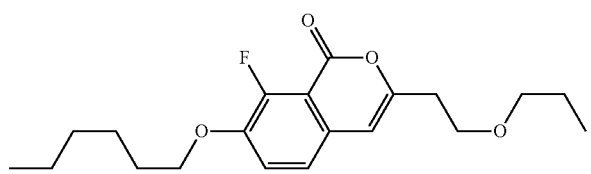 |
| 247 | 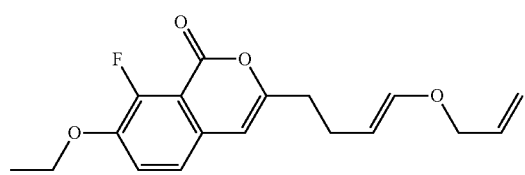 [SMILES: C=CCO/C=C/CCc1cc2ccc(OCC)c(F)c2c(=O)o1] |
| 248 | 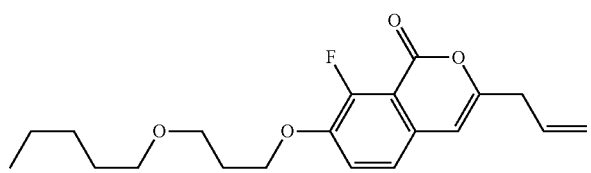 |
| 249 | 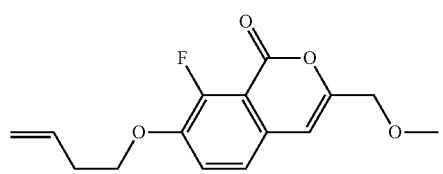 |
| 250 | 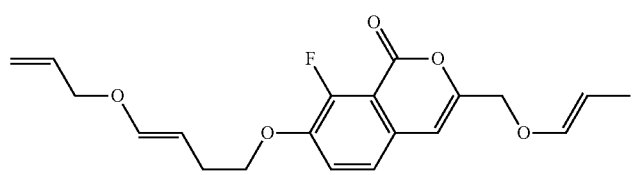 |
| 251 |  |
| 252 | 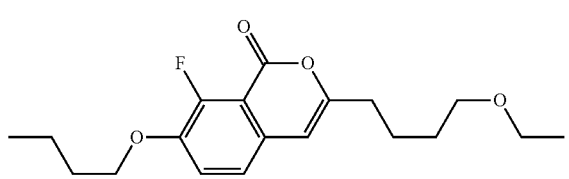 |

| No. | |
|---|---|
| 253 | 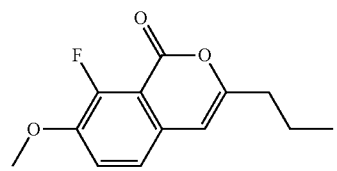 [SMILES: CCCc1cc2ccc(OC)c(F)c2c(=O)o1] |
| 254 | 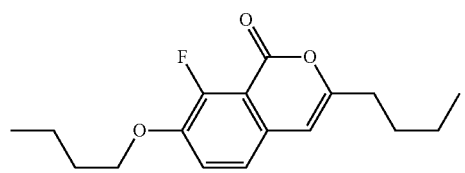 [SMILES: CCCCOc1ccc2cc(CCCC)oc(=O)c2c1F] |
| 255 | 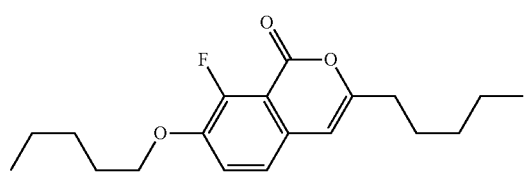 |
| 256 | 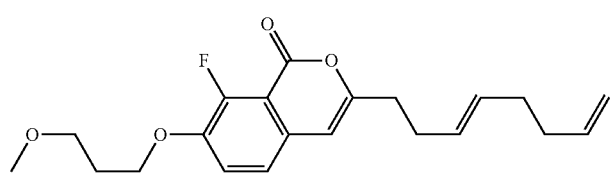 [SMILES: C=CCC/C=C/CCc1cc2ccc(OCCCOC)c(F)c2c(=O)o1] |
| 257 | 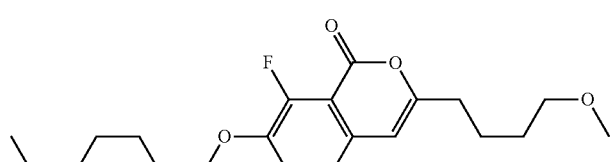 |
| 258 | 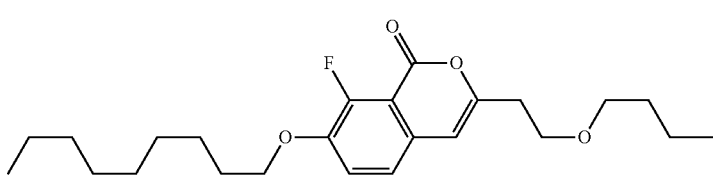 |
| 259 | 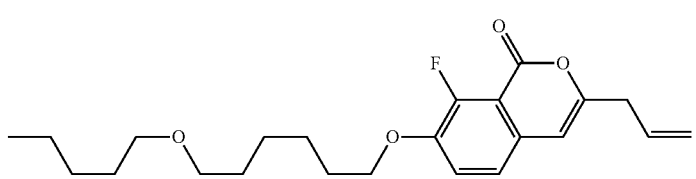 |
| 260 | 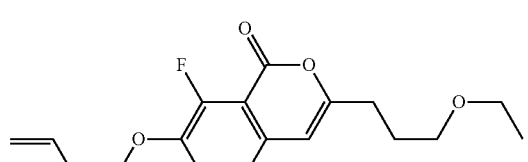 |
| 261 | 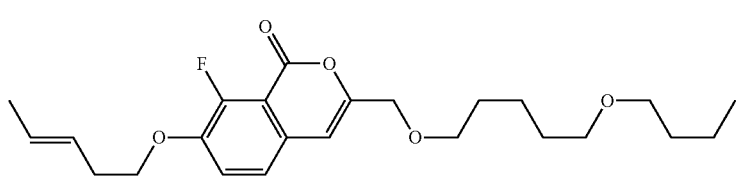 [SMILES: C/C=C/CCOc1ccc2cc(COCCCCCOCCCC)oc(=O)c2c1F] |

| No. | |
|---|---|
| 262 | 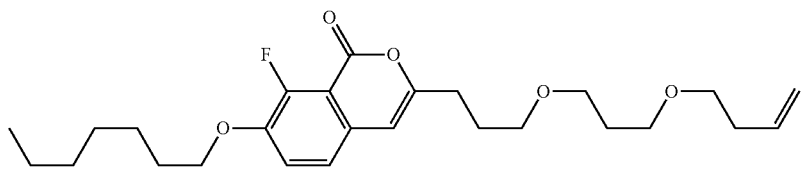 |
| 263 | 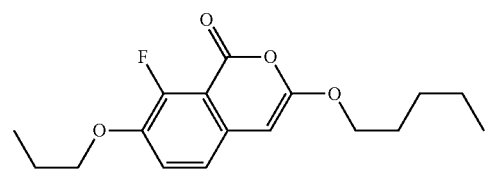 |
| 264 | 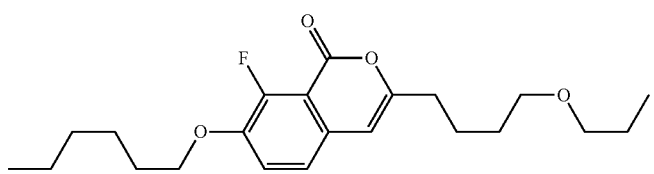 |
| 265 | 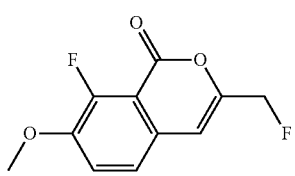 |
| 266 | 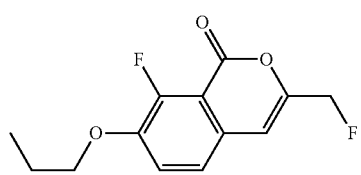 [SMILES: CCCOc1ccc2cc(CF)oc(=O)c2c1F] |
| 267 | 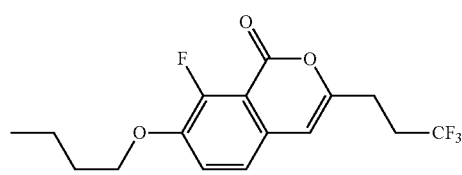 |
| 268 | 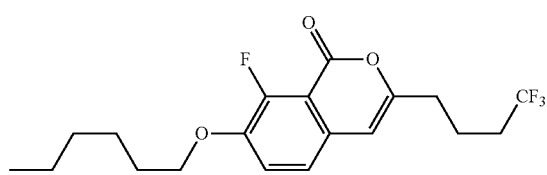 [SMILES: CCCCCCOc1ccc2cc(CCCC(F)(F)F)oc(=O)c2c1F] |
| 269 | 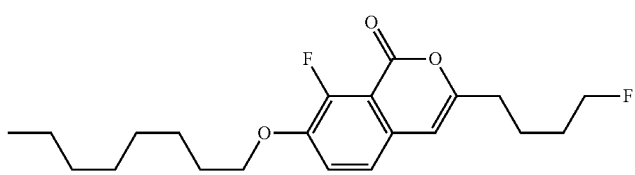 |
| 270 |  |

| No. |  |
|---|---|
| 271 | 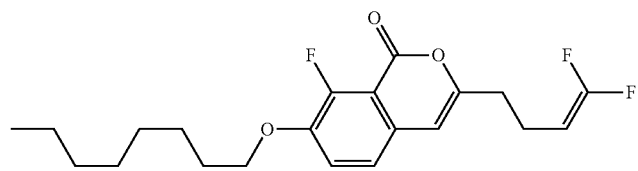 [SMILES: CCCCCCCCOc1ccc2cc(CCC=C(F)F)oc(=O)c2c1F] |
| 272 | 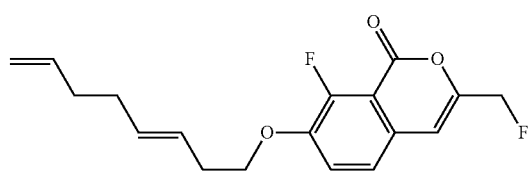 [SMILES: C=CCC/C=C/CCOc1ccc2cc(CF)oc(=O)c2c1F] |
| 273 | 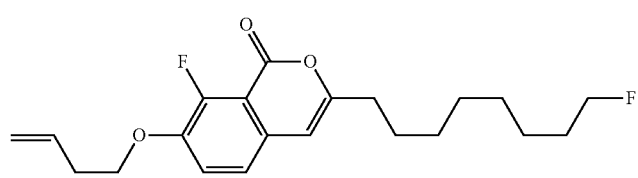 [SMILES: C=CCCOc1ccc2cc(CCCCCCCCF)oc(=O)c2c1F] |
| 274 | 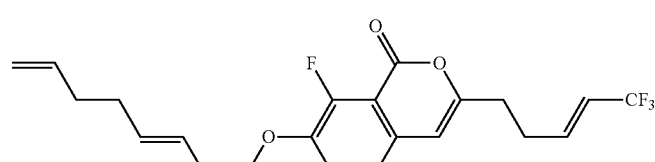 |
| 275 | 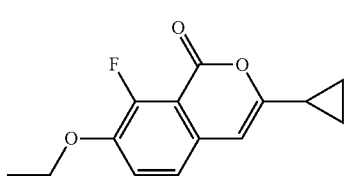 [SMILES: CCOc1ccc2cc(C3CC3)oc(=O)c2c1F] |
| 276 | 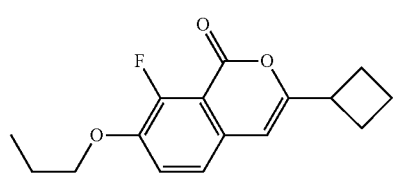 [SMILES: CCCOc1ccc2cc(C3CCC3)oc(=O)c2c1F] |
| 277 | 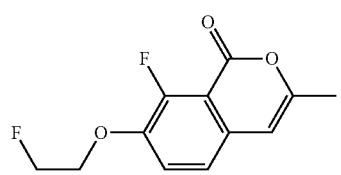 [SMILES: Cc1cc2ccc(OCCF)c(F)c2c(=O)o1] |
| 278 | 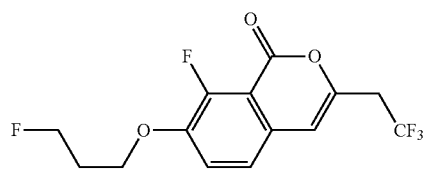 [SMILES: O=c1oc(CC(F)(F)F)cc2ccc(OCCCF)c(F)c12] |
| 279 | 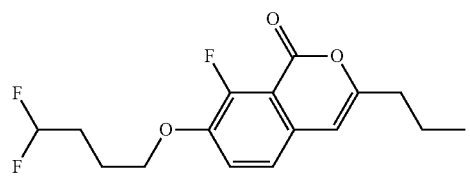 [SMILES: CCCc1cc2ccc(OCCCC(F)F)c(F)c2c(=O)o1] |

-continued
| No. | |
|---|---|
| 280 | 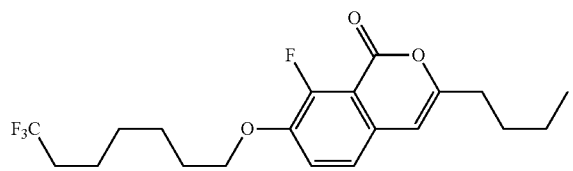 [SMILES: CCCCc1cc2ccc(OCCCCCCC(F)(F)F)c(F)c2c(=O)o1] |
| 281 | 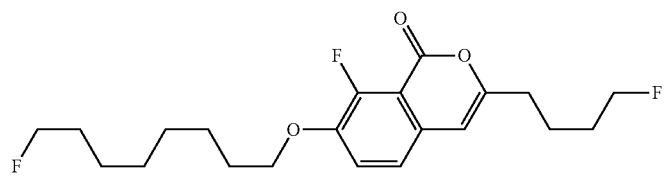 |
| 282 | 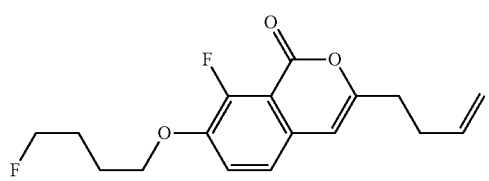 [SMILES: C=CCCc1cc2ccc(OCCCCF)c(F)c2c(=O)o1] |
| 283 | 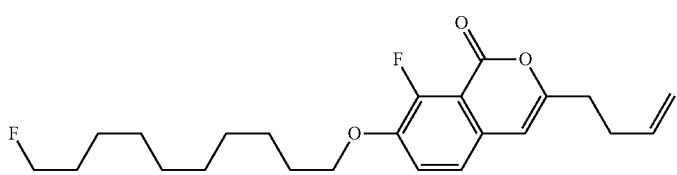 |
| 284 | 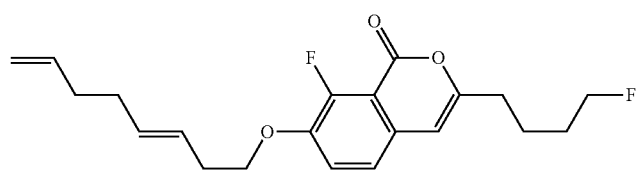 [SMILES: C=CCC/C=C/CCOc1ccc2cc(CCCCF)oc(=O)c2c1F] |
| 285 | 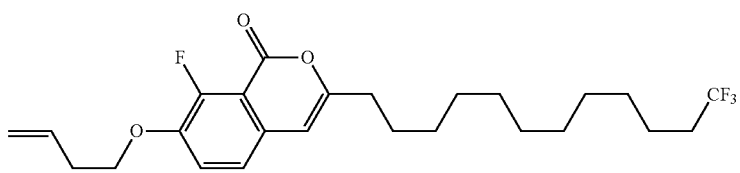 [SMILES: C=CCCOc1ccc2cc(CCCCCCCCCCCC(F)(F)F)oc(=O)c2c1F] |
| 286 | 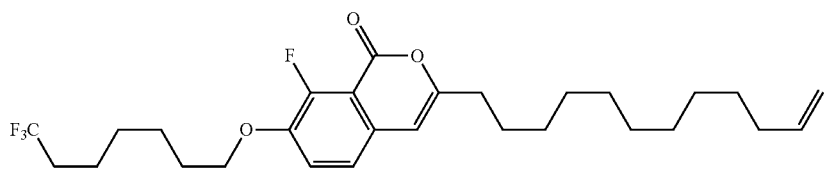 [SMILES: C=CCCCCCCCCCCc1cc2ccc(OCCCCCCC(F)(F)F)c(F)c2c(=O)o1] |
| 287 | 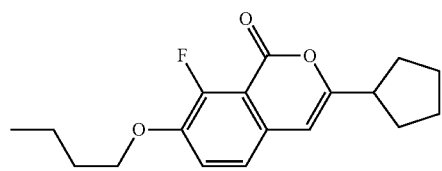 [SMILES: CCCCOc1ccc2cc(C3CCCC3)oc(=O)c2c1F] |

| No. | |
|---|---|
| 288 | 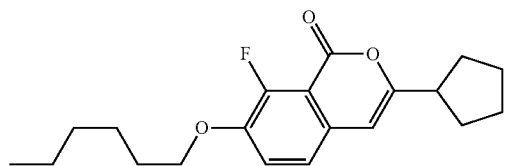 [SMILES: CCCCCCOc1ccc2cc(C3CCCC3)oc(=O)c2c1F] |
| 289 |  |
| 290 | 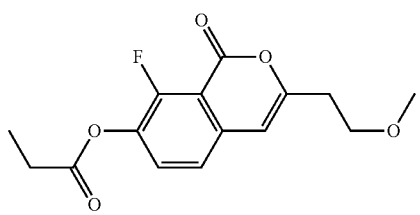 [SMILES: CCC(=O)Oc1ccc2cc(CCOC)oc(=O)c2c1F] |
| 291 | 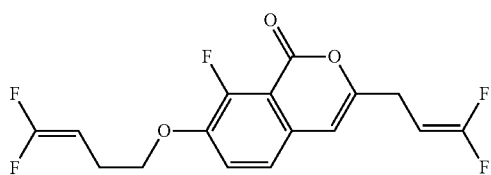 [SMILES: O=c1oc(CC=C(F)F)cc2ccc(OCCC=C(F)F)c(F)c12] |
| 292 | 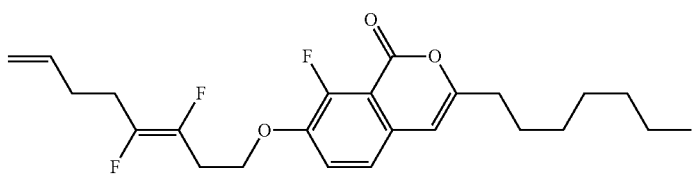 [SMILES: C=CCC/C(F)=C(\F)CCOc1ccc2cc(CCCCCCC)oc(=O)c2c1F] |
| 293 | 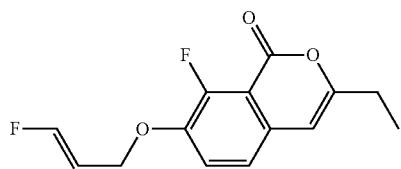 [SMILES: CCc1cc2ccc(OC/C=C/F)c(F)c2c(=O)o1] |
| 294 | 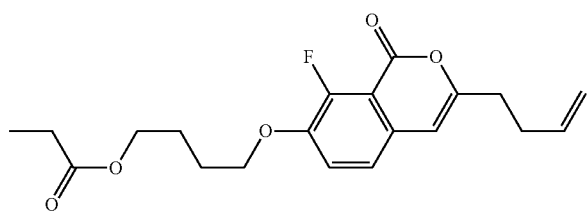 [SMILES: C=CCCc1cc2ccc(OCCCCOC(=O)CC)c(F)c2c(=O)o1] |
| 295 | 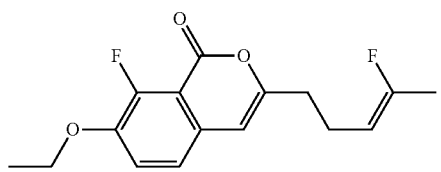 |

-continued
| No. | |
|---|---|
| 296 | 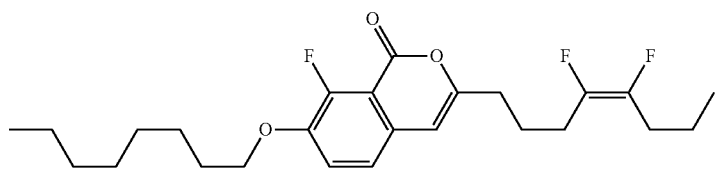 [SMILES: CCCCCCCCOc1ccc2cc(CCC/C(F)=C(/F)CCC)oc(=O)c2c1F] |
| 297 | 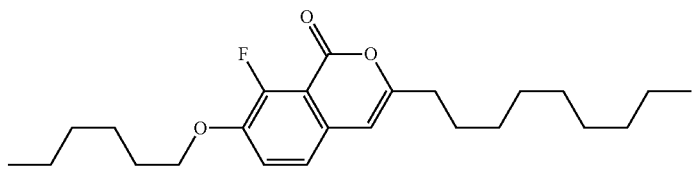 [SMILES: CCCCCCCCCc1cc2ccc(OCCCCCC)c(F)c2c(=O)o1] |
| 298 | 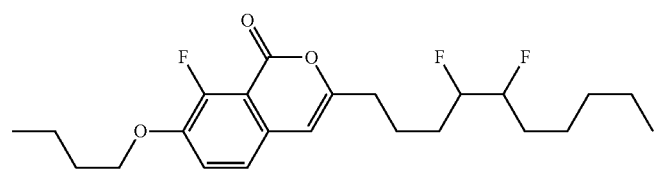 |
| 299 | 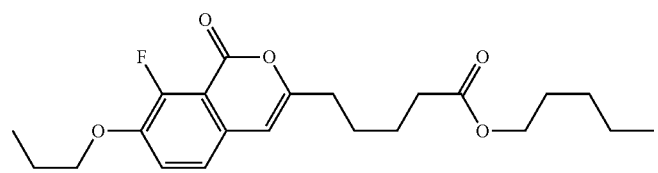 [SMILES: CCCCCOC(=O)CCCCc1cc2ccc(OCCC)c(F)c2c(=O)o1] |
| 300 | 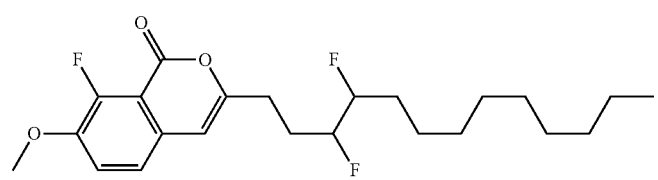 [SMILES: CCCCCCCCCC(F)C(F)CCc1cc2ccc(OC)c(F)c2c(=O)o1] |
| 301 | 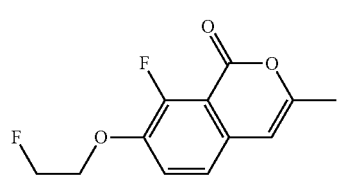 |
| 302 | 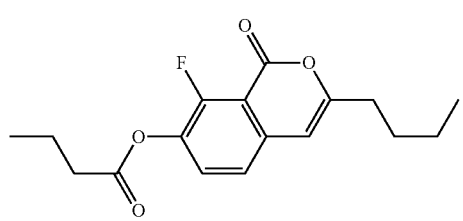 [SMILES: CCCCc1cc2ccc(OC(=O)CCC)c(F)c2c(=O)o1] |
| 303 | 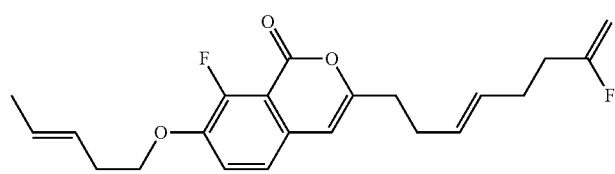 [SMILES: C=C(F)CC/C=C/CCc1cc2ccc(OCC/C=C/C)c(F)c2c(=O)o1] |

-continued
| No. | |
|---|---|
| 304 | 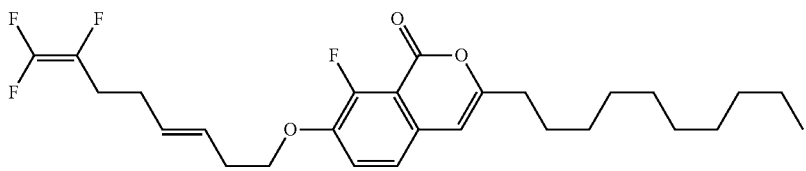 [SMILES: CCCCCCCCCCc1cc2ccc(OCC/C=C/CCC(F)=C(F)F)c(F)c2c(=O)o1] |
| 305 | 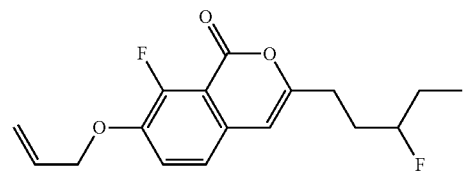 [SMILES: C=CCOc1ccc2cc(CCC(F)CC)oc(=O)c2c1F] |
| 306 | 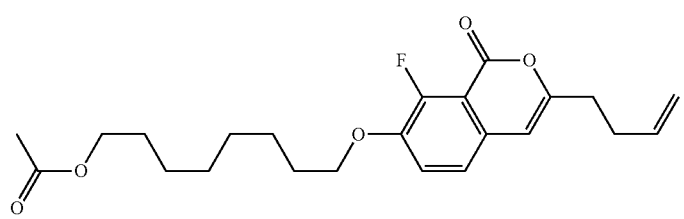 [SMILES: C=CCCc1cc2ccc(OCCCCCCCCOC(C)=O)c(F)c2c(=O)o1] |
| 307 | 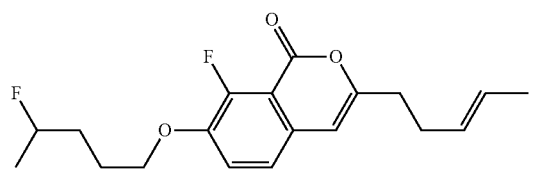 [SMILES: C/C=C/CCc1cc2ccc(OCCCC(C)F)c(F)c2c(=O)o1] |
| 308 | 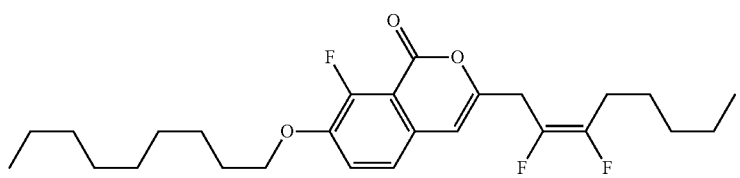 [SMILES: CCCCCCCCCOc1ccc2cc(C/C(F)=C(/F)CCCCC)oc(=O)c2c1F] |
| 309 | 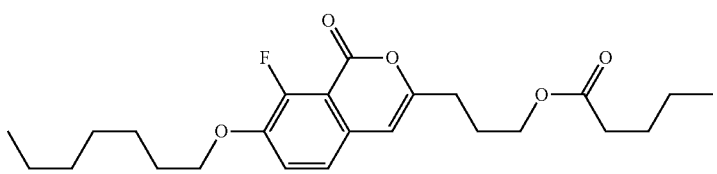 |
| 310 | 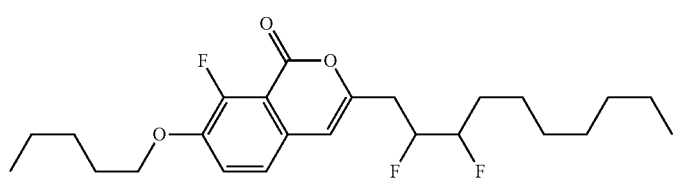 [SMILES: CCCCCCCC(F)C(F)Cc1cc2ccc(OCCCCC)c(F)c2c(=O)o1] |
| 311 | 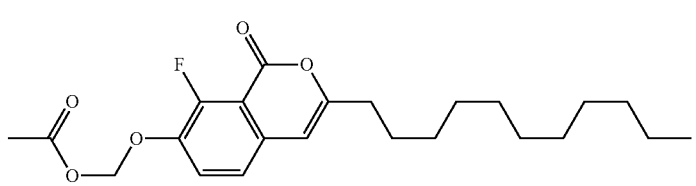 |

-continued
| No. | |
|---|---|
| 312 | 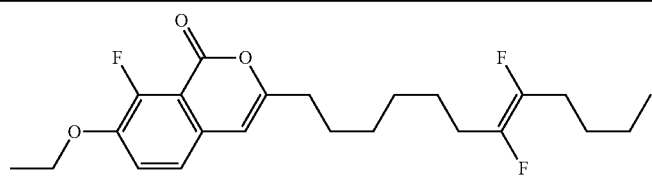 |
| 313 | 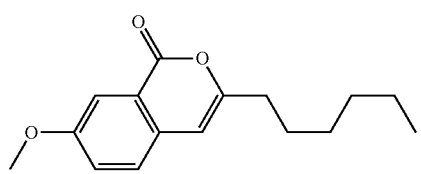 [SMILES: CCCCCCc1cc2ccc(OC)cc2c(=O)o1] |
| 314 | 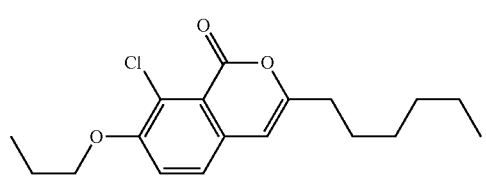 [SMILES: CCCCCCc1cc2ccc(OCCC)c(Cl)c2c(=O)o1] |
| 315 | 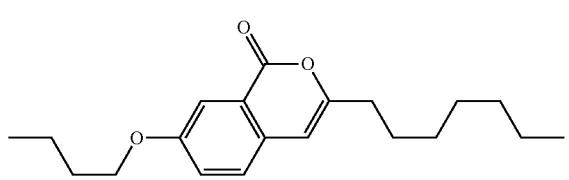 |
| 316 | 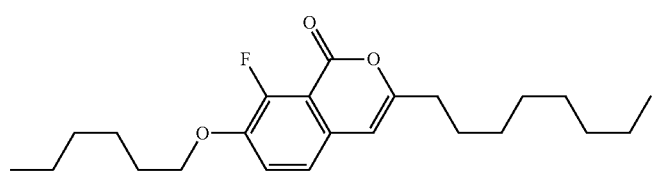 |
| 317 | 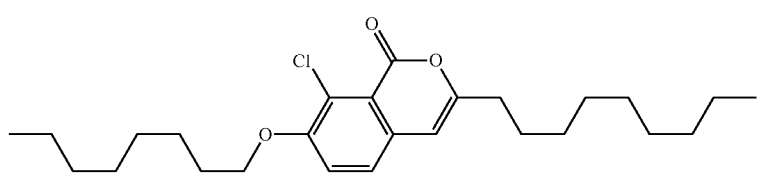 [SMILES: CCCCCCCCCc1cc2ccc(OCCCCCCCC)c(Cl)c2c(=O)o1] |
| 318 | 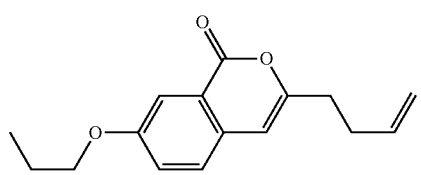 [SMILES: C=CCCc1cc2ccc(OCCC)cc2c(=O)o1] |
| 319 | 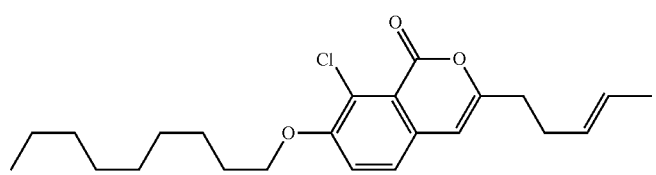 |
| 320 | 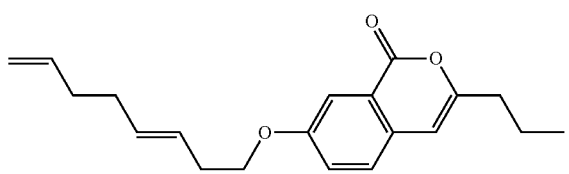 |

-continued
| No. | |
|---|---|
| 321 | 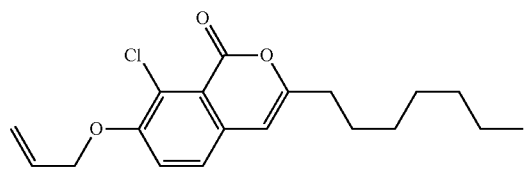 |
| 322 | 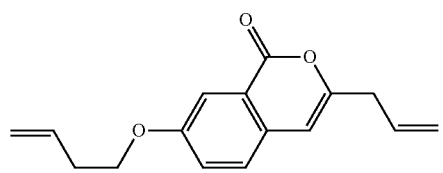 [SMILES: C=CCCOc1ccc2cc(CC=C)oc(=O)c2c1] |
| 323 | 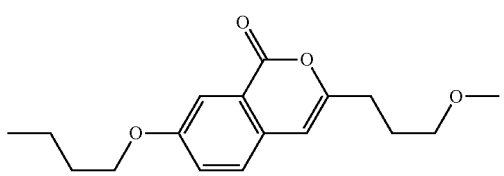 [SMILES: CCCCOc1ccc2cc(CCCOC)oc(=O)c2c1] |
| 324 | 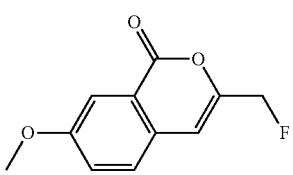 |
| 325 | 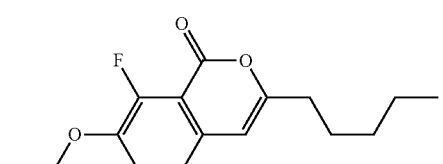 |
| 326 | 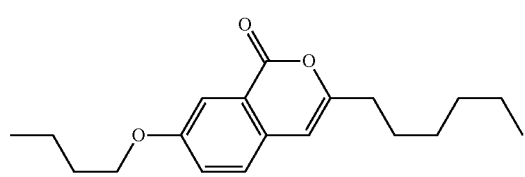 |
| 327 | 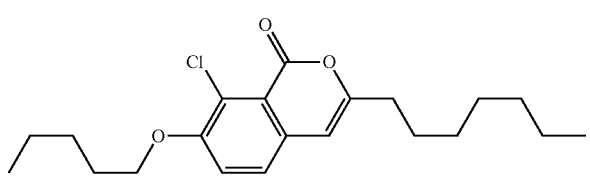 |
| 328 | 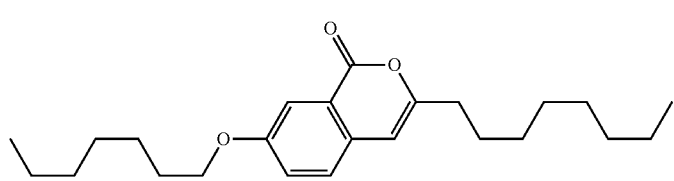 |
| 329 | 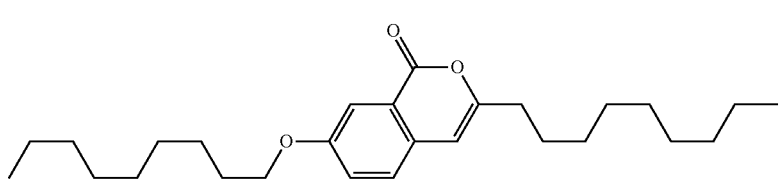 [SMILES: CCCCCCCCCOc1ccc2cc(CCCCCCCCC)oc(=O)c2c1] |

| No. |
|---|
| 330 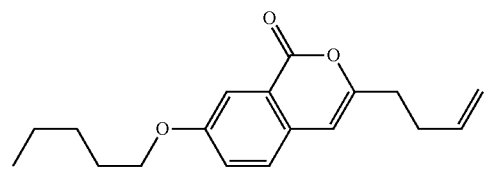 [SMILES: C=CCCc1cc2ccc(OCCCCC)cc2c(=O)o1] |
| 331 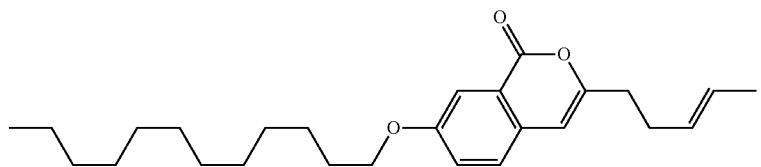 [SMILES: C/C=C/CCc1cc2ccc(OCCCCCCCCCCCC)cc2c(=O)o1] |
| 332 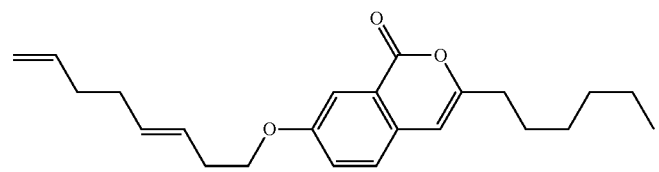 |
| 333 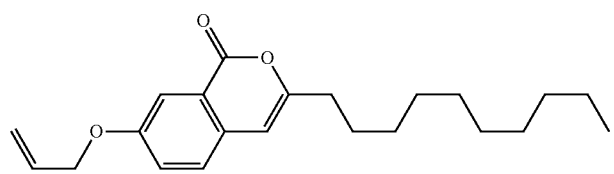 [SMILES: C=CCOc1ccc2cc(CCCCCCCCCC)oc(=O)c2c1] |
| 334 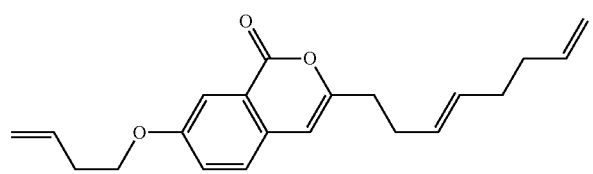 [SMILES: C=CCC/C=C/CCc1cc2ccc(OCCC=C)cc2c(=O)o1] |
| 335 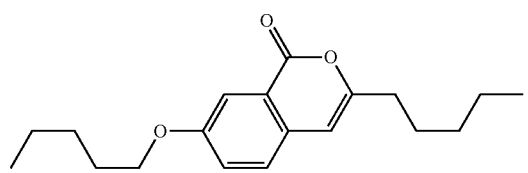 [SMILES: CCCCCOc1ccc2cc(CCCCC)oc(=O)c2c1] |
| 336 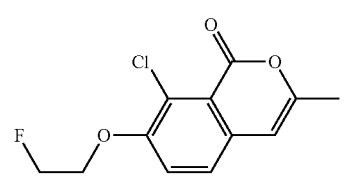 [SMILES: Cc1cc2ccc(OCCF)c(Cl)c2c(=O)o1] |
| 337 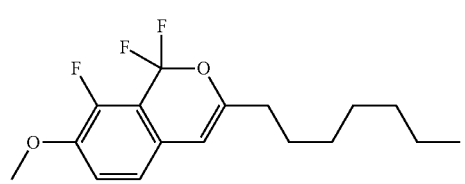 [SMILES: CCCCCCCC1=Cc2ccc(OC)c(F)c2C(F)(F)O1] |

-continued
| No. | |
|---|---|
| 338 | 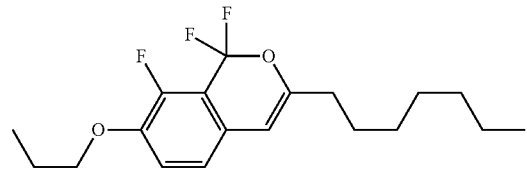 [SMILES: CCCCCCCC1=Cc2ccc(OCCC)c(F)c2C(F)(F)O1] |
| 339 | 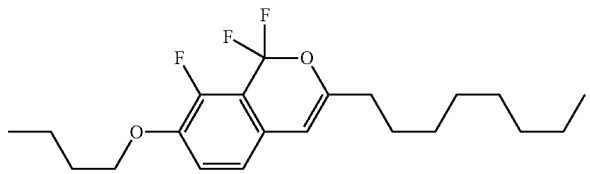 [SMILES: CCCCCCCCC1=Cc2ccc(OCCCC)c(F)c2C(F)(F)O1] |
| 340 | 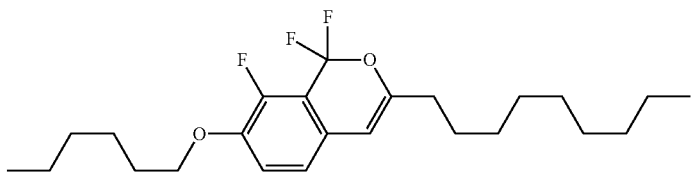 [SMILES: CCCCCCCCCC1=Cc2ccc(OCCCCCC)c(F)c2C(F)(F)O1] |
| 341 | 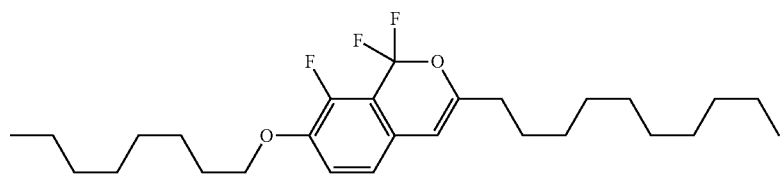 [SMILES: CCCCCCCCCCC1=Cc2ccc(OCCCCCCCC)c(F)c2C(F)(F)O1] |
| 342 | 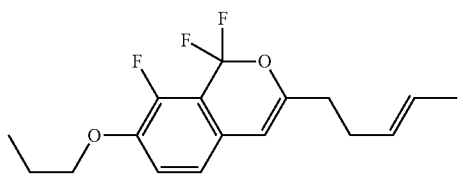 [SMILES: C/C=C/CCC1=Cc2ccc(OCCC)c(F)c2C(F)(F)O1] |
| 343 | 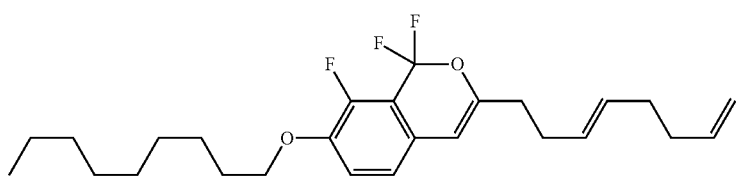 [SMILES: C=CCC/C=C/CCC1=Cc2ccc(OCCCCCCCCC)c(F)c2C(F)(F)O1] |
| 344 | 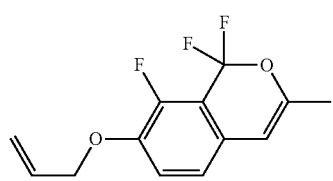 [SMILES: C=CCOc1ccc2c(c1F)C(F)(F)OC(C)=C2] |
| 345 | 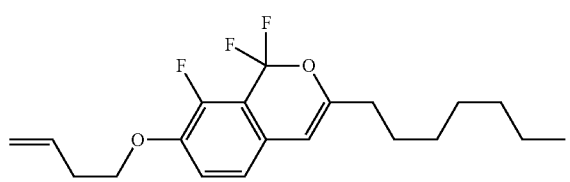 |

| No. |
|---|
| 346 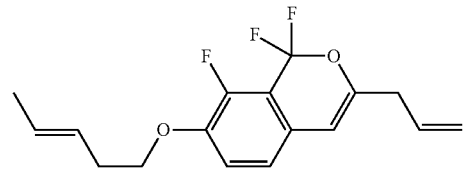 [SMILES: C=CCC1=Cc2ccc(OCC/C=C/C)c(F)c2C(F)(F)O1] |
| 347 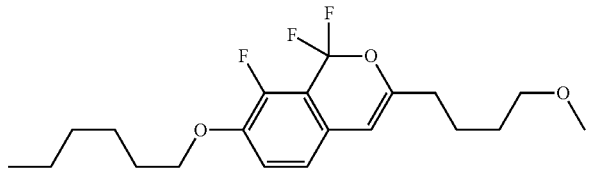 [SMILES: CCCCCCOc1ccc2c(c1F)C(F)(F)OC(CCCCOC)=C2] |
| 348 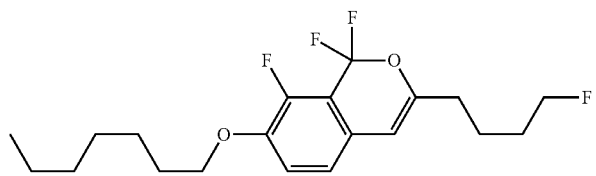 [SMILES: CCCCCCCOc1ccc2c(c1F)C(F)(F)OC(CCCCF)=C2] |
| 349 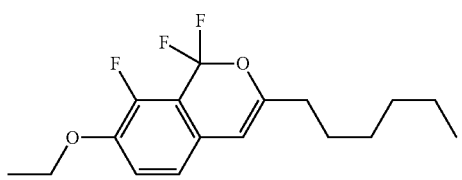 [SMILES: CCCCCCC1=Cc2ccc(OCC)c(F)c2C(F)(F)O1] |
| 350 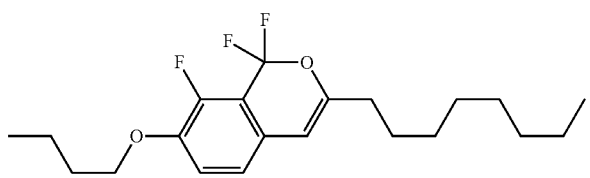 [SMILES: CCCCCCCCC1=Cc2ccc(OCCCC)c(F)c2C(F)(F)O1] |
| 351 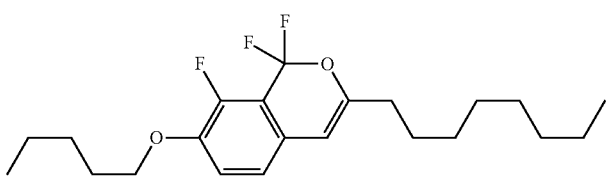 [SMILES: CCCCCCCCC1=Cc2ccc(OCCCCC)c(F)c2C(F)(F)O1] |
| 352 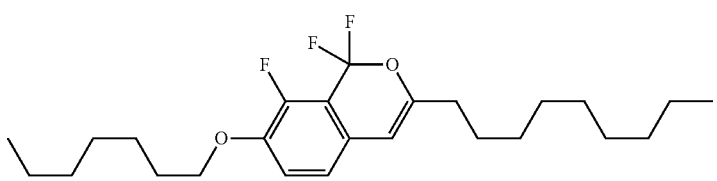 [SMILES: CCCCCCCCCC1=Cc2ccc(OCCCCCCC)c(F)c2C(F)(F)O1] |
| 353 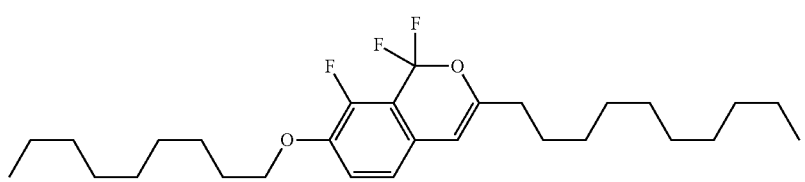 [SMILES: CCCCCCCCCCC1=Cc2ccc(OCCCCCCCCC)c(F)c2C(F)(F)O1] |

| No. |
|---|
| 354 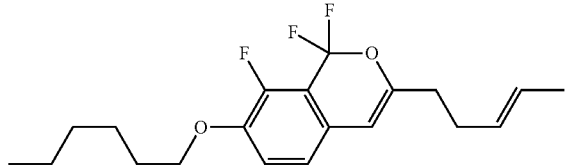 [SMILES: C/C=C/CCC1=Cc2ccc(OCCCCCC)c(F)c2C(F)(F)O1] |
| 355 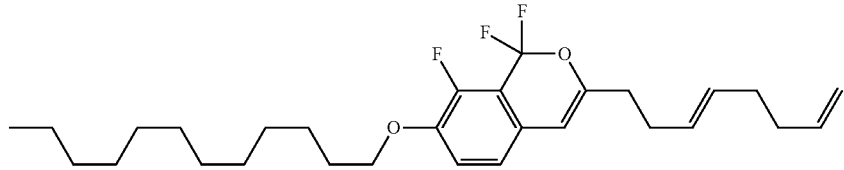 [SMILES: C=CCC/C=C/CCC1=Cc2ccc(OCCCCCCCCCCCC)c(F)c2C(F)(F)O1] |
| 356 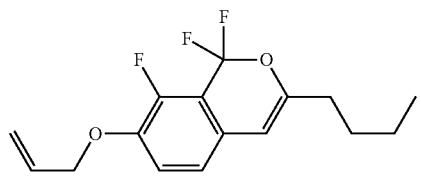 |
| 357 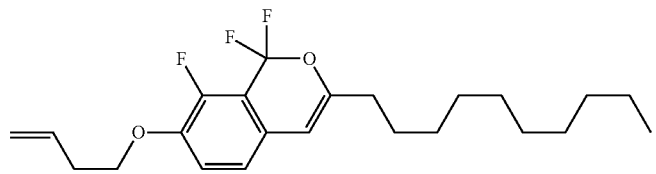 [SMILES: C=CCCOc1ccc2c(c1F)C(F)(F)OC(CCCCCCCCCC)=C2] |
| 358 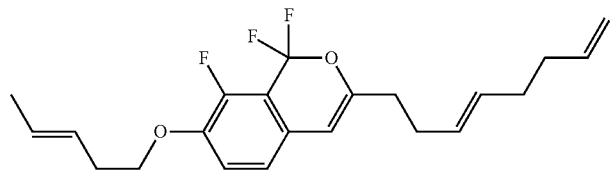 [SMILES: C=CCC/C=C/CCC1=Cc2ccc(OCC/C=C/C)c(F)c2C(F)(F)O1] |
| 359 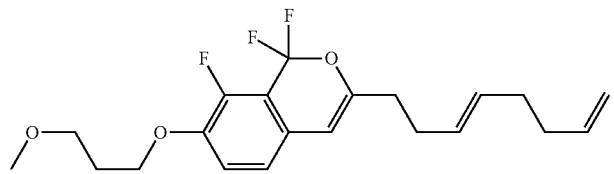 [SMILES: C=CCC/C=C/CCC1=Cc2ccc(OCCCOC)c(F)c2C(F)(F)O1] |
| 360 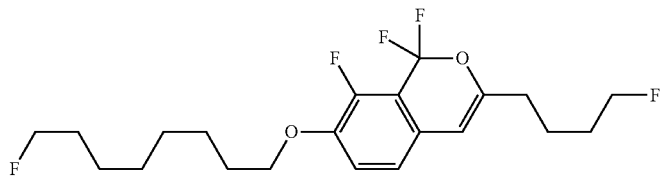 [SMILES: FCCCCCCCCOc1ccc2c(c1F)C(F)(F)OC(CCCCF)=C2] |
| 361 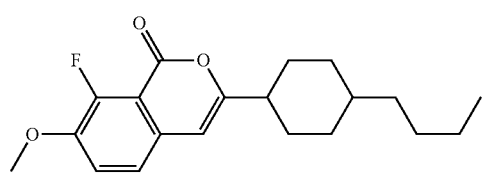 |

| No. | |
|---|---|
| 362 | 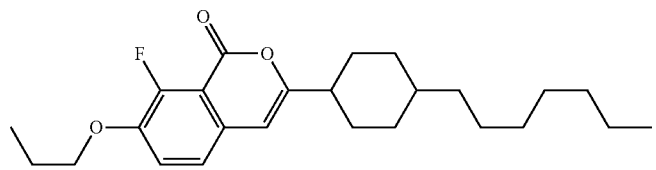 |
| 363 | 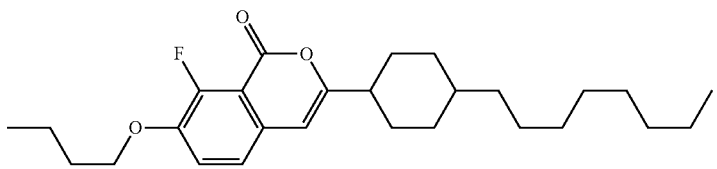 |
| 364 | 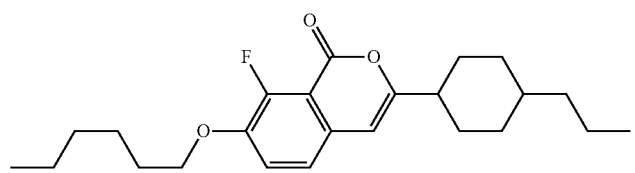 [SMILES: CCCCCCOc1ccc2cc(C3CCC(CCC)CC3)oc(=O)c2c1F] |
| 365 | 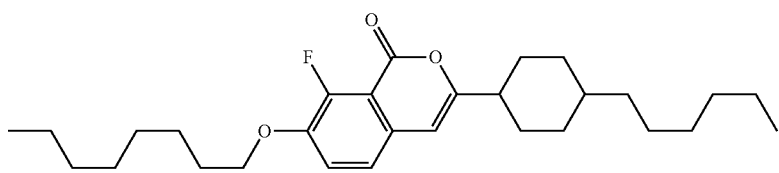 [SMILES: CCCCCCCCOc1ccc2cc(C3CCC(CCCCCC)CC3)oc(=O)c2c1F] |
| 366 | 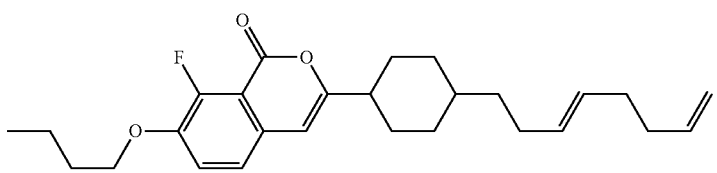 [SMILES: C=CCC/C=C/CCC1CCC(c2cc3ccc(OCCCC)c(F)c3c(=O)o2)CC1] |
| 367 | 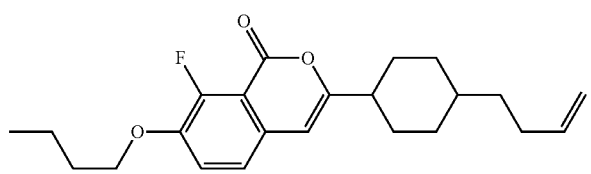 |
| 368 | 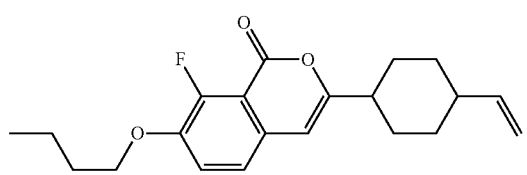 [SMILES: C=CC1CCC(c2cc3ccc(OCCCC)c(F)c3c(=O)o2)CC1] |
| 369 | 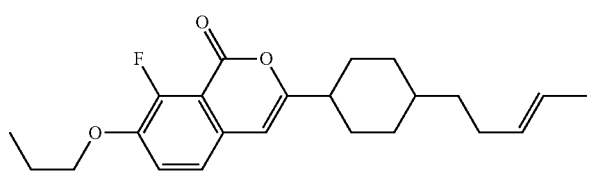 |
| 370 | 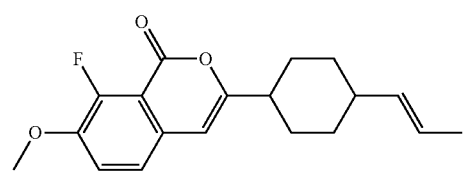 [SMILES: C/C=C/C1CCC(c2cc3ccc(OC)c(F)c3c(=O)o2)CC1] |

| No. | |
|---|---|
| 371 | 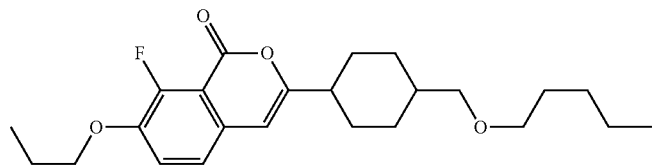 |
| 372 | 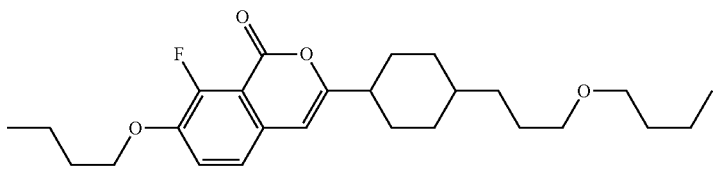 [SMILES: CCCCOCCCC1CCC(c2cc3ccc(OCCCC)c(F)c3c(=O)o2)CC1] |
| 373 | 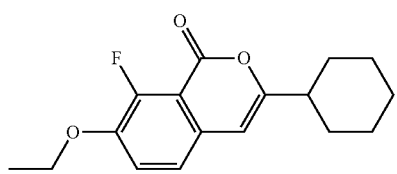 [SMILES: CCOc1ccc2cc(C3CCCCC3)oc(=O)c2c1F] |
| 374 | 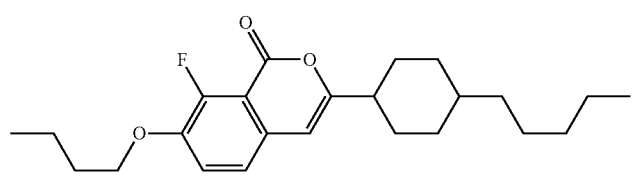 |
| 375 | 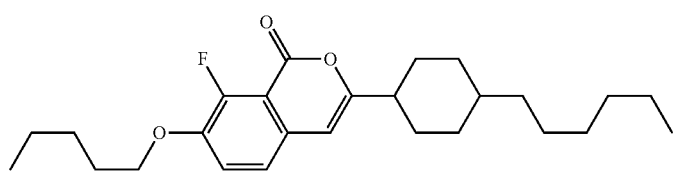 |
| 376 | 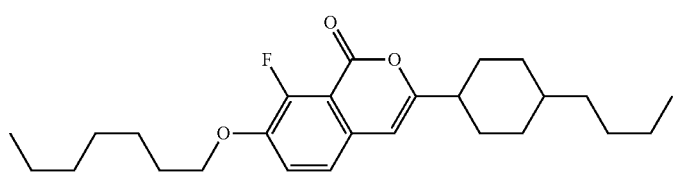 [SMILES: CCCCCCCOc1ccc2cc(C3CCC(CCCC)CC3)oc(=O)c2c1F] |
| 377 | 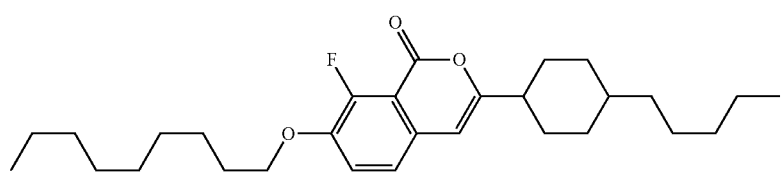 [SMILES: CCCCCCCCCOc1ccc2cc(C3CCC(CCCCC)CC3)oc(=O)c2c1F] |
| 378 | 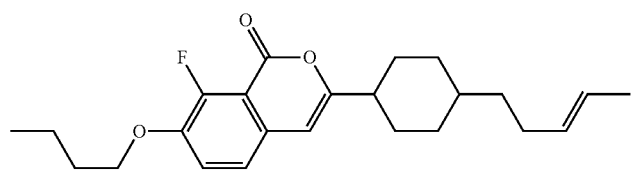 [SMILES: C/C=C/CCC1CCC(c2cc3ccc(OCCCC)c(F)c3c(=O)o2)CC1] |
| 379 | 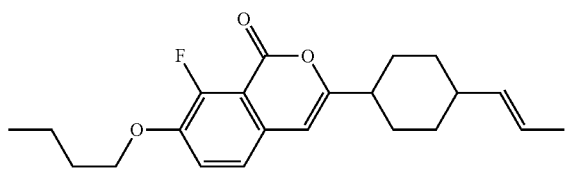 |

-continued
| No. | |
|---|---|
| 380 | 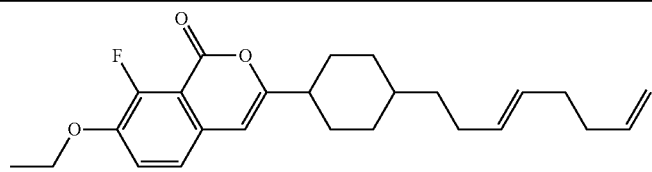 |
| 381 | 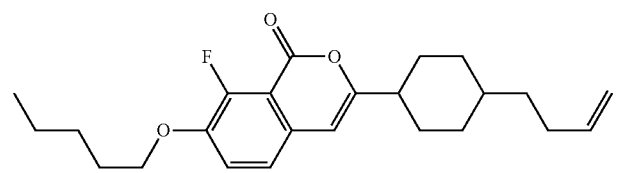 |
| 382 | 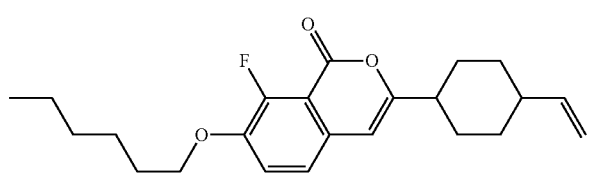 |
| 383 | 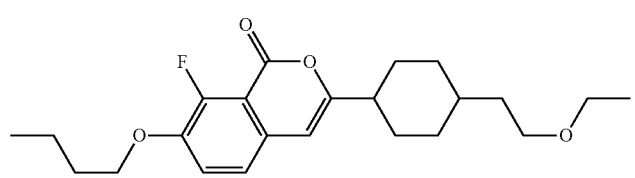 [SMILES: CCCCOc1ccc2cc(C3CCC(CCOCC)CC3)oc(=O)c2c1F] |
| 384 | 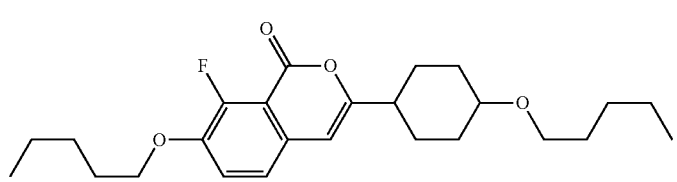 [SMILES: CCCCCOc1ccc2cc(C3CCC(OCCCCC)CC3)oc(=O)c2c1F] |
| 361 | 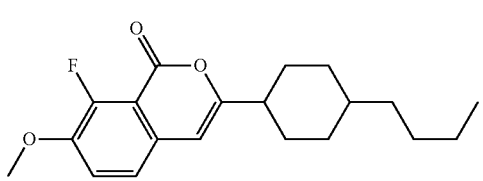 [SMILES: CCCCC1CCC(c2cc3ccc(OC)c(F)c3c(=O)o2)CC1] |
| 362 | 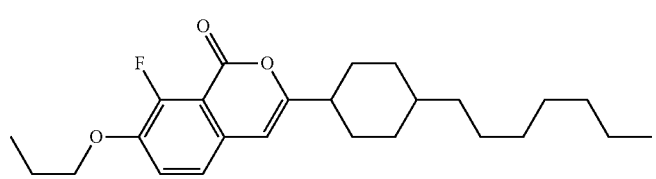 [SMILES: CCCCCCCC1CCC(c2cc3ccc(OCCC)c(F)c3c(=O)o2)CC1] |
| 263 | 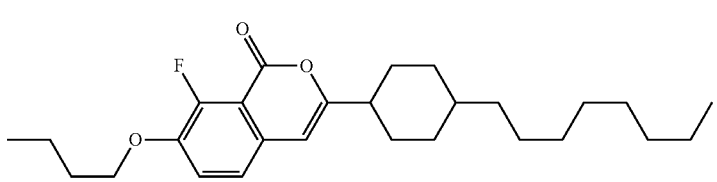 [SMILES: CCCCCCCCC1CCC(c2cc3ccc(OCCCC)c(F)c3c(=O)o2)CC1] |
| 364 | 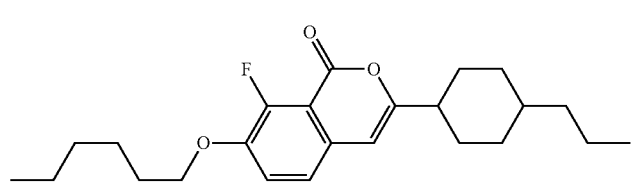 [SMILES: CCCCCCOc1ccc2cc(C3CCC(CCC)CC3)oc(=O)c2c1F] |

| No. | |
|---|---|
| 365 | 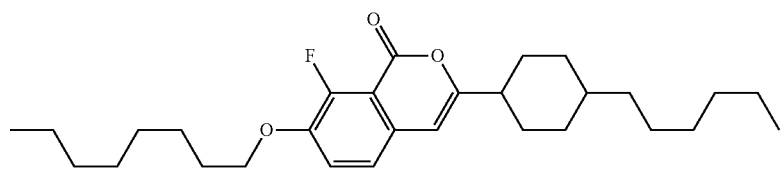 |
| 366 | 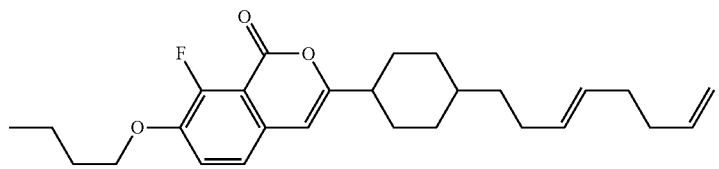 |
| 367 | 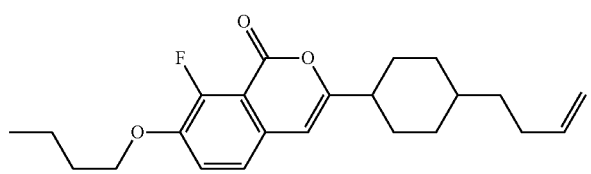 [SMILES: C=CCCC1CCC(c2cc3ccc(OCCCC)c(F)c3c(=O)o2)CC1] |
| 368 | 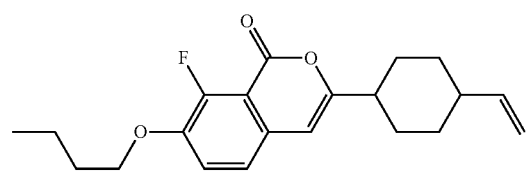 |
| 369 | 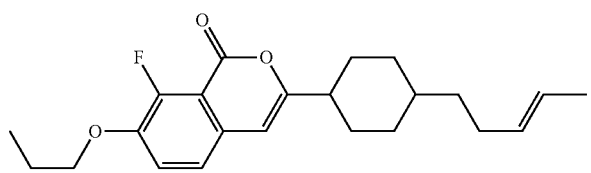 [SMILES: C/C=C/CCC1CCC(c2cc3ccc(OCCC)c(F)c3c(=O)o2)CC1] |
| 370 | 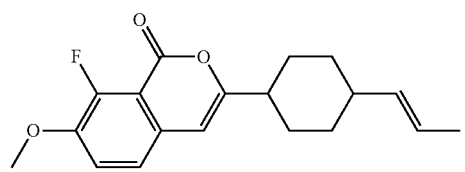 [SMILES: C/C=C/C1CCC(c2cc3ccc(OC)c(F)c3c(=O)o2)CC1] |
| 371 | 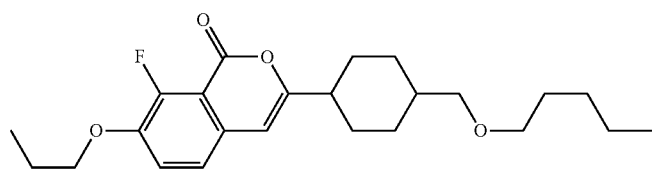 |
| 372 | 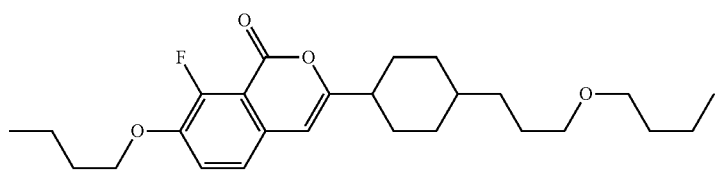 |
| 373 | 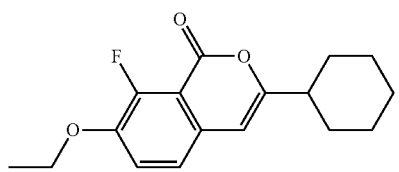 [SMILES: CCOc1ccc2cc(C3CCCCC3)oc(=O)c2c1F] |

| No. | |
|---|---|
| 374 | 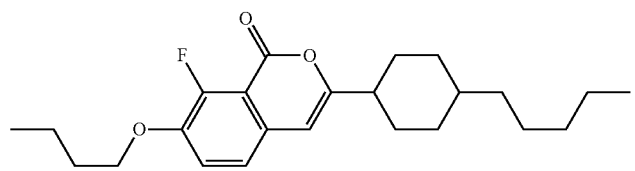 |
| 375 | 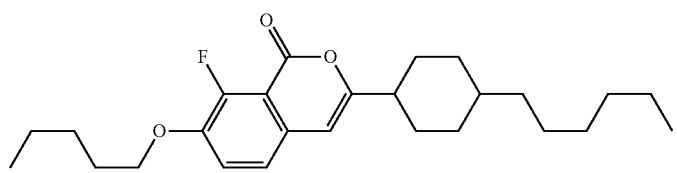 [SMILES: CCCCCCC1CCC(c2cc3ccc(OCCCCC)c(F)c3c(=O)o2)CC1] |
| 376 | 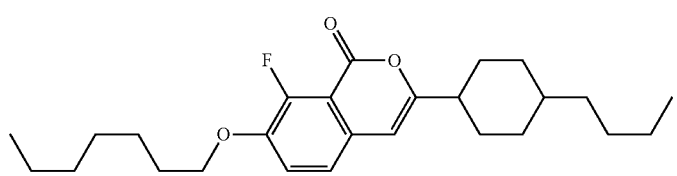 [SMILES: CCCCCCCOc1ccc2cc(C3CCC(CCCC)CC3)oc(=O)c2c1F] |
| 377 | 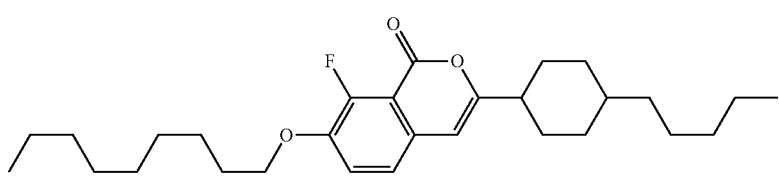 [SMILES: CCCCCCCCCOc1ccc2cc(C3CCC(CCCCC)CC3)oc(=O)c2c1F] |
| 378 | 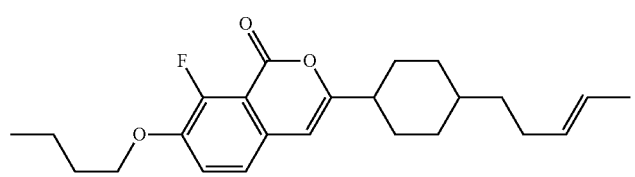 |
| 379 | 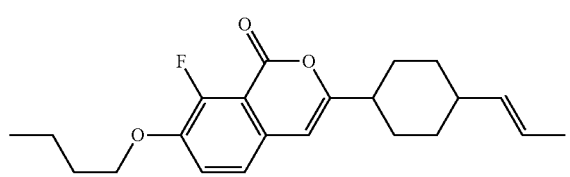 [SMILES: C/C=C/C1CCC(c2cc3ccc(OCCCC)c(F)c3c(=O)o2)CC1] |
| 380 | 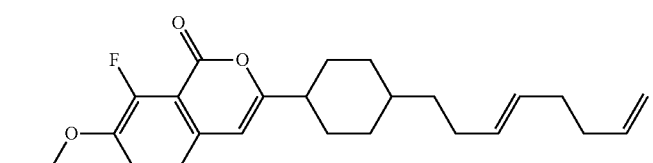 |
| 381 | 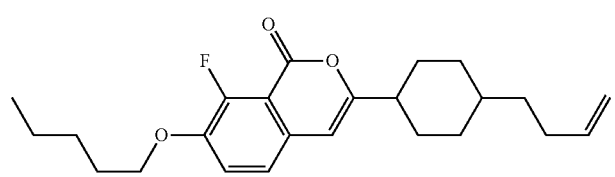 [SMILES: C=CCCC1CCC(c2cc3ccc(OCCCCC)c(F)c3c(=O)o2)CC1] |
| 382 | 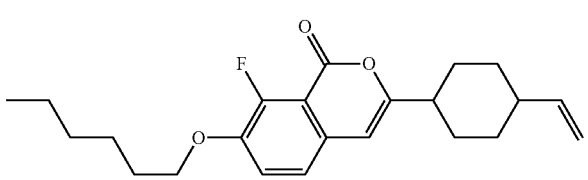 |

| No. |
|---|
| 383 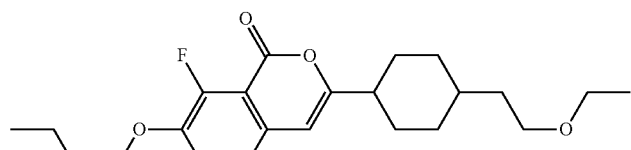 |
| 384 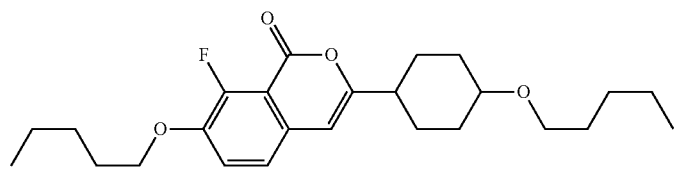 |
| 385 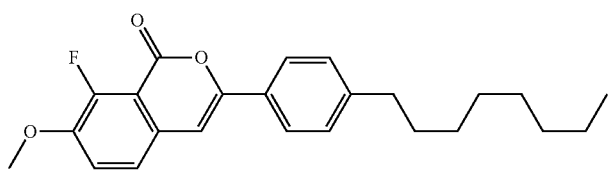 [SMILES: CCCCCCCCc1ccc(-c2cc3ccc(OC)c(F)c3c(=O)o2)cc1] |
| 386 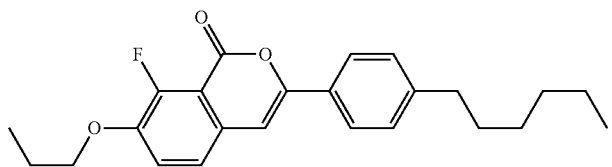 [SMILES: CCCCCCc1ccc(-c2cc3ccc(OCCC)c(F)c3c(=O)o2)cc1] |
| 387 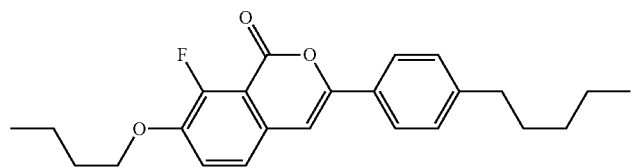 |
| 388 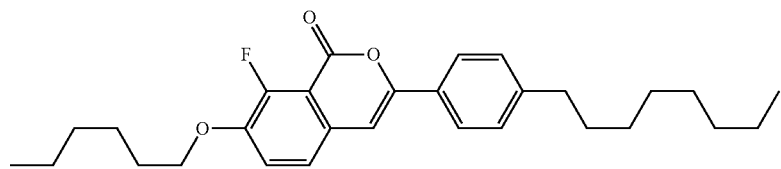 [SMILES: CCCCCCCCc1ccc(-c2cc3ccc(OCCCCCC)c(F)c3c(=O)o2)cc1] |
| 389 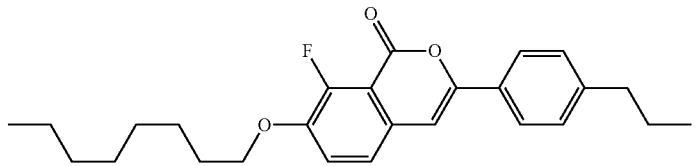 [SMILES: CCCCCCCCOc1ccc2cc(-c3ccc(CCC)cc3)oc(=O)c2c1F] |
| 390 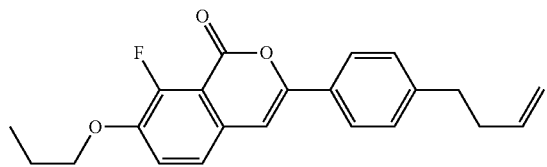 [SMILES: C=CCCc1ccc(-c2cc3ccc(OCCC)c(F)c3c(=O)o2)cc1] |
| 391 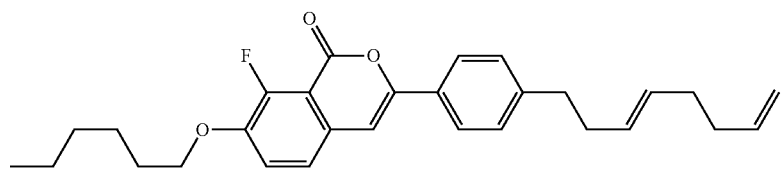 |

| No. | |
|---|---|
| 392 | 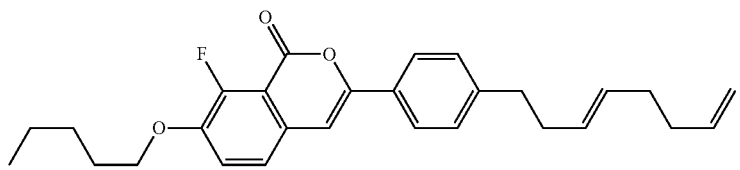 [SMILES: C=CCC/C=C/CCc1ccc(-c2cc3ccc(OCCCCC)c(F)c3c(=O)o2)cc1] |
| 393 | 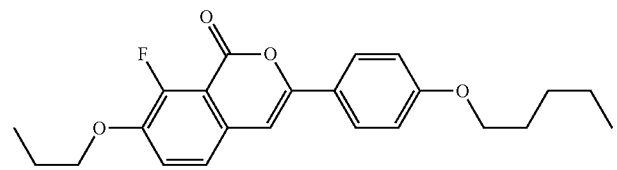 [SMILES: CCCCCOc1ccc(-c2cc3ccc(OCCC)c(F)c3c(=O)o2)cc1] |
| 394 | 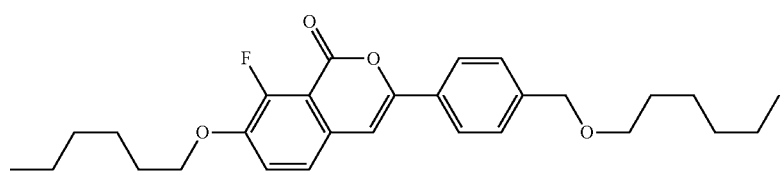 |
| 395 | 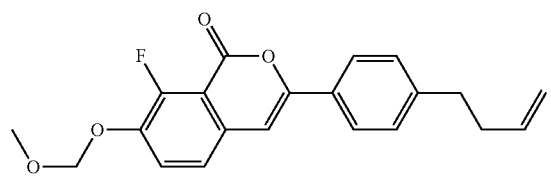 [SMILES: C=CCCc1ccc(-c2cc3ccc(OCOC)c(F)c3c(=O)o2)cc1] |
| 396 | 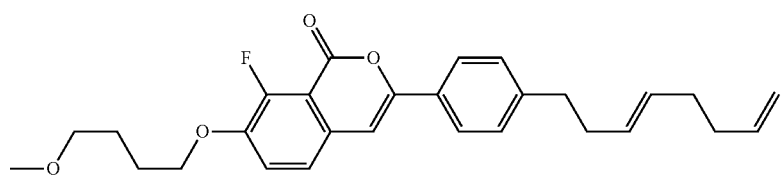 [SMILES: C=CCC/C=C/CCc1ccc(-c2cc3ccc(OCCCCOC)c(F)c3c(=O)o2)cc1] |
| 397 | 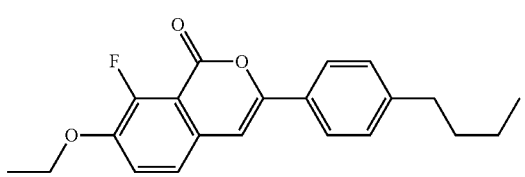 [SMILES: CCCCc1ccc(-c2cc3ccc(OCC)c(F)c3c(=O)o2)cc1] |
| 398 | 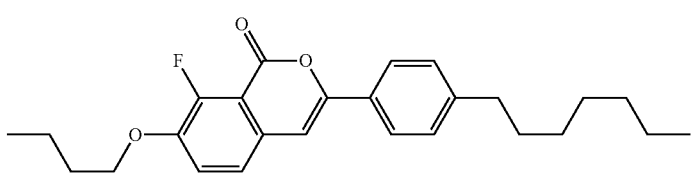 |
| 399 | 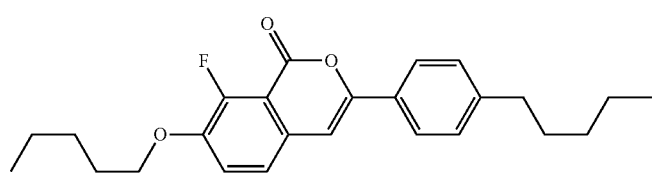 [SMILES: CCCCCOc1ccc2cc(-c3ccc(CCCCC)cc3)oc(=O)c2c1F] |
| 400 | 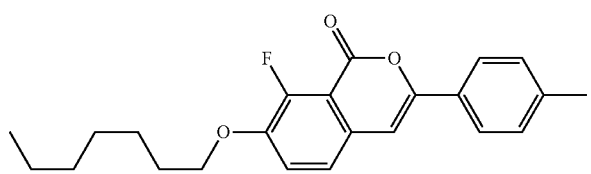 [SMILES: CCCCCCCOc1ccc2cc(-c3ccc(C)cc3)oc(=O)c2c1F] |

-continued
| No. | |
|---|---|
| 401 | 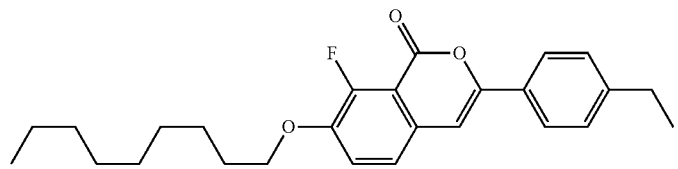 [SMILES: CCCCCCCCCOc1ccc2cc(-c3ccc(CC)cc3)oc(=O)c2c1F] |
| 402 | 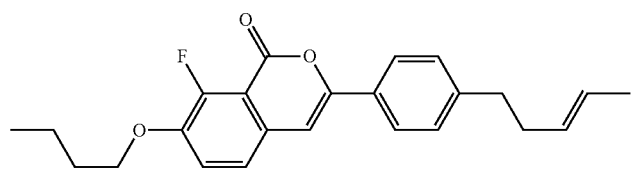 [SMILES: C/C=C/CCc1ccc(-c2cc3ccc(OCCCC)c(F)c3c(=O)o2)cc1] |
| 403 | 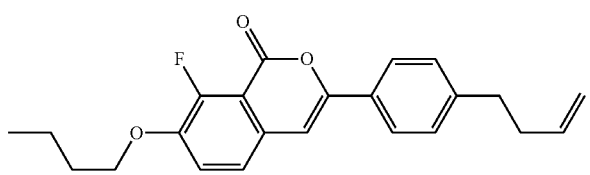 [SMILES: C=CCCc1ccc(-c2cc3ccc(OCCCC)c(F)c3c(=O)o2)cc1] |
| 404 | 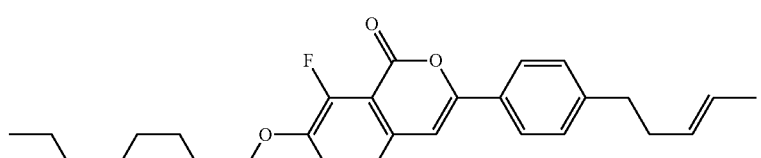 |
| 405 | 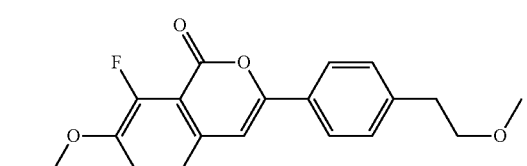 |
| 406 | 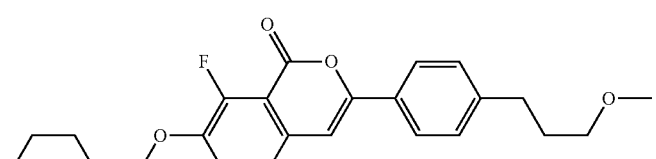 |
| 407 | 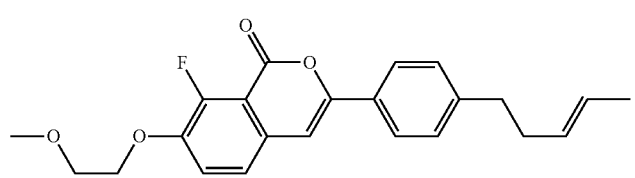 [SMILES: C/C=C/CCc1ccc(-c2cc3ccc(OCCOC)c(F)c3c(=O)o2)cc1] |
| 408 | 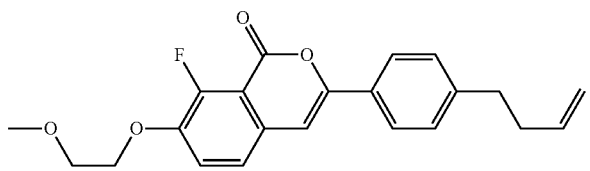 [SMILES: C=CCCc1ccc(-c2cc3ccc(OCCOC)c(F)c3c(=O)o2)cc1] |
| 409 | 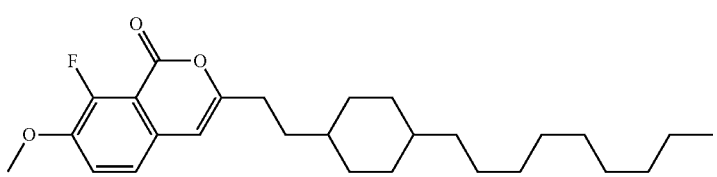 [SMILES: CCCCCCCCCC1CCC(CCc2cc3ccc(OC)c(F)c3c(=O)o2)CC1] |

-continued
| No. | |
|---|---|
| 410 | 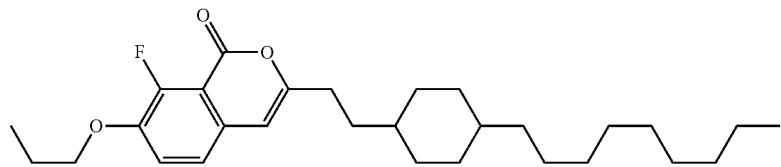 |
| 411 | 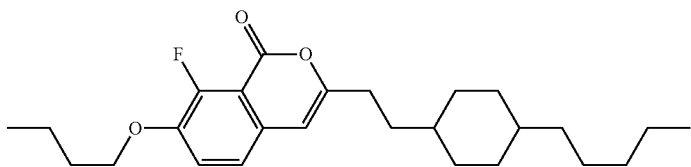 [SMILES: CCCCCC1CCC(CCc2cc3ccc(OCCCC)c(F)c3c(=O)o2)CC1] |
| 412 | 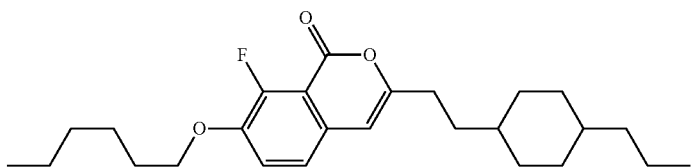 [SMILES: CCCCCCOc1ccc2cc(CCC3CCC(CCC)CC3)oc(=O)c2c1F] |
| 413 | 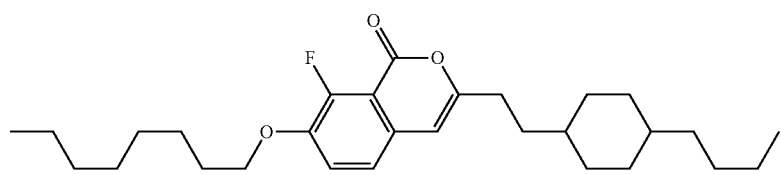 [SMILES: CCCCCCCCOc1ccc2cc(CCC3CCC(CCCC)CC3)oc(=O)c2c1F] |
| 414 | 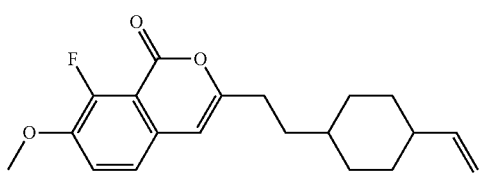 [SMILES: C=CC1CCC(CCc2cc3ccc(OC)c(F)c3c(=O)o2)CC1] |
| 415 | 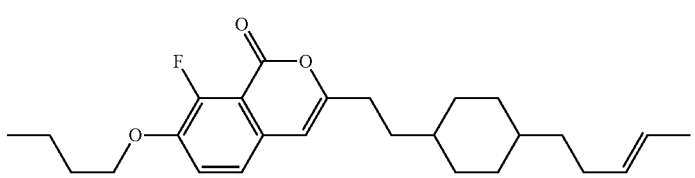 [SMILES: C/C=C/CCC1CCC(CCc2cc3ccc(OCCCC)c(F)c3c(=O)o2)CC1] |
| 416 | 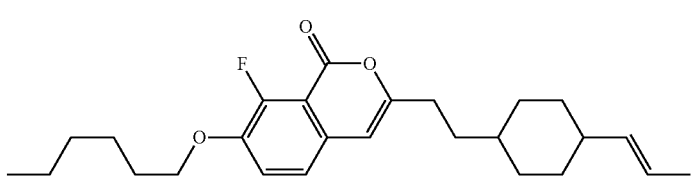 |
| 417 | 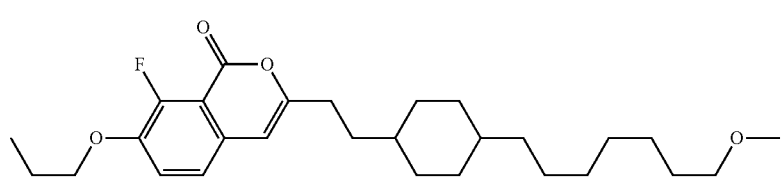 [SMILES: CCCOc1ccc2cc(CCC3CCC(CCCCCCCOC)CC3)oc(=O)c2c1F] |

| No. |
|---|
| 418 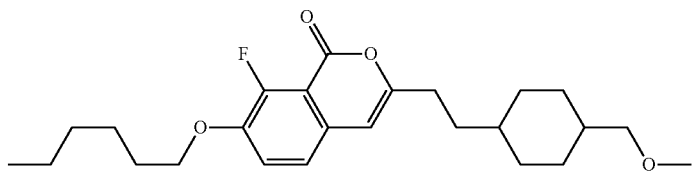 [SMILES: CCCCCCOc1ccc2cc(CCC3CCC(COC)CC3)oc(=O)c2c1F] |
| 419 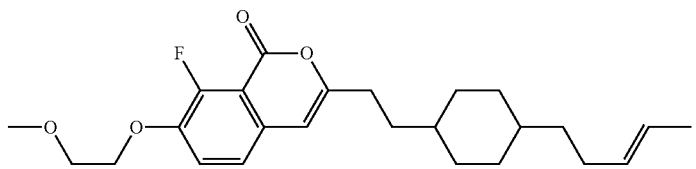 [SMILES: C/C=C/CCC1CCC(CCc2cc3ccc(OCCOC)c(F)c3c(=O)o2)CC1] |
| 420 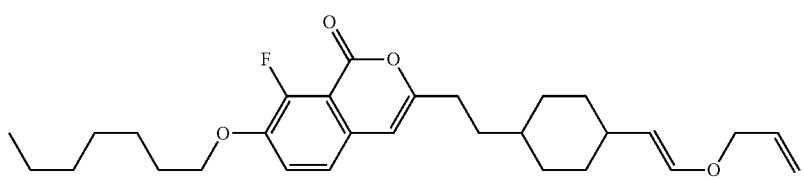 [SMILES: C=CCO/C=C/C1CCC(CCc2cc3ccc(OCCCCCCC)c(F)c3c(=O)o2)CC1] |
| 421 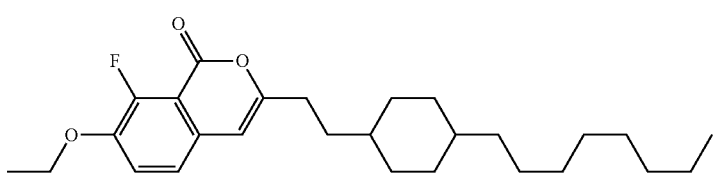 [SMILES: CCCCCCCCC1CCC(CCc2cc3ccc(OCC)c(F)c3c(=O)o2)CC1] |
| 422 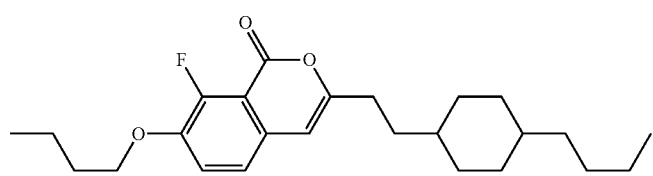 |
| 423 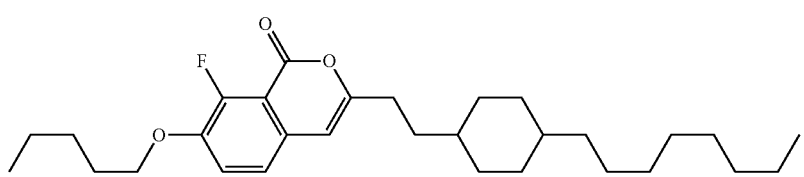 [SMILES: CCCCCCCCC1CCC(CCc2cc3ccc(OCCCCC)c(F)c3c(=O)o2)CC1] |
| 424 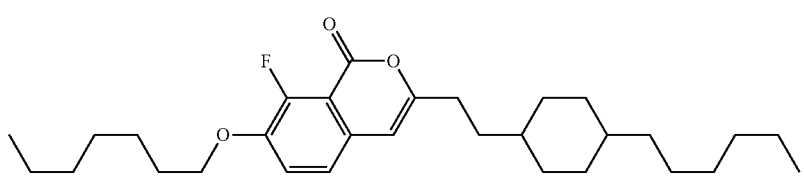 [SMILES: CCCCCCCOc1ccc2cc(CCC3CCC(CCCCCC)CC3)oc(=O)c2c1F] |
| 425 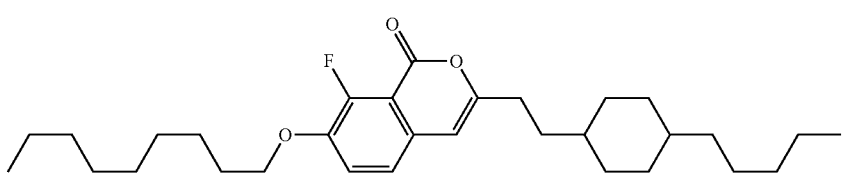 [SMILES: CCCCCCCCCOc1ccc2cc(CCC3CCC(CCCCC)CC3)oc(=O)c2c1F] |
| 426 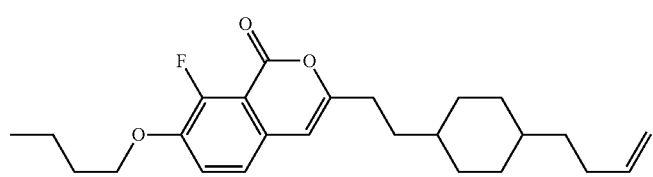 [SMILES: C=CCCC1CCC(CCc2cc3ccc(OCCCC)c(F)c3c(=O)o2)CC1] |

-continued
| No. | |
|---|---|
| 427 | 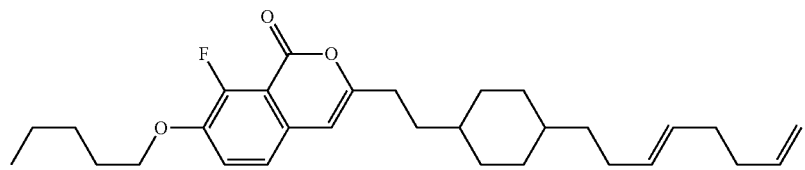 [SMILES: C=CCC/C=C/CCC1CCC(CCc2cc3ccc(OCCCCC)c(F)c3c(=O)o2)CC1] |
| 428 | 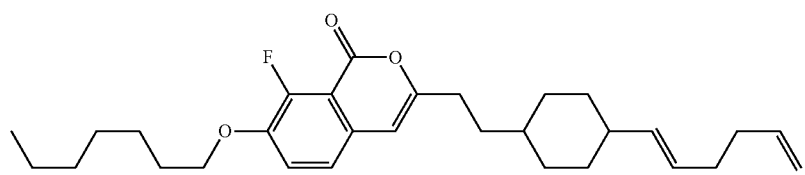 [SMILES: C=CCC/C=C/C1CCC(CCc2cc3ccc(OCCCCCCC)c(F)c3c(=O)o2)CC1] |
| 429 | 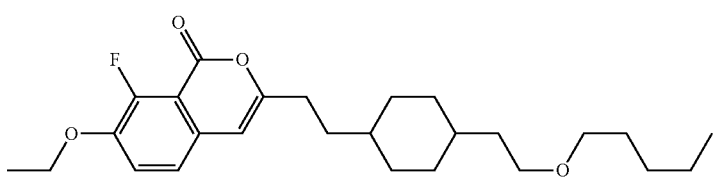 [SMILES: CCCCCOCCC1CCC(CCc2cc3ccc(OCC)c(F)c3c(=O)o2)CC1] |
| 430 | 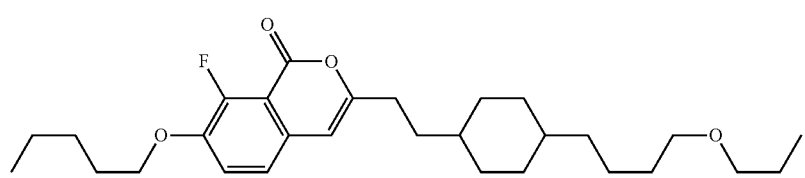 |
| 431 | 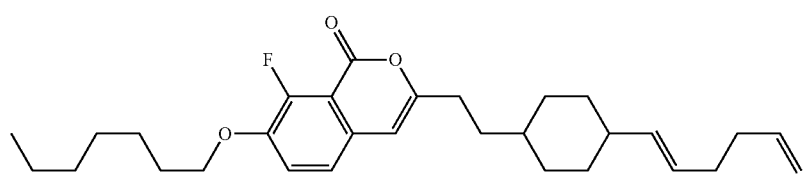 [SMILES: C=CCC/C=C/C1CCC(CCc2cc3ccc(OCCCCCCC)c(F)c3c(=O)o2)CC1] |
| 432 | 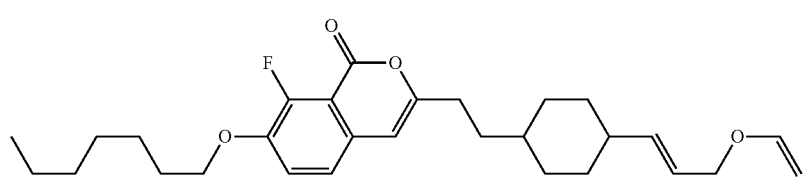 |
| 433 | 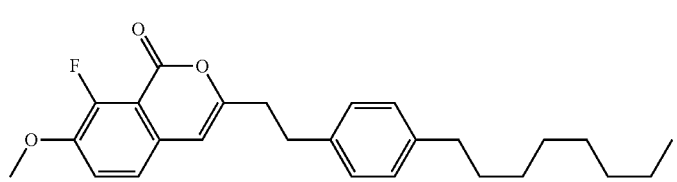 |
| 434 | 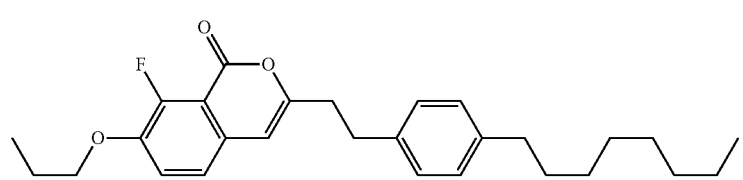 [SMILES: CCCCCCCCc1ccc(CCc2cc3ccc(OCCC)c(F)c3c(=O)o2)cc1] |

| No. | |
|---|---|
| 435 | 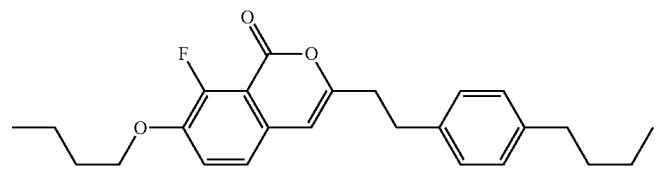 |
| 436 | 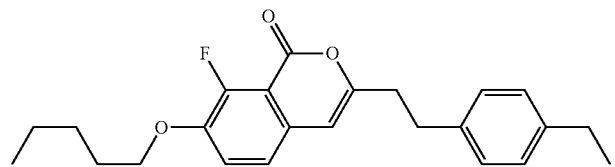 [SMILES: CCCCCOc1ccc2cc(CCc3ccc(CC)cc3)oc(=O)c2c1F] |
| 437 | 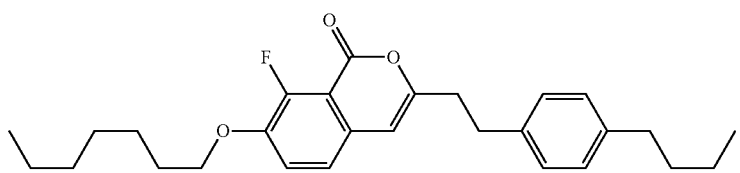 [SMILES: CCCCCCCOc1ccc2cc(CCc3ccc(CCCC)cc3)oc(=O)c2c1F] |
| 438 | 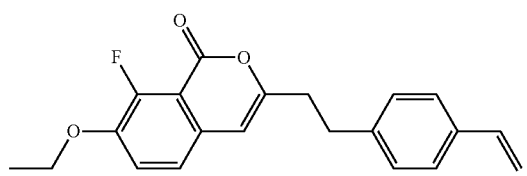 [SMILES: C=Cc1ccc(CCc2cc3ccc(OCC)c(F)c3c(=O)o2)cc1] |
| 439 | 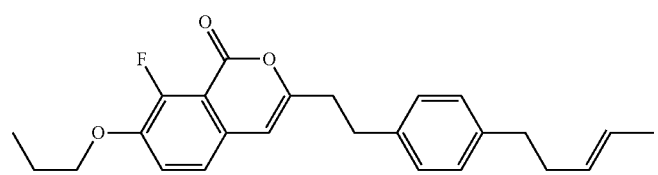 [SMILES: C/C=C/CCc1ccc(CCc2cc3ccc(OCCC)c(F)c3c(=O)o2)cc1] |
| 440 | 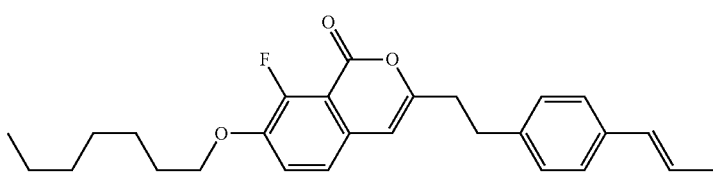 [SMILES: C/C=C/c1ccc(CCc2cc3ccc(OCCCCCCC)c(F)c3c(=O)o2)cc1] |
| 441 | 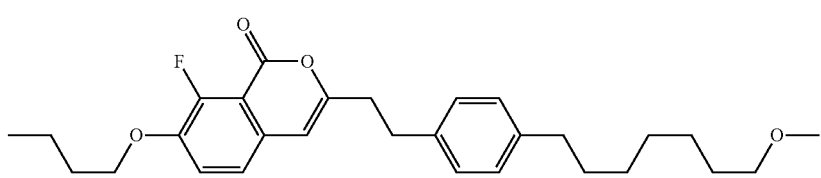 [SMILES: CCCCOc1ccc2cc(CCc3ccc(CCCCCCCOC)cc3)oc(=O)c2c1F] |
| 442 | 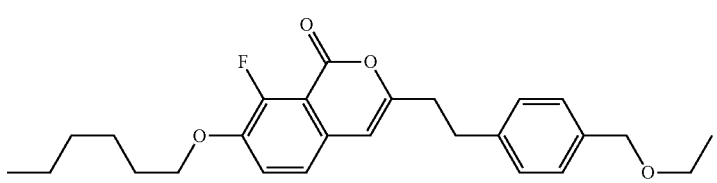 [SMILES: CCCCCCOc1ccc2cc(CCc3ccc(COCC)cc3)oc(=O)c2c1F] |
| 443 | 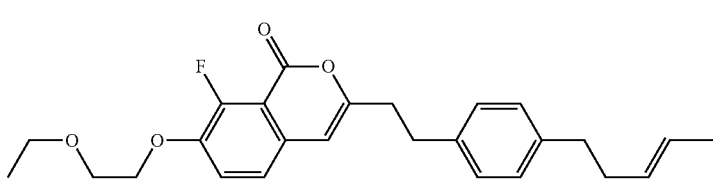 [SMILES: C/C=C/CCc1ccc(CCc2cc3ccc(OCCOCC)c(F)c3c(=O)o2)cc1] |

| No. |
|---|
| 444 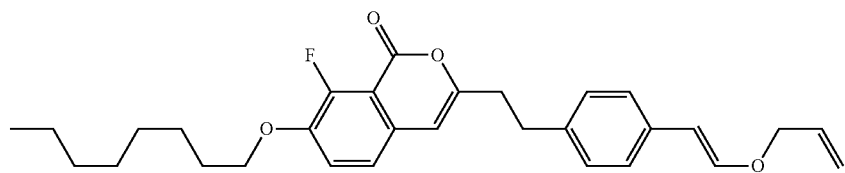 [SMILES: C=CCO/C=C/c1ccc(CCc2cc3ccc(OCCCCCCCC)c(F)c3c(=O)o2)cc1] |
| 445 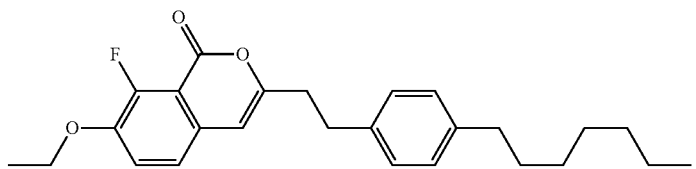 [SMILES: CCCCCCCc1ccc(CCc2cc3ccc(OCC)c(F)c3c(=O)o2)cc1] |
| 446 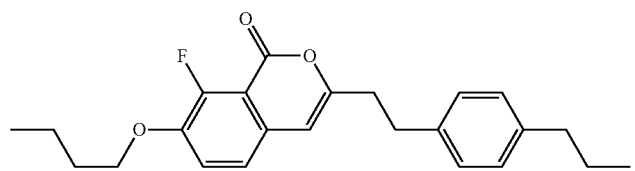 |
| 447 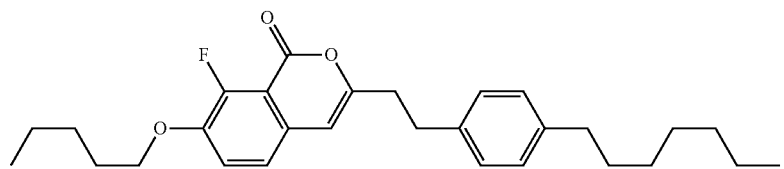 |
| 448 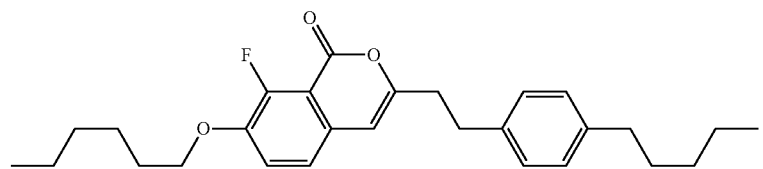 [SMILES: CCCCCCOc1ccc2cc(CCc3ccc(CCCCC)cc3)oc(=O)c2c1F] |
| 449 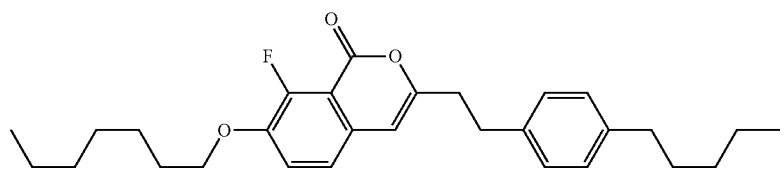 [SMILES: CCCCCCCOc1ccc2cc(CCc3ccc(CCCCC)cc3)oc(=O)c2c1F] |
| 450 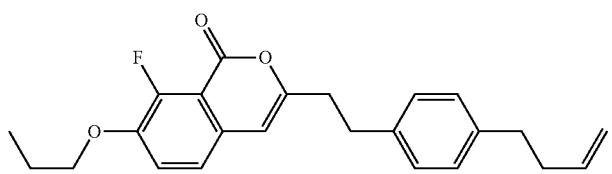 [SMILES: C=CCCc1ccc(CCc2cc3ccc(OCCC)c(F)c3c(=O)o2)cc1] |
| 451 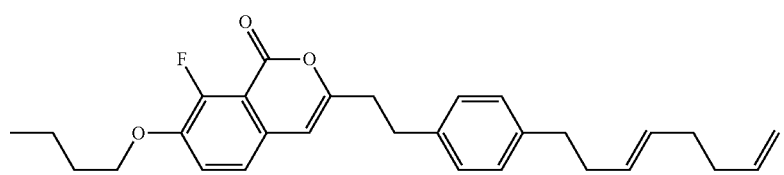 [SMILES: C=CCC/C=C/CCc1ccc(CCc2cc3ccc(OCCCC)c(F)c3c(=O)o2)cc1] |

| No. |
|---|
| 452 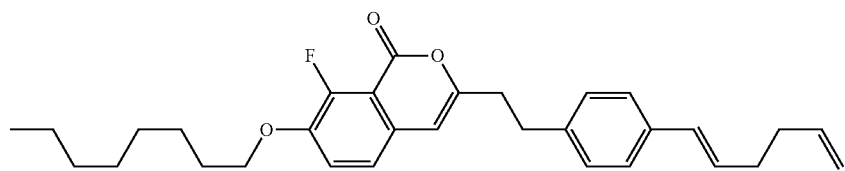 [SMILES: C=CCC/C=C/c1ccc(CCc2cc3ccc(OCCCCCCCC)c(F)c3c(=O)o2)cc1] |
| 453 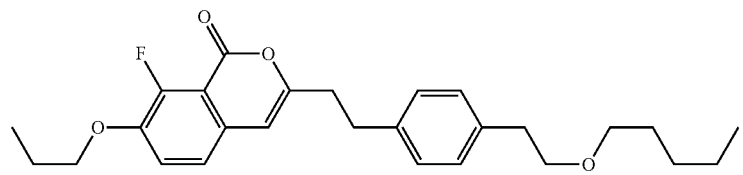 [SMILES: CCCCCOCCc1ccc(CCc2cc3ccc(OCCC)c(F)c3c(=O)o2)cc1] |
| 454 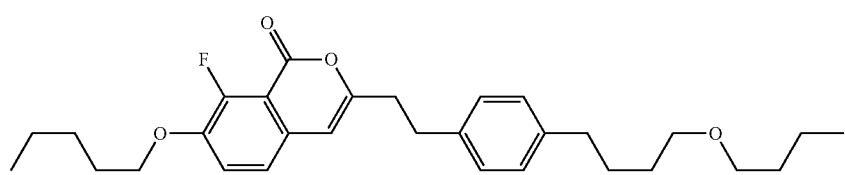 [SMILES: CCCCCOc1ccc2cc(CCc3ccc(CCCCOCCCC)cc3)oc(=O)c2c1F] |
| 455 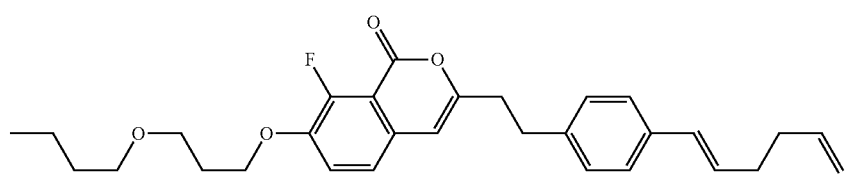 [SMILES: C=CCC/C=C/c1ccc(CCc2cc3ccc(OCCCOCCCC)c(F)c3c(=O)o2)cc1] |
| 456 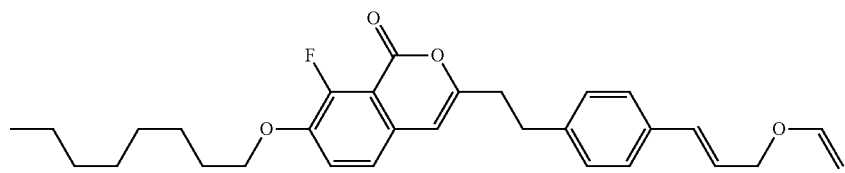 |
| 481 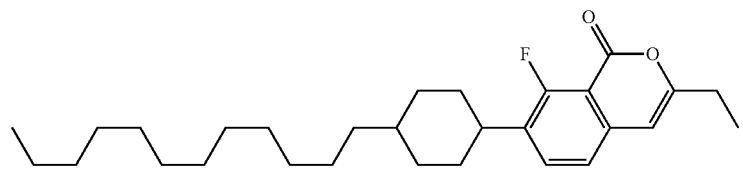 [SMILES: CCCCCCCCCCCCC1CCC(c2ccc3cc(CC)oc(=O)c3c2F)CC1] |
| 482 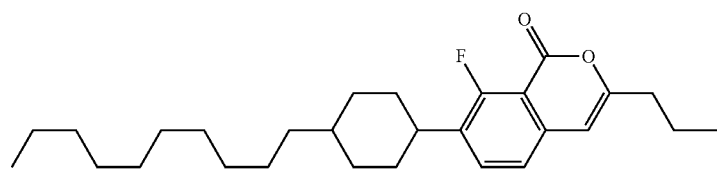 |
| 483 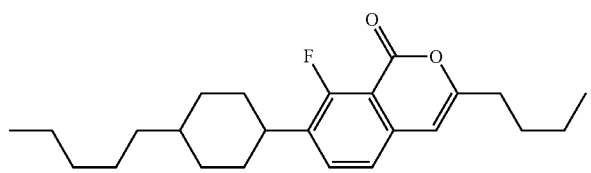 [SMILES: CCCCCC1CCC(c2ccc3cc(CCCC)oc(=O)c3c2F)CC1] |
| 484 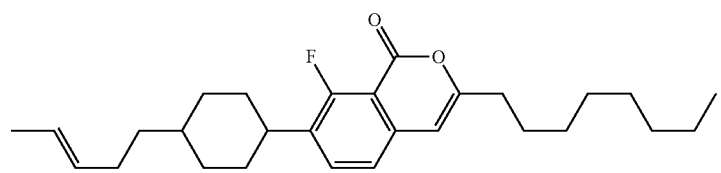 |

-continued
| No. |
|---|
| 485 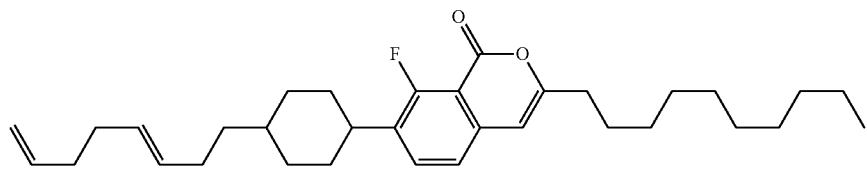 [SMILES: C=CCC/C=C/CCC1CCC(c2ccc3cc(CCCCCCCCCC)oc(=O)c3c2F)CC1] |
| 486 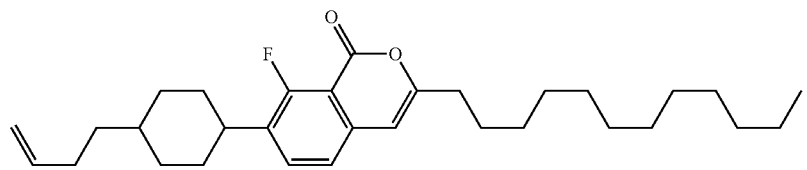 |
| 487 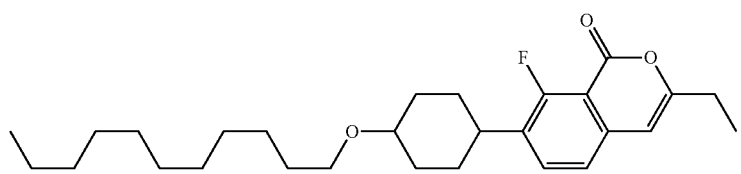 [SMILES: CCCCCCCCCCCOC1CCC(c2ccc3cc(CC)oc(=O)c3c2F)CC1] |
| 488 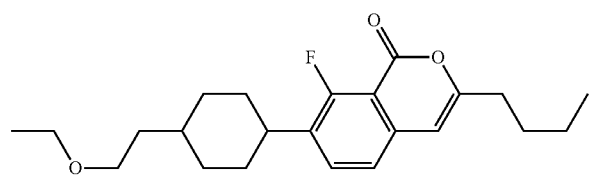 [SMILES: CCCCc1cc2ccc(C3CCC(CCOCC)CC3)c(F)c2c(=O)o1] |
| 489 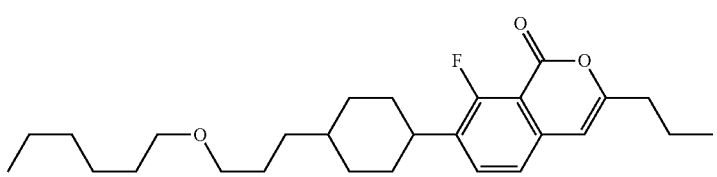 |
| 490 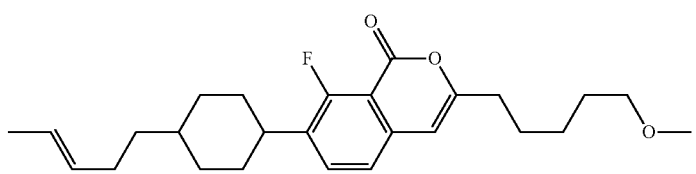 [SMILES: C/C=C/CCC1CCC(c2ccc3cc(CCCCCOC)oc(=O)c3c2F)CC1] |
| 491 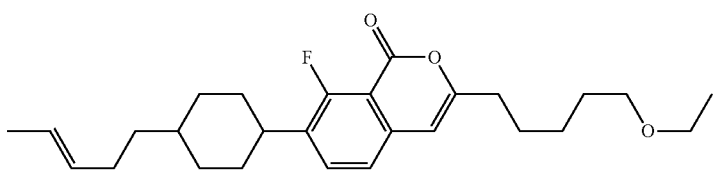 |
| 492 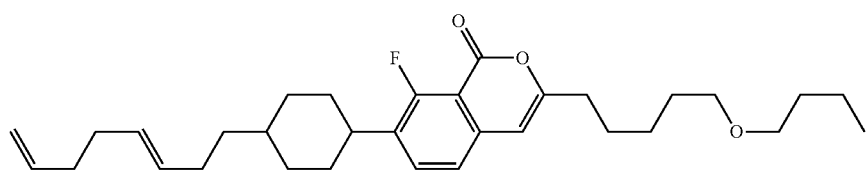 [SMILES: C=CCC/C=C/CCC1CCC(c2ccc3cc(CCCCCOCCCC)oc(=O)c3c2F)CC1] |
| 493 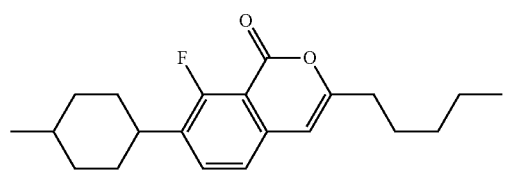 |

| No. |
|---|
| 494 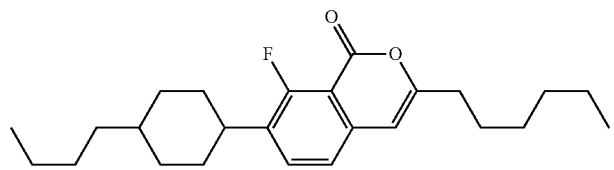 [SMILES: CCCCCCc1cc2ccc(C3CCC(CCCC)CC3)c(F)c2c(=O)o1] |
| 495 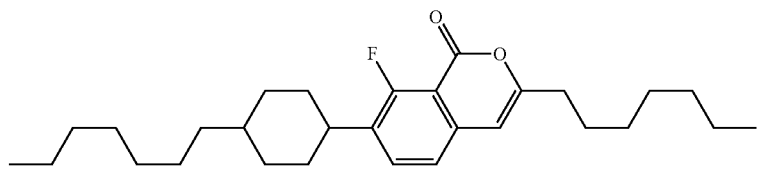 |
| 496 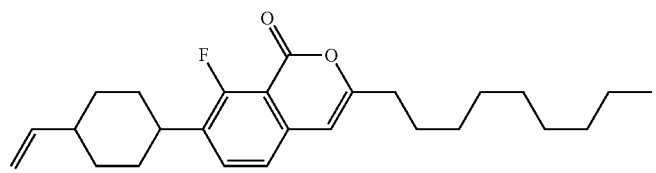 [SMILES: C=CC1CCC(c2ccc3cc(CCCCCCCCC)oc(=O)c3c2F)CC1] |
| 497 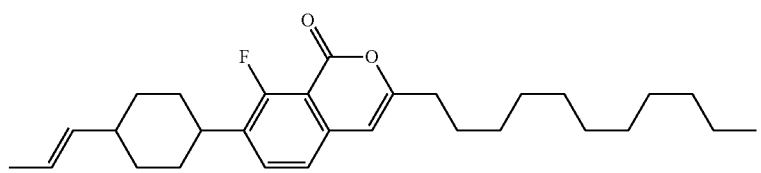 |
| 498 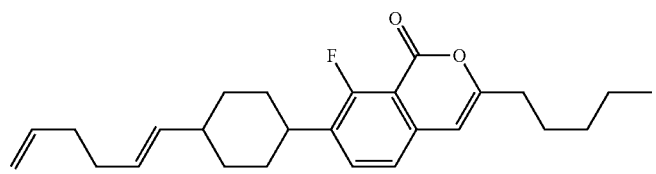 |
| 499 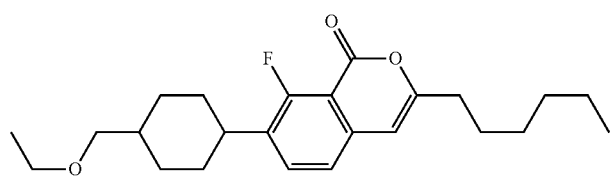 [SMILES: CCCCCCc1cc2ccc(C3CCC(COCC)CC3)c(F)c2c(=O)o1] |
| 500 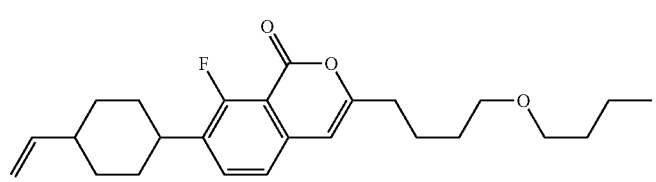 |
| 501 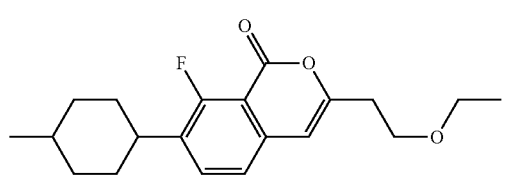 [SMILES: CCOCCc1cc2ccc(C3CCC(C)CC3)c(F)c2c(=O)o1] |

| No. |
|---|
| 502 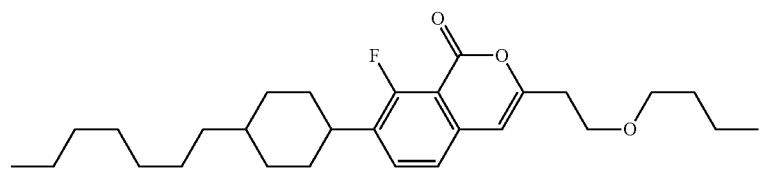 |
| 503 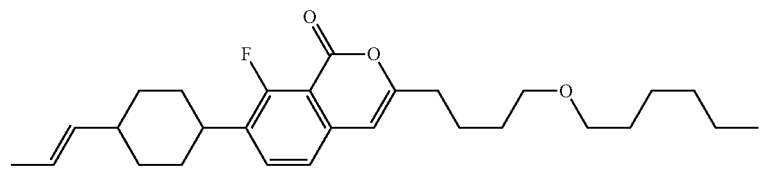 |
| 504 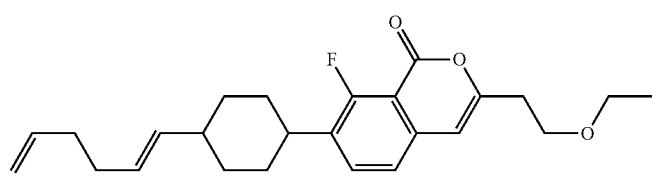 [SMILES: C=CCC/C=C/C1CCC(c2ccc3cc(CCOCC)oc(=O)c3c2F)CC1] |
| 505 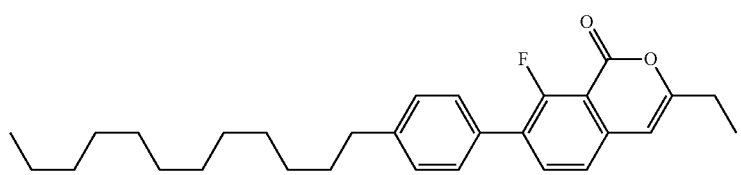 [SMILES: CCCCCCCCCCCCc1ccc(-c2ccc3cc(CC)oc(=O)c3c2F)cc1] |
| 506 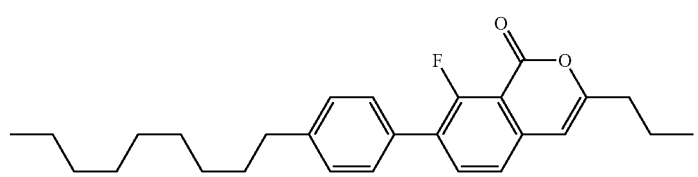 |
| 507 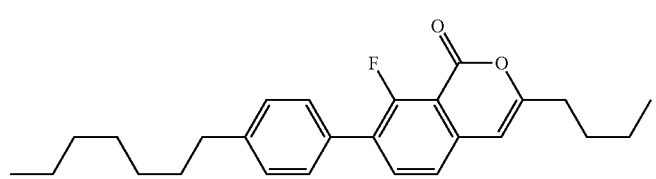 [SMILES: CCCCCCCc1ccc(-c2ccc3cc(CCCC)oc(=O)c3c2F)cc1] |
| 508 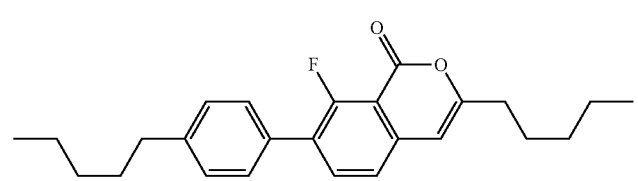 |
| 509 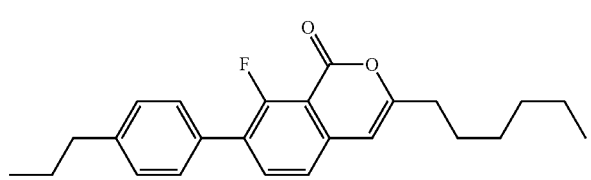 |
| 510 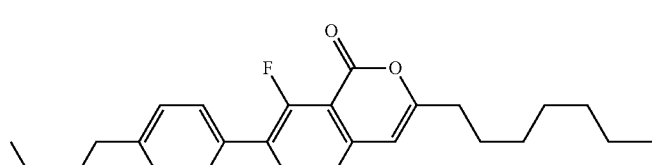 |

-continued
| No. | |
|---|---|
| 511 | 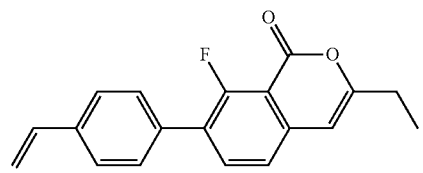 |
| 512 | 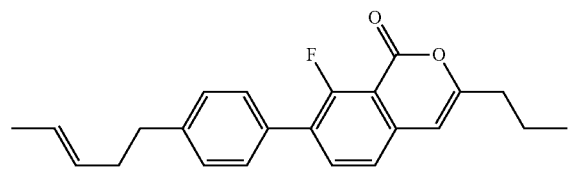 [SMILES: C/C=C/CCc1ccc(-c2ccc3cc(CCC)oc(=O)c3c2F)cc1] |
| 513 | 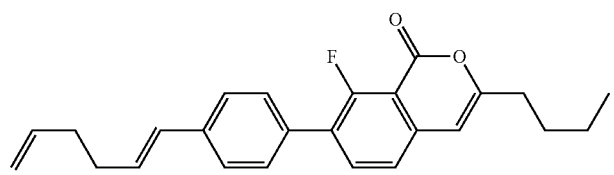 [SMILES: C=CCC/C=C/c1ccc(-c2ccc3cc(CCCC)oc(=O)c3c2F)cc1] |
| 514 | 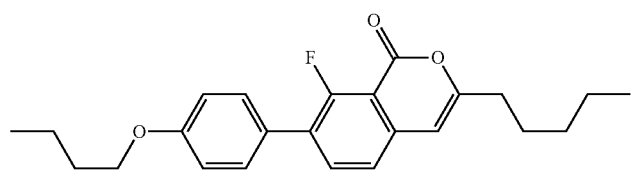 [SMILES: CCCCCc1cc2ccc(-c3ccc(OCCCC)cc3)c(F)c2c(=O)o1] |
| 515 | 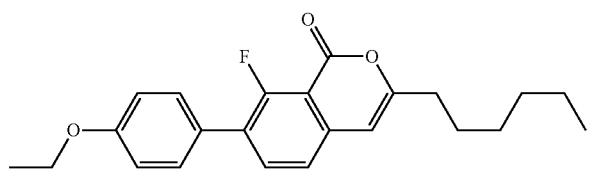 [SMILES: CCCCCCc1cc2ccc(-c3ccc(OCC)cc3)c(F)c2c(=O)o1] |
| 516 | 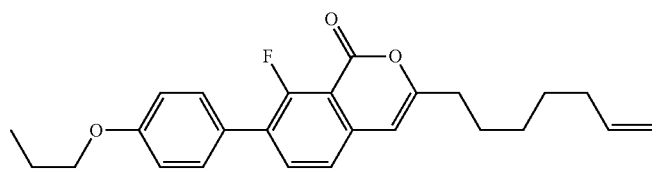 [SMILES: C=CCCCCCc1cc2ccc(-c3ccc(OCCC)cc3)c(F)c2c(=O)o1] |
| 517 | 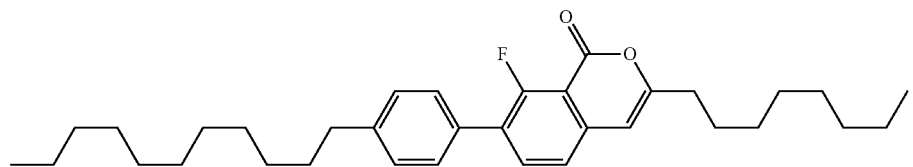 [SMILES: CCCCCCCCCCCc1ccc(-c2ccc3cc(CCCCCCCC)oc(=O)c3c2F)cc1] |
| 518 | 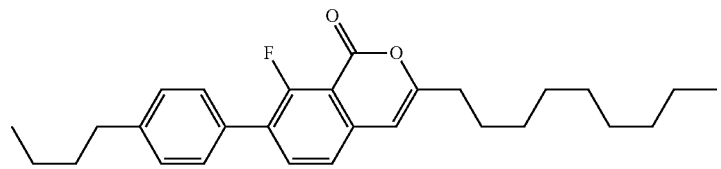 [SMILES: CCCCCCCCCc1cc2ccc(-c3ccc(CCCC)cc3)c(F)c2c(=O)o1] |
| 519 | 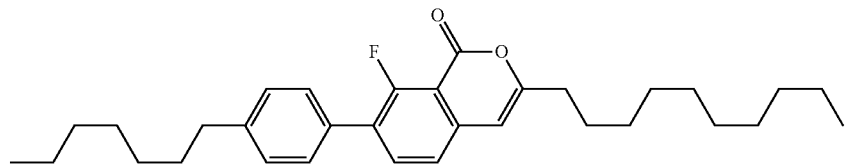 |

| No. |
|---|
| 520 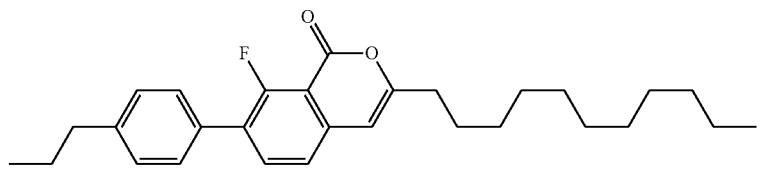 [SMILES: CCCCCCCCCCCc1cc2ccc(-c3ccc(CCC)cc3)c(F)c2c(=O)o1] |
| 521 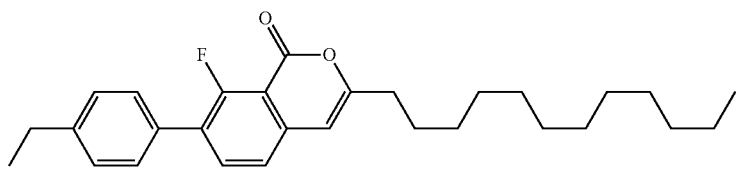 |
| 522 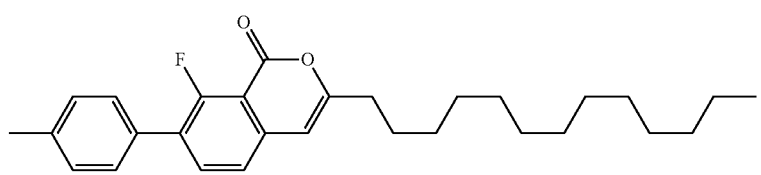 |
| 523 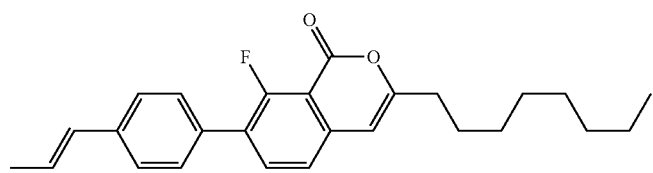 [SMILES: C/C=C/c1ccc(-c2ccc3cc(CCCCCCCC)oc(=O)c3c2F)cc1] |
| 524 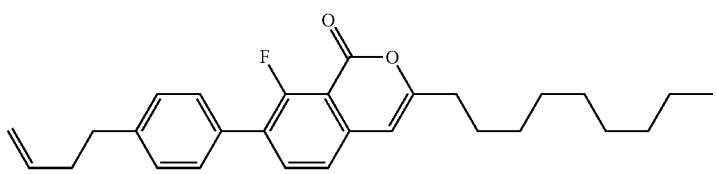 [SMILES: C=CCCc1ccc(-c2ccc3cc(CCCCCCCCC)oc(=O)c3c2F)cc1] |
| 525 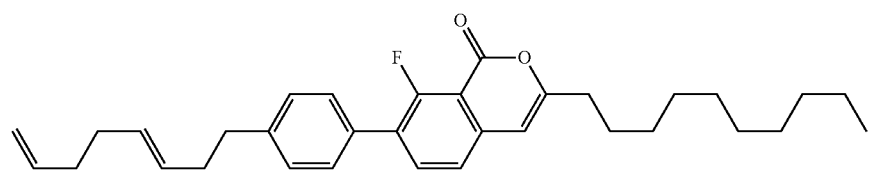 [SMILES: C=CCC/C=C/CCc1ccc(-c2ccc3cc(CCCCCCCCCC)oc(=O)c3c2F)cc1] |
| 526 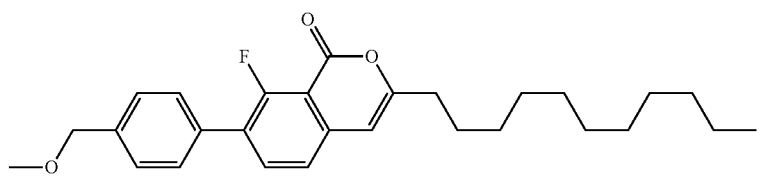 [SMILES: CCCCCCCCCCCc1cc2ccc(-c3ccc(COC)cc3)c(F)c2c(=O)o1] |
| 527 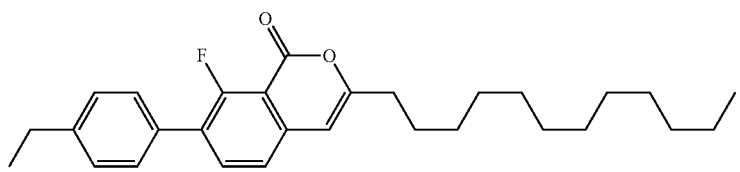 [SMILES: CCCCCCCCCCCCc1cc2ccc(-c3ccc(CC)cc3)c(F)c2c(=O)o1] |
| 528 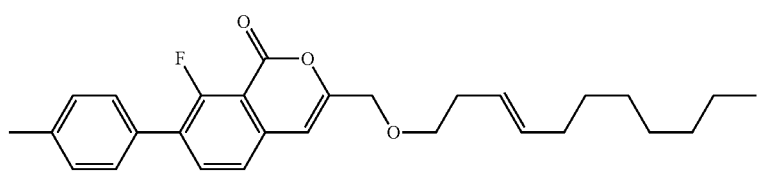 |

| No. |
|---|
| 529 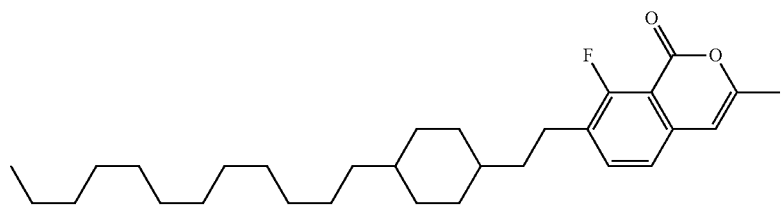 |
| 530 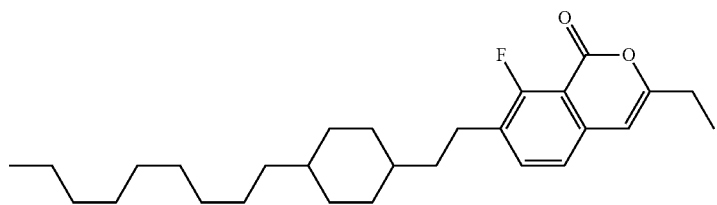 [SMILES: CCCCCCCCCC1CCC(CCc2ccc3cc(CC)oc(=O)c3c2F)CC1] |
| 531 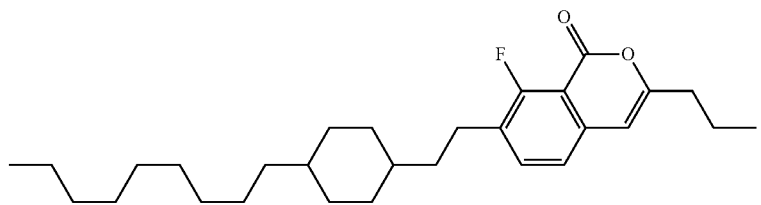 |
| 532 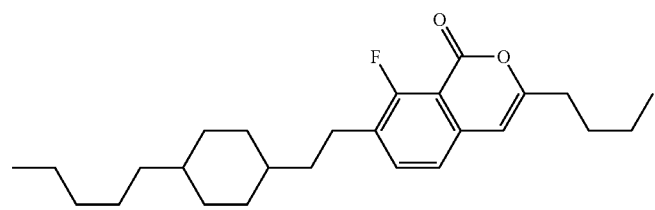 |
| 533 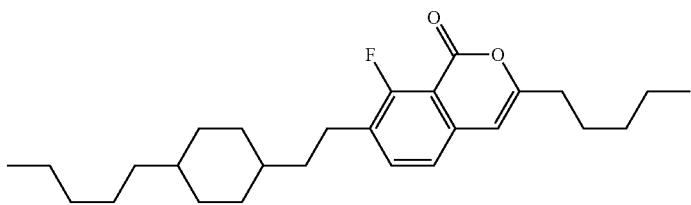 [SMILES: CCCCCc1cc2ccc(CCC3CCC(CCCCC)CC3)c(F)c2c(=O)o1] |
| 534 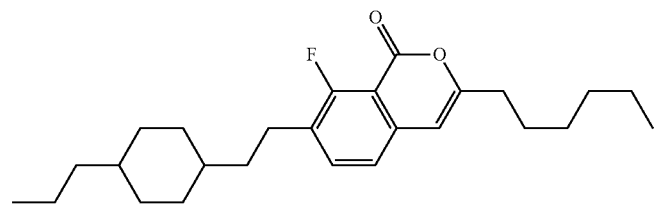 [SMILES: CCCCCCc1cc2ccc(CCC3CCC(CCC)CC3)c(F)c2c(=O)o1] |
| 535 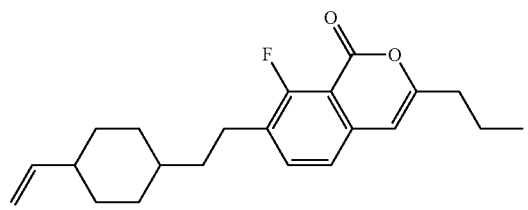 [SMILES: C=CC1CCC(CCc2ccc3cc(CCC)oc(=O)c3c2F)CC1] |

| No. |
|---|
| 536 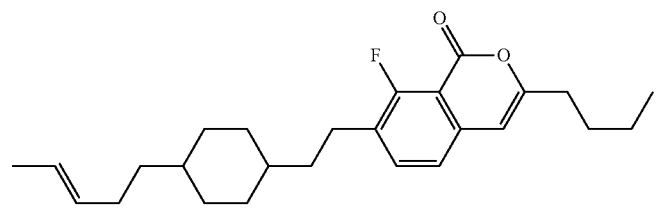 |
| 537 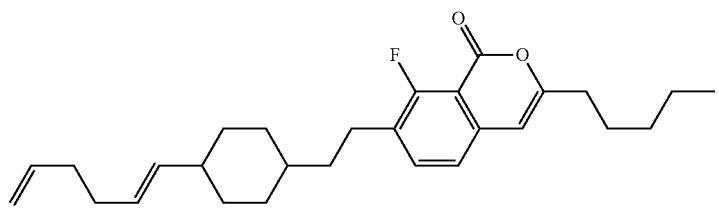 [SMILES: C=CCC/C=C/C1CCC(CCc2ccc3cc(CCCCC)oc(=O)c3c2F)CC1] |
| 538 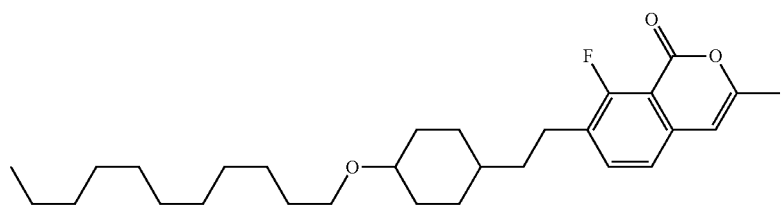 [SMILES: CCCCCCCCCCCOC1CCC(CCc2ccc3cc(C)oc(=O)c3c2F)CC1] |
| 539 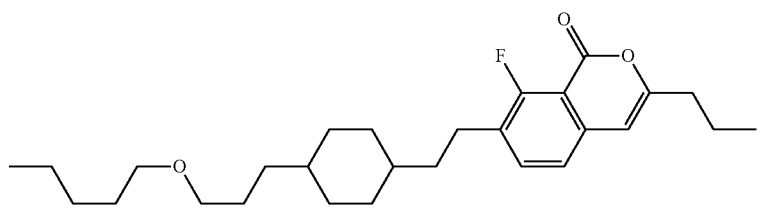 |
| 540 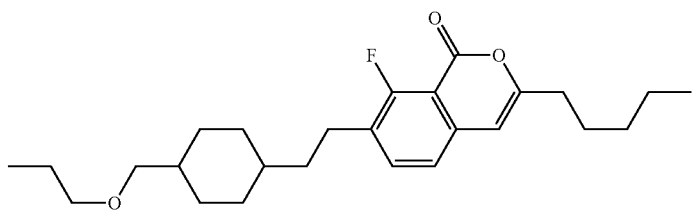 [SMILES: CCCCCc1cc2ccc(CCC3CCC(COCCC)CC3)c(F)c2c(=O)o1] |
| 541 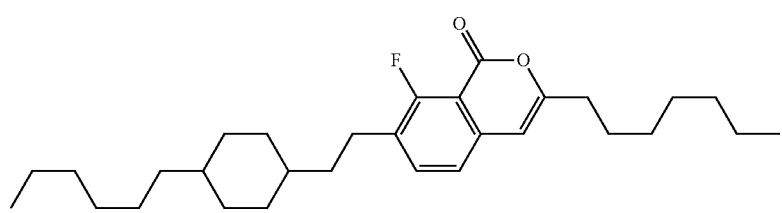 [SMILES: CCCCCCCc1cc2ccc(CCC3CCC(CCCCCC)CC3)c(F)c2c(=O)o1] |
| 542 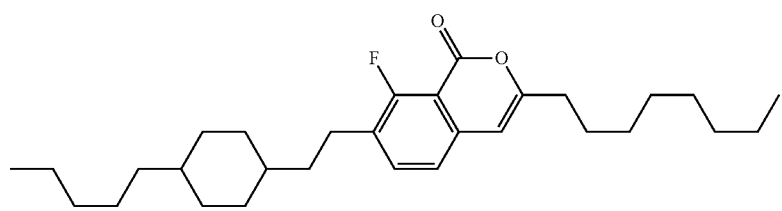 [SMILES: CCCCCCCCc1cc2ccc(CCC3CCC(CCCCC)CC3)c(F)c2c(=O)o1] |

| No. |
|---|
| 543 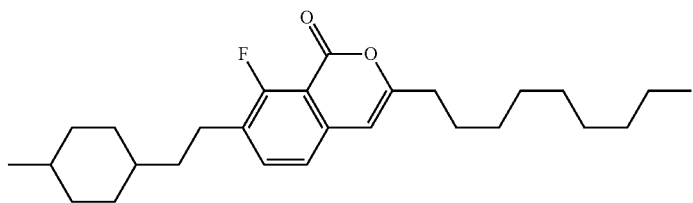 [SMILES: CCCCCCCCCc1cc2ccc(CCC3CCC(C)CC3)c(F)c2c(=O)o1] |
| 544 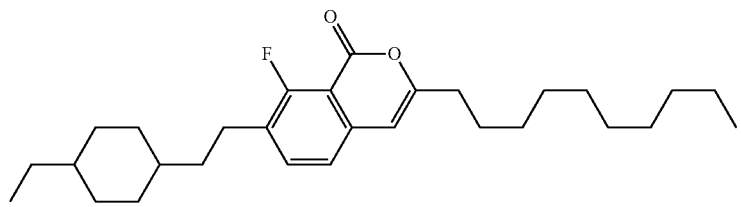 [SMILES: CCCCCCCCCCc1cc2ccc(CCC3CCC(CC)CC3)c(F)c2c(=O)o1] |
| 545 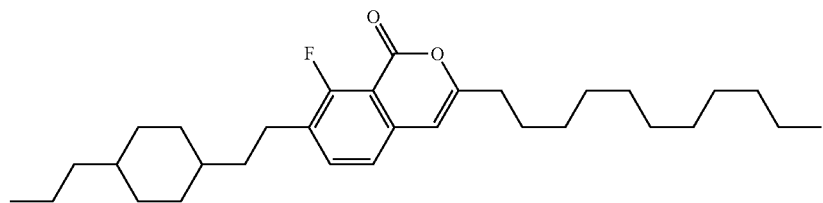 [SMILES: CCCCCCCCCCCc1cc2ccc(CCC3CCC(CCC)CC3)c(F)c2c(=O)o1] |
| 546 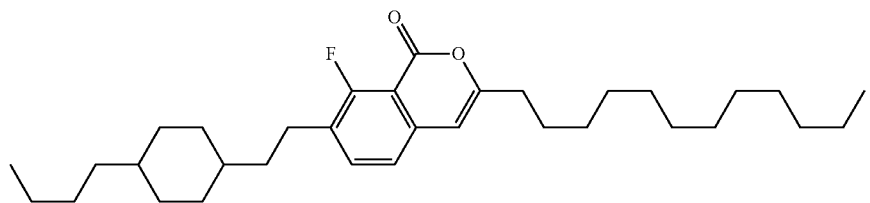 [SMILES: CCCCCCCCCCCCc1cc2ccc(CCC3CCC(CCCC)CC3)c(F)c2c(=O)o1] |
| 547 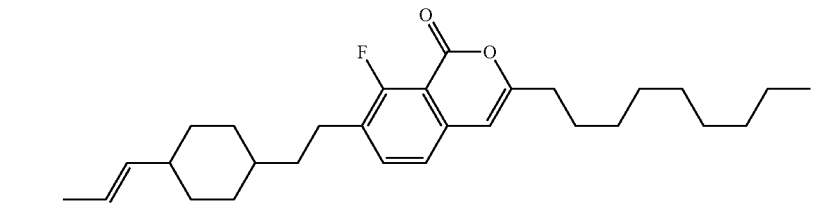 |
| 548 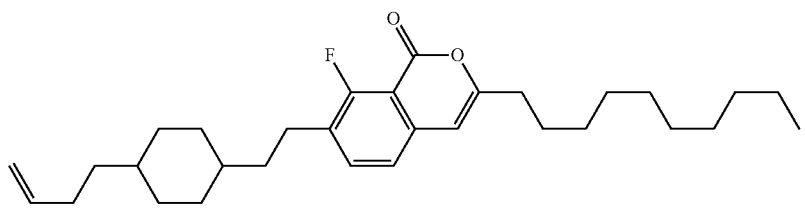 [SMILES: C=CCCC1CCC(CCc2ccc3cc(CCCCCCCCCC)oc(=O)c3c2F)CC1] |
| 549 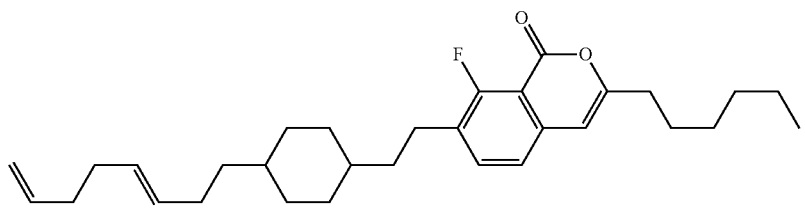 [SMILES: C=CCC/C=C/CCC1CCC(CCc2ccc3cc(CCCCCC)oc(=O)c3c2F)CC1] |

| No. |
|---|
| 550 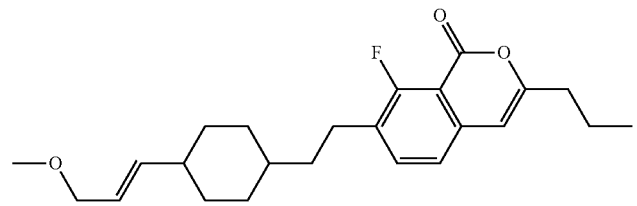 [SMILES: CCCc1cc2ccc(CCC3CCC(/C=C/COC)CC3)c(F)c2c(=O)o1] |
| 551 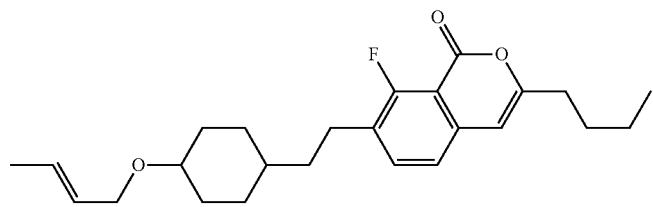 [SMILES: C/C=C/COC1CCC(CCc2ccc3cc(CCCC)oc(=O)c3c2F)CC1] |
| 552 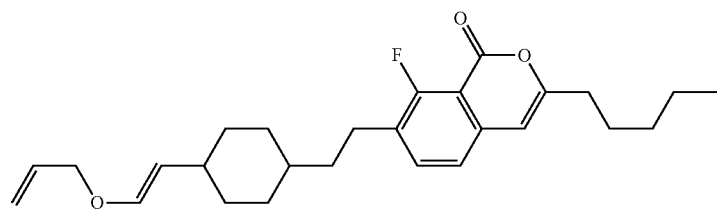 [SMILES: C=CCO/C=C/C1CCC(CCc2ccc3cc(CCCCC)oc(=O)c3c2F)CC1] |
| 553 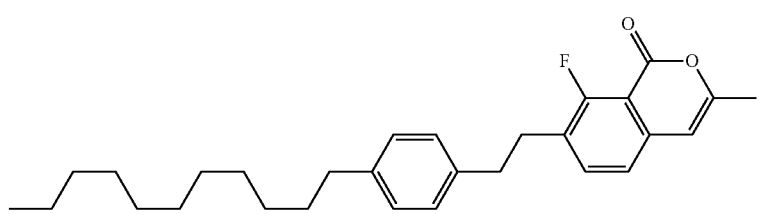 [SMILES: CCCCCCCCCCCc1ccc(CCc2ccc3cc(C)oc(=O)c3c2F)cc1] |
| 554 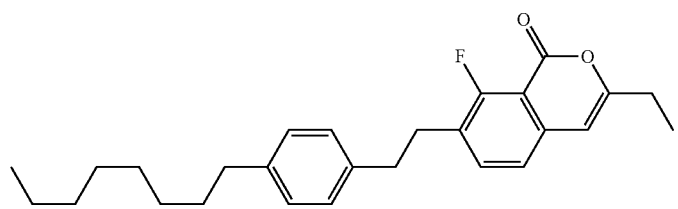 [SMILES: CCCCCCCCc1ccc(CCc2ccc3cc(CC)oc(=O)c3c2F)cc1] |
| 555 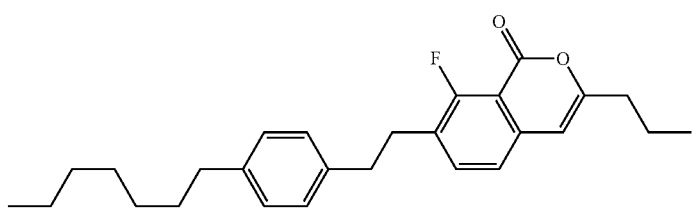 [SMILES: CCCCCCCc1ccc(CCc2ccc3cc(CCC)oc(=O)c3c2F)cc1] |
| 556 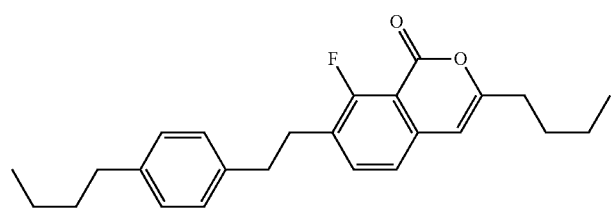 [SMILES: CCCCc1ccc(CCc2ccc3cc(CCCC)oc(=O)c3c2F)cc1] |

| No. |
|---|
| 557 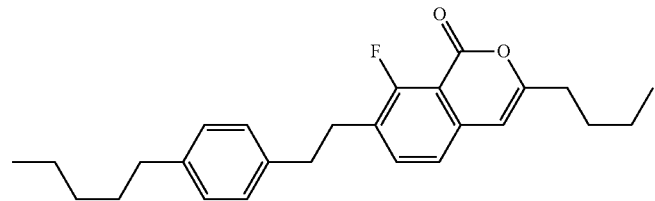 [SMILES: CCCCCc1ccc(CCc2ccc3cc(CCCC)oc(=O)c3c2F)cc1] |
| 558 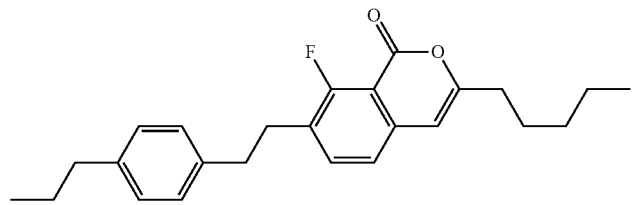 [SMILES: CCCCCc1cc2ccc(CCc3ccc(CCC)cc3)c(F)c2c(=O)o1] |
| 559 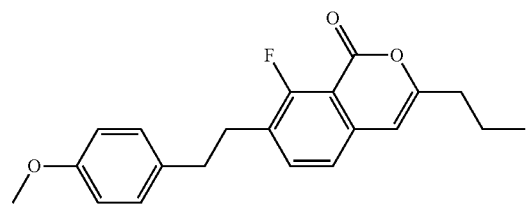 [SMILES: CCCc1cc2ccc(CCc3ccc(OC)cc3)c(F)c2c(=O)o1] |
| 560 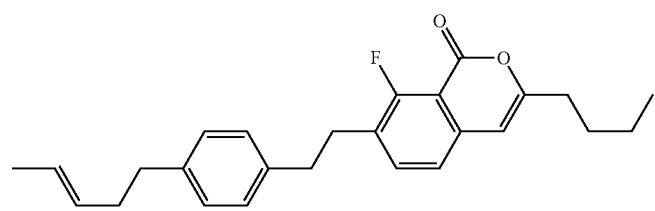 |
| 561 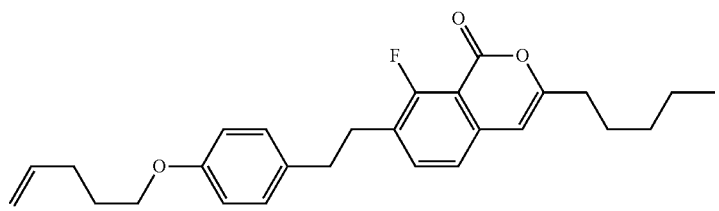 [SMILES: C=CCCCOc1ccc(CCc2ccc3cc(CCCCC)oc(=O)c3c2F)cc1] |
| 562 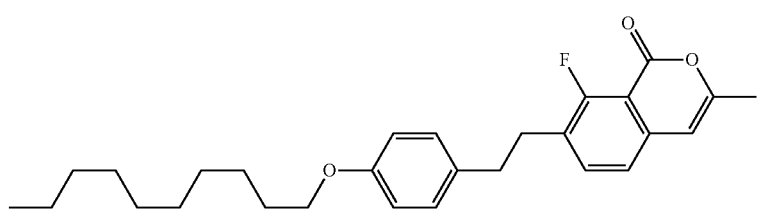 |
| 563 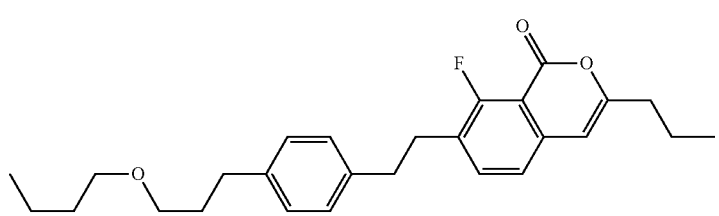 [SMILES: CCCCOCCCc1ccc(CCc2ccc3cc(CCC)oc(=O)c3c2F)cc1] |

| No. |
|---|
| 564 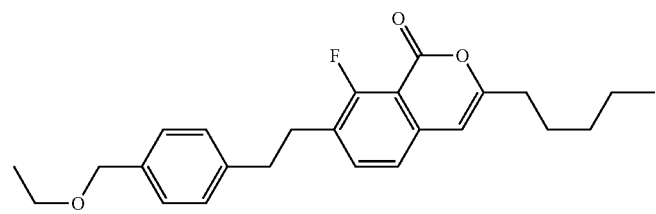 [SMILES: CCCCCc1cc2ccc(CCc3ccc(COCC)cc3)c(F)c2c(=O)o1] |
| 565 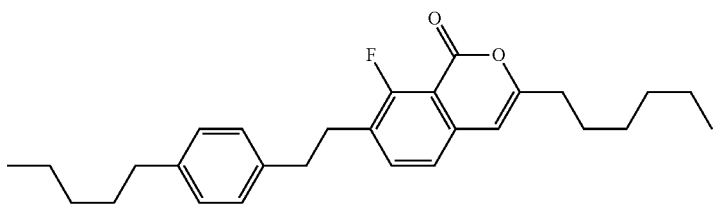 [SMILES: CCCCCCc1cc2ccc(CCc3ccc(CCCCC)cc3)c(F)c2c(=O)o1] |
| 566 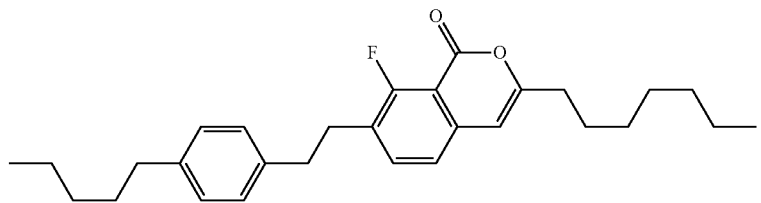 [SMILES: CCCCCCCc1cc2ccc(CCc3ccc(CCCCC)cc3)c(F)c2c(=O)o1] |
| 567 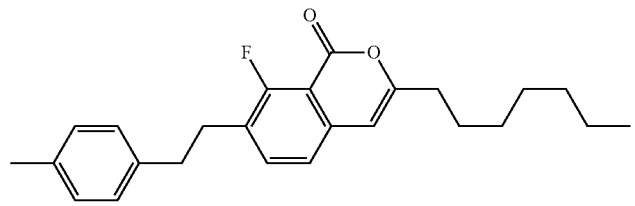 [SMILES: CCCCCCCc1cc2ccc(CCc3ccc(C)cc3)c(F)c2c(=O)o1] |
| 568 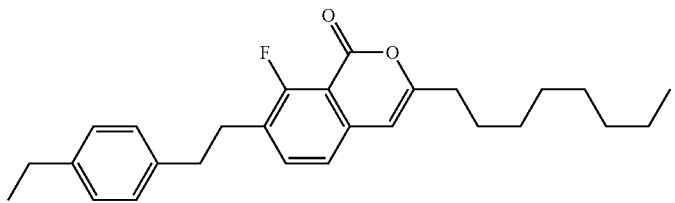 [SMILES: CCCCCCCCc1cc2ccc(CCc3ccc(CC)cc3)c(F)c2c(=O)o1] |
| 569 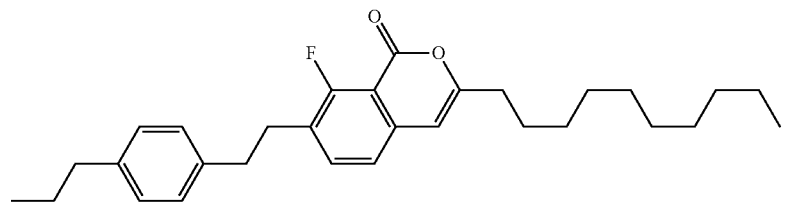 [SMILES: CCCCCCCCCCc1cc2ccc(CCc3ccc(CCC)cc3)c(F)c2c(=O)o1] |
| 570 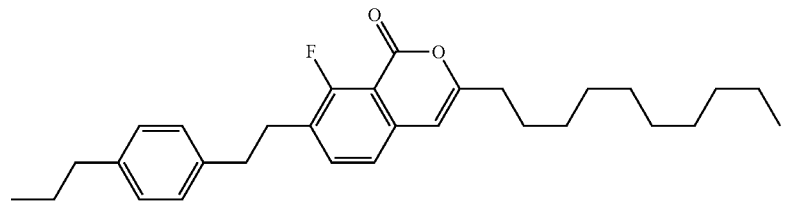 |

-continued
| No. |
|---|
| 571 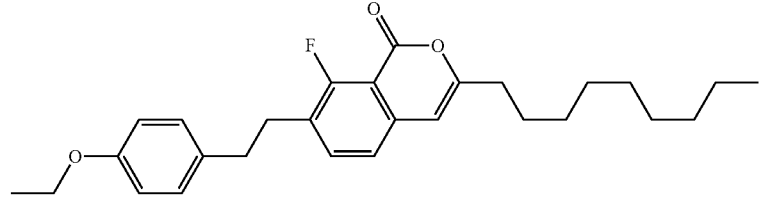 |
| 572 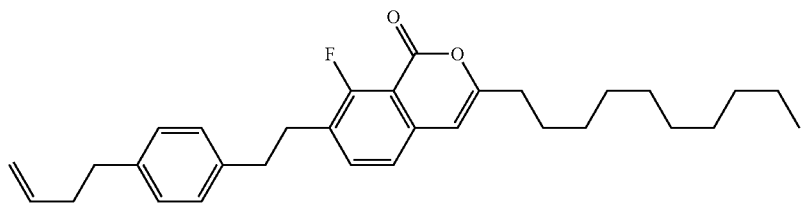 |
| 573 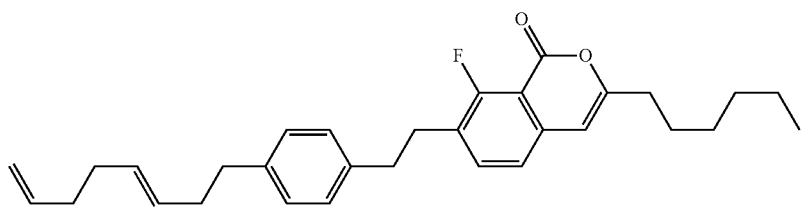 |
| 574 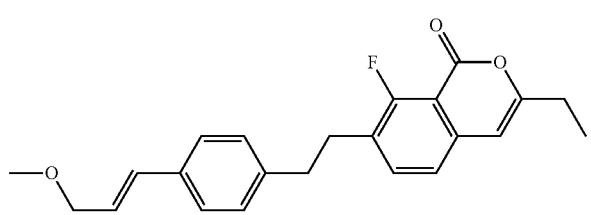 [SMILES: CCc1cc2ccc(CCc3ccc(/C=C/COC)cc3)c(F)c2c(=O)o1] |
| 575 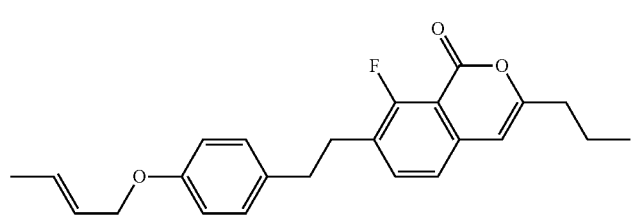 |
| 576 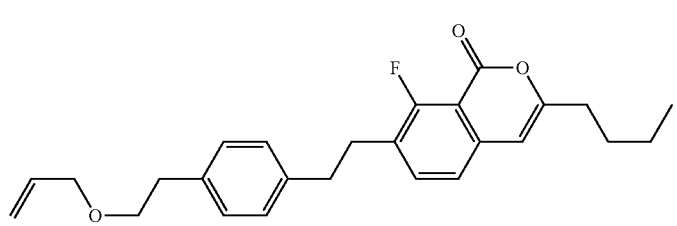 [SMILES: C=CCOCCc1ccc(CCc2ccc3cc(CCCC)oc(=O)c3c2F)cc1] |
| 577 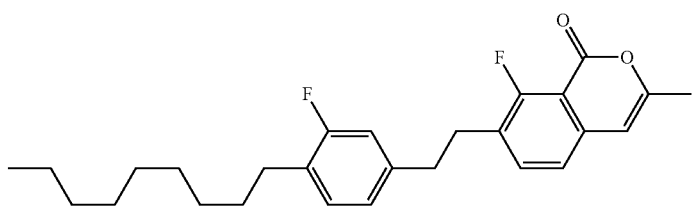 [SMILES: CCCCCCCCCc1ccc(CCc2ccc3cc(C)oc(=O)c3c2F)cc1F] |

-continued
| No. |
| --- |
578
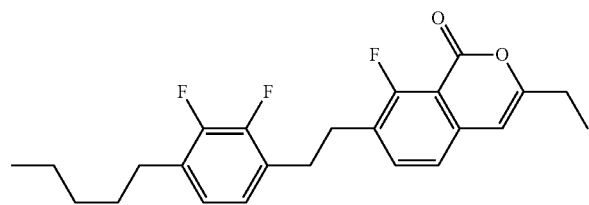
579
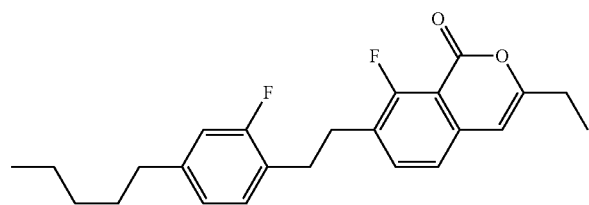
580
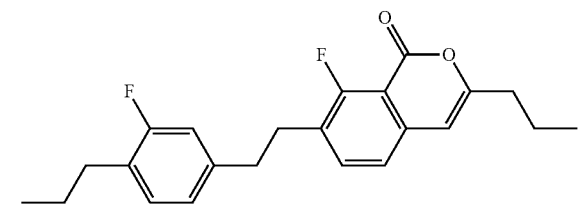 [SMILES: CCCc1cc2ccc(CCc3ccc(CCC)c(F)c3)c(F)c2c(=O)o1]
581
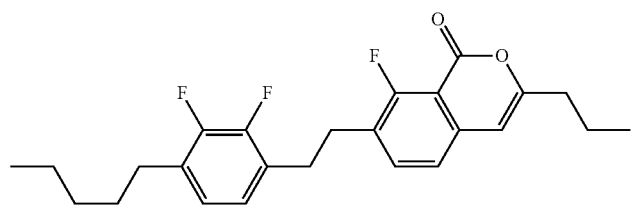
582
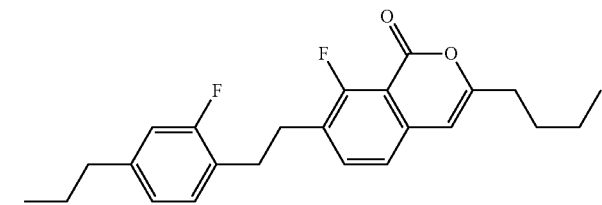
583
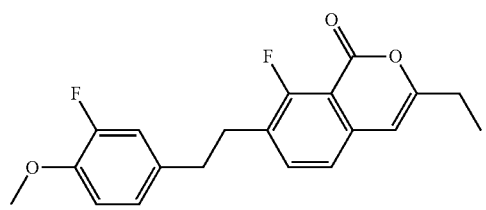 [SMILES: CCc1cc2ccc(CCc3ccc(OC)c(F)c3)c(F)c2c(=O)o1]
584
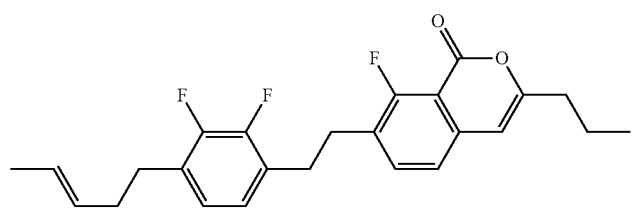 [SMILES: C/C=C/CCc1ccc(CCc2ccc3cc(CCC)oc(=O)c3c2F)c(F)c1F]

| No. | |
|---|---|
| 585 | 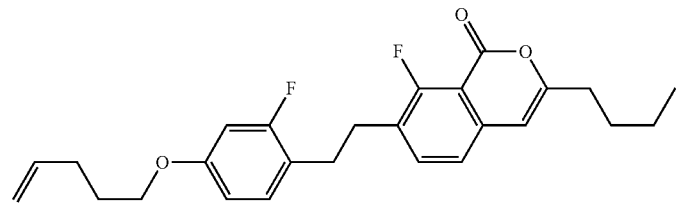 [SMILES: C=CCCCOc1ccc(CCc2ccc3cc(CCCC)oc(=O)c3c2F)c(F)c1] |
| 586 | 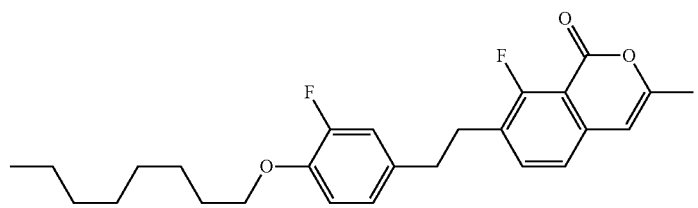 [SMILES: CCCCCCCCOc1ccc(CCc2ccc3cc(C)oc(=O)c3c2F)cc1F] |
| 587 | 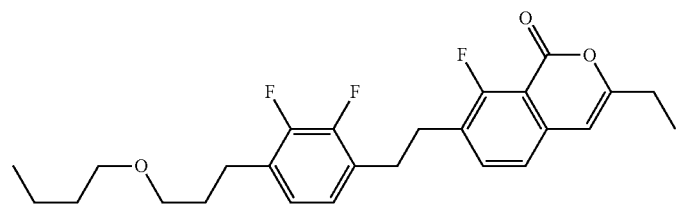 [SMILES: CCCCOCCCc1ccc(CCc2ccc3cc(CC)oc(=O)c3c2F)c(F)c1F] |
| 588 | 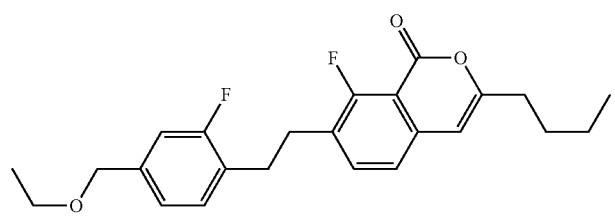 [SMILES: CCCCc1cc2ccc(CCc3ccc(COCC)cc3F)c(F)c2c(=O)o1] |
| 589 | 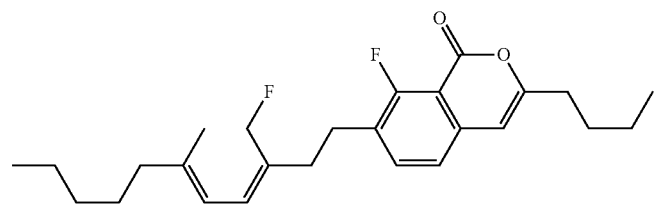 [SMILES: CCCCC/C(C)=C/C=C(\CF)CCc1ccc2cc(CCCC)oc(=O)c2c1F] |
| 590 | 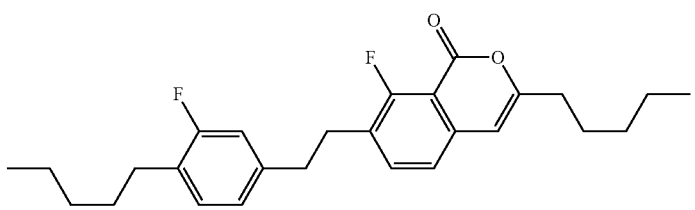 [SMILES: CCCCCc1cc2ccc(CCc3ccc(CCCCC)c(F)c3)c(F)c2c(=O)o1] |
| 591 | 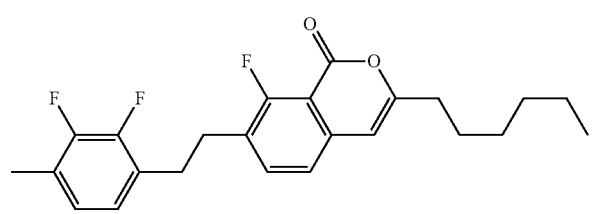 [SMILES: CCCCCCc1cc2ccc(CCc3ccc(C)c(F)c3F)c(F)c2c(=O)o1] |

-continued
| No. |
|---|
| 592 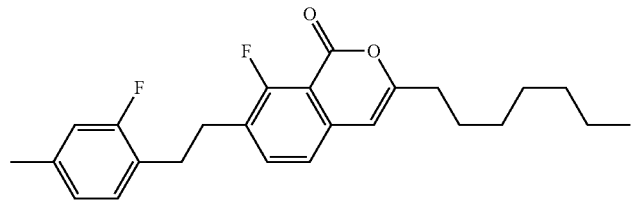 [SMILES: CCCCCCCc1cc2ccc(CCc3ccc(C)cc3F)c(F)c2c(=O)o1] |
| 593 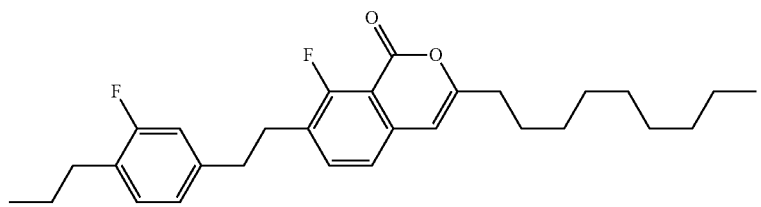 [SMILES: CCCCCCCCCc1cc2ccc(CCc3ccc(CCC)c(F)c3)c(F)c2c(=O)o1] |
| 594 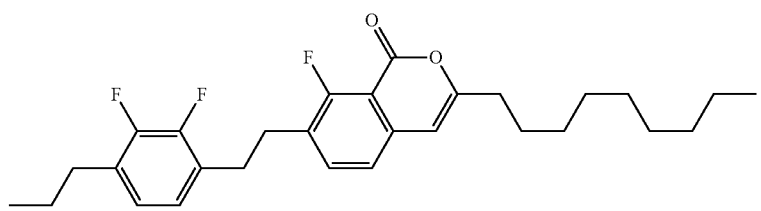 [SMILES: CCCCCCCCCc1cc2ccc(CCc3ccc(CCC)c(F)c3F)c(F)c2c(=O)o1] |
| 595 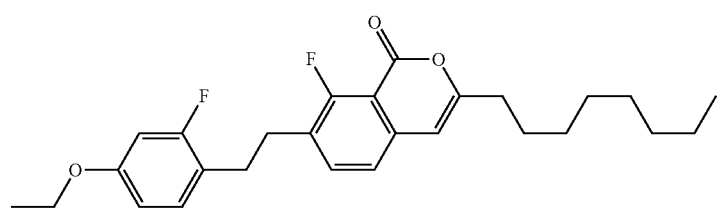 [SMILES: CCCCCCCCc1cc2ccc(CCc3ccc(OCC)cc3F)c(F)c2c(=O)o1] |
| 596 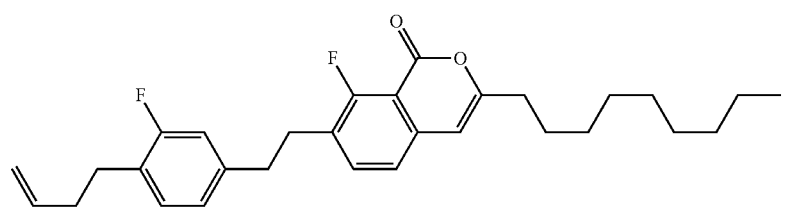 [SMILES: C=CCCc1ccc(CCc2ccc3cc(CCCCCCCCC)oc(=O)c3c2F)cc1F] |
| 597 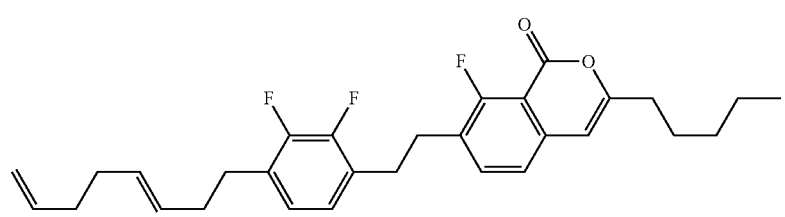 |
| 598 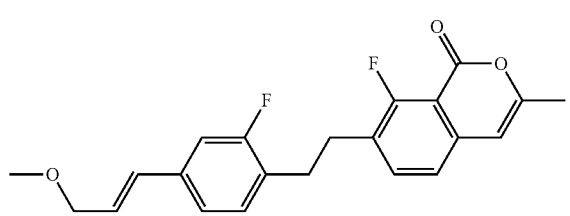 |

US 10,428,273 B2
247 248
-continued
| No. |
|---|
| 599 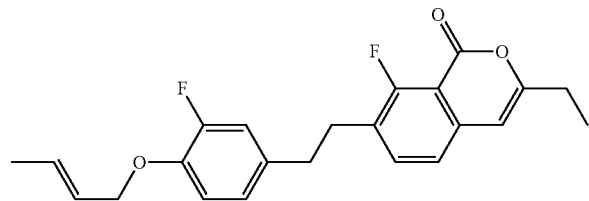 [SMILES: C/C=C/COc1ccc(CCc2ccc3cc(CC)oc(=O)c3c2F)cc1F] |
| 600 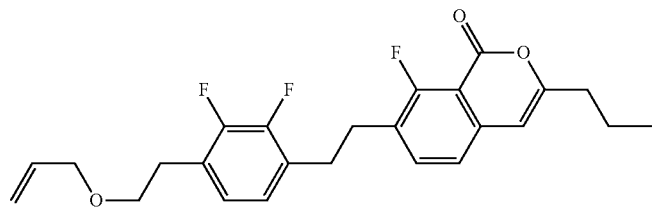 [SMILES: C=CCOCCc1ccc(CCc2ccc3cc(CCC)oc(=O)c3c2F)c(F)c1F] |
| 601 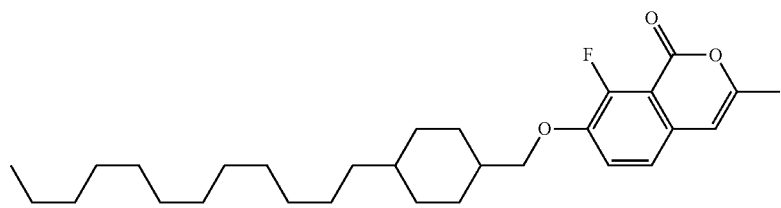 |
| 602 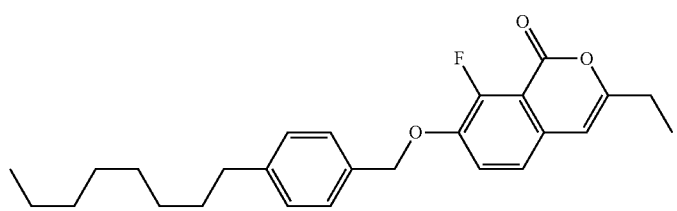 [SMILES: CCCCCCCCc1ccc(COc2ccc3cc(CC)oc(=O)c3c2F)cc1] |
| 603 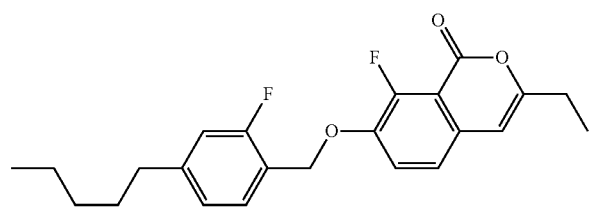 |
| 604 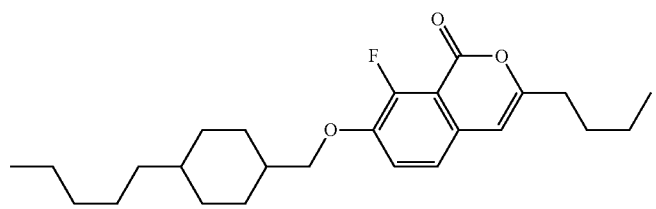 |
| 605 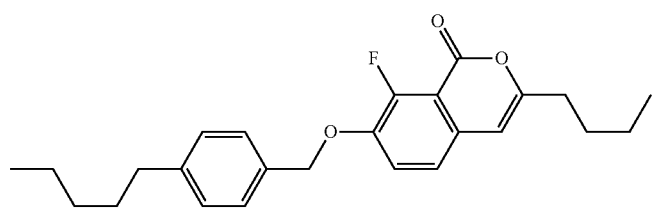 |

| No. |
|---|
| 606 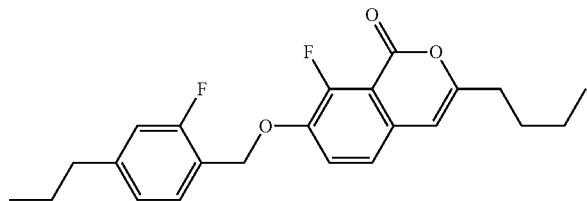 |
| 607 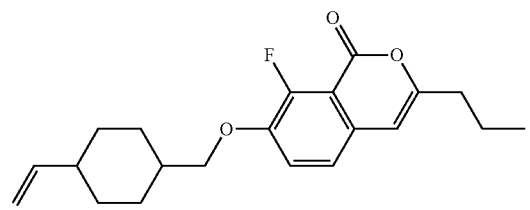 |
| 608 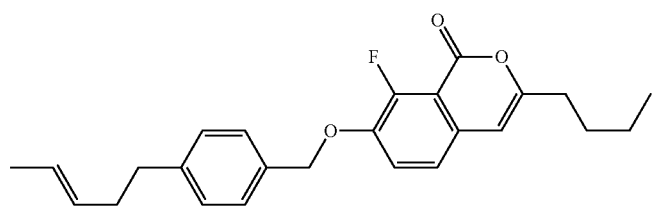 |
| 609 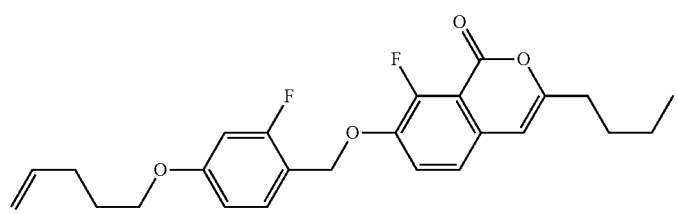 |
| 610 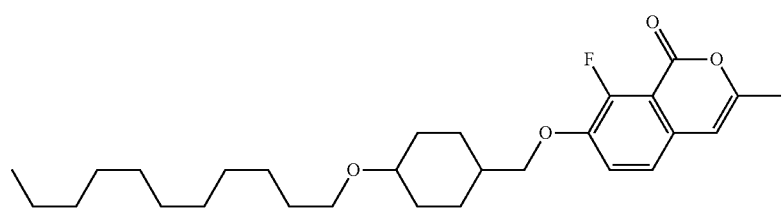 |
| 611 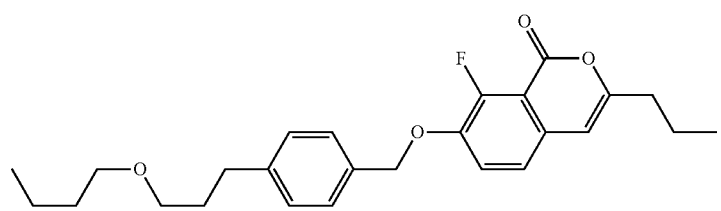 |
| 612 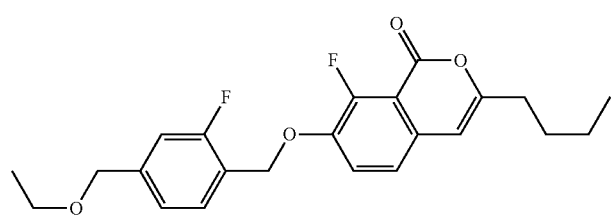 |

US 10,428,273 B2
251                                                                                   252
-continued
| No. |
|---|
| 612 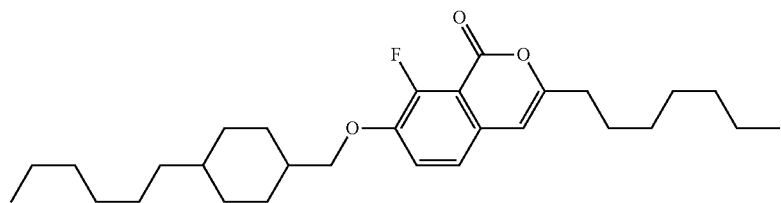 |
| 614 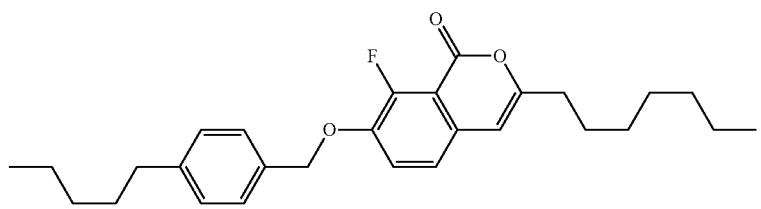 [SMILES: CCCCCCCc1cc2ccc(OCc3ccc(CCCCC)cc3)c(F)c2c(=O)o1] |
| 615 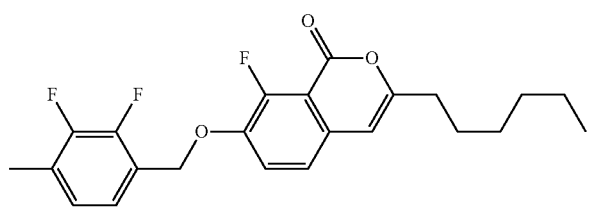 [SMILES: CCCCCCc1cc2ccc(OCc3ccc(C)c(F)c3F)c(F)c2c(=O)o1] |
| 616 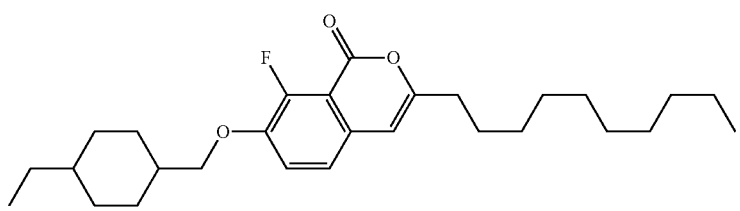 [SMILES: CCCCCCCCCCc1cc2ccc(OCC3CCC(CC)CC3)c(F)c2c(=O)o1] |
| 617 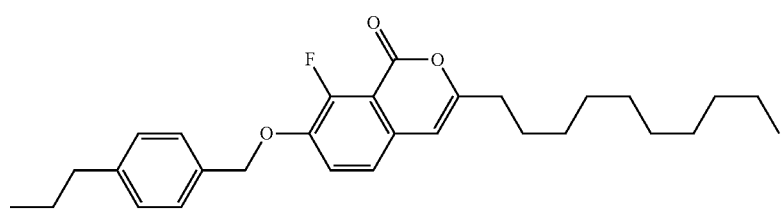 |
| 618 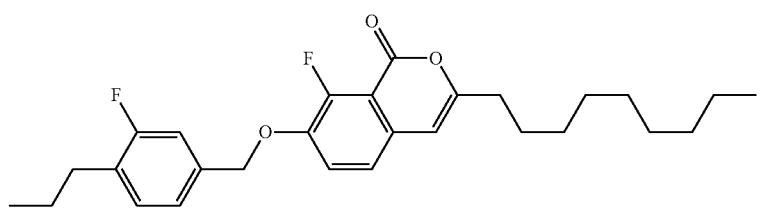 |
| 619 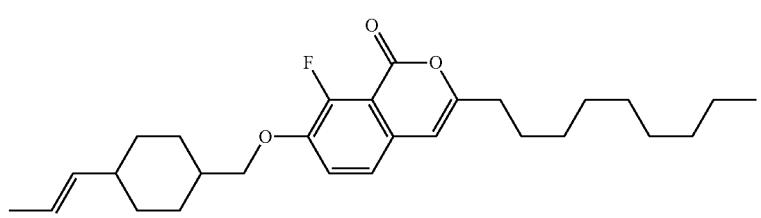 [SMILES: C/C=C/C1CCC(COc2ccc3cc(CCCCCCCCC)oc(=O)c3c2F)CC1] |

| No. |
|---|
| 620 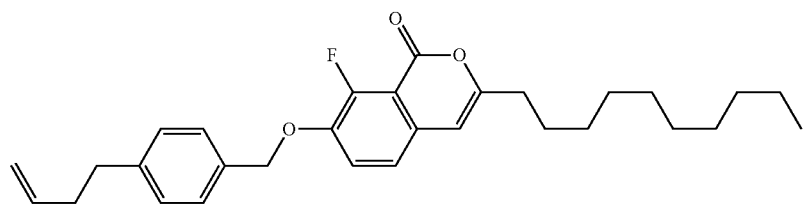 [SMILES: C=CCCc1ccc(COc2ccc3cc(CCCCCCCCCC)oc(=O)c3c2F)cc1] |
| 621 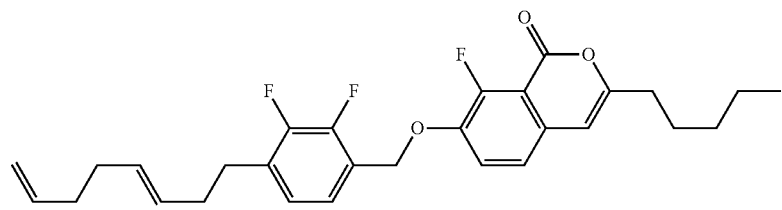 |
| 622 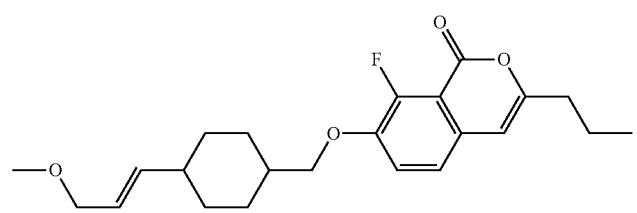 |
| 623 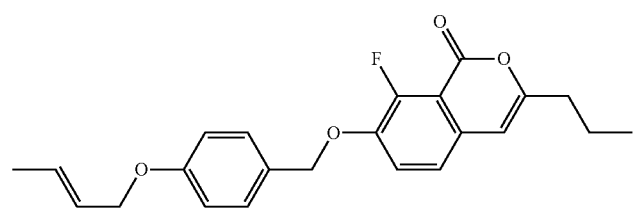 |
| 624 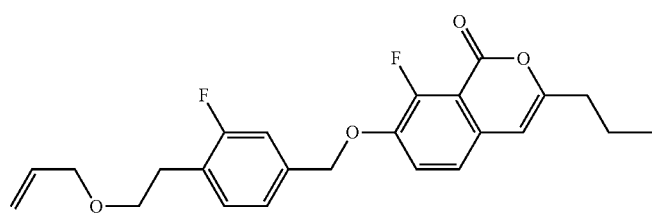 [SMILES: C=CCOCCc1ccc(COc2ccc3cc(CCC)oc(=O)c3c2F)cc1F] |
| 625 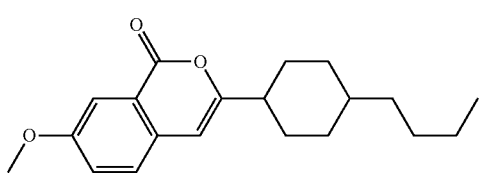 [SMILES: CCCCC1CCC(c2cc3ccc(OC)cc3c(=O)o2)CC1] |
| 626 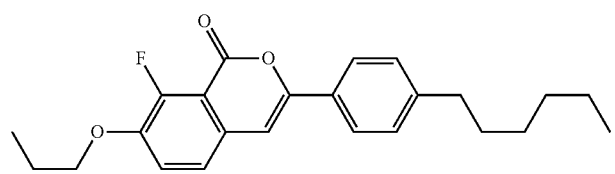 |
| 627 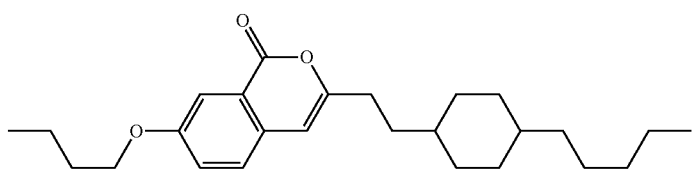 |

-continued
| No. | |
|---|---|
| 628 | 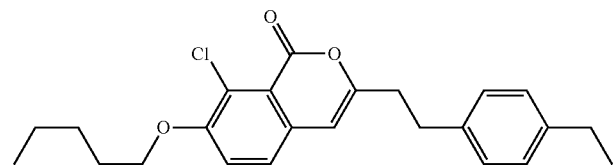 |
| 629 | 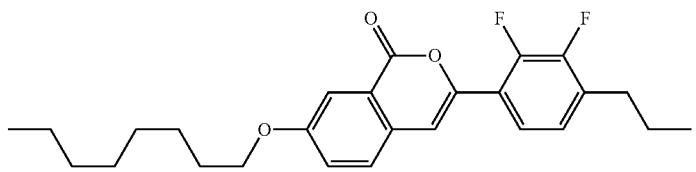 [SMILES: CCCCCCCCOc1ccc2cc(-c3ccc(CCC)c(F)c3F)oc(=O)c2c1] |
| 630 | 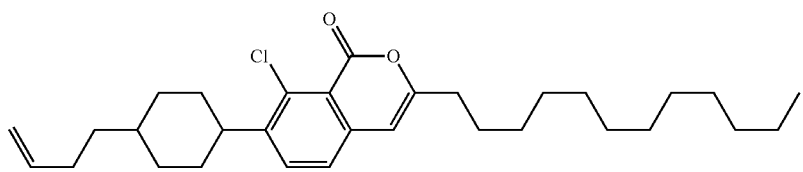 [SMILES: C=CCCC1CCC(c2ccc3cc(CCCCCCCCCCCC)oc(=O)c3c2Cl)CC1] |
| 631 | 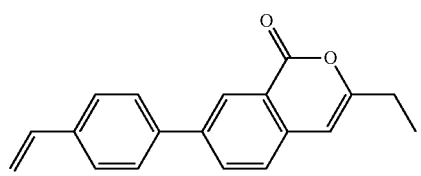 [SMILES: C=Cc1ccc(-c2ccc3cc(CC)oc(=O)c3c2)cc1] |
| 632 | 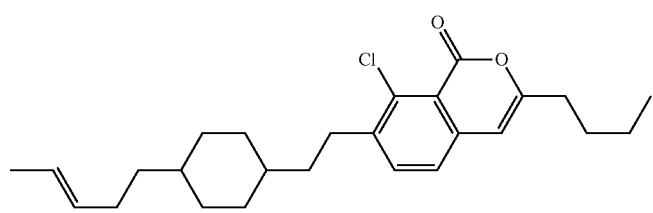 |
| 633 | 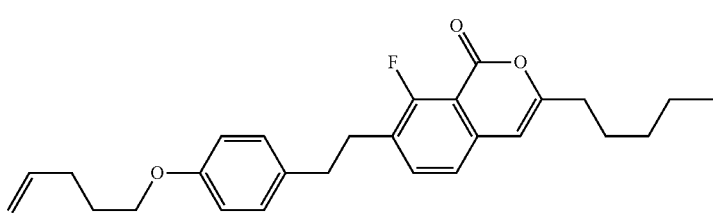 [SMILES: C=CCCCOc1ccc(CCc2ccc3cc(CCCCC)oc(=O)c3c2F)cc1] |
| 634 | 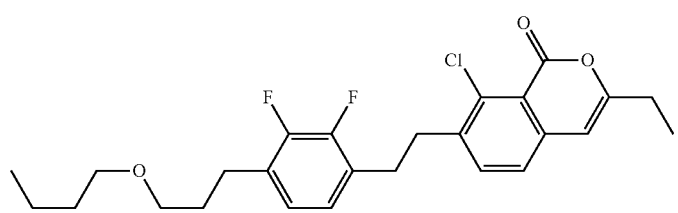 |
| 635 | 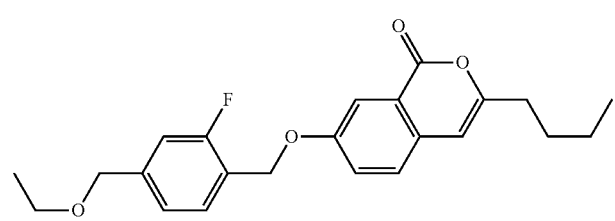 [SMILES: CCCCc1cc2ccc(OCc3ccc(COCC)cc3F)cc2c(=O)o1] |

| No. | |
|---|---|
| 636 | 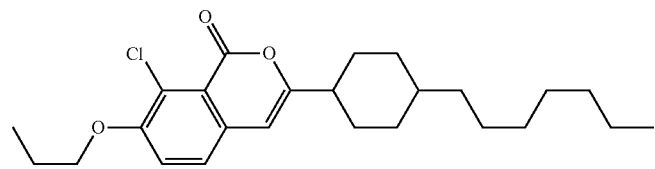 |
| 637 | 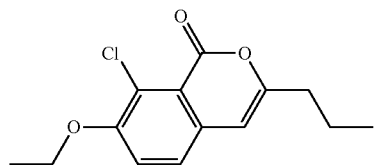 |
| 638 | 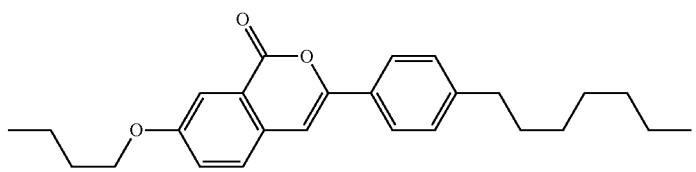 |
| 639 | 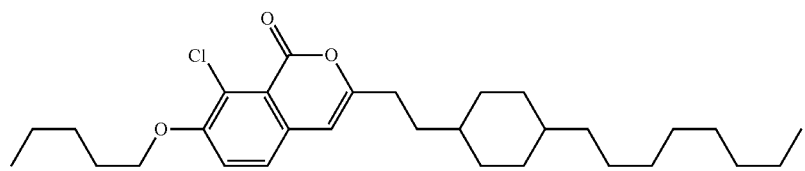 |
| 640 | 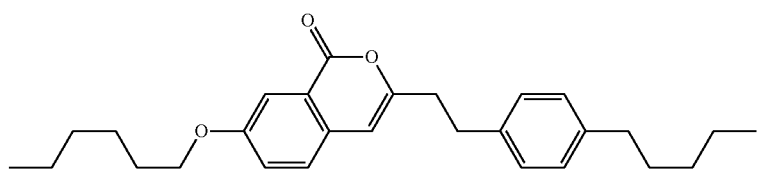 |
| 641 | 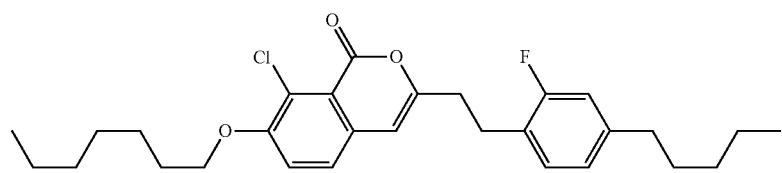 |
| 642 | 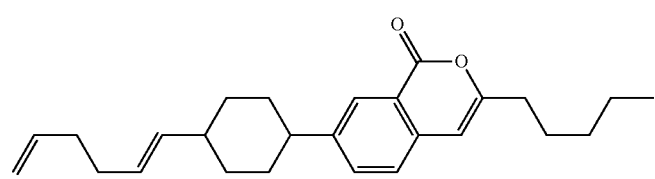 |
| 643 | 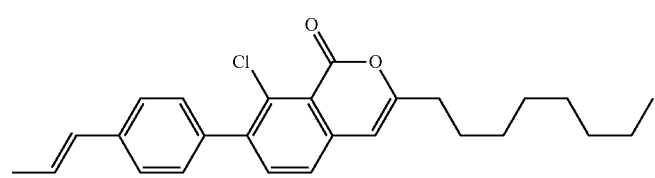 |

| No. |
|---|
| 644 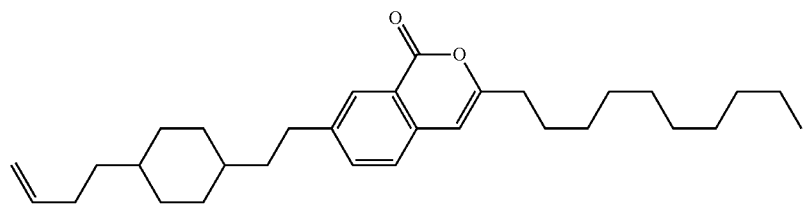 |
| 645 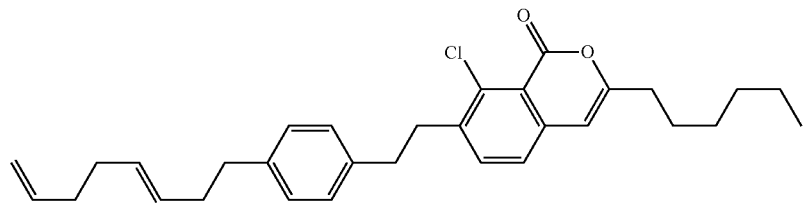 [SMILES: C=CCC/C=C/CCc1ccc(CCc2ccc3cc(CCCCCC)oc(=O)c3c2Cl)cc1] |
| 646 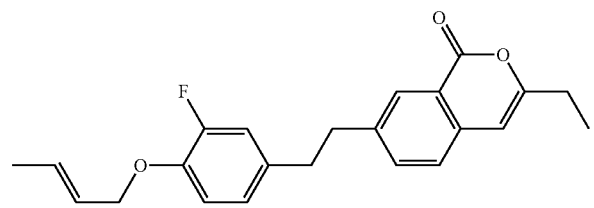 [SMILES: C/C=C/COc1ccc(CCc2ccc3cc(CC)oc(=O)c3c2)cc1F] |
| 647 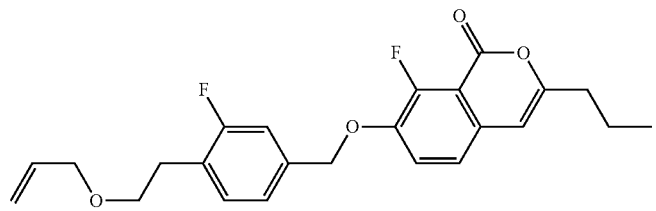 |
| 648 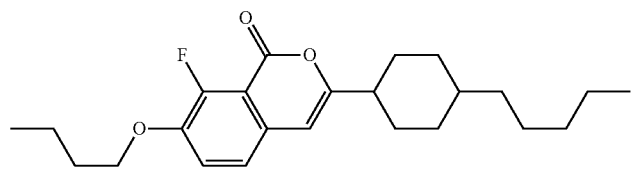 |
| 649 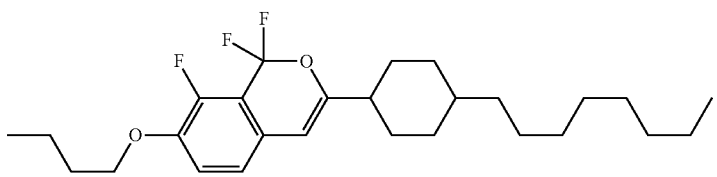 [SMILES: CCCCCCCCC1CCC(C2=Cc3ccc(OCCCC)c(F)c3C(F)(F)O2)CC1] |
| 650 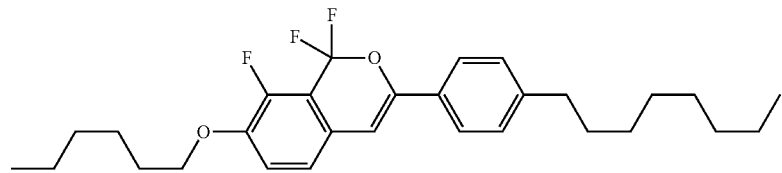 [SMILES: CCCCCCCCc1ccc(C2=Cc3ccc(OCCCCCC)c(F)c3C(F)(F)O2)cc1] |
| 651 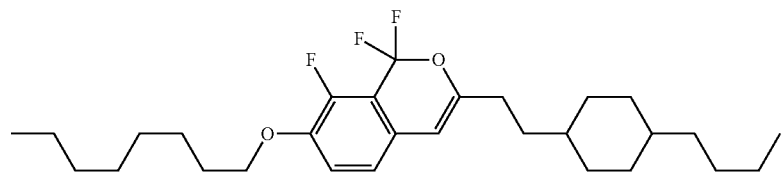 [SMILES: CCCCCCCCOc1ccc2c(c1F)C(F)(F)OC(CCC1CCC(CCCC)CC1)=C2] |

-continued
| No. | |
|---|---|
| 652 | 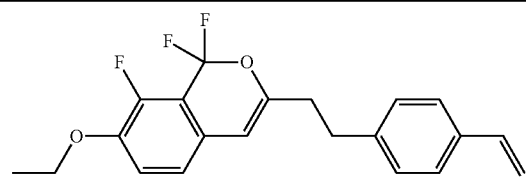 |
| 653 | 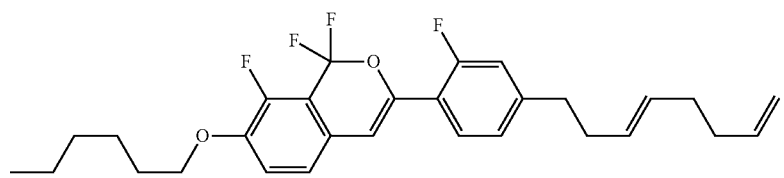 [SMILES: C=CCC/C=C/CCc1ccc(C2=Cc3ccc(OCCCCCC)c(F)c3C(F)(F)O2)c(F)c1] |
| 654 | 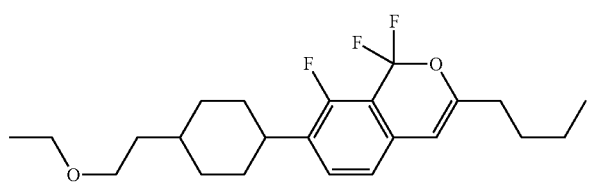 [SMILES: CCCCC1=Cc2ccc(C3CCC(CCOCC)CC3)c(F)c2C(F)(F)O1] |
| 655 | 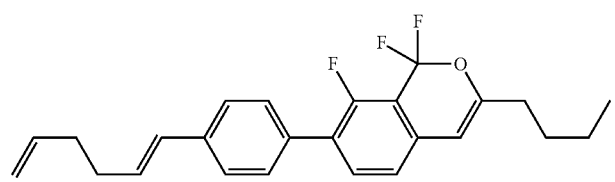 |
| 656 | 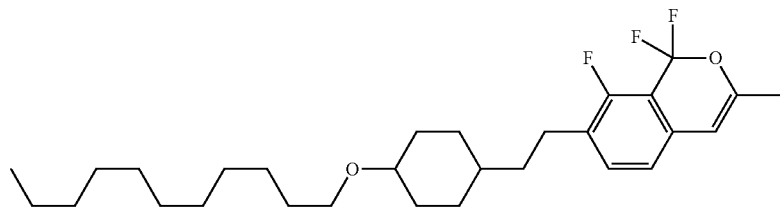 [SMILES: CCCCCCCCCCCOC1CCC(CCc2ccc3c(c2F)C(F)(F)OC(C)=C3)CC1] |
| 657 | 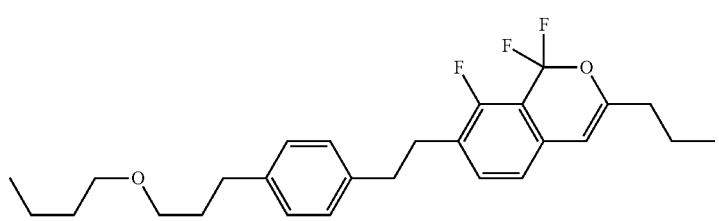 [SMILES: CCCCOCCCc1ccc(CCc2ccc3c(c2F)C(F)(F)OC(CCC)=C3)cc1] |
| 658 | 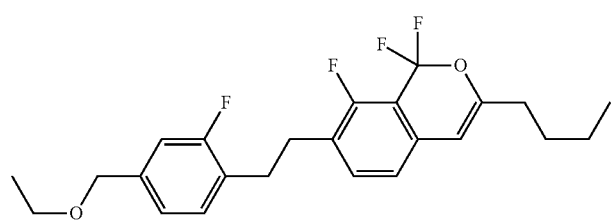 [SMILES: CCCCC1=Cc2ccc(CCc3ccc(COCC)cc3F)c(F)c2C(F)(F)O1] |
| 659 | 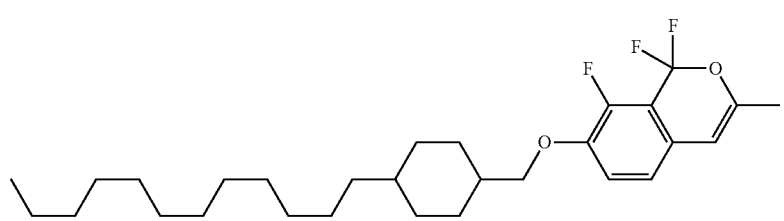 [SMILES: CCCCCCCCCCCCC1CCC(COc2ccc3c(c2F)C(F)(F)OC(C)=C3)CC1] |

| No. |
|---|
| 660 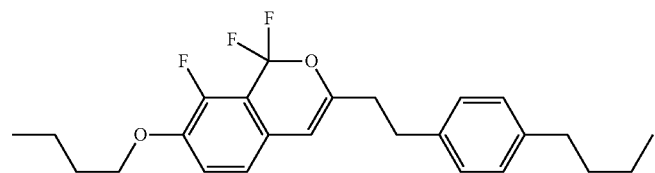 [SMILES: CCCCOc1ccc2c(c1F)C(F)(F)OC(CCc1ccc(CCCC)cc1)=C2] |
| 661 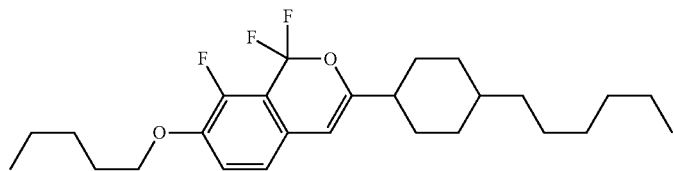 [SMILES: CCCCCCC1CCC(C2=Cc3ccc(OCCCCC)c(F)c3C(F)(F)O2)CC1] |
| 662 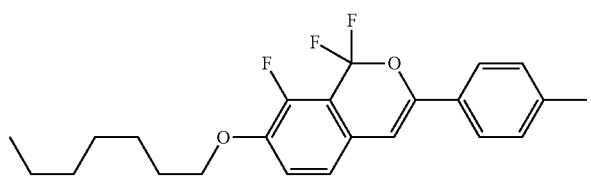 [SMILES: CCCCCCCOc1ccc2c(c1F)C(F)(F)OC(c1ccc(C)cc1)=C2] |
| 663 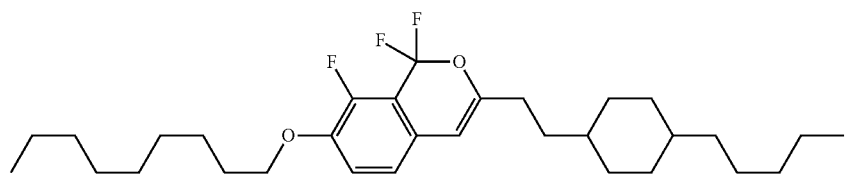 [SMILES: CCCCCCCCCOc1ccc2c(c1F)C(F)(F)OC(CCC1CCC(CCCCC)CC1)=C2] |
| 664 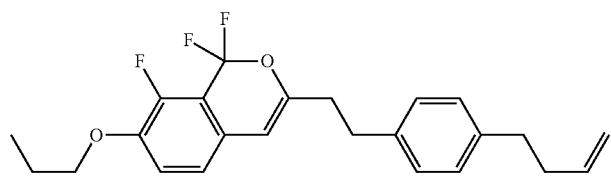 [SMILES: C=CCCc1ccc(CCC2=Cc3ccc(OCCC)c(F)c3C(F)(F)O2)cc1] |
| 665 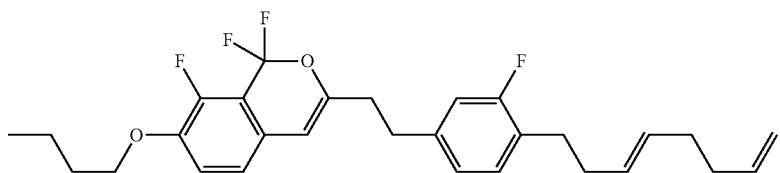 [SMILES: C=CCC/C=C/CCc1ccc(CCC2=Cc3ccc(OCCCC)c(F)c3C(F)(F)O2)cc1F] |
| 666 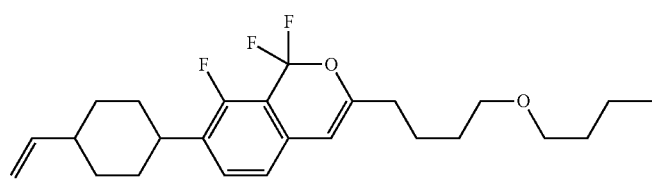 [SMILES: C=CC1CCC(c2ccc3c(c2F)C(F)(F)OC(CCCCOCCCC)=C3)CC1] |
| 667 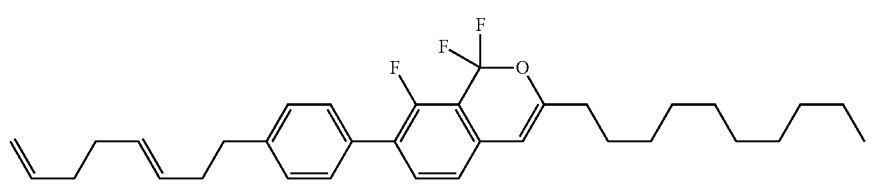 [SMILES: C=CCC/C=C/CCc1ccc(-c2ccc3c(c2F)C(F)(F)OC(CCCCCCCCCC)=C3)cc1] |

-continued
| No. | |
|---|---|
| 668 | 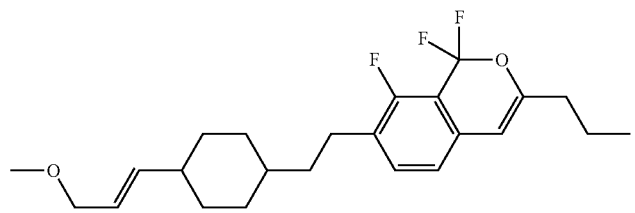 [SMILES: CCCC1=Cc2ccc(CCC3CCC(/C=C/COC)CC3)c(F)c2C(F)(F)O1] |
| 669 | 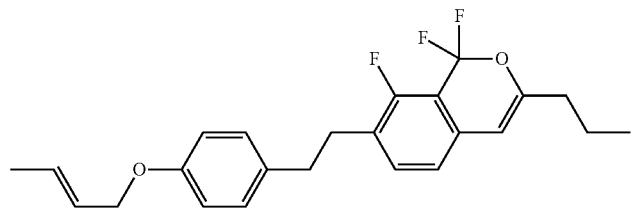 [SMILES: C/C=C/COc1ccc(CCc2ccc3c(c2F)C(F)(F)OC(CCC)=C3)cc1] |
| 670 | 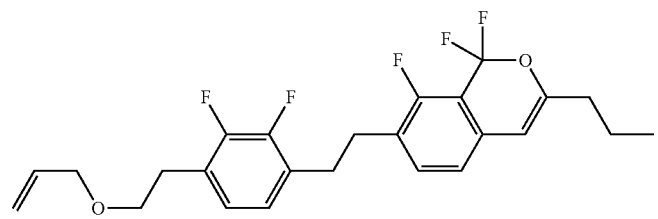 [SMILES: C=CCOCCc1ccc(CCc2ccc3c(c2F)C(F)(F)OC(CCC)=C3)c(F)c1F] |
| 671 | 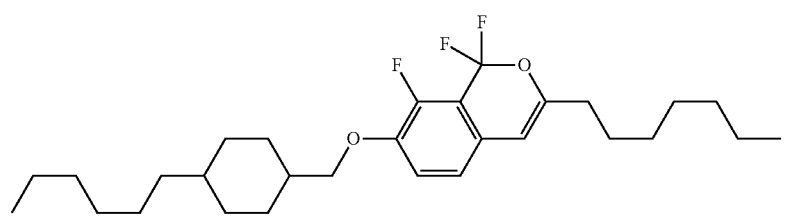 [SMILES: CCCCCCCC1=Cc2ccc(OCC3CCC(CCCCCC)CC3)c(F)c2C(F)(F)O1] |
| 672 | 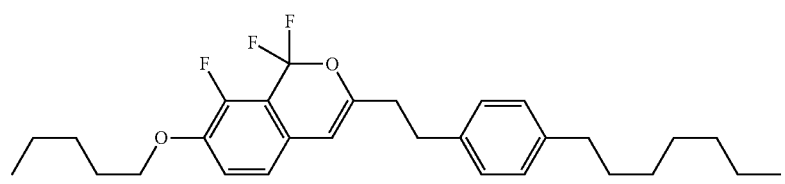 [SMILES: CCCCCCCc1ccc(CCC2=Cc3ccc(OCCCCC)c(F)c3C(F)(F)O2)cc1] |
| 673 | 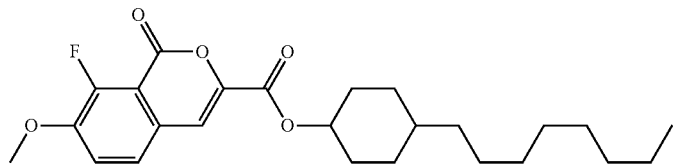 |
| 674 | 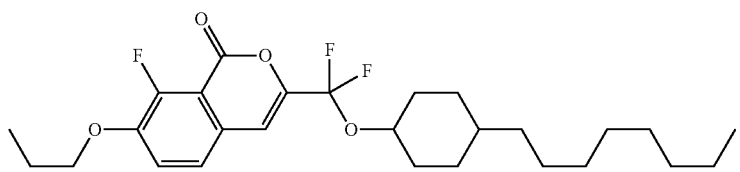 [SMILES: CCCCCCCCC1CCC(OC(F)(F)c2cc3ccc(OCCC)c(F)c3c(=O)o2)CC1] |
| 675 | 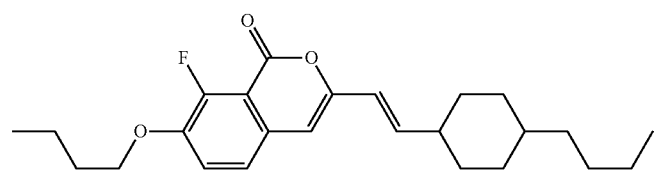 |

| No. | |
|---|---|
| 676 | 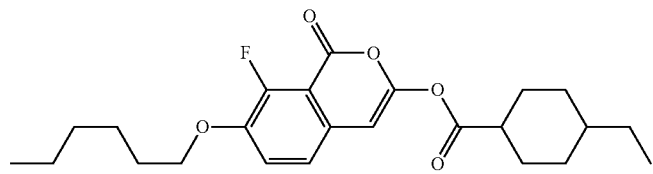 [SMILES: CCCCCCOc1ccc2cc(OC(=O)C3CCC(CC)CC3)oc(=O)c2c1F] |
| 677 | 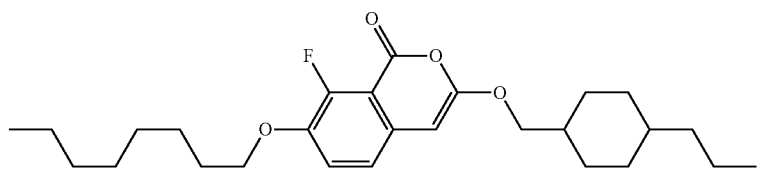 |
| 678 | 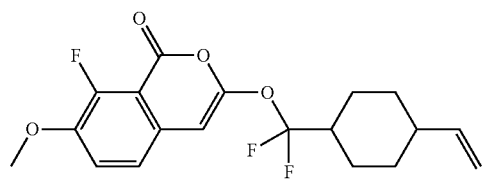 [SMILES: C=CC1CCC(C(F)(F)Oc2cc3ccc(OC)c(F)c3c(=O)o2)CC1] |
| 679 | 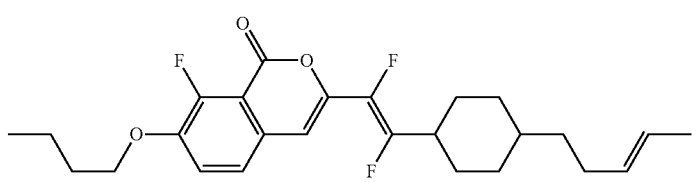 [SMILES: C/C=C/CCC1CCC(/C(F)=C(\F)c2cc3ccc(OCCCC)c(F)c3c(=O)o2)CC1] |
| 680 | 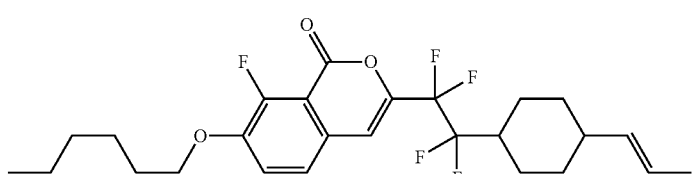 |
| 681 | 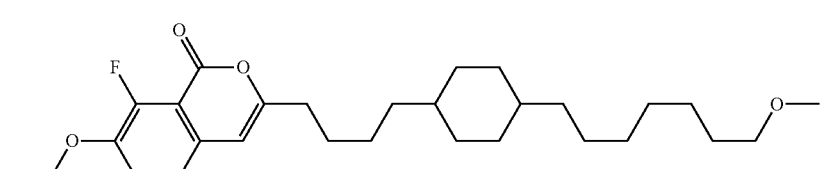 |
| 682 | 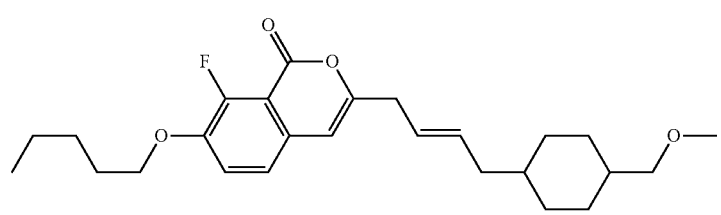 [SMILES: CCCCCOc1ccc2cc(C/C=C/CC3CCC(COC)CC3)oc(=O)c2c1F] |
| 683 | 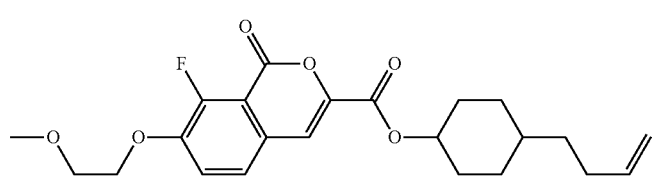 [SMILES: C=CCCC1CCC(OC(=O)c2cc3ccc(OCCOC)c(F)c3c(=O)o2)CC1] |

-continued
| No. | |
|---|---|
| 684 | 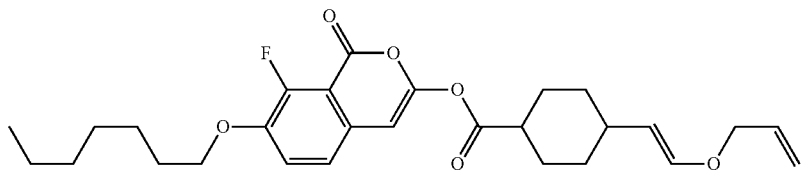 [SMILES: C=CCO/C=C/C1CCC(C(=O)Oc2cc3ccc(OCCCCCCC)c(F)c3c(=O)o2)CC1] |
| 685 | 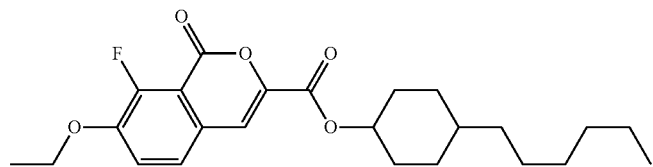 [SMILES: CCCCCCC1CCC(OC(=O)c2cc3ccc(OCC)c(F)c3c(=O)o2)CC1] |
| 686 | 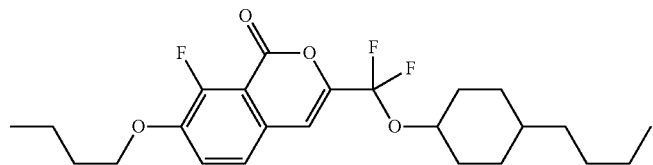 |
| 687 | 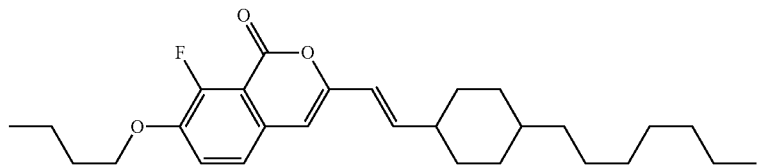 [SMILES: CCCCCCCC1CCC(/C=C/c2cc3ccc(OCCCC)c(F)c3c(=O)o2)CC1] |
| 688 | 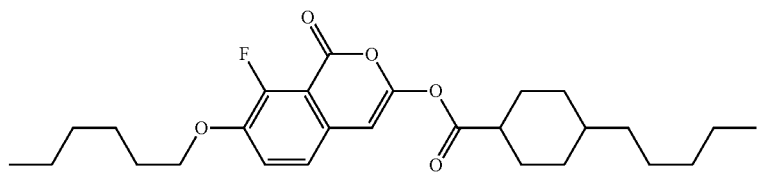 [SMILES: CCCCCCOc1ccc2cc(OC(=O)C3CCC(CCCCC)CC3)oc(=O)c2c1F] |
| 689 | 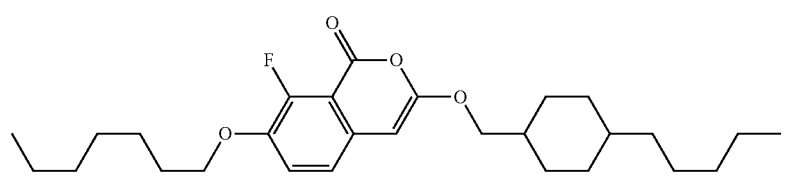 |
| 690 | 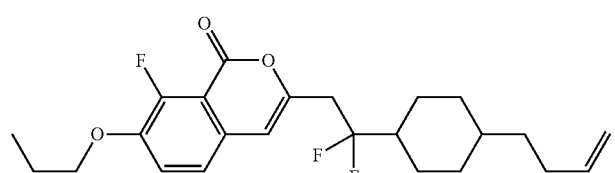 |
| 691 | 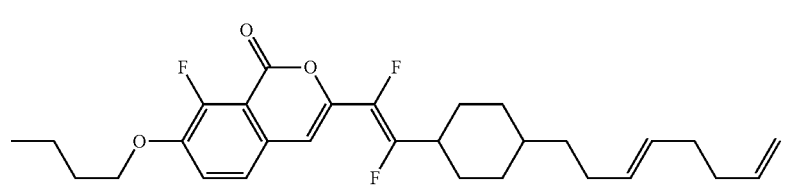 [SMILES: C=CCC/C=C/CCC1CCC(/C(F)=C(\F)c2cc3ccc(OCCCC)c(F)c3c(=O)o2)CC1] |

| No. |
|---|
| 692 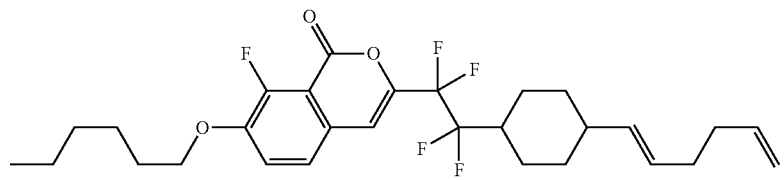 [SMILES: C=CCC/C=C/C1CCC(C(F)(F)C(F)(F)c2cc3ccc(OCCCCCC)c(F)c3c(=O)o2)CC1] |
| 693 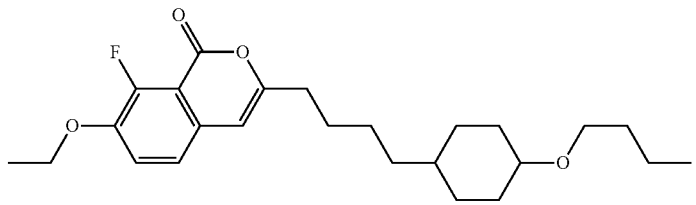 [SMILES: CCCCOC1CCC(CCCCc2cc3ccc(OCC)c(F)c3c(=O)o2)CC1] |
| 694 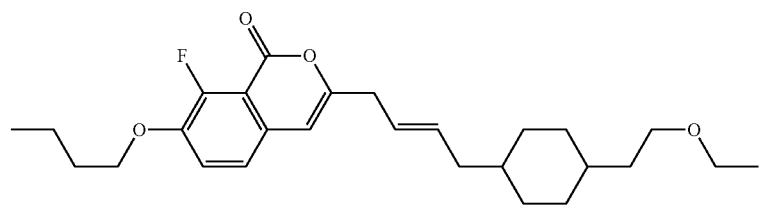 [SMILES: CCCCOc1ccc2cc(C/C=C/CC3CCC(CCOCC)CC3)oc(=O)c2c1F] |
| 695 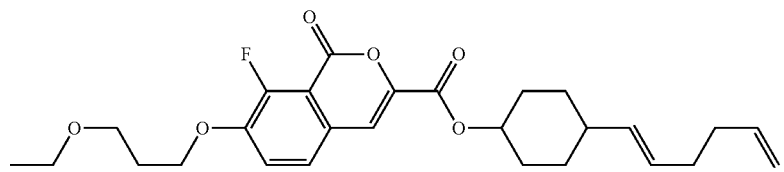 [SMILES: C=CCC/C=C/C1CCC(OC(=O)c2cc3ccc(OCCCOCC)c(F)c3c(=O)o2)CC1] |
| 696 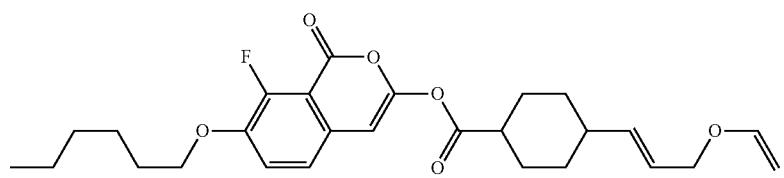 [SMILES: C=COC/C=C/C1CCC(C(=O)Oc2cc3ccc(OCCCCCC)c(F)c3c(=O)o2)CC1] |
| 697 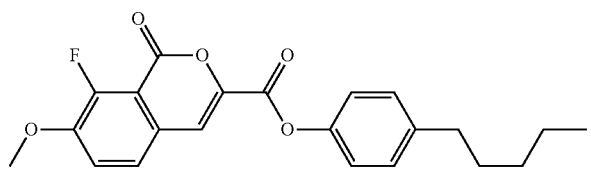 [SMILES: CCCCCc1ccc(OC(=O)c2cc3ccc(OC)c(F)c3c(=O)o2)cc1] |
| 698 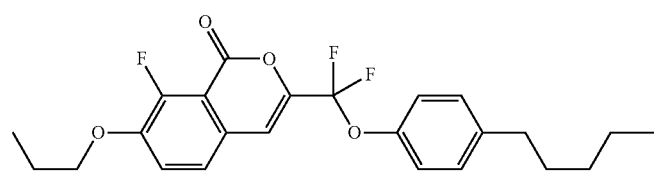 |
| 699 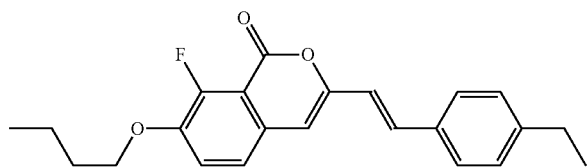 [SMILES: CCCCOc1ccc2cc(/C=C/c3ccc(CC)cc3)oc(=O)c2c1F] |

-continued
| No. | |
|---|---|
| 700 | 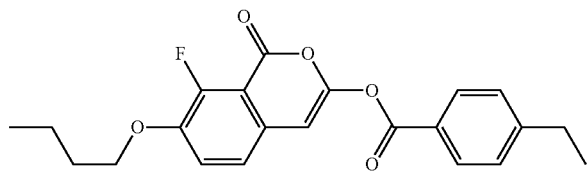 |
| 701 | 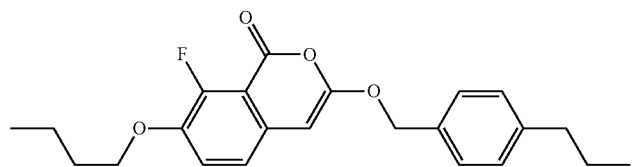 [SMILES: CCCCOc1ccc2cc(OCc3ccc(CCC)cc3)oc(=O)c2c1F] |
| 702 | 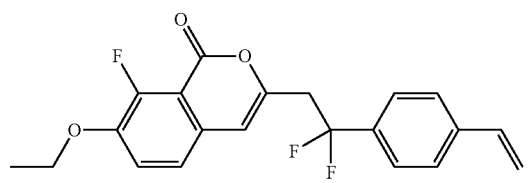 [SMILES: C=Cc1ccc(C(F)(F)Cc2cc3ccc(OCC)c(F)c3c(=O)o2)cc1] |
| 703 | 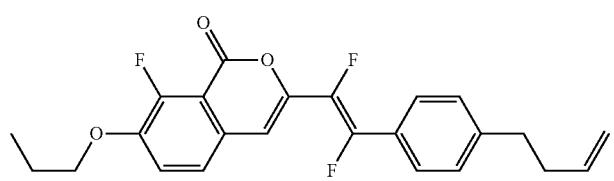 [SMILES: C=CCCc1ccc(/C(F)=C(\F)c2cc3ccc(OCCC)c(F)c3c(=O)o2)cc1] |
| 704 | 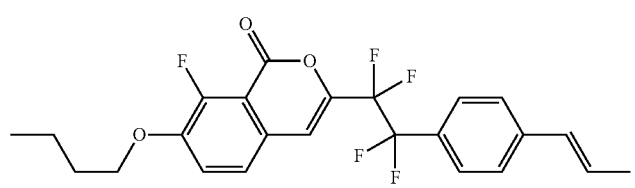 [SMILES: C/C=C/c1ccc(C(F)(F)C(F)(F)c2cc3ccc(OCCCC)c(F)c3c(=O)o2)cc1] |
| 705 | 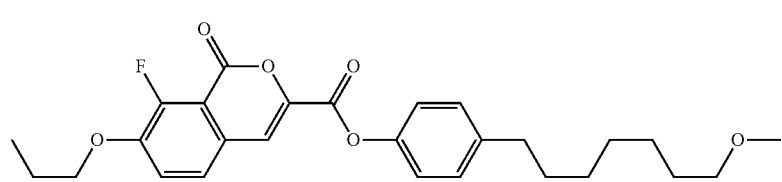 [SMILES: CCCOc1ccc2cc(C(=O)Oc3ccc(CCCCCCCOC)cc3)oc(=O)c2c1F] |
| 706 | 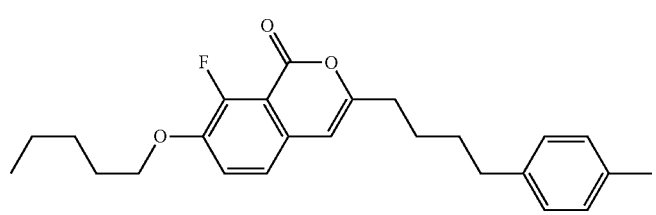 [SMILES: CCCCCOc1ccc2cc(CCCCc3ccc(C)cc3)oc(=O)c2c1F] |
| 707 | 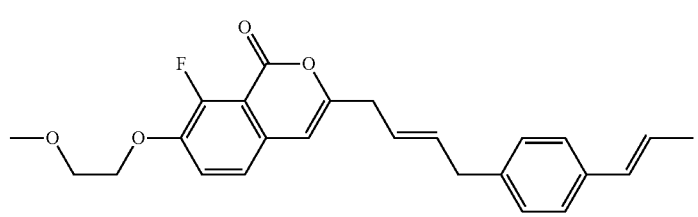 [SMILES: C/C=C/c1ccc(C/C=C/Cc2cc3ccc(OCCOC)c(F)c3c(=O)o2)cc1] |

| No. | |
|---|---|
| 708 | 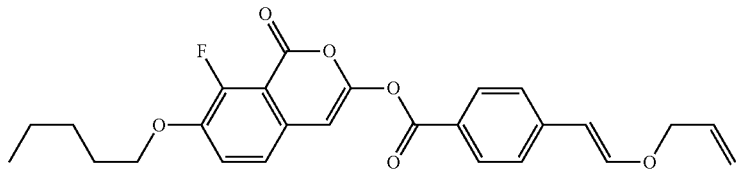 [SMILES: C=CCO/C=C/c1ccc(C(=O)Oc2cc3ccc(OCCCCC)c(F)c3c(=O)o2)cc1] |
| 709 | 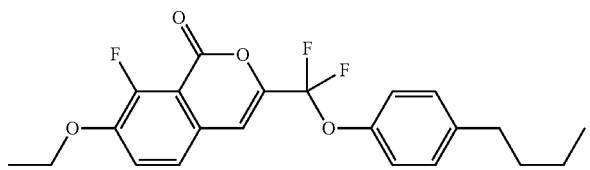 [SMILES: CCCCc1ccc(OC(F)(F)c2cc3ccc(OCC)c(F)c3c(=O)o2)cc1] |
| 710 | 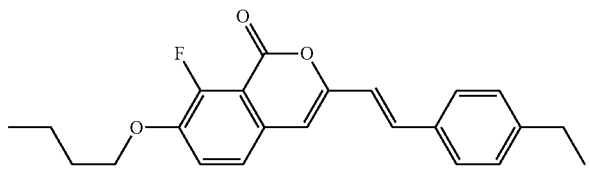 [SMILES: CCCCOc1ccc2cc(/C=C/c3ccc(CC)cc3)oc(=O)c2c1F] |
| 711 | 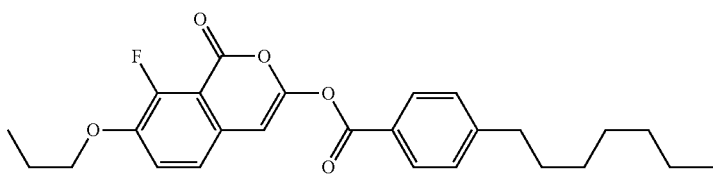 [SMILES: CCCCCCCc1ccc(C(=O)Oc2cc3ccc(OCCC)c(F)c3c(=O)o2)cc1] |
| 712 | 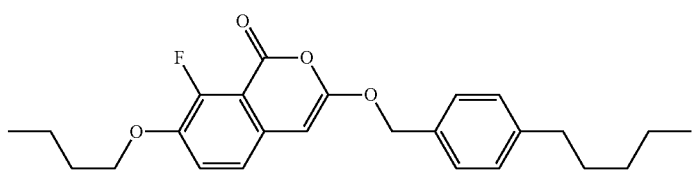 [SMILES: CCCCCc1ccc(COc2cc3ccc(OCCCC)c(F)c3c(=O)o2)cc1] |
| 713 | 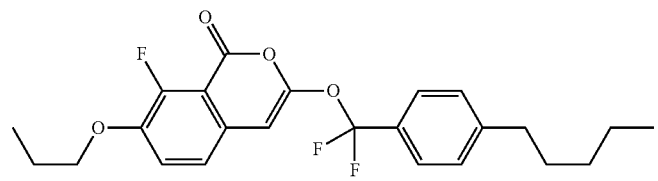 [SMILES: CCCCCc1ccc(C(F)(F)Oc2cc3ccc(OCCC)c(F)c3c(=O)o2)cc1] |
| 714 | 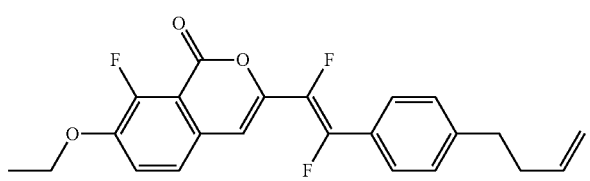 [SMILES: C=CCCc1ccc(/C(F)=C(\F)c2cc3ccc(OCC)c(F)c3c(=O)o2)cc1] |
| 715 | 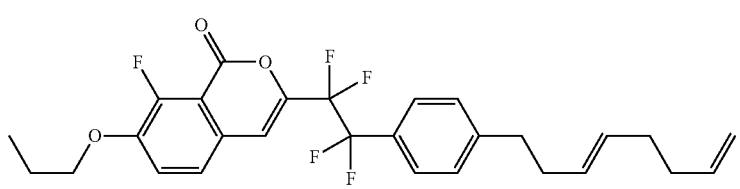 [SMILES: C=CCC/C=C/CCc1ccc(C(F)(F)C(F)(F)c2cc3ccc(OCCC)c(F)c3c(=O)o2)cc1] |

| No. |
|---|
| 716 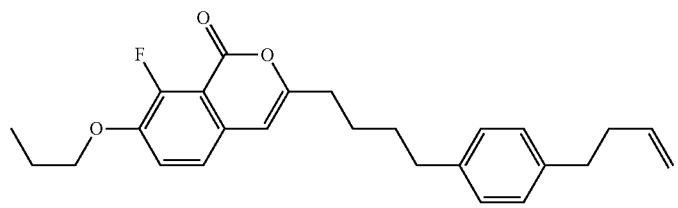 [SMILES: C=CCCc1ccc(CCCCc2cc3ccc(OCCC)c(F)c3c(=O)o2)cc1] |
| 717 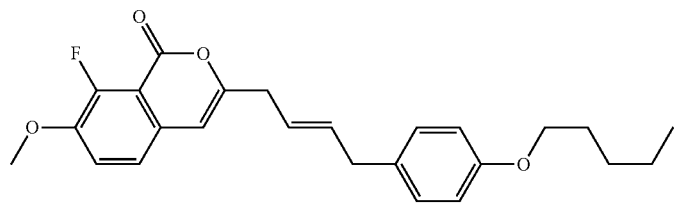 [SMILES: CCCCCOc1ccc(C/C=C/Cc2cc3ccc(OC)c(F)c3c(=O)o2)cc1] |
| 718 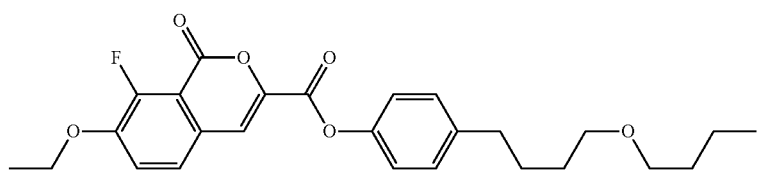 [SMILES: CCCCOCCCCc1ccc(OC(=O)c2cc3ccc(OCC)c(F)c3c(=O)o2)cc1] |
| 719 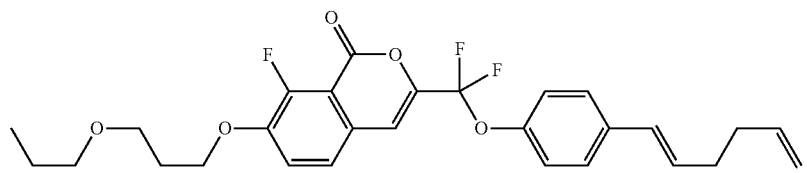 [SMILES: C=CCC/C=C/c1ccc(OC(F)(F)c2cc3ccc(OCCCOCCC)c(F)c3c(=O)o2)cc1] |
| 720 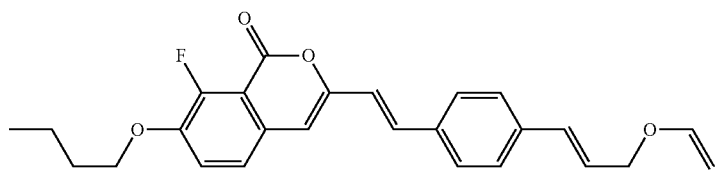 [SMILES: C=COC/C=C/c1ccc(/C=C/c2cc3ccc(OCCCC)c(F)c3c(=O)o2)cc1] |
| 721 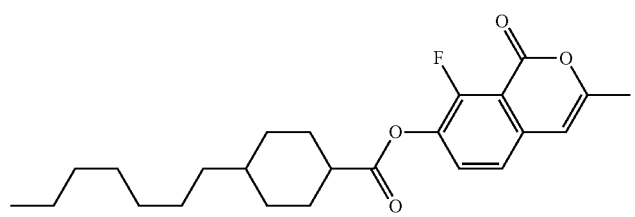 [SMILES: CCCCCCCC1CCC(C(=O)Oc2ccc3cc(C)oc(=O)c3c2F)CC1] |
| 722 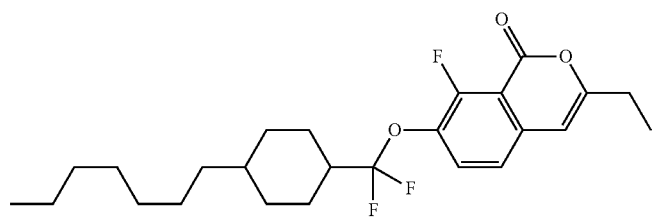 [SMILES: CCCCCCCC1CCC(C(F)(F)Oc2ccc3cc(CC)oc(=O)c3c2F)CC1] |
| 723 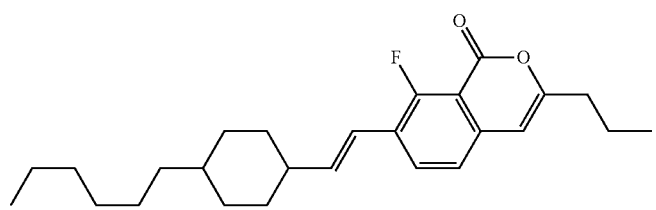 [SMILES: CCCCCCC1CCC(/C=C/c2ccc3cc(CCC)oc(=O)c3c2F)CC1] |

-continued
| No. |
|---|
| 724 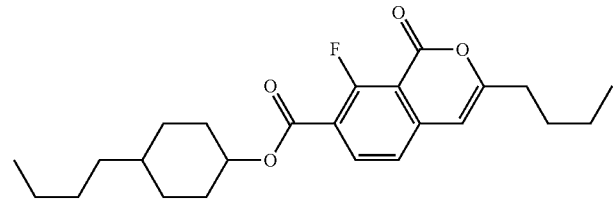 [SMILES: CCCCc1cc2ccc(C(=O)OC3CCC(CCCC)CC3)c(F)c2c(=O)o1] |
| 726 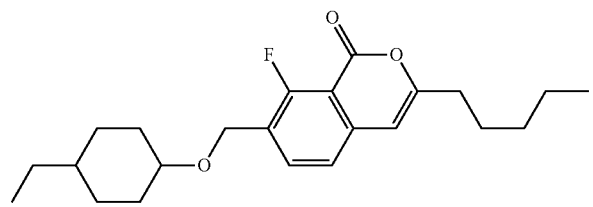 [SMILES: CCCCCc1cc2ccc(COC3CCC(CC)CC3)c(F)c2c(=O)o1] |
| 727 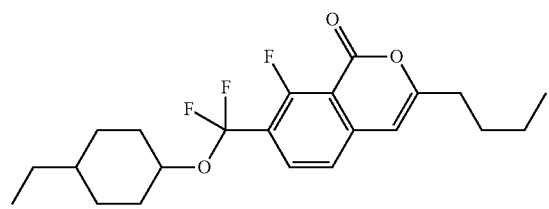 [SMILES: CCCCc1cc2ccc(C(F)(F)OC3CCC(CC)CC3)c(F)c2c(=O)o1] |
| 728 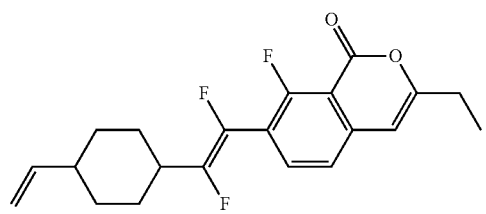 [SMILES: C=CC1CCC(/C(F)=C(\F)c2ccc3cc(CC)oc(=O)c3c2F)CC1] |
| 729 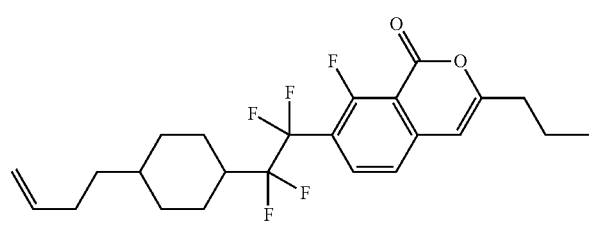 |
| 730 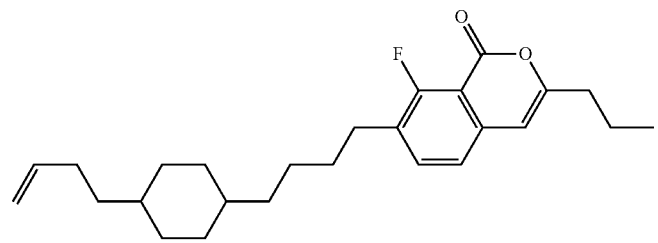 [SMILES: C=CCCC1CCC(CCCCc2ccc3cc(CCC)oc(=O)c3c2F)CC1] |
| 731 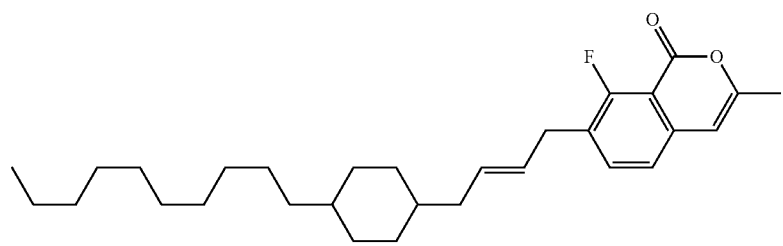 [SMILES: CCCCCCCCCCC1CCC(C/C=C/Cc2ccc3cc(C)oc(=O)c3c2F)CC1] |

| No. | |
|---|---|
| 732 | 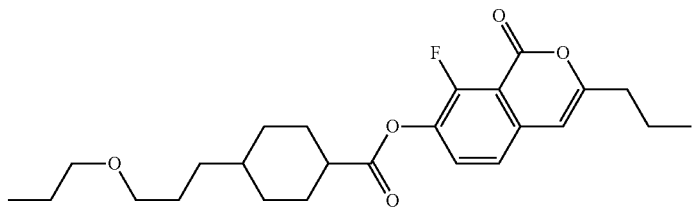 [SMILES: CCCOCCCC1CCC(C(=O)Oc2ccc3cc(CCC)oc(=O)c3c2F)CC1] |
| 733 | 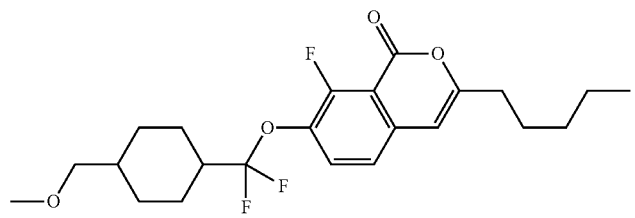 [SMILES: CCCCCc1cc2ccc(OC(F)(F)C3CCC(COC)CC3)c(F)c2c(=O)o1] |
| 733 | 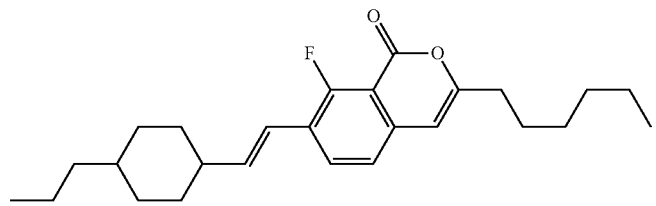 |
| 734 | 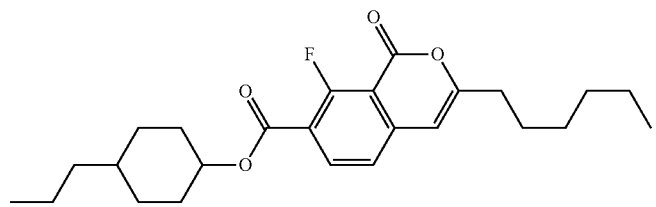 [SMILES: CCCCCCc1cc2ccc(C(=O)OC3CCC(CCC)CC3)c(F)c2c(=O)o1] |
| 735 | 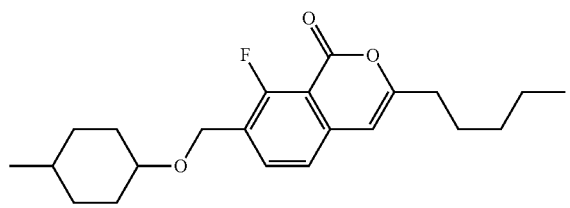 [SMILES: CCCCCc1cc2ccc(COC3CCC(C)CC3)c(F)c2c(=O)o1] |
| 736 | 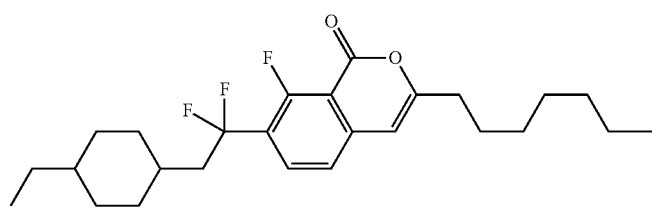 [SMILES: CCCCCCCc1cc2ccc(C(F)(F)CC3CCC(CC)CC3)c(F)c2c(=O)o1] |
| 737 | 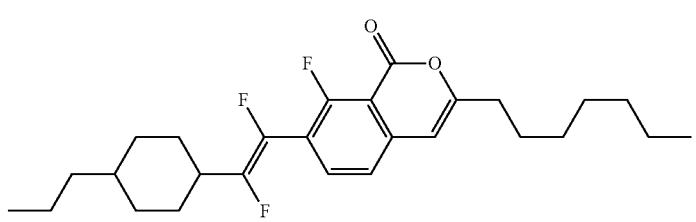 [SMILES: CCCCCCCc1cc2ccc(/C(F)=C(\F)C3CCC(CCC)CC3)c(F)c2c(=O)o1] |

| No. |
|---|
| 738 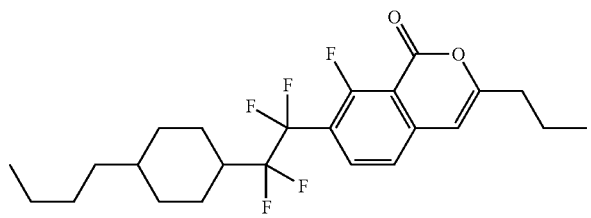 [SMILES: CCCCC1CCC(C(F)(F)C(F)(F)c2ccc3cc(CCC)oc(=O)c3c2F)CC1] |
| 739 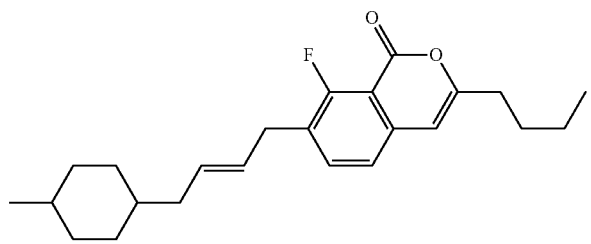 [SMILES: CCCCc1cc2ccc(C/C=C/CC3CCC(C)CC3)c(F)c2c(=O)o1] |
| 740 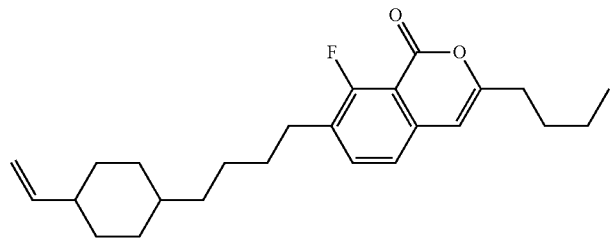 [SMILES: C=CC1CCC(CCCCc2ccc3cc(CCCC)oc(=O)c3c2F)CC1] |
| 741 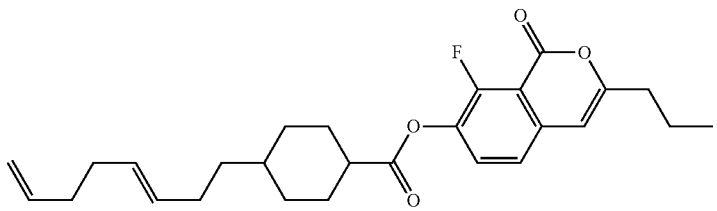 |
| 742 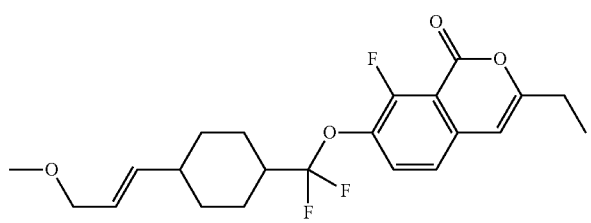 [SMILES: CCc1cc2ccc(OC(F)(F)C3CCC(/C=C/COC)CC3)c(F)c2c(=O)o1] |
| 743 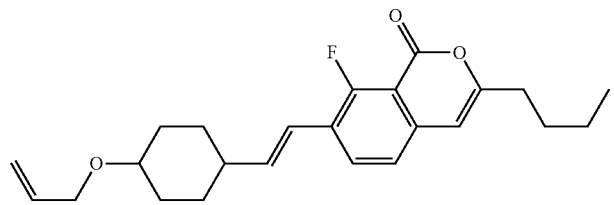 [SMILES: C=CCOC1CCC(/C=C/c2ccc3cc(CCCC)oc(=O)c3c2F)CC1] |
| 744 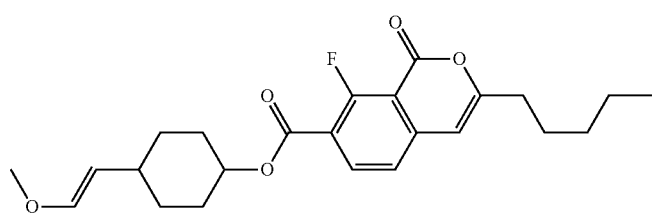 [SMILES: CCCCCc1cc2ccc(C(=O)OC3CCC(/C=C/OC)CC3)c(F)c2c(=O)o1] |

| No. |
|---|
| 745 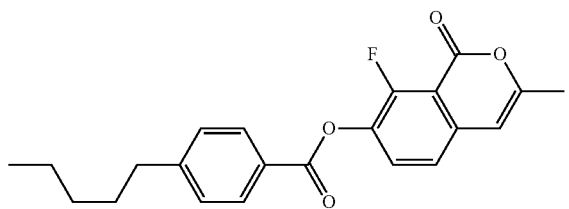 [SMILES: CCCCCc1ccc(C(=O)Oc2ccc3cc(C)oc(=O)c3c2F)cc1] |
| 746 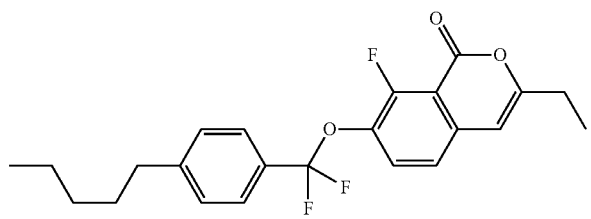 [SMILES: CCCCCc1ccc(C(F)(F)Oc2ccc3cc(CC)oc(=O)c3c2F)cc1] |
| 747 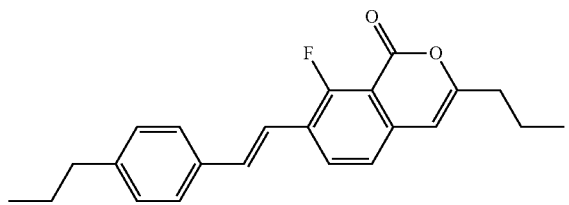 [SMILES: CCCc1ccc(/C=C/c2ccc3cc(CCC)oc(=O)c3c2F)cc1] |
| 748 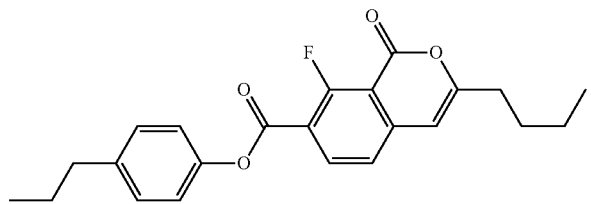 [SMILES: CCCCc1cc2ccc(C(=O)Oc3ccc(CCC)cc3)c(F)c2c(=O)o1] |
| 749 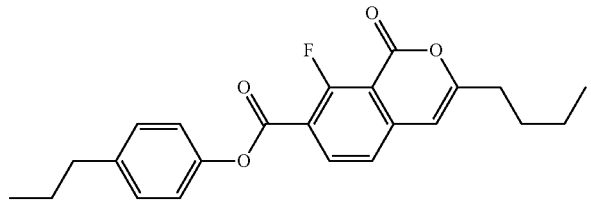 [SMILES: CCCCc1cc2ccc(C(=O)Oc3ccc(CCC)cc3)c(F)c2c(=O)o1] |
| 750 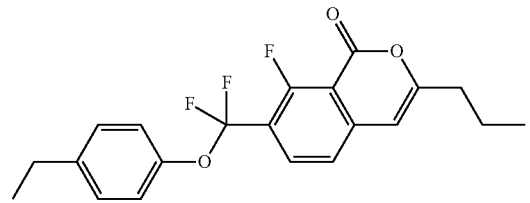 |
| 751 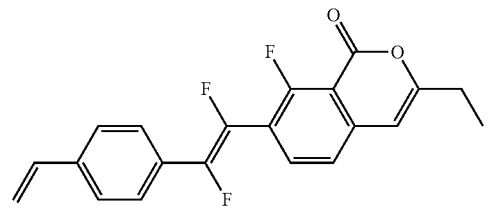 [SMILES: C=Cc1ccc(/C(F)=C(\F)c2ccc3cc(CC)oc(=O)c3c2F)cc1] |

-continued
| No. | |
|---|---|
| 752 | 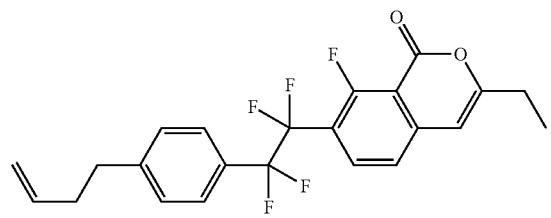 [SMILES: C=CCCc1ccc(C(F)(F)C(F)(F)c2ccc3cc(CC)oc(=O)c3c2F)cc1] |
| 753 | 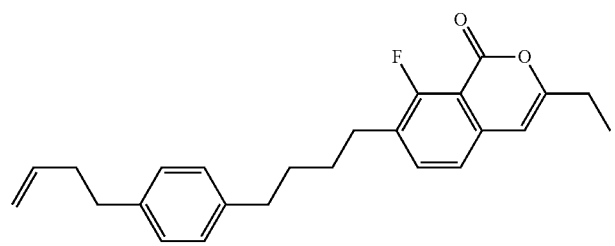 [SMILES: C=CCCc1ccc(CCCCc2ccc3cc(CC)oc(=O)c3c2F)cc1] |
| 754 | 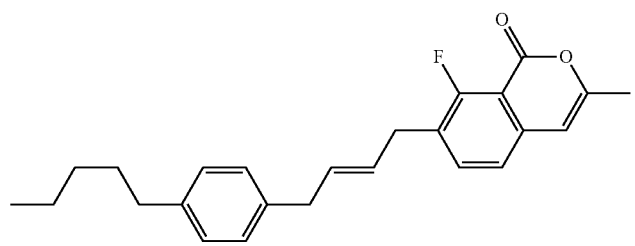 [SMILES: CCCCCc1ccc(C/C=C/Cc2ccc3cc(C)oc(=O)c3c2F)cc1] |
| 755 | 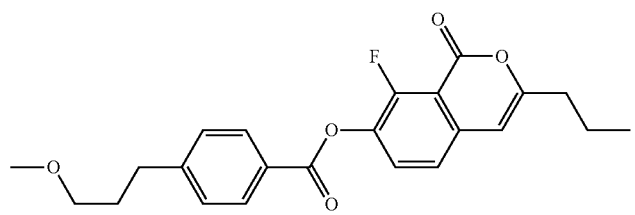 |
| 756 | 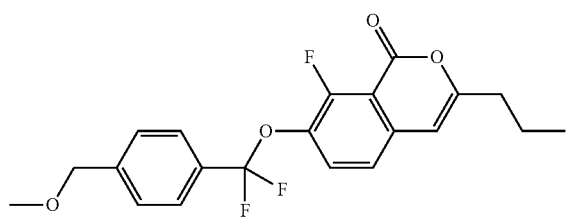 [SMILES: CCCc1cc2ccc(OC(F)(F)c3ccc(COC)cc3)c(F)c2c(=O)o1] |
| 757 | 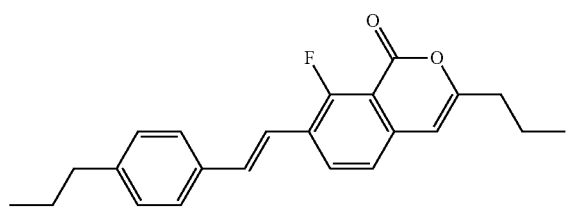 [SMILES: CCCc1ccc(/C=C/c2ccc3cc(CCC)oc(=O)c3c2F)cc1] |
| 758 | 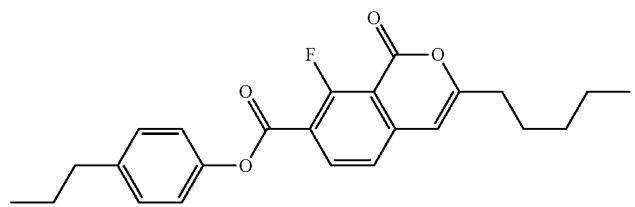 [SMILES: CCCCCc1cc2ccc(C(=O)Oc3ccc(CCC)cc3)c(F)c2c(=O)o1] |

-continued
| No. | |
|---|---|
| 759 | 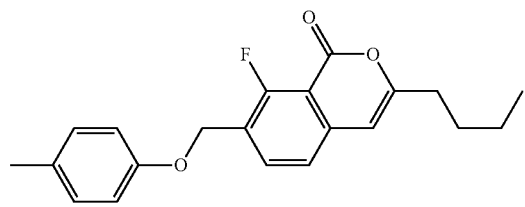 [SMILES: CCCCc1cc2ccc(COc3ccc(C)cc3)c(F)c2c(=O)o1] |
| 760 | 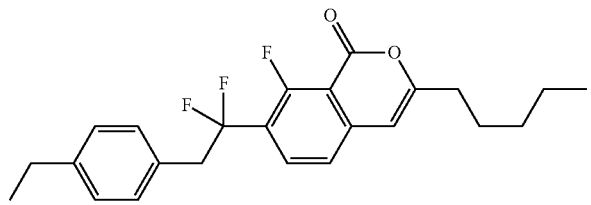 [SMILES: CCCCCc1cc2ccc(C(F)(F)Cc3ccc(CC)cc3)c(F)c2c(=O)o1] |
| 761 | 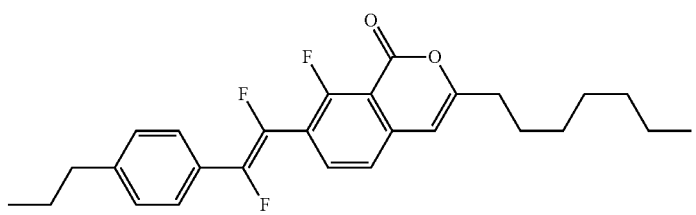 |
| 762 | 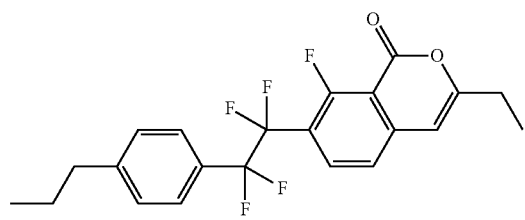 [SMILES: CCCc1ccc(C(F)(F)C(F)(F)c2ccc3cc(CC)oc(=O)c3c2F)cc1] |
| 763 | 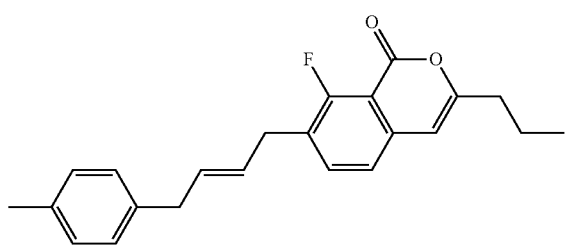 [SMILES: CCCc1cc2ccc(C/C=C/Cc3ccc(C)cc3)c(F)c2c(=O)o1] |
| 764 | 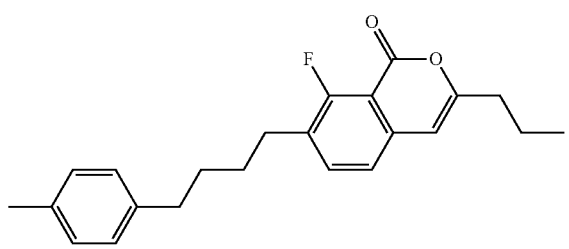 |
| 765 | 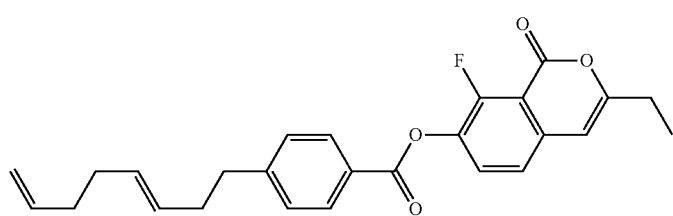 |

-continued
| No. |
|---|
| 766 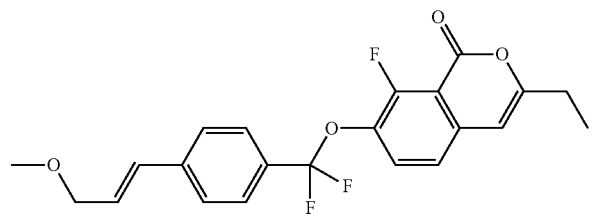 [SMILES: CCc1cc2ccc(OC(F)(F)c3ccc(/C=C/COC)cc3)c(F)c2c(=O)o1] |
| 767 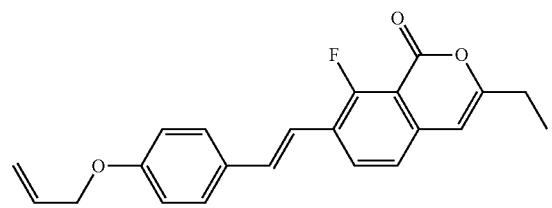 [SMILES: C=CCOc1ccc(/C=C/c2ccc3cc(CC)oc(=O)c3c2F)cc1] |
| 768 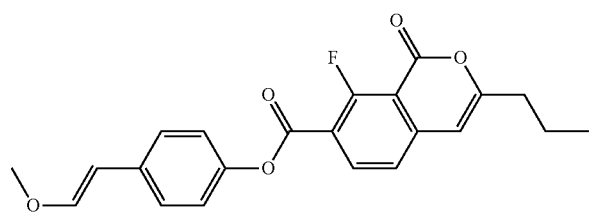 [SMILES: CCCc1cc2ccc(C(=O)Oc3ccc(/C=C/OC)cc3)c(F)c2c(=O)o1] |
| 769 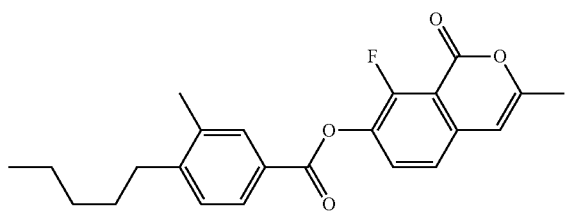 [SMILES: CCCCCc1ccc(C(=O)Oc2ccc3cc(C)oc(=O)c3c2F)cc1C] |
| 770 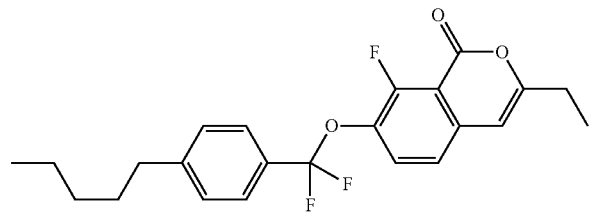 |
| 771 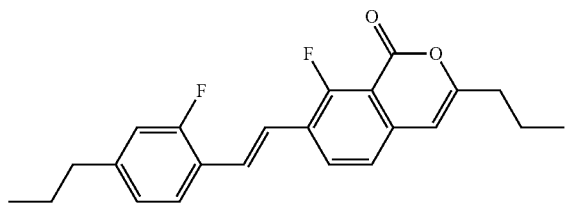 [SMILES: CCCc1ccc(/C=C/c2ccc3cc(CCC)oc(=O)c3c2F)c(F)c1] |
| 772 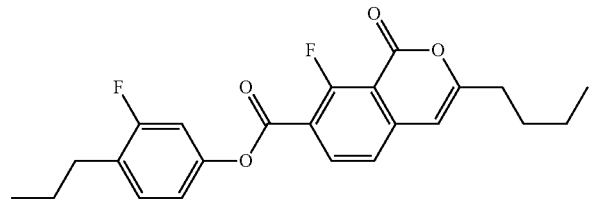 [SMILES: CCCCc1cc2ccc(C(=O)Oc3ccc(CCC)c(F)c3)c(F)c2c(=O)o1] |

-continued
| No. | |
|---|---|
| 773 | 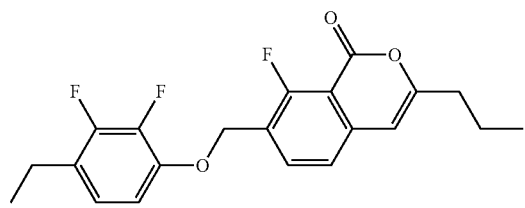 [SMILES: CCCc1cc2ccc(COc3ccc(CC)c(F)c3F)c(F)c2c(=O)o1] |
| 774 | 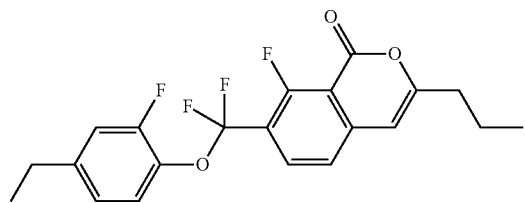 |
| 775 | 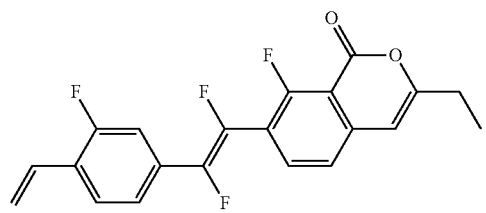 [SMILES: C=Cc1ccc(/C(F)=C(\F)c2ccc3cc(CC)oc(=O)c3c2F)cc1F] |
| 776 | 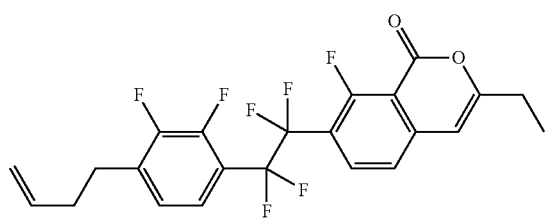 [SMILES: C=CCCc1ccc(C(F)(F)C(F)(F)c2ccc3cc(CC)oc(=O)c3c2F)c(F)c1F] |
| 777 | 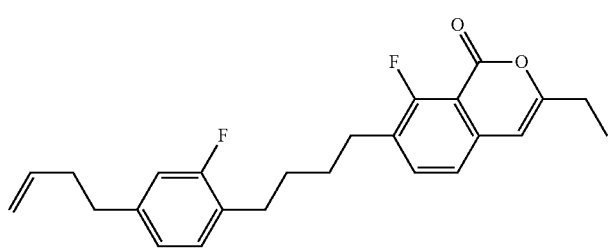 [SMILES: C=CCCc1ccc(CCCCc2ccc3cc(CC)oc(=O)c3c2F)c(F)c1] |
| 778 | 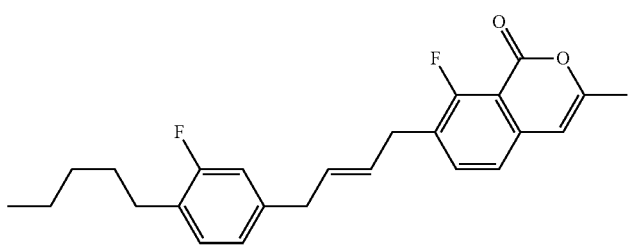 [SMILES: CCCCCc1ccc(C/C=C/Cc2ccc3cc(C)oc(=O)c3c2F)cc1F] |
| 779 | 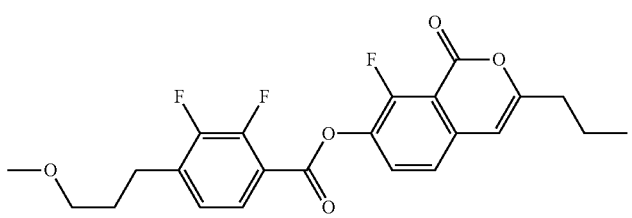 [SMILES: CCCc1cc2ccc(OC(=O)c3ccc(CCCOC)c(F)c3F)c(F)c2c(=O)o1] |

-continued
| No. | |
|---|---|
| 780 | 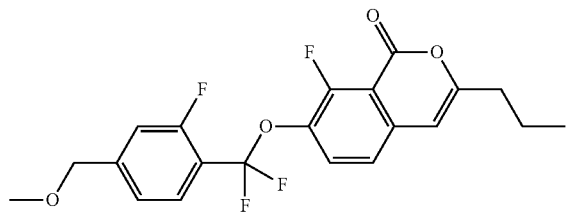 [SMILES: CCCc1cc2ccc(OC(F)(F)c3ccc(COC)cc3F)c(F)c2c(=O)o1] |
| 781 | 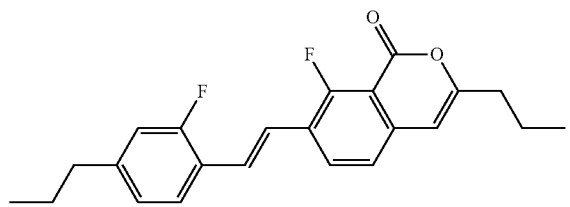 [SMILES: CCCc1ccc(/C=C/c2ccc3cc(CCC)oc(=O)c3c2F)c(F)c1] |
| 782 | 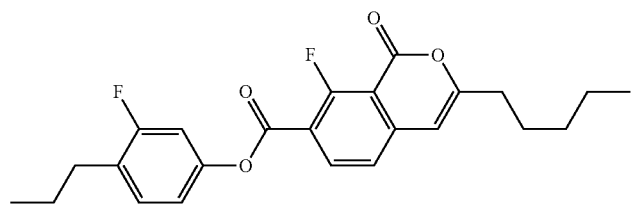 |
| 783 | 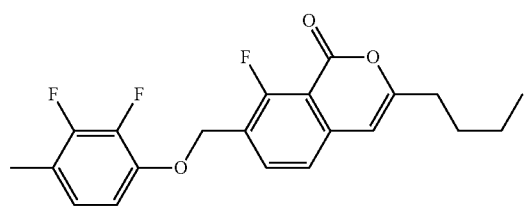 [SMILES: CCCCc1cc2ccc(COc3ccc(C)c(F)c3F)c(F)c2c(=O)o1] |
| 784 | 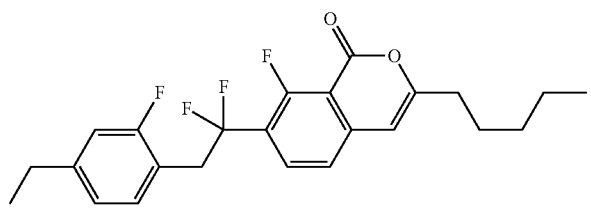 [SMILES: CCCCCc1cc2ccc(C(F)(F)Cc3ccc(CC)cc3F)c(F)c2c(=O)o1] |
| 785 | 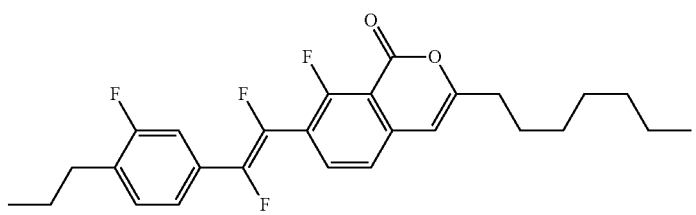 |
| 786 | 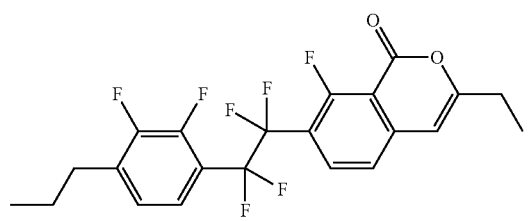 [SMILES: CCCc1ccc(C(F)(F)C(F)(F)c2ccc3cc(CC)oc(=O)c3c2F)c(F)c1F] |

-continued
| No. | |
|---|---|
| 787 | 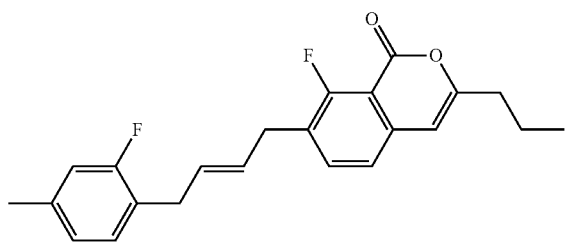 [SMILES: CCCc1cc2ccc(C/C=C/Cc3ccc(C)cc3F)c(F)c2c(=O)o1] |
| 788 | 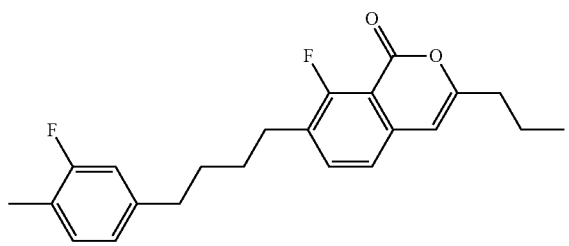 [SMILES: CCCc1cc2ccc(CCCCc3ccc(C)c(F)c3)c(F)c2c(=O)o1] |
| 789 | 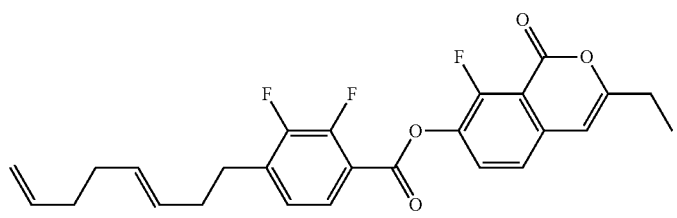 [SMILES: C=CCC/C=C/CCc1ccc(C(=O)Oc2ccc3cc(CC)oc(=O)c3c2F)c(F)c1F] |
| 790 | 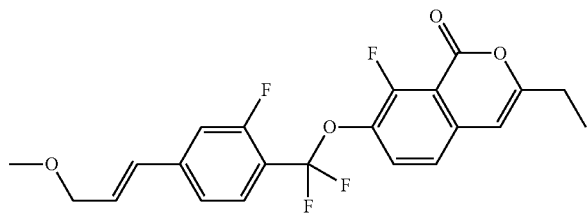 [SMILES: CCc1cc2ccc(OC(F)(F)c3ccc(/C=C/COC)cc3F)c(F)c2c(=O)o1] |
| 791 | 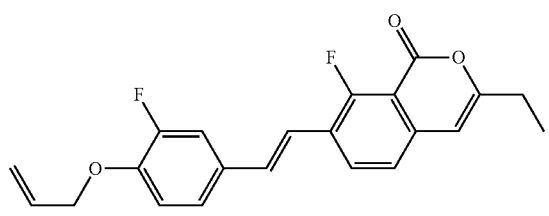 [SMILES: C=CCOc1ccc(/C=C/c2ccc3cc(CC)oc(=O)c3c2F)cc1F] |
| 792 | 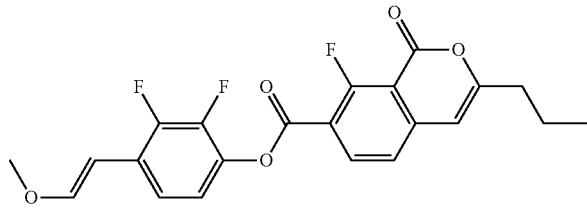 [SMILES: CCCc1cc2ccc(C(=O)Oc3ccc(/C=C/OC)c(F)c3F)c(F)c2c(=O)o1] |
| 793 | 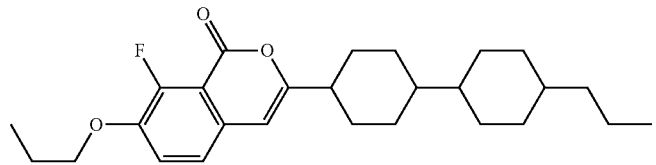 |

| No. |
|---|
| 794 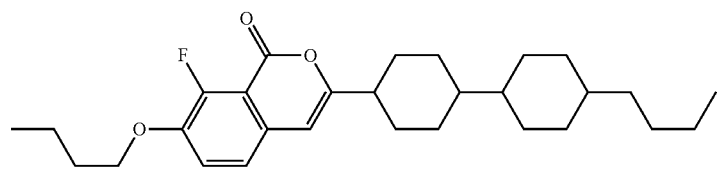 |
| 795 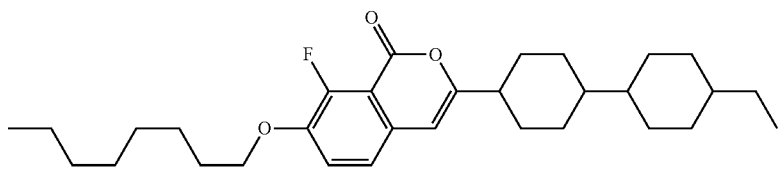 |
| 796 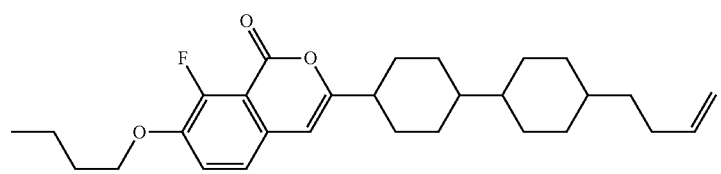 [SMILES: CCCCOc1ccc2cc(C3CCC(C4CCC(CCCC)CC4)CC3)oc(=O)c2c1F] |
| 797 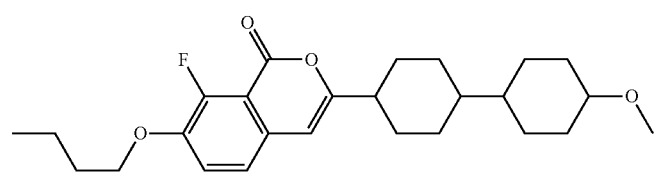 |
| 798 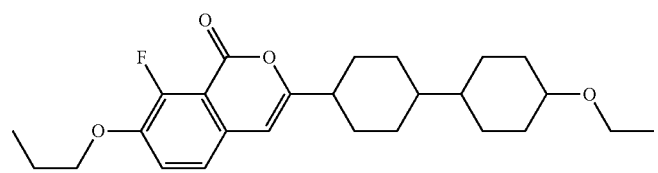 [SMILES: CCCOc1ccc2cc(C3CCC(C4CCC(OCC)CC4)CC3)oc(=O)c2c1F] |
| 799 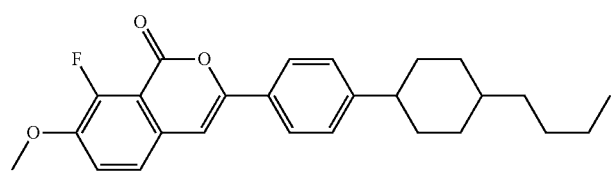 [SMILES: CCCCC1CCC(c2ccc(-c3cc4ccc(OC)c(F)c4c(=O)o3)cc2)CC1] |
| 800 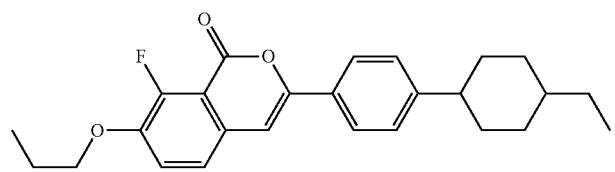 [SMILES: CCCOc1ccc2cc(-c3ccc(C4CCC(CC)CC4)cc3)oc(=O)c2c1F] |
| 801 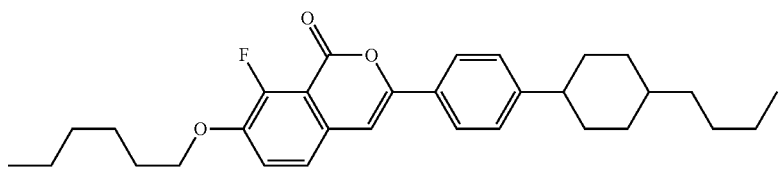 [SMILES: CCCCCCOc1ccc2cc(-c3ccc(C4CCC(CCCC)CC4)cc3)oc(=O)c2c1F] |
| 802 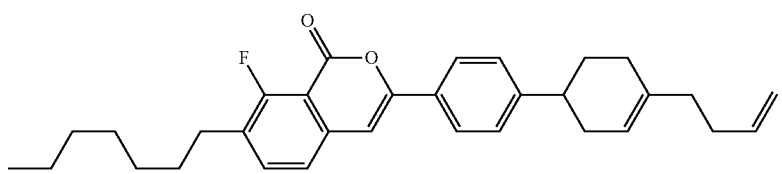 |

| No. |
|---|
| 803 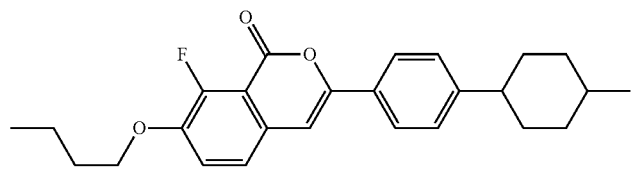 [SMILES: CCCCOc1ccc2cc(-c3ccc(C4CCC(C)CC4)cc3)oc(=O)c2c1F] |
| 804 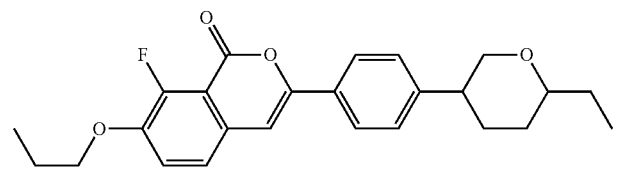 |
| 805 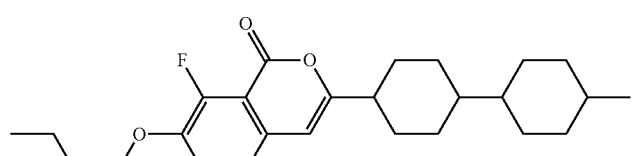 |
| 806 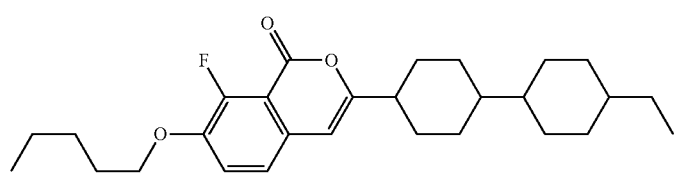 [SMILES: CCCCCOc1ccc2cc(C3CCC(C4CCC(CC)CC4)CC3)oc(=O)c2c1F] |
| 807 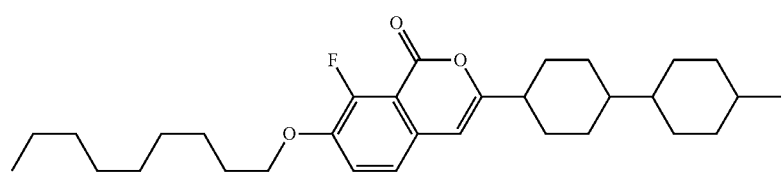 [SMILES: CCCCCCCCCOc1ccc2cc(C3CCC(C4CCC(C)CC4)CC3)oc(=O)c2c1F] |
| 808 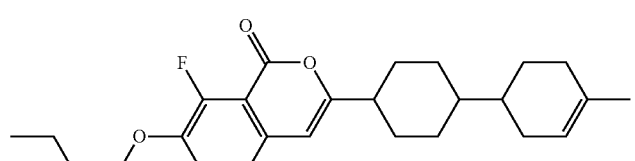 |
| 809 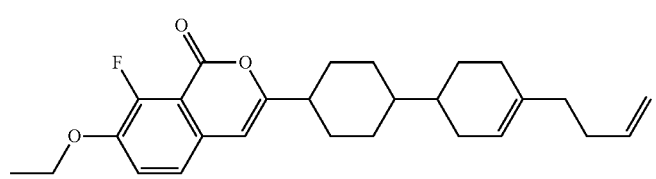 [SMILES: C=CCCC1=CCC(C2CCC(c3cc4ccc(OCC)c(F)c4c(=O)o3)CC2)CC1] |
| 810 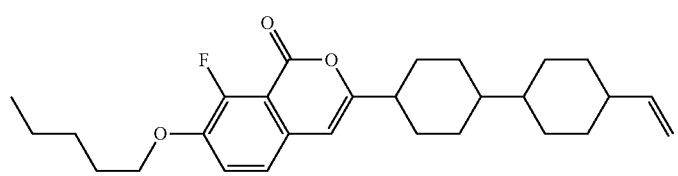 [SMILES: C=CC1CCC(C2CCC(c3cc4ccc(OCCCCC)c(F)c4c(=O)o3)CC2)CC1] |
| 811 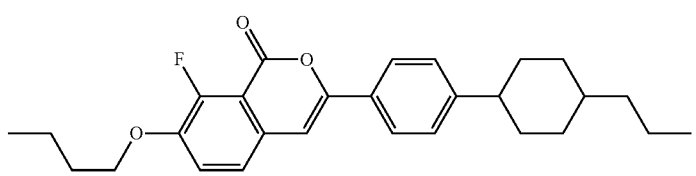 |

-continued
| No. |
|---|
| 812 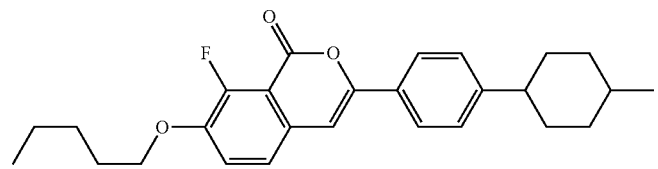 [SMILES: CCCCCOc1ccc2cc(-c3ccc(C4CCC(C)CC4)cc3)oc(=O)c2c1F] |
| 813 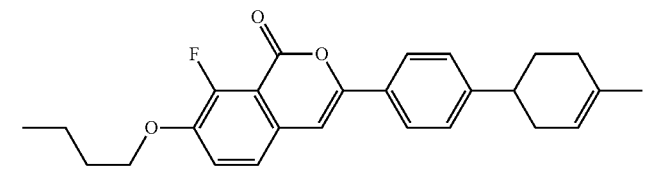 [SMILES: CCCCOc1ccc2cc(-c3ccc(C4CC=C(C)CC4)cc3)oc(=O)c2c1F] |
| 814 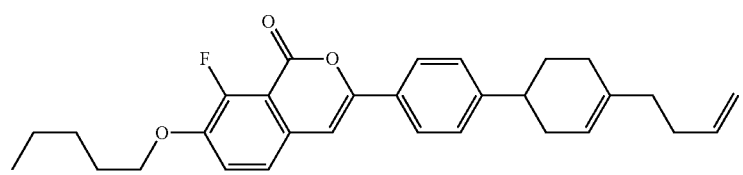 |
| 815 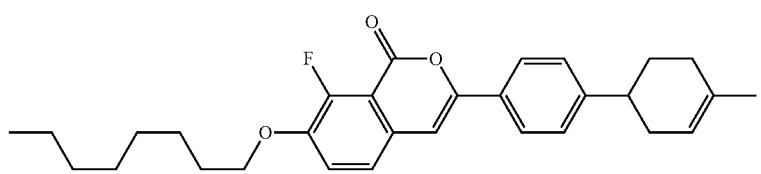 |
| 816 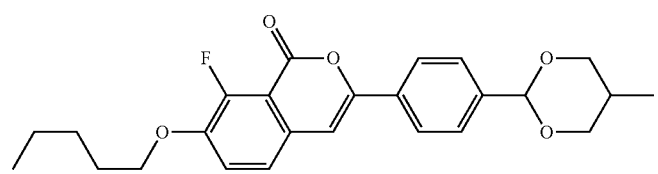 |
| 817 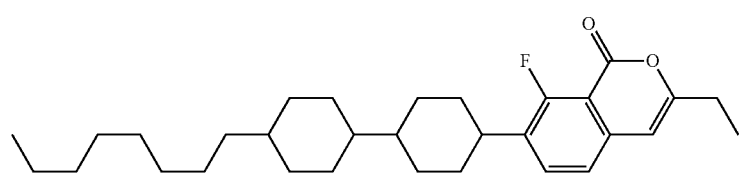 [SMILES: CCCCCCCCC1CCC(C2CCC(c3ccc4cc(CC)oc(=O)c4c3F)CC2)CC1] |
| 818 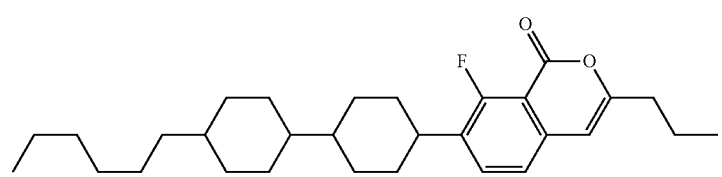 [SMILES: CCCCCCC1CCC(C2CCC(c3ccc4cc(CCC)oc(=O)c4c3F)CC2)CC1] |
| 819 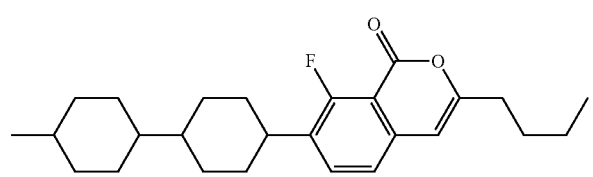 [SMILES: CCCCc1cc2ccc(C3CCC(C4CCC(C)CC4)CC3)c(F)c2c(=O)o1] |
| 820 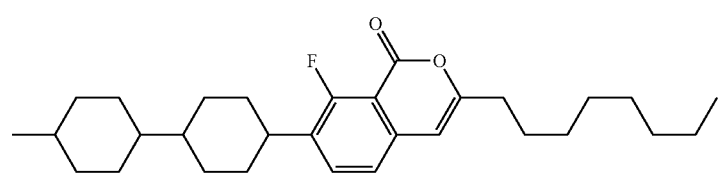 |

-continued
| No. |
|---|
| 821 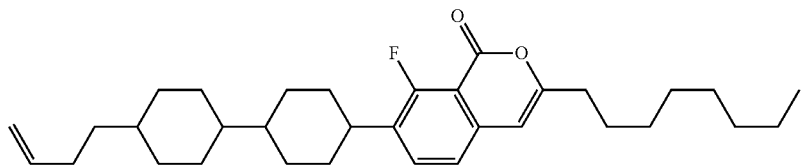 [SMILES: C=CCCC1CCC(C2CCC(c3ccc4cc(CCCCCCCC)oc(=O)c4c3F)CC2)CC1] |
| 822 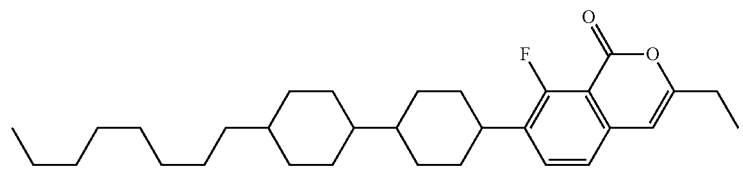 [SMILES: CCCCCCCCC1CCC(C2CCC(c3ccc4cc(CC)oc(=O)c4c3F)CC2)CC1] |
| 823 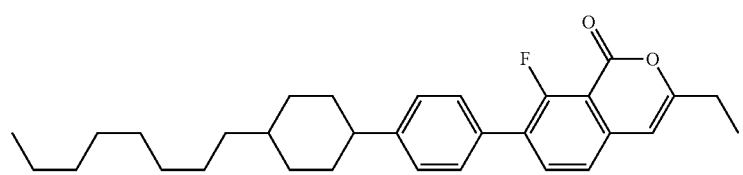 [SMILES: CCCCCCCCC1CCC(c2ccc(-c3ccc4cc(CC)oc(=O)c4c3F)cc2)CC1] |
| 824 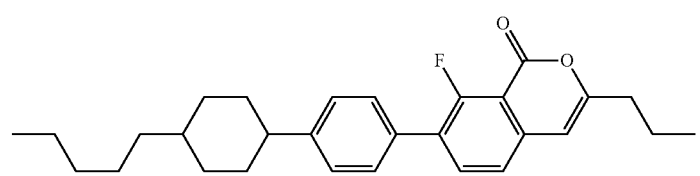 [SMILES: CCCCCC1CCC(c2ccc(-c3ccc4cc(CCC)oc(=O)c4c3F)cc2)CC1] |
| 825 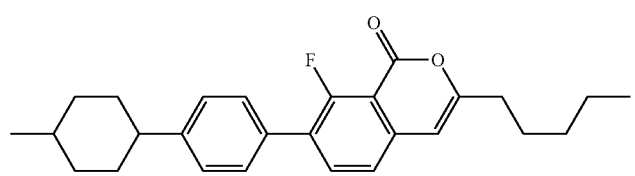 |
| 826 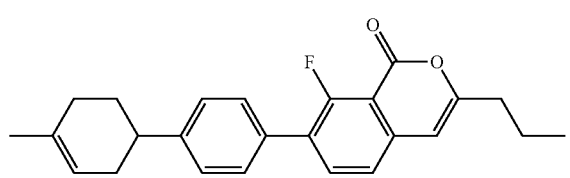 [SMILES: CCCc1cc2ccc(-c3ccc(C4CC=C(C)CC4)cc3)c(F)c2c(=O)o1] |
| 827 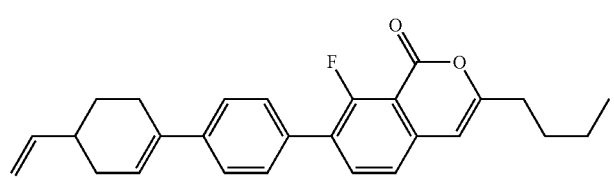 [SMILES: C=CC1CC=C(c2ccc(-c3ccc4cc(CCCC)oc(=O)c4c3F)cc2)CC1] |
| 828 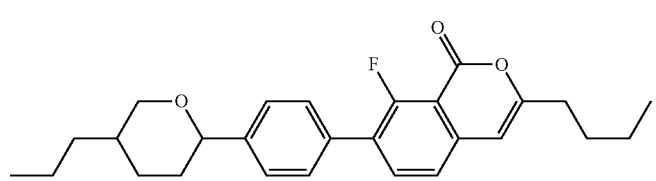 |
| 829 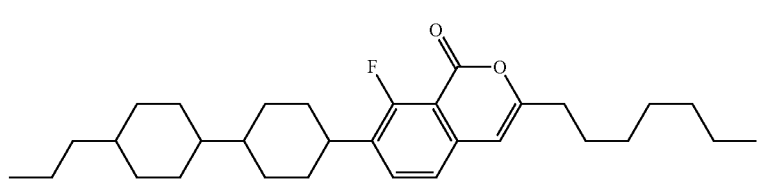 |

| No. |
|---|
| 830 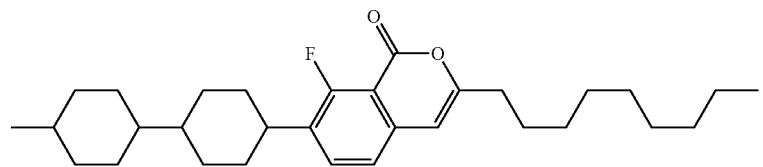 |
| 831 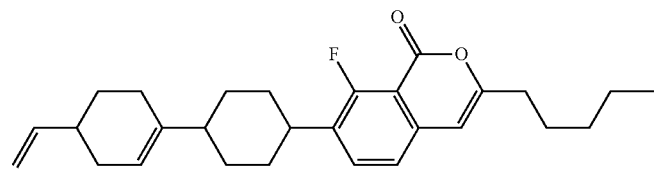 [SMILES: C=CC1CC=C(C2CCC(c3ccc4cc(CCCCC)oc(=O)c4c3F)CC2)CC1] |
| 832 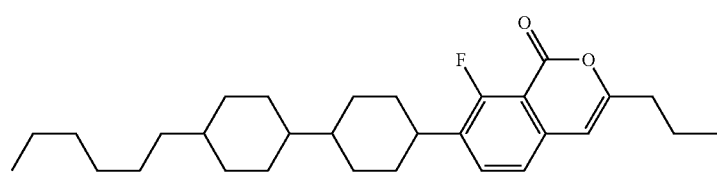 [SMILES: CCCCCCC1CCC(C2CCC(c3ccc4cc(CCC)oc(=O)c4c3F)CC2)CC1] |
| 833 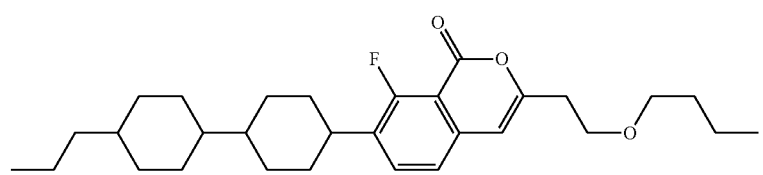 [SMILES: CCCCOCCc1cc2ccc(C3CCC(C4CCC(CCC)CC4)CC3)c(F)c2c(=O)o1] |
| 834 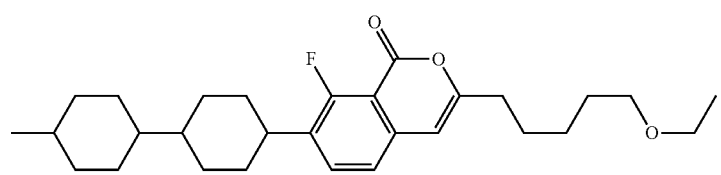 |
| 835 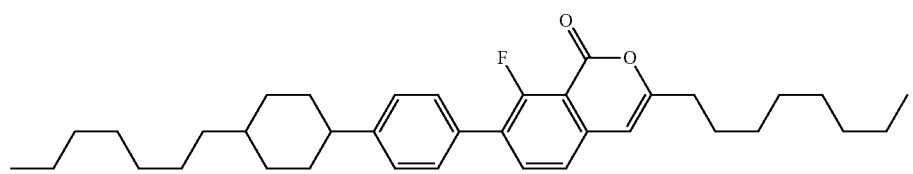 |
| 836 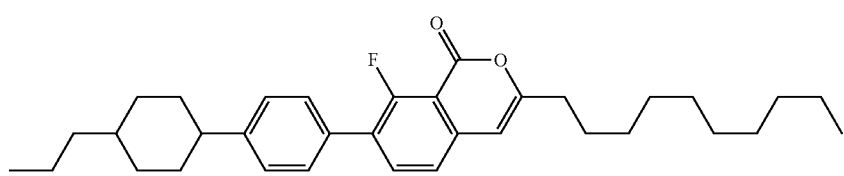 |
| 837 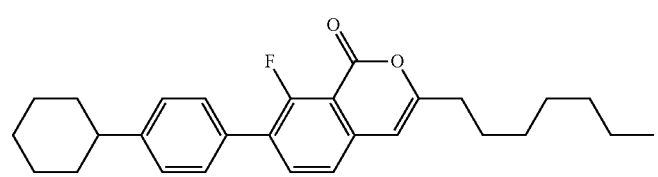 [SMILES: CCCCCCCc1cc2ccc(-c3ccc(C4CCCCC4)cc3)c(F)c2c(=O)o1] |
| 838 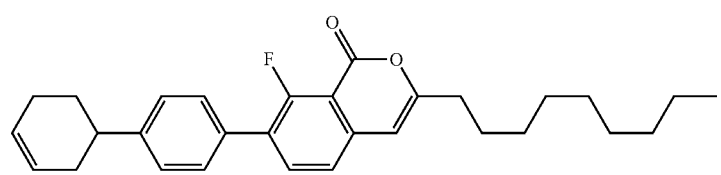 [SMILES: CCCCCCCCCc1cc2ccc(-c3ccc(C4CC=CCC4)cc3)c(F)c2c(=O)o1] |

-continued
| No. |
|---|
| 839 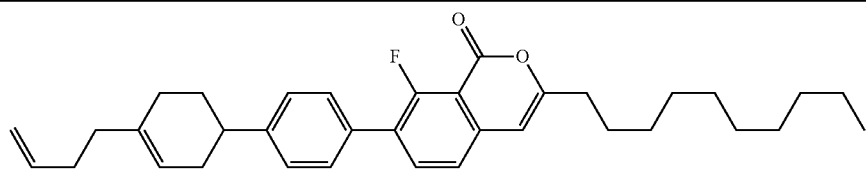 |
| 840 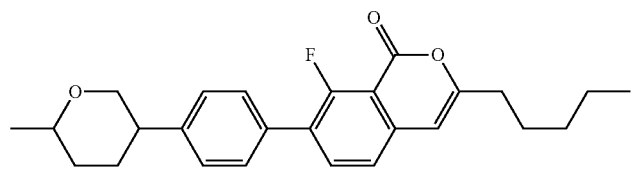 |
| 841 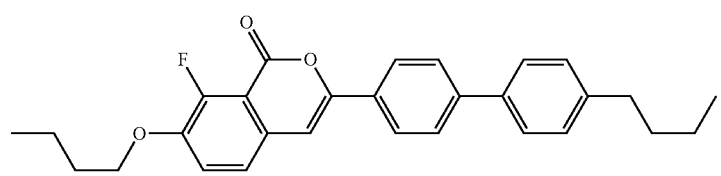 [SMILES: CCCCOc1ccc2cc(-c3ccc(-c4ccc(CCCC)cc4)cc3)oc(=O)c2c1F] |
| 842 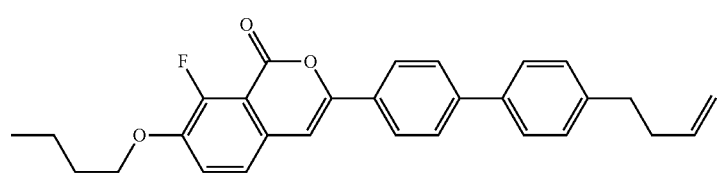 |
| 843 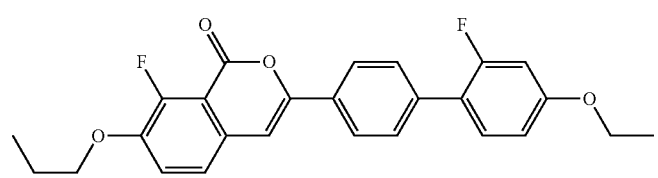 [SMILES: CCCOc1ccc2cc(-c3ccc(-c4ccc(OCC)cc4F)cc3)oc(=O)c2c1F] |
| 844 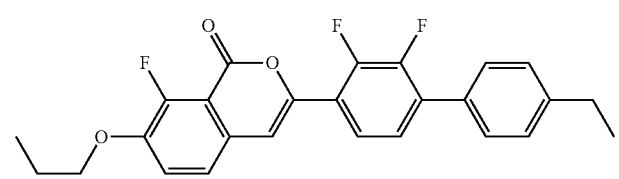 [SMILES: CCCOc1ccc2cc(-c3ccc(-c4ccc(CC)cc4)c(F)c3F)oc(=O)c2c1F] |
| 845 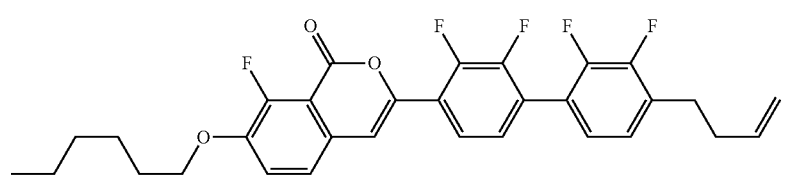 [SMILES: C=CCCc1ccc(-c2ccc(-c3cc4ccc(OCCCCCC)c(F)c4c(=O)o3)c(F)c2F)c(F)c1F] |
| 846 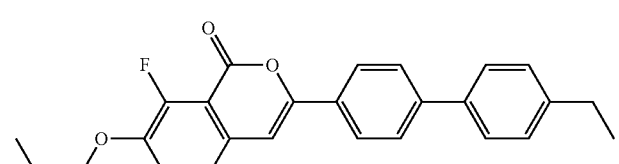 |
| 847 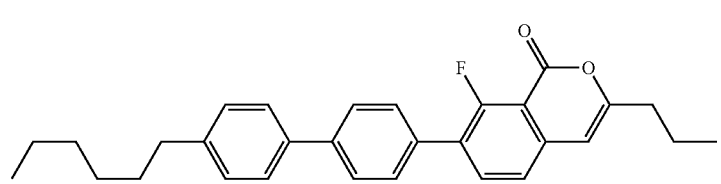 [SMILES: CCCCCCc1ccc(-c2ccc(-c3ccc4cc(CCC)oc(=O)c4c3F)cc2)cc1] |

| No. |
|---|
| 848 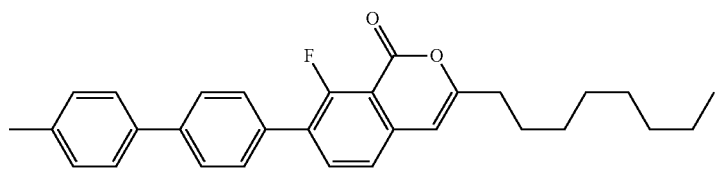 |
| 849 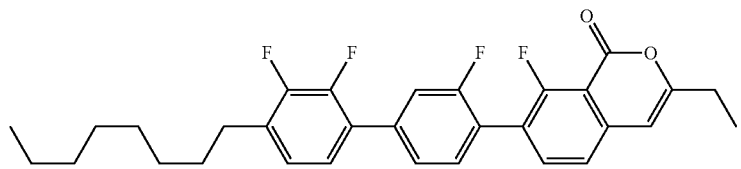 [SMILES: CCCCCCCCc1ccc(-c2ccc(-c3ccc4cc(CC)oc(=O)c4c3F)c(F)c2)c(F)c1F] |
| 850 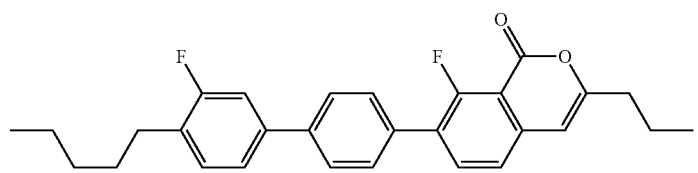 |
| 851 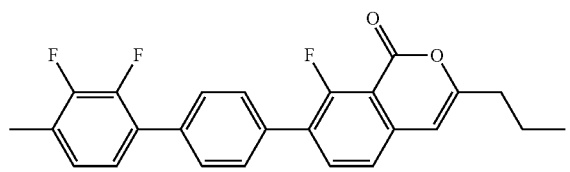 [SMILES: CCCc1cc2ccc(-c3ccc(-c4ccc(C)c(F)c4F)cc3)c(F)c2c(=O)o1] |
| 852 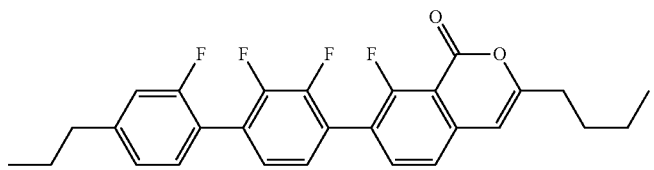 [SMILES: CCCCc1cc2ccc(-c3ccc(-c4ccc(CCC)cc4F)c(F)c3F)c(F)c2c(=O)o1] |
| 853 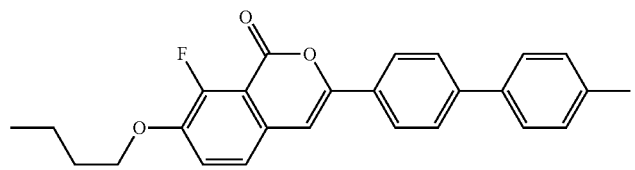 |
| 854 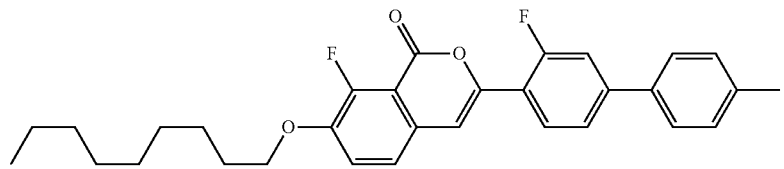 [SMILES: CCCCCCCCCOc1ccc2cc(-c3ccc(-c4ccc(C)cc4)cc3F)oc(=O)c2c1F] |
| 855 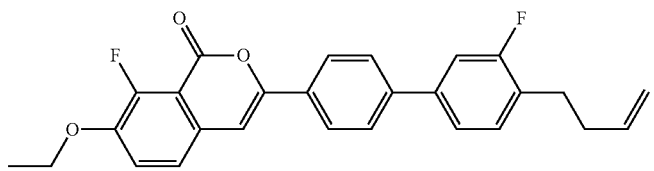 [SMILES: C=CCCc1ccc(-c2ccc(-c3cc4ccc(OCC)c(F)c4c(=O)o3)cc2)cc1F] |
| 856 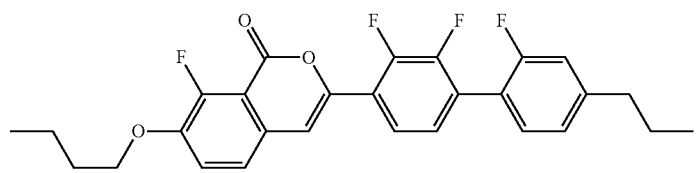 [SMILES: CCCCOc1ccc2cc(-c3ccc(-c4ccc(CCC)cc4F)c(F)c3F)oc(=O)c2c1F] |

-continued
| No. | |
|---|---|
| 857 | 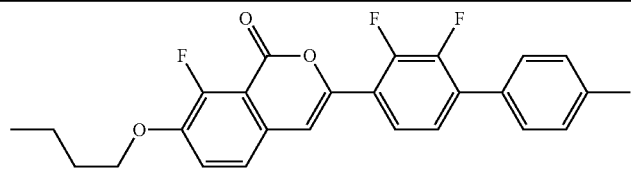 |
| 858 | 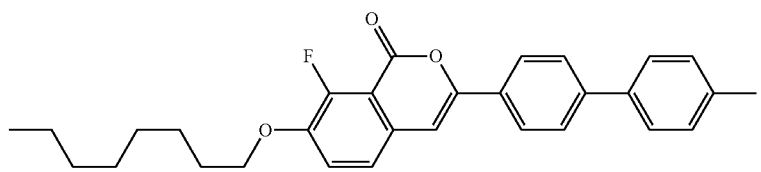 [SMILES: CCCCCCCCOc1ccc2cc(-c3ccc(-c4ccc(C)cc4)cc3)oc(=O)c2c1F] |
| 859 | 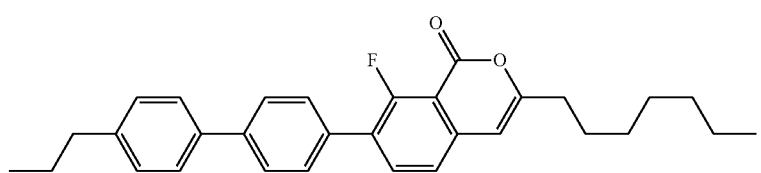 [SMILES: CCCCCCCc1cc2ccc(-c3ccc(-c4ccc(CCC)cc4)cc3)c(F)c2c(=O)o1] |
| 860 | 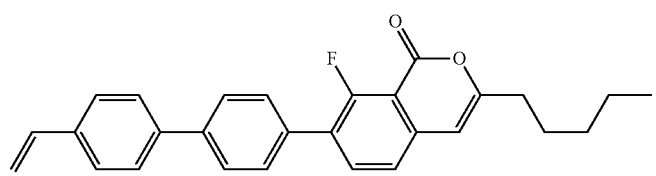 [SMILES: C=Cc1ccc(-c2ccc(-c3ccc4cc(CCCCC)oc(=O)c4c3F)cc2)cc1] |
| 861 | 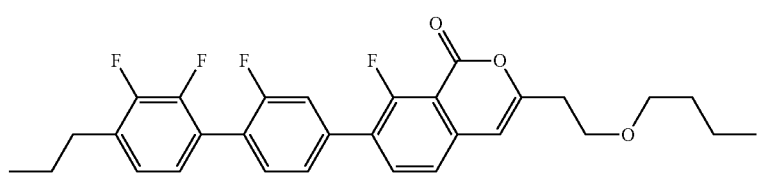 |
| 862 | 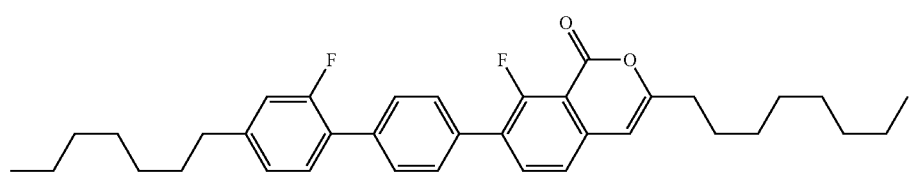 [SMILES: CCCCCCCCc1cc2ccc(-c3ccc(-c4ccc(CCCCCCC)cc4F)cc3)c(F)c2c(=O)o1] |
| 863 | 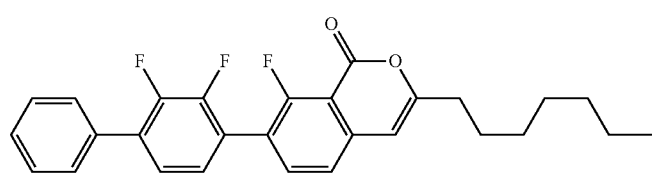 [SMILES: CCCCCCCc1cc2ccc(-c3ccc(-c4ccccc4)c(F)c3F)c(F)c2c(=O)o1] |
| 864 | 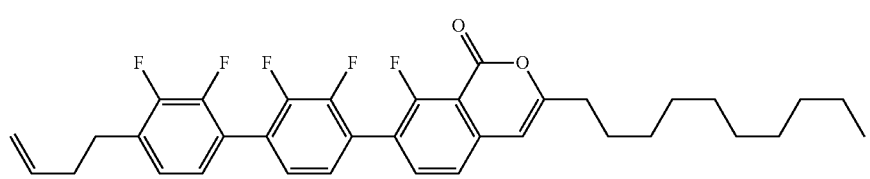 |
| 865 | 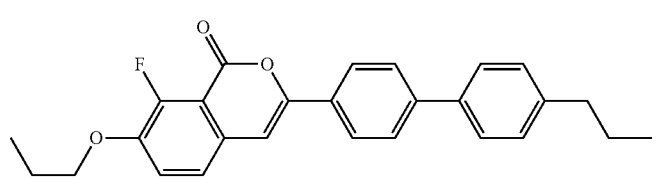 |

| No. | |
|---|---|
| 866 | 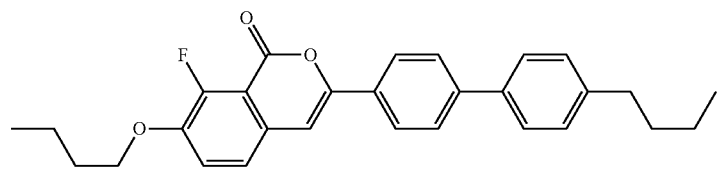 [SMILES: CCCCOc1ccc2cc(-c3ccc(-c4ccc(CCCC)cc4)cc3)oc(=O)c2c1F] |
| 867 | 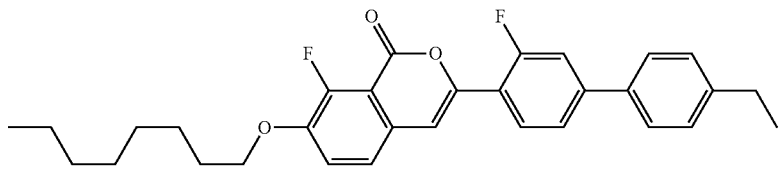 [SMILES: CCCCCCCCOc1ccc2cc(-c3ccc(-c4ccc(CC)cc4)cc3F)oc(=O)c2c1F] |
| 868 | 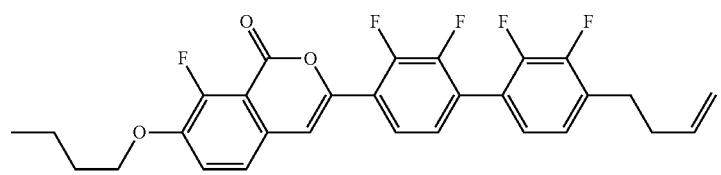 |
| 869 | 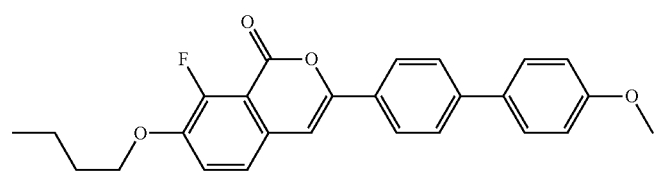 [SMILES: CCCCOc1ccc2cc(-c3ccc(-c4ccc(OC)cc4)cc3)oc(=O)c2c1F] |
| 870 | 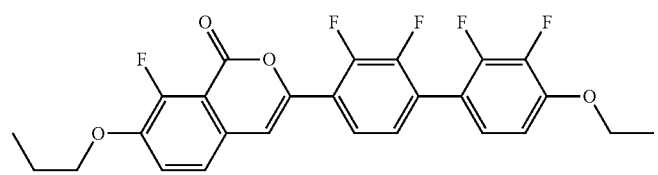 |
| 871 | 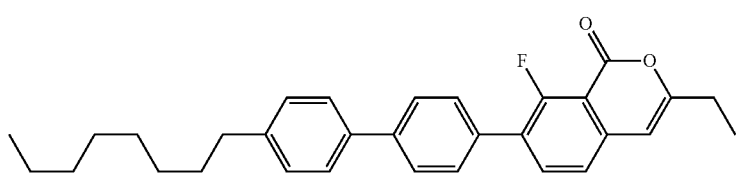 |
| 872 | 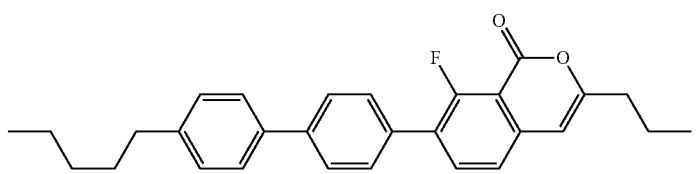 |
| 873 | 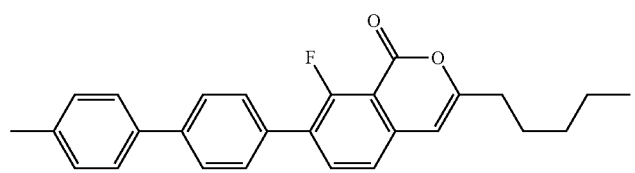 |
| 874 | 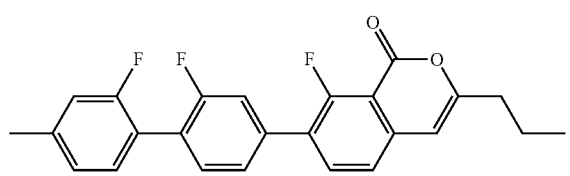 |

-continued
| No. | |
|---|---|
| 875 | 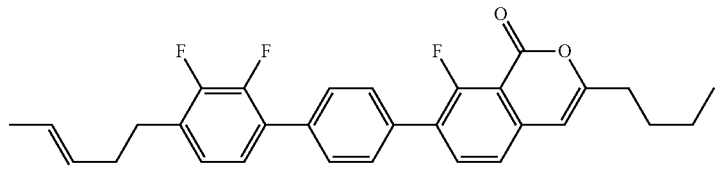 [SMILES: C/C=C/CCc1ccc(-c2ccc(-c3ccc4cc(CCCC)oc(=O)c4c3F)cc2)c(F)c1F] |
| 876 | 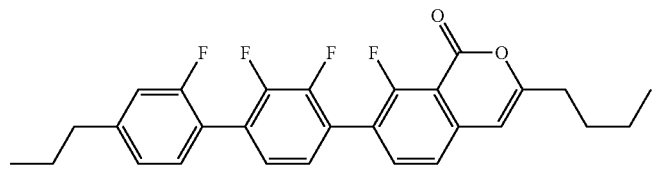 [SMILES: CCCCc1cc2ccc(-c3ccc(-c4ccc(CCC)cc4F)c(F)c3F)c(F)c2c(=O)o1] |
| 877 | 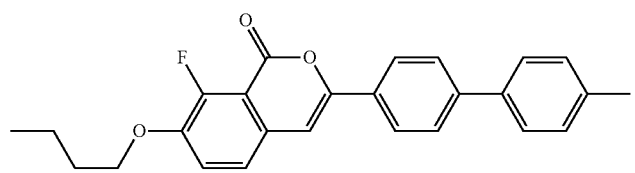 [SMILES: CCCCOc1ccc2cc(-c3ccc(-c4ccc(C)cc4)cc3)oc(=O)c2c1F] |
| 878 | 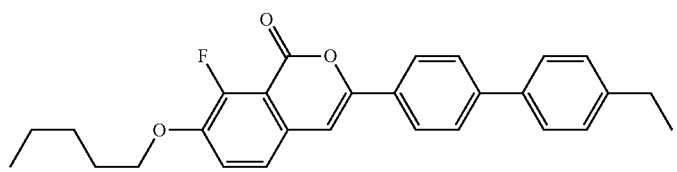 [SMILES: CCCCCOc1ccc2cc(-c3ccc(-c4ccc(CC)cc4)cc3)oc(=O)c2c1F] |
| 879 | 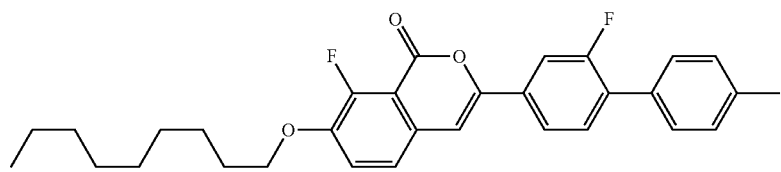 [SMILES: CCCCCCCCCOc1ccc2cc(-c3ccc(-c4ccc(C)cc4)c(F)c3)oc(=O)c2c1F] |
| 880 | 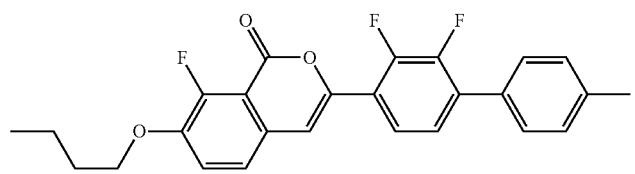 |
| 881 | 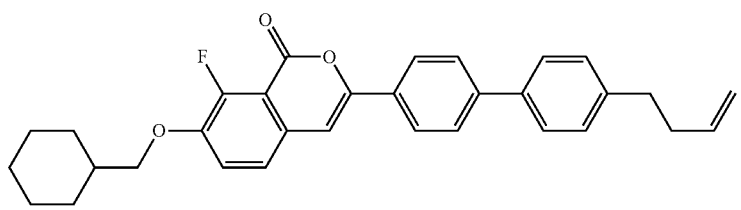 [SMILES: C=CCCc1ccc(-c2ccc(-c3cc4ccc(OCC5CCCCC5)c(F)c4c(=O)o3)cc2)cc1] |
| 882 | 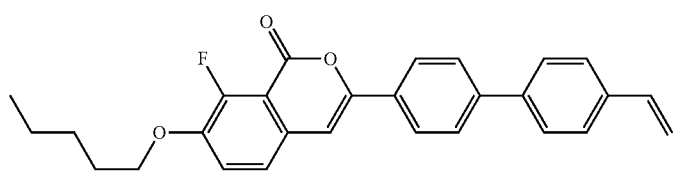 |

| No. |
|---|
| 883 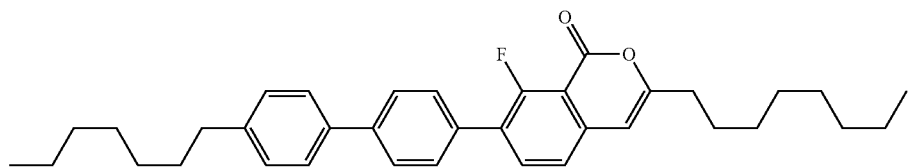 [SMILES: CCCCCCCCc1cc2ccc(-c3ccc(-c4ccc(CCCCCCC)cc4)cc3)c(F)c2c(=O)o1] |
| 884 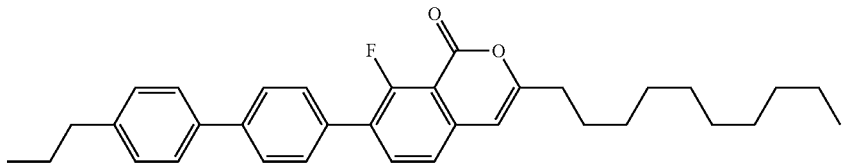 [SMILES: CCCCCCCCCCc1cc2ccc(-c3ccc(-c4ccc(CCC)cc4)cc3)c(F)c2c(=O)o1] |
| 885 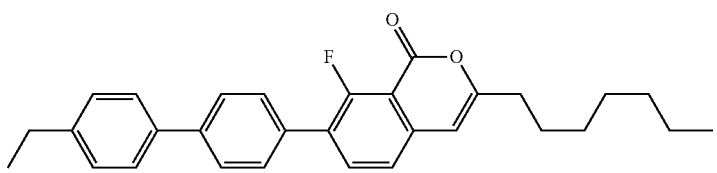 [SMILES: CCCCCCCc1cc2ccc(-c3ccc(-c4ccc(CC)cc4)cc3)c(F)c2c(=O)o1] |
| 886 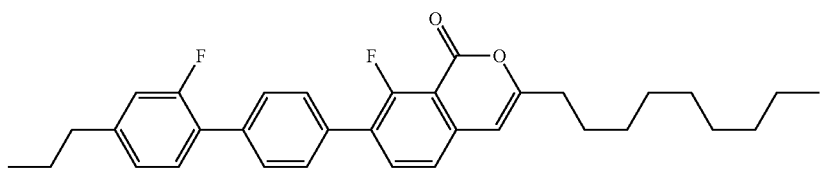 [SMILES: CCCCCCCCCc1cc2ccc(-c3ccc(-c4ccc(CCC)cc4F)cc3)c(F)c2c(=O)o1] |
| 887 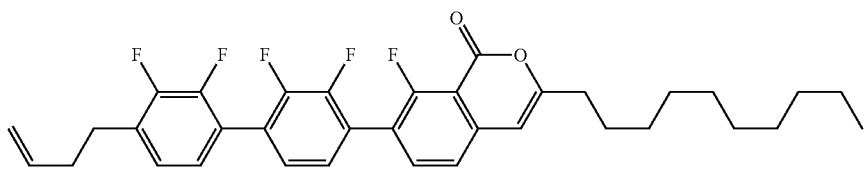 |
| 888 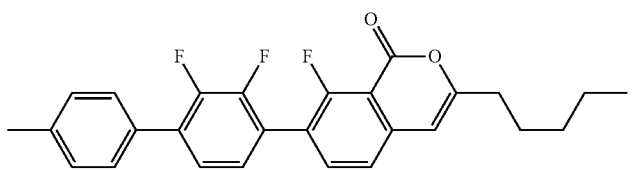 [SMILES: CCCCCc1cc2ccc(-c3ccc(-c4ccc(C)cc4)c(F)c3F)c(F)c2c(=O)o1] |
| 889 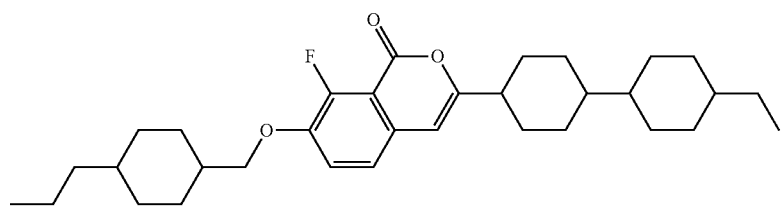 [SMILES: CCCC1CCC(COc2ccc3cc(C4CCC(C5CCC(CC)CC5)CC4)oc(=O)c3c2F)CC1] |
| 890 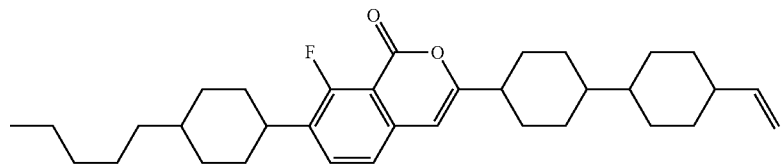 [SMILES: C=CC1CCC(C2CCC(c3cc4ccc(C5CCC(CCCCC)CC5)c(F)c4c(=O)o3)CC2)CC1] |

| No. | |
|---|---|
| 891 | 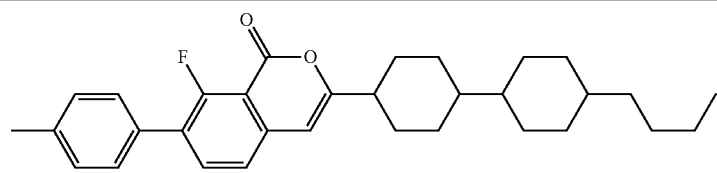 [SMILES: CCCCC1CCC(C2CCC(c3cc4ccc(-c5ccc(C)cc5)c(F)c4c(=O)o3)CC2)CC1] |
| 892 | 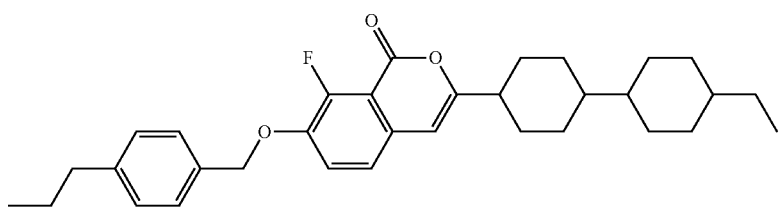 [SMILES: CCCc1ccc(COc2ccc3cc(C4CCC(C5CCC(CC)CC5)CC4)oc(=O)c3c2F)cc1] |
| 893 | 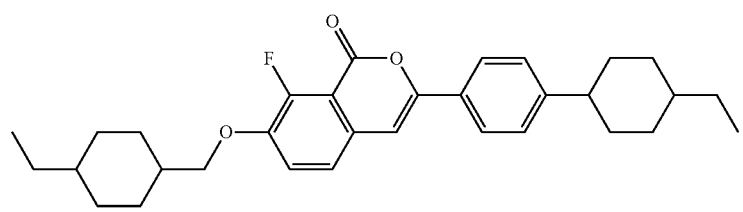 [SMILES: CCC1CCC(COc2ccc3cc(-c4ccc(C5CCC(CC)CC5)cc4)oc(=O)c3c2F)CC1] |
| 894 | 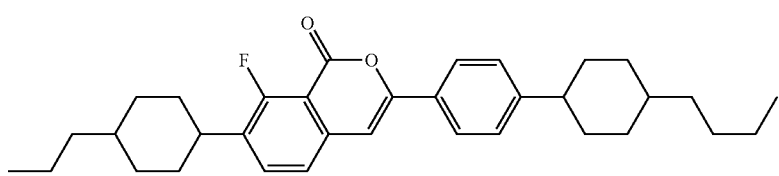 [SMILES: CCCCC1CCC(c2ccc(-c3cc4ccc(C5CCC(CCC)CC5)c(F)c4c(=O)o3)cc2)CC1] |
| 895 | 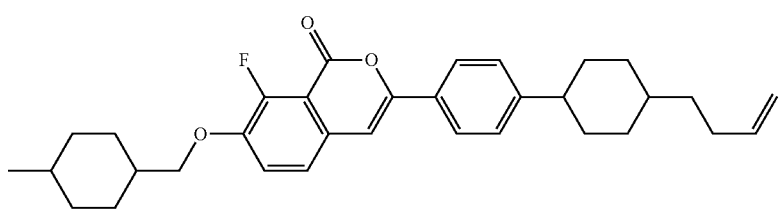 [SMILES: C=CCCC1CCC(c2ccc(-c3cc4ccc(OCC5CCC(C)CC5)c(F)c4c(=O)o3)cc2)CC1] |
| 896 | 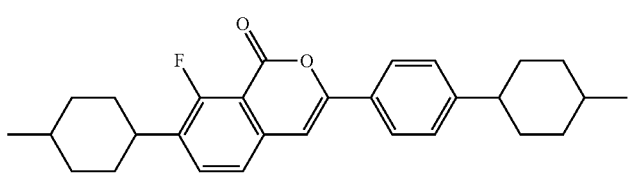 |
| 897 | 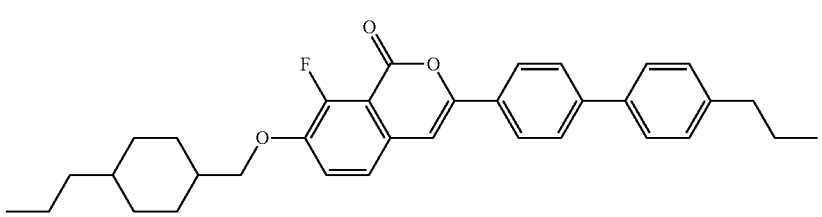 [SMILES: CCCc1ccc(-c2ccc(-c3cc4ccc(OCC5CCC(CCC)CC5)c(F)c4c(=O)o3)cc2)cc1] |
| 898 | 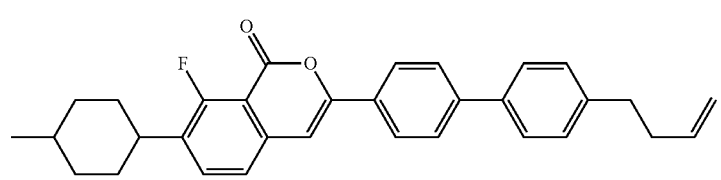 [SMILES: C=CCCc1ccc(-c2ccc(-c3cc4ccc(C5CCC(C)CC5)c(F)c4c(=O)o3)cc2)cc1] |

-continued
| No. |
|---|
| 899 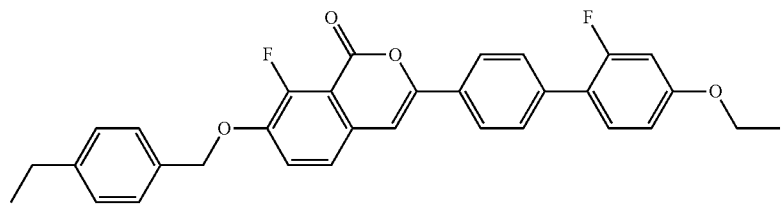 [SMILES: CCOc1ccc(-c2ccc(-c3cc4ccc(OCc5ccc(CC)cc5)c(F)c4c(=O)o3)cc2)c(F)c1] |
| 900 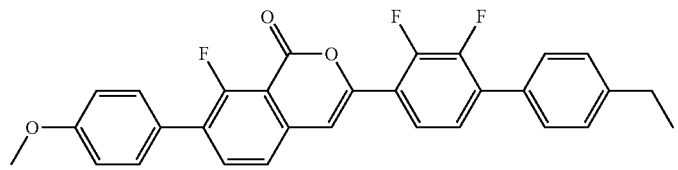 [SMILES: CCc1ccc(-c2ccc(-c3cc4ccc(-c5ccc(OC)cc5)c(F)c4c(=O)o3)c(F)c2F)cc1] |
| 901 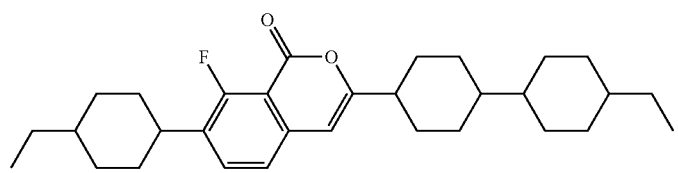 [SMILES: CCC1CCC(c2ccc3cc(C4CCC(C5CCC(CC)CC5)CC4)oc(=O)c3c2F)CC1] |
| 902 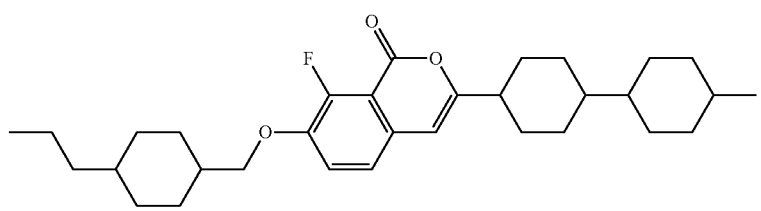 [SMILES: CCCC1CCC(COc2ccc3cc(C4CCC(C5CCC(C)CC5)CC4)oc(=O)c3c2F)CC1] |
| 903 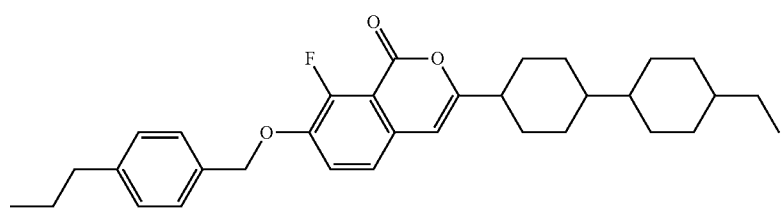 [SMILES: CCCc1ccc(COc2ccc3cc(C4CCC(C5CCC(CC)CC5)CC4)oc(=O)c3c2F)cc1] |
| 904 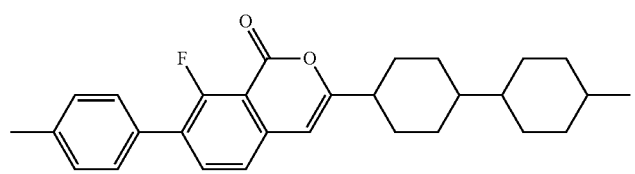 |
| 905 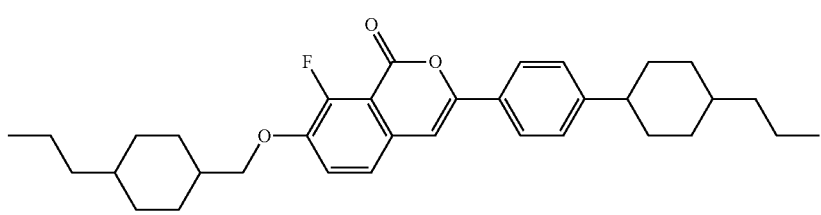 [SMILES: CCCC1CCC(COc2ccc3cc(-c4ccc(C5CCC(CCC)CC5)cc4)oc(=O)c3c2F)CC1] |
| 906 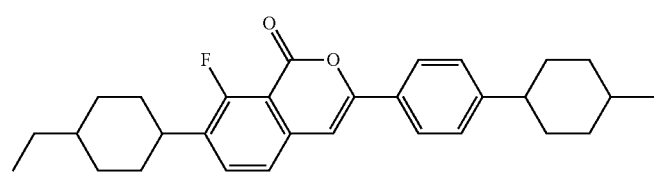 [SMILES: CCC1CCC(c2ccc3cc(-c4ccc(C5CCC(C)CC5)cc4)oc(=O)c3c2F)CC1] |

US 10,428,273 B2
325                                                                         326
-continued
| No. |
|---|
| 907 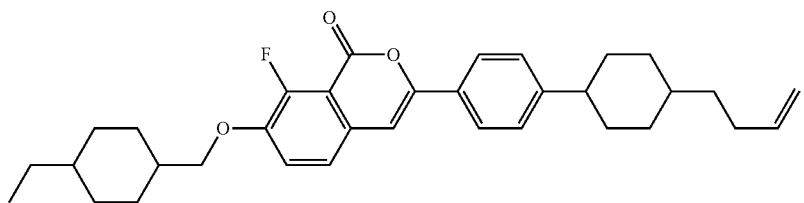 [SMILES: C=CCCC1CCC(c2ccc(-c3cc4ccc(OCC5CCC(CC)CC5)c(F)c4c(=O)o3)cc2)CC1] |
| 908 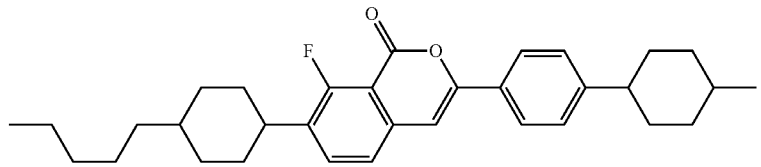 [SMILES: CCCCCC1CCC(c2ccc3cc(-c4ccc(C5CCC(C)CC5)cc4)oc(=O)c3c2F)CC1] |
| 909 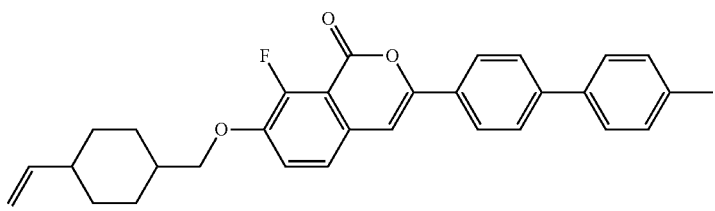 [SMILES: C=CC1CCC(COc2ccc3cc(-c4ccc(-c5ccc(C)cc5)cc4)oc(=O)c3c2F)CC1] |
| 910 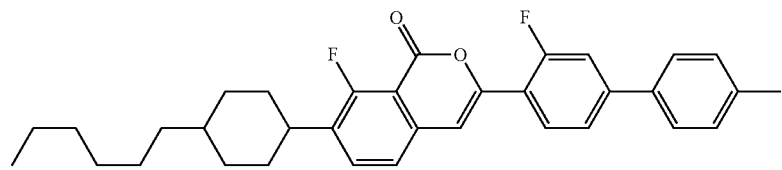 |
| 911 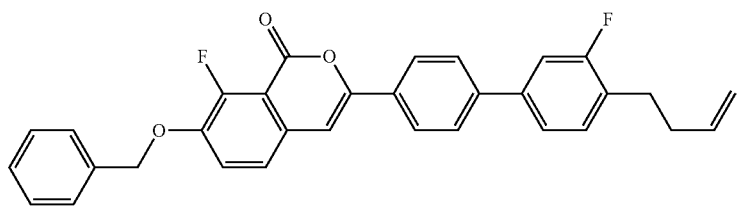 [SMILES: C=CCCc1ccc(-c2ccc(-c3cc4ccc(OCc5ccccc5)c(F)c4c(=O)o3)cc2)cc1F] |
| 912 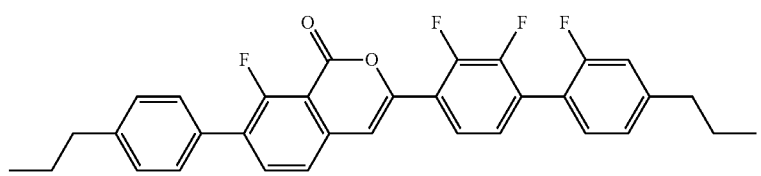 [SMILES: CCCc1ccc(-c2ccc3cc(-c4ccc(-c5ccc(CCC)cc5F)c(F)c4F)oc(=O)c3c2F)cc1] |
| 913 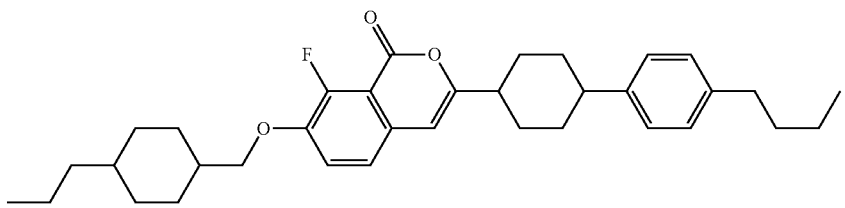 [SMILES: CCCCc1ccc(C2CCC(c3cc4ccc(OCC5CCC(CCC)CC5)c(F)c4c(=O)o3)CC2)cc1] |
| 914 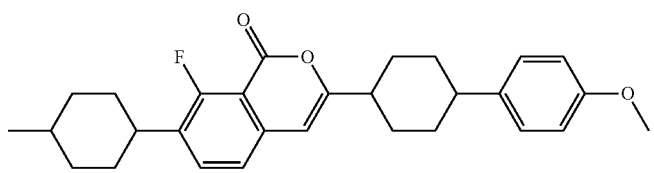 |

| No. |
|---|
| 915 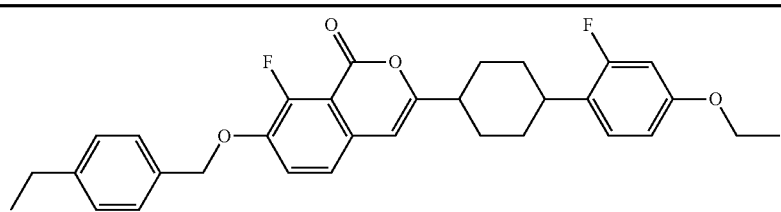 |
| 916 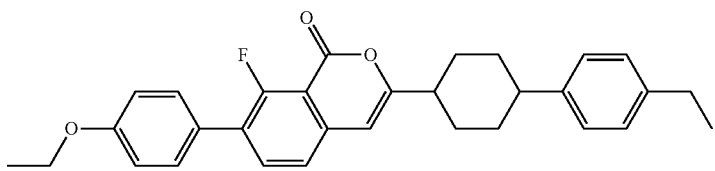 [SMILES: CCOc1ccc(-c2ccc3cc(C4CCC(c5ccc(CC)cc5)CC4)oc(=O)c3c2F)cc1] |
| 917 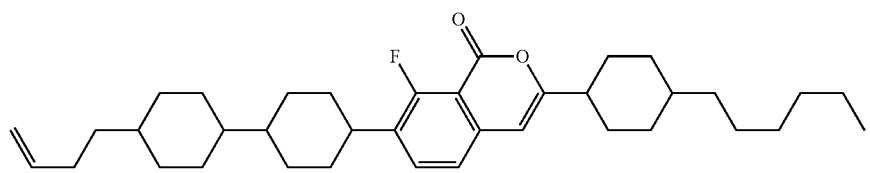 [SMILES: C=CCCC1CCC(C2CCC(c3ccc4cc(C5CCC(CCCCCC)CC5)oc(=O)c4c3F)CC2)CC1] |
| 918 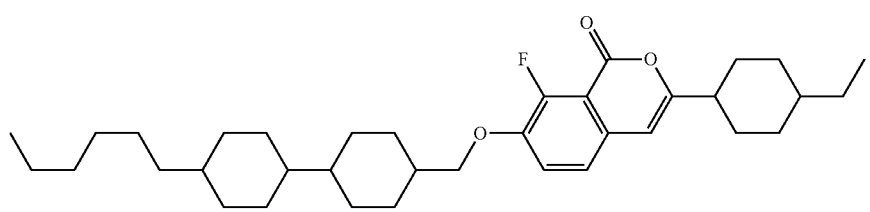 [SMILES: CCCCCCC1CCC(C2CCC(COc3ccc4cc(C5CCC(CC)CC5)oc(=O)c4c3F)CC2)CC1] |
| 919 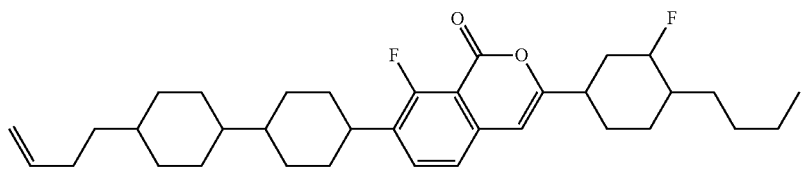 [SMILES: C=CCCC1CCC(C2CCC(c3ccc4cc(C5CCC(CCCC)C(F)C5)oc(=O)c4c3F)CC2)CC1] |
| 920 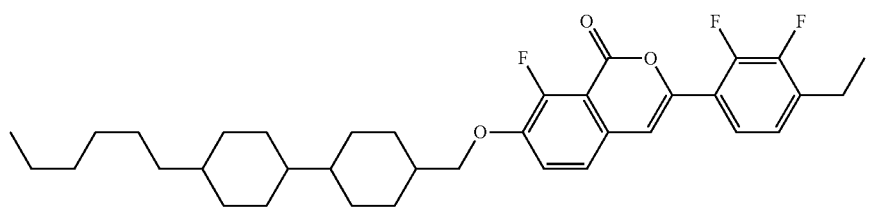 [SMILES: CCCCCCC1CCC(C2CCC(COc3ccc4cc(-c5ccc(CC)c(F)c5F)oc(=O)c4c3F)CC2)CC1] |
| 921 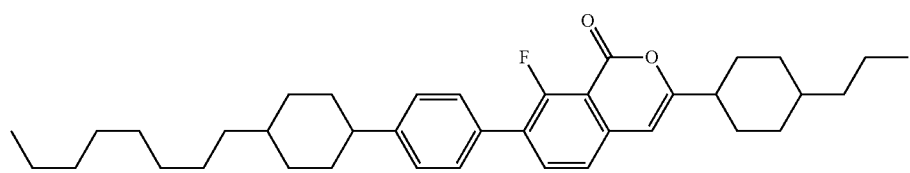 [SMILES: CCCCCCCCC1CCC(c2ccc(-c3ccc4cc(C5CCC(CCC)CC5)oc(=O)c4c3F)cc2)CC1] |
| 922 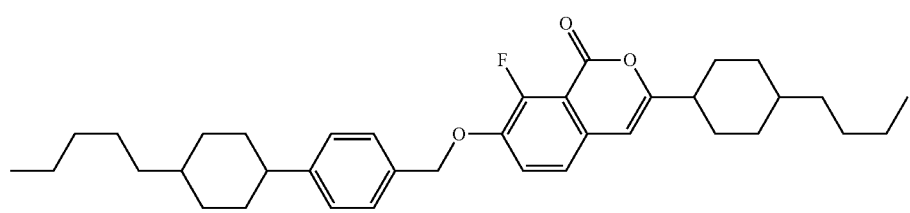 [SMILES: CCCCCC1CCC(c2ccc(COc3ccc4cc(C5CCC(CCCC)CC5)oc(=O)c4c3F)cc2)CC1] |

-continued
| No. | |
|---|---|
| 923 | 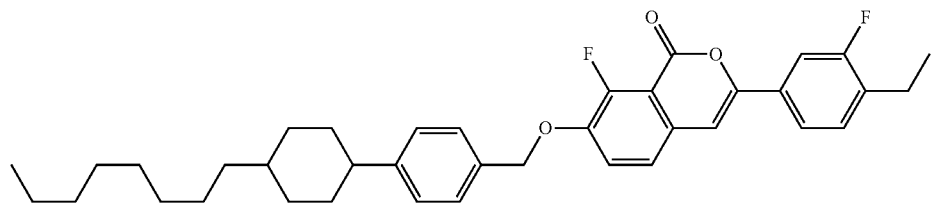 [SMILES: CCCCCCCCC1CCC(c2ccc(COc3ccc4cc(-c5ccc(CC)c(F)c5)oc(=O)c4c3F)cc2)CC1] |
| 924 | 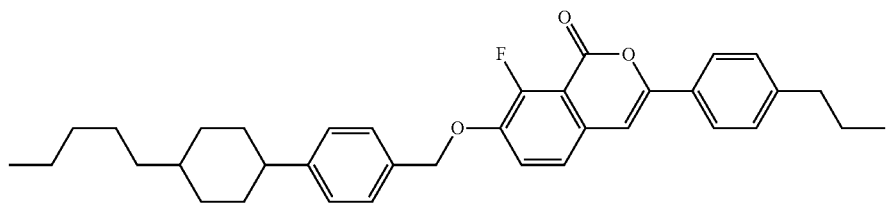 [SMILES: CCCCCC1CCC(c2ccc(COc3ccc4cc(-c5ccc(CCC)cc5)oc(=O)c4c3F)cc2)CC1] |
| 925 | 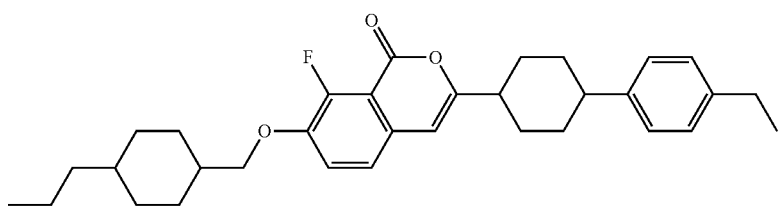 [SMILES: CCCC1CCC(COc2ccc3cc(C4CCC(c5ccc(CC)cc5)CC4)oc(=O)c3c2F)CC1] |
| 926 | 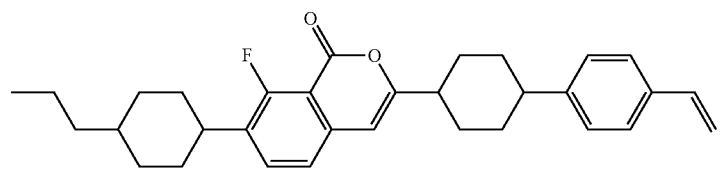 [SMILES: C=Cc1ccc(C2CCC(c3cc4ccc(C5CCC(CCC)CC5)c(F)c4c(=O)o3)CC2)cc1] |
| 927 | 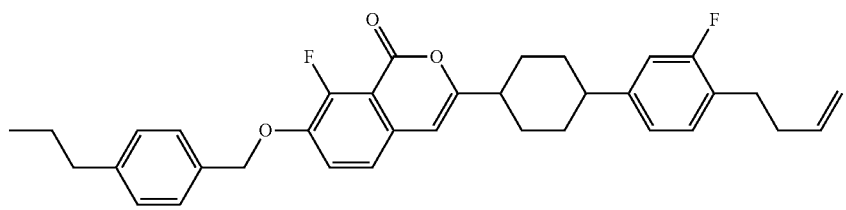 [SMILES: C=CCCc1ccc(C2CCC(c3cc4ccc(OCc5ccc(CCC)cc5)c(F)c4c(=O)o3)CC2)cc1F] |
| 928 | 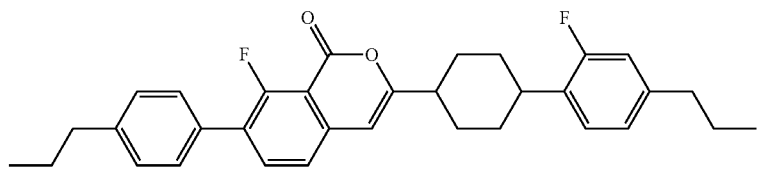 [SMILES: CCCc1ccc(-c2ccc3cc(C4CCC(c5ccc(CCC)cc5F)CC4)oc(=O)c3c2F)cc1] |
| 929 | 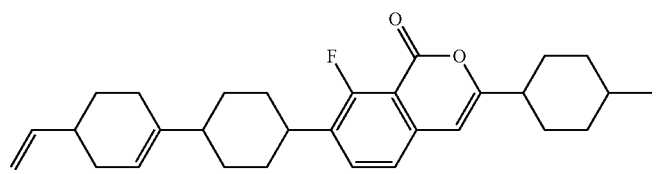 [SMILES: C=CC1CC=C(C2CCC(c3ccc4cc(C5CCC(C)CC5)oc(=O)c4c3F)CC2)CC1] |
| 930 | 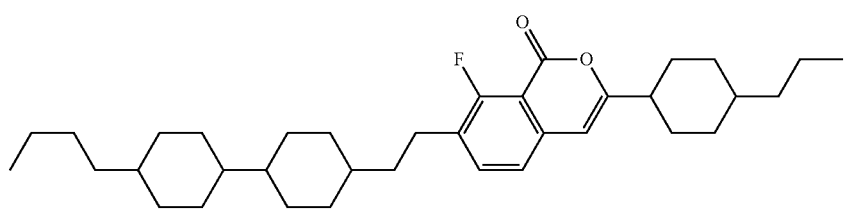 [SMILES: CCCCC1CCC(C2CCC(CCc3ccc4cc(C5CCC(CCC)CC5)oc(=O)c4c3F)CC2)CC1] |

-continued
| No. | |
|---|---|
| 931 | 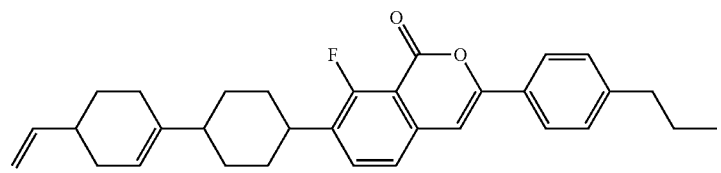 [SMILES: C=CC1CC=C(C2CCC(c3ccc4cc(-c5ccc(CCC)cc5)oc(=O)c4c3F)CC2)CC1] |
| 932 | 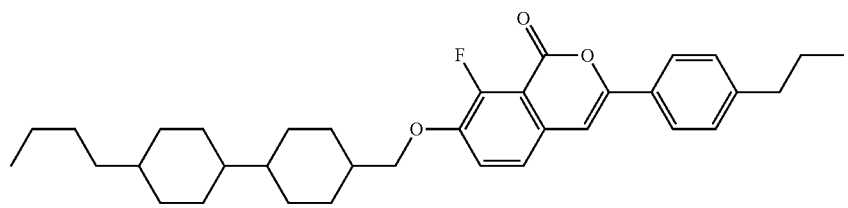 [SMILES: CCCCC1CCC(C2CCC(COc3ccc4cc(-c5ccc(CCC)cc5)oc(=O)c4c3F)CC2)CC1] |
| 933 | 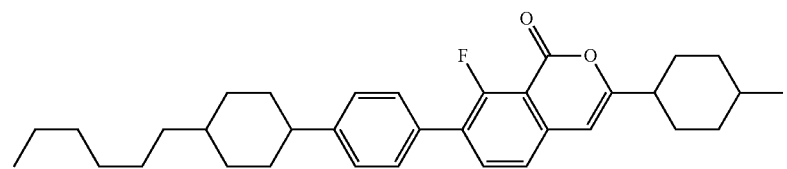 |
| 934 | 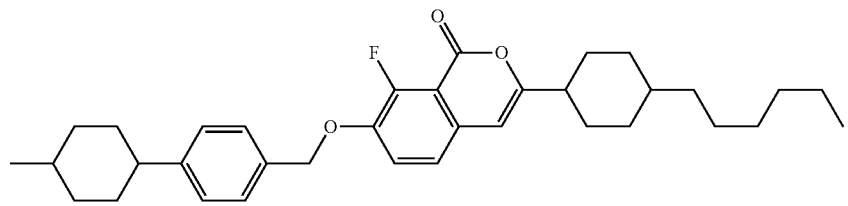 |
| 935 | 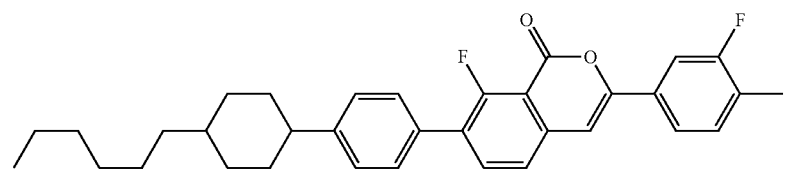 [SMILES: CCCCCCC1CCC(c2ccc(-c3ccc4cc(-c5ccc(C)c(F)c5)oc(=O)c4c3F)cc2)CC1] |
| 936 | 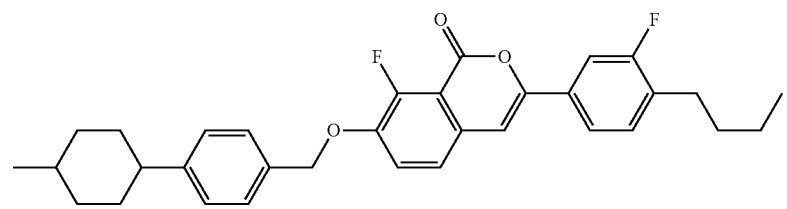 [SMILES: CCCCc1ccc(-c2cc3ccc(OCc4ccc(C5CCC(C)CC5)cc4)c(F)c3c(=O)o2)cc1F] |
| 937 | 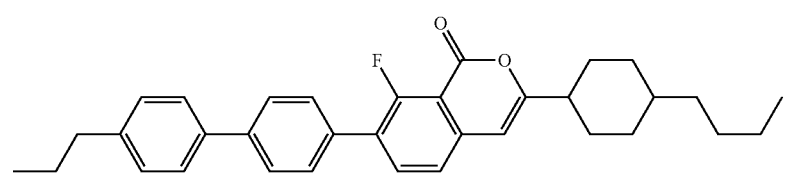 [SMILES: CCCCC1CCC(c2cc3ccc(-c4ccc(-c5ccc(CCC)cc5)cc4)c(F)c3c(=O)o2)CC1] |
| 938 | 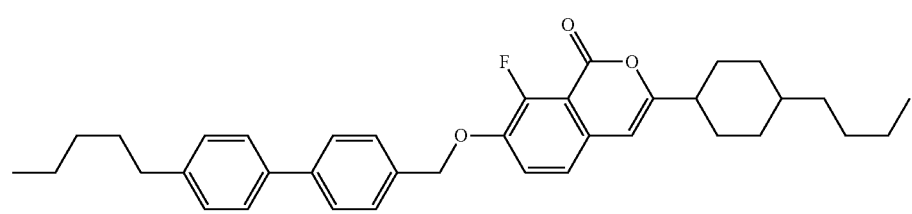 [SMILES: CCCCCc1ccc(-c2ccc(COc3ccc4cc(C5CCC(CCCC)CC5)oc(=O)c4c3F)cc2)cc1] |

| No. |
|---|
| 939 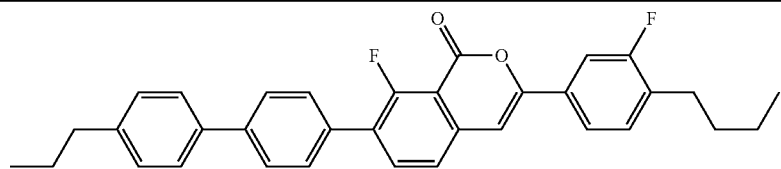 |
| 940 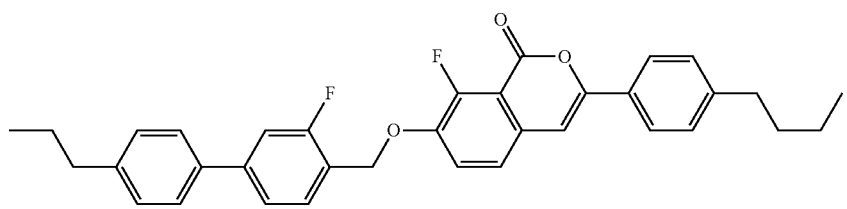 [SMILES: CCCCc1ccc(-c2cc3ccc(OCc4ccc(-c5ccc(CCC)cc5)cc4F)c(F)c3c(=O)o2)cc1] |
| 941 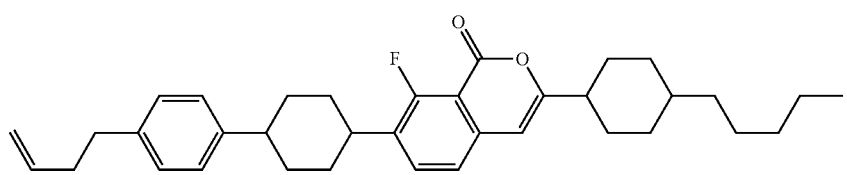 |
| 942 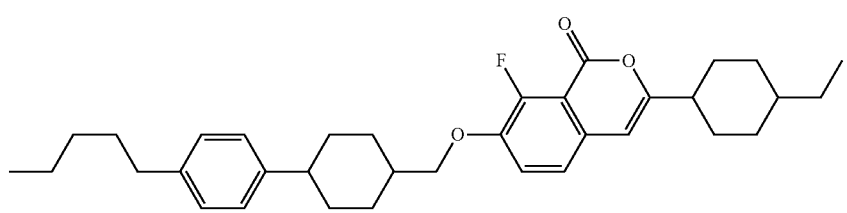 [SMILES: CCCCCc1ccc(C2CCC(COc3ccc4cc(C5CCC(CC)CC5)oc(=O)c4c3F)CC2)cc1] |
| 943 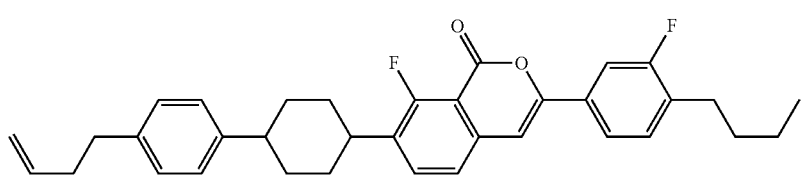 |
| 944 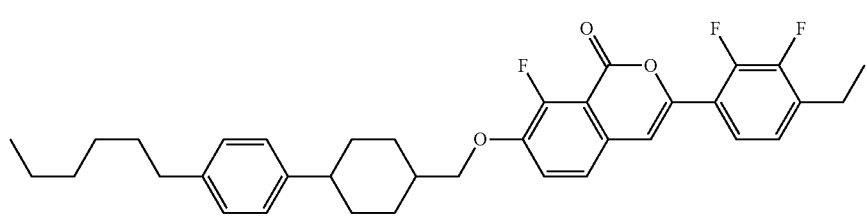 [SMILES: CCCCCCc1ccc(C2CCC(COc3ccc4cc(-c5ccc(CC)c(F)c5F)oc(=O)c4c3F)CC2)cc1] |
| 945 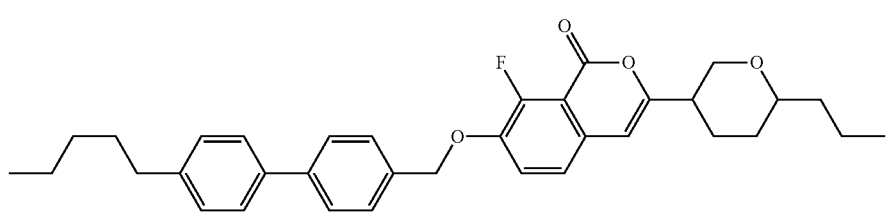 [SMILES: CCCCCc1ccc(-c2ccc(COc3ccc4cc(C5CCC(CCC)OC5)oc(=O)c4c3F)cc2)cc1] |
| 946 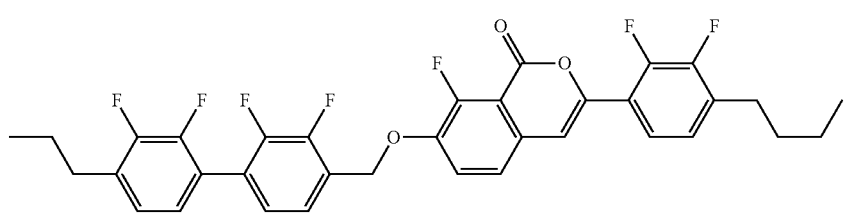 [SMILES: CCCCc1ccc(-c2cc3ccc(OCc4ccc(-c5ccc(CCC)c(F)c5F)c(F)c4F)c(F)c3c(=O)o2)c(F)c1F] |

-continued
| No. | |
|---|---|
| 947 | 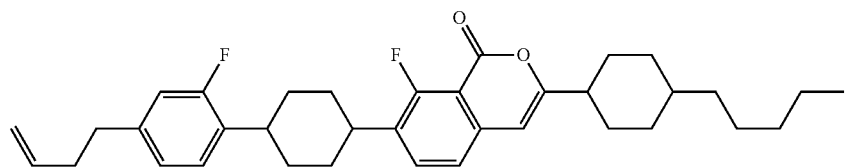 |
| 948 | 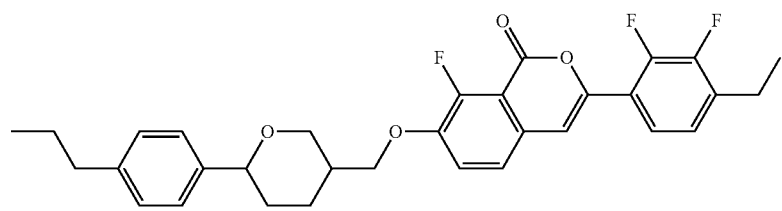 [SMILES: CCCc1ccc(C2CCC(COc3ccc4cc(-c5ccc(CC)c(F)c5F)oc(=O)c4c3F)CO2)cc1] |
| 949 | 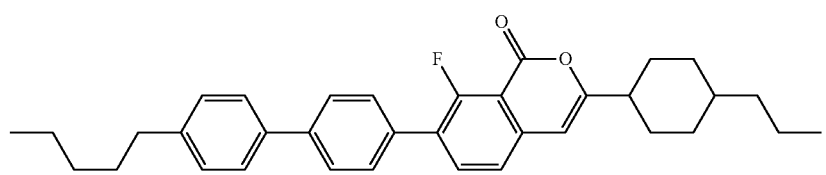 [SMILES: CCCCCc1ccc(-c2ccc(-c3ccc4cc(C5CCC(CCC)CC5)oc(=O)c4c3F)cc2)cc1] |
| 950 | 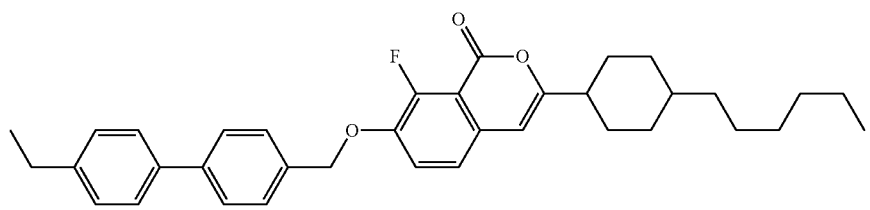 [SMILES: CCCCCCC1CCC(c2cc3ccc(OCc4ccc(-c5ccc(CC)cc5)cc4)c(F)c3c(=O)o2)CC1] |
| 951 | 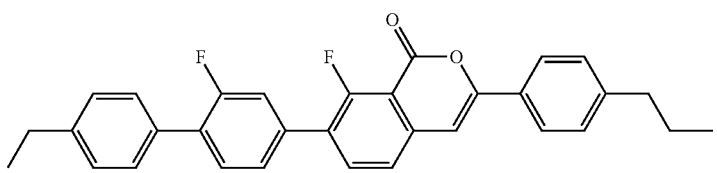 [SMILES: CCCc1ccc(-c2cc3ccc(-c4ccc(-c5ccc(CC)cc5)c(F)c4)c(F)c3c(=O)o2)cc1] |
| 952 | 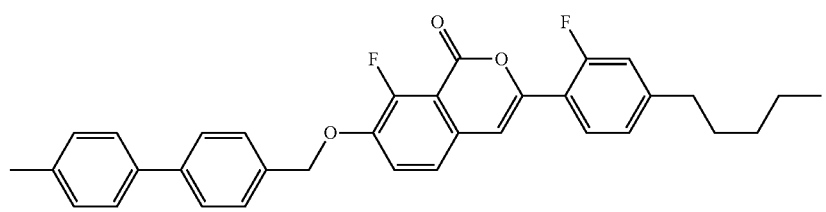 [SMILES: CCCCCc1ccc(-c2cc3ccc(OCc4ccc(-c5ccc(C)cc5)cc4)c(F)c3c(=O)o2)c(F)c1] |
| 953 | 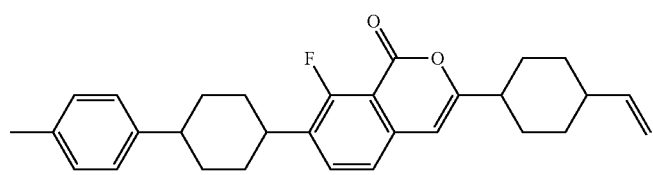 [SMILES: C=CC1CCC(c2cc3ccc(C4CCC(c5ccc(C)cc5)CC4)c(F)c3c(=O)o2)CC1] |
| 954 | 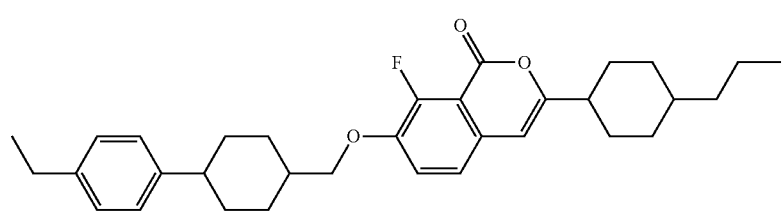 [SMILES: CCCC1CCC(c2cc3ccc(OCC4CCC(c5ccc(CC)cc5)CC4)c(F)c3c(=O)o2)CC1] |

| No. |
|---|
| 955 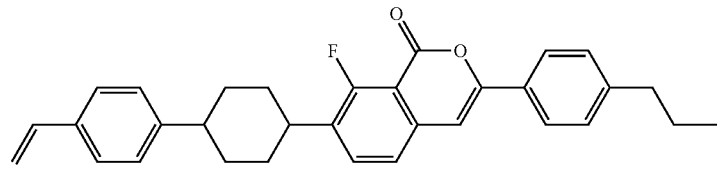 [SMILES: C=Cc1ccc(C2CCC(c3ccc4cc(-c5ccc(CCC)cc5)oc(=O)c4c3F)CC2)cc1] |
| 956 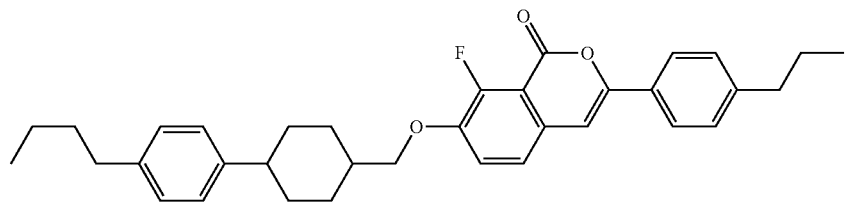 [SMILES: CCCCc1ccc(C2CCC(COc3ccc4cc(-c5ccc(CCC)cc5)oc(=O)c4c3F)CC2)cc1] |
| 957 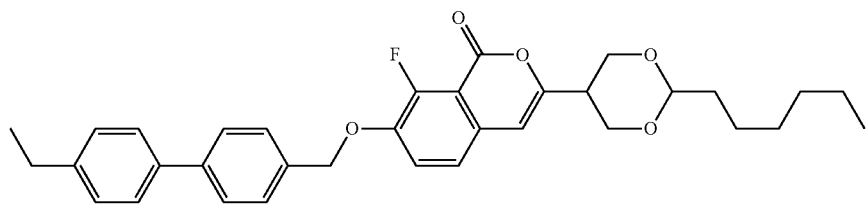 [SMILES: CCCCCCC1OCC(c2cc3ccc(OCc4ccc(-c5ccc(CC)cc5)cc4)c(F)c3c(=O)o2)CO1] |
| 958 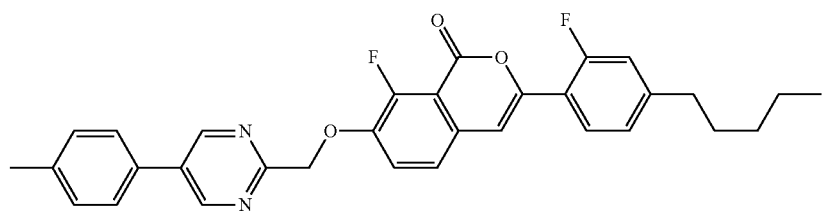 [SMILES: CCCCCc1ccc(-c2cc3ccc(OCc4ncc(-c5ccc(C)cc5)cn4)c(F)c3c(=O)o2)c(F)c1] |
| 959 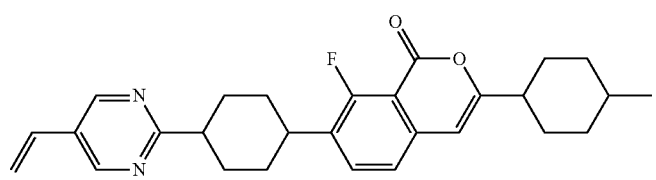 [SMILES: C=Cc1cnc(C2CCC(c3ccc4cc(C5CCC(C)CC5)oc(=O)c4c3F)CC2)nc1] |
| 960 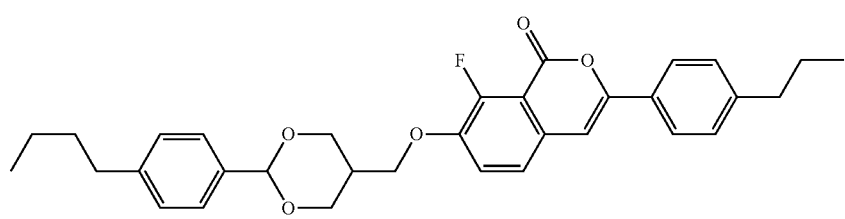 [SMILES: CCCCc1ccc(C2OCC(COc3ccc4cc(-c5ccc(CCC)cc5)oc(=O)c4c3F)CO2)cc1] |
| 961 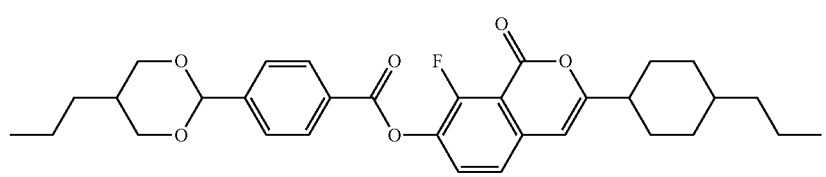 |

-continued
| No. | |
|---|---|
| 962 | 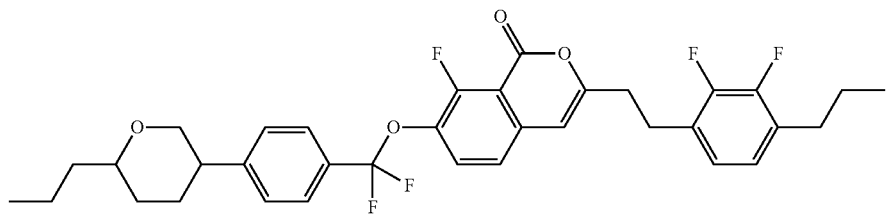 [SMILES: CCCc1ccc(CCc2cc3ccc(OC(F)(F)c4ccc(C5CCC(CCC)OC5)cc4)c(F)c3c(=O)o2)c(F)c1F] |
| 963 | 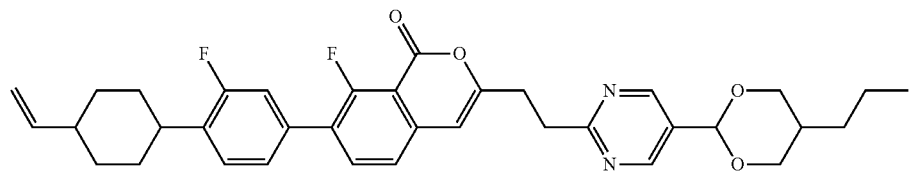 [SMILES: C=CC1CCC(c2ccc(-c3ccc4cc(CCc5ncc(C6OCC(CCC)CO6)cn5)oc(=O)c4c3F)cc2F)CC1] |
| 964 | 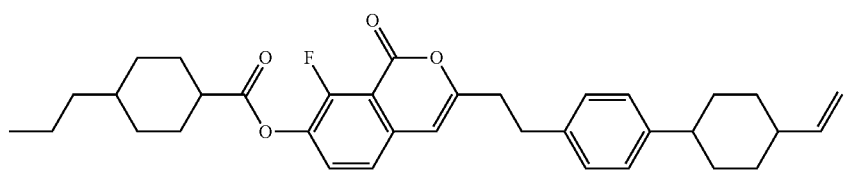 |
| 965 | 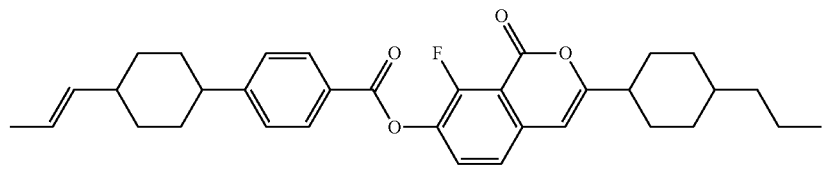 [SMILES: C/C=C/C1CCC(c2ccc(C(=O)Oc3ccc4cc(C5CCC(CCC)CC5)oc(=O)c4c3F)cc2)CC1] |
| 966 | 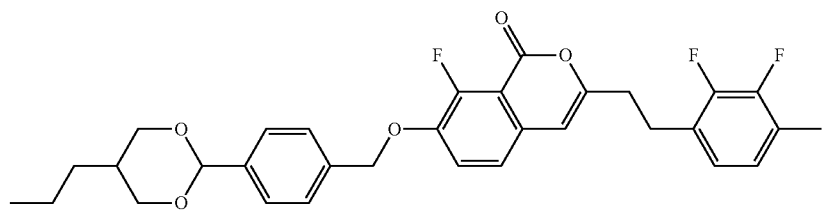 [SMILES: CCCC1COC(c2ccc(COc3ccc4cc(CCc5ccc(C)c(F)c5F)oc(=O)c4c3F)cc2)OC1] |
| 967 | 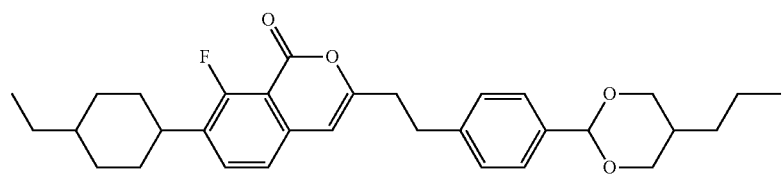 |
| 968 | 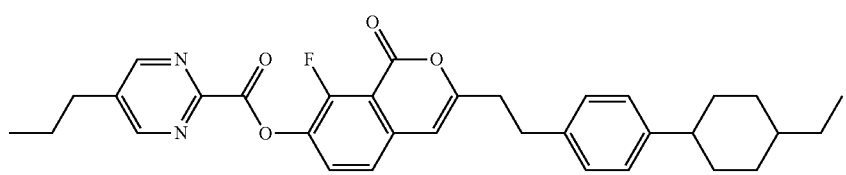 [SMILES: CCCc1cnc(C(=O)Oc2ccc3cc(CCc4ccc(C5CCC(CC)CC5)cc4)oc(=O)c3c2F)nc1] |
| 969 | 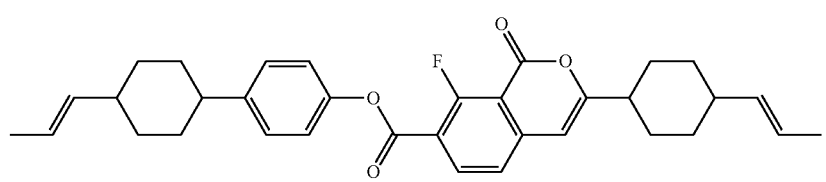 [SMILES: C/C=C/C1CCC(c2ccc(OC(=O)c3ccc4cc(C5CCC(/C=C/C)CC5)oc(=O)c4c3F)cc2)CC1] |

| No. |
|---|
| 970 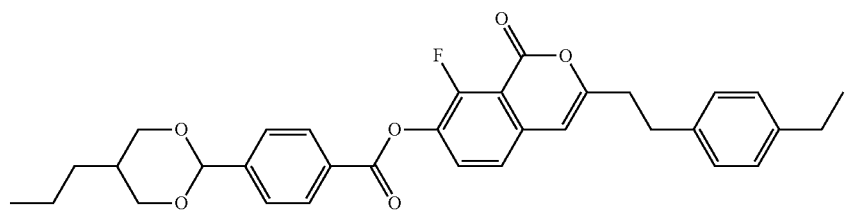 [SMILES: CCCC1COC(c2ccc(C(=O)Oc3ccc4cc(CCc5ccc(CC)cc5)oc(=O)c4c3F)cc2)OC1] |
| 971 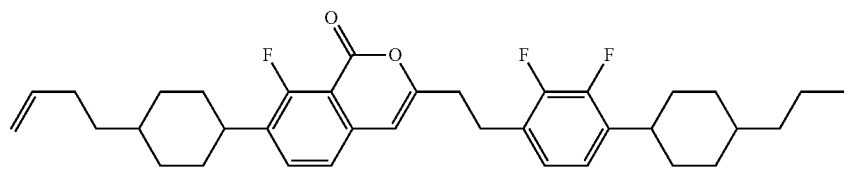 [SMILES: C=CCCC1CCC(c2ccc3cc(CCc4ccc(C5CCC(CCC)CC5)c(F)c4F)oc(=O)c3c2F)CC1] |
| 972 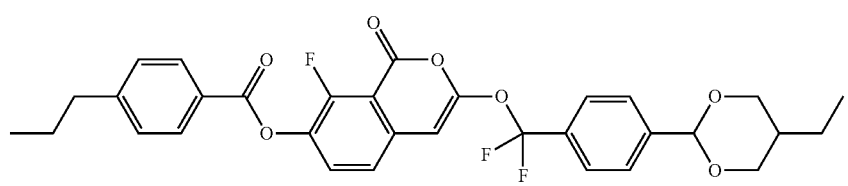 [SMILES: CCCc1ccc(C(=O)Oc2ccc3cc(OC(F)(F)c4ccc(C5OCC(CC)CO5)cc4)oc(=O)c3c2F)cc1] |
| 973 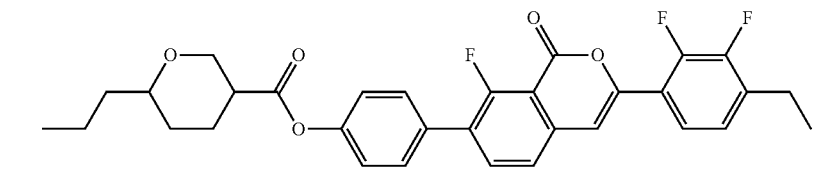 [SMILES: CCCC1CCC(C(=O)Oc2ccc(-c3ccc4cc(-c5ccc(CC)c(F)c5F)oc(=O)c4c3F)cc2)CO1] |
| 974 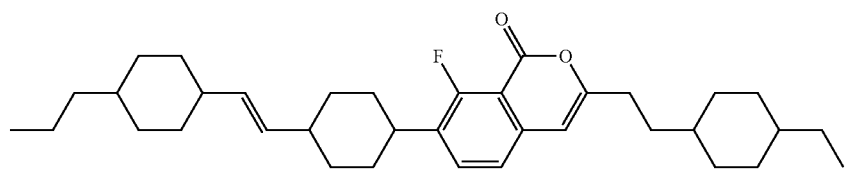 [SMILES: CCCC1CCC(/C=C/C2CCC(c3ccc4cc(CCC5CCC(CC)CC5)oc(=O)c4c3F)CC2)CC1] |
| 975 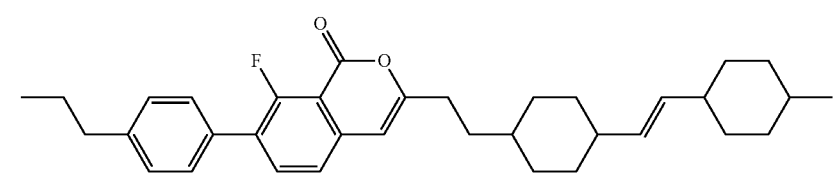 |
| 976 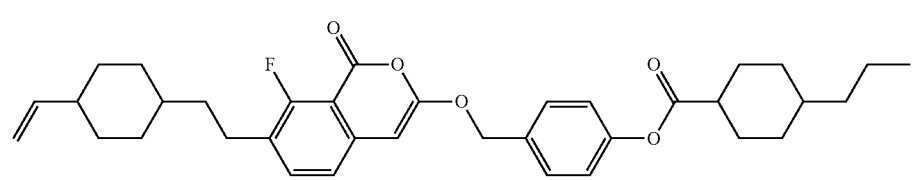 [SMILES: C=CC1CCC(CCc2ccc3cc(OCc4ccc(OC(=O)C5CCC(CCC)CC5)cc4)oc(=O)c3c2F)CC1] |
| 977 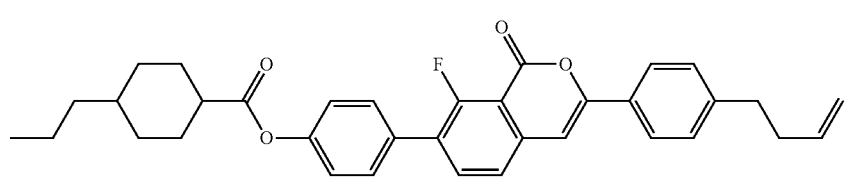 [SMILES: C=CCCc1ccc(-c2cc3ccc(-c4ccc(OC(=O)C5CCC(CCC)CC5)cc4)c(F)c3c(=O)o2)cc1] |

| No. |
|---|
| 978 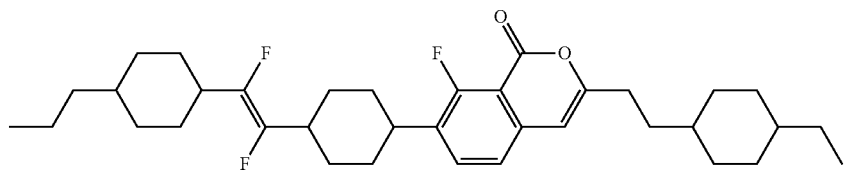 [SMILES: CCCC1CCC(/C(F)=C(\F)C2CCC(c3ccc4cc(CCC5CCC(CC)CC5)oc(=O)c4c3F)CC2)CC1] |
| 979 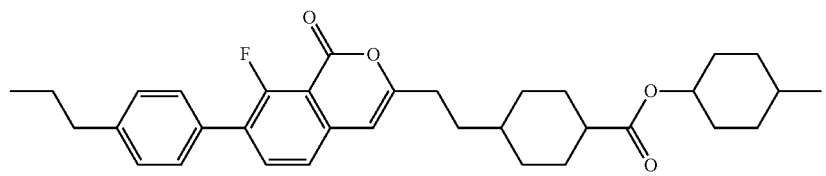 [SMILES: CCCc1ccc(-c2ccc3cc(CCC4CCC(C(=O)OC5CCC(C)CC5)CC4)oc(=O)c3c2F)cc1] |
| 980 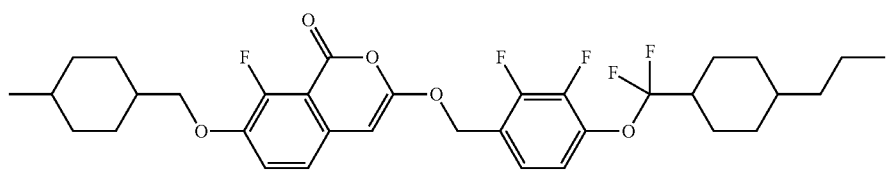 [SMILES: CCCC1CCC(C(F)(F)Oc2ccc(COc3cc4ccc(OCC5CCC(C)CC5)c(F)c4c(=O)o3)c(F)c2F)CC1] |
| 981 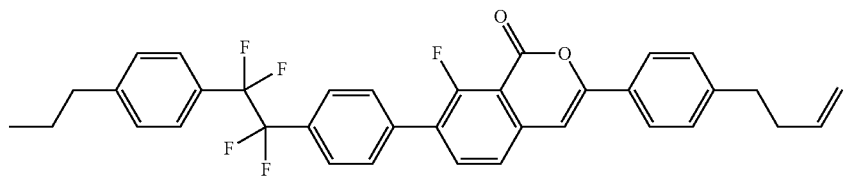 [SMILES: C=CCCc1ccc(-c2cc3ccc(-c4ccc(C(F)(F)C(F)(F)c5ccc(CCC)cc5)cc4)c(F)c3c(=O)o2)cc1] |
| 982 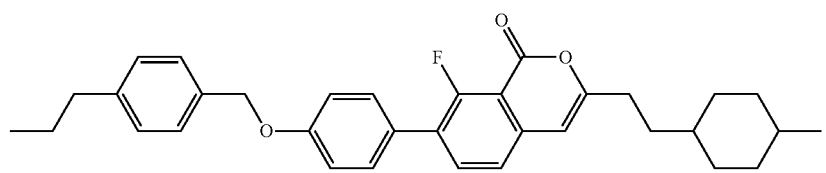 [SMILES: CCCc1ccc(COc2ccc(-c3ccc4cc(CCC5CCC(C)CC5)oc(=O)c4c3F)cc2)cc1] |
| 983 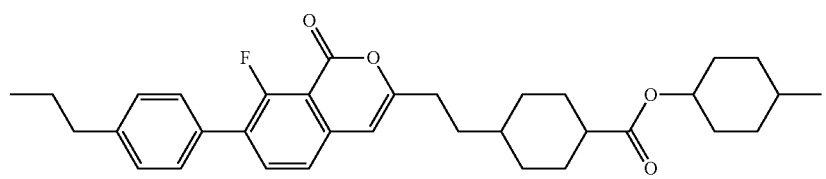 [SMILES: CCCc1ccc(-c2ccc3cc(CCC4CCC(C(=O)OC5CCC(C)CC5)CC4)oc(=O)c3c2F)cc1] |
| 984 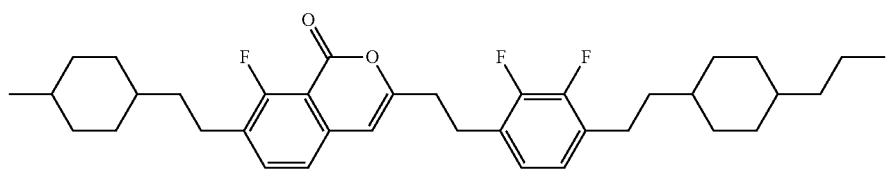 [SMILES: CCCC1CCC(CCc2ccc(CCc3cc4ccc(CCC5CCC(C)CC5)c(F)c4c(=O)o3)c(F)c2F)CC1] |

Examples of compositions are described below. The invention includes a mixture in Use Example 1 and Use Example 2. The invention also includes a mixture of at least two compositions in Use Examples. Component compounds were expressed using symbols according to definitions of Table 3 described below. In Table 3, a configuration of 1,4-cyclohexylene is trans. A parenthesized number next to a symbolized compound represents a chemical formula to which the compound belongs. A symbol (-) means a liquid crystal compound different from compounds (1) to (15). A proportion (percentage) of the liquid crystal compound is expressed in terms of weight percent (% by weight) based on the weight of the liquid crystal composition containing no additive. Values of the physical properties of the composition are summarized in a last part. The physical properties were measured according to the methods described above, and measured values are directly described (without extrapolation).

TABLE 3

Method for Description of Compounds using Symbols
R—(A₁)—Z₁ ... —Zₙ—(Aₙ)—R'

1) Left-terminal Group R—             Symbol $C_nH_{2n+1}$—                         n-
$C_nH_{2n+1}O$—                        nO—
$C_mH_{2m+1}OC_nH_{2n}$—               mOn—
$CH_2$=CH—                             V—
$C_nH_{2n+1}$—CH=CH—                   nV—
$CH_2$=CH—$C_nH_{2n}$—                 Vn—
$C_mH_{2m+1}$—CH=CH—$C_nH_{2n}$—       mVn—
$CF_2$=CH—                             VFF—
$CF_2$=CH—$C_nH_{2n}$—                 VFFn—

2) Right-terminal Group —R'           Symbol

—$C_nH_{2n+1}$                         -n
—$OC_nH_{2n+1}$                        —On
—$COOCH_3$                             —EMe
—CH=$CH_2$                             —V
—CH=CH—$C_nH_{2n+1}$                   —Vn
—$C_nH_{2n}$—CH=$CH_2$                 —nV
—$C_mH_{2m}$—CH=CH—$C_nH_{2n+1}$       —mVn
—CH=$CF_2$                             —VFF
—F                                     —F
—Cl                                    —CL
—$OCF_3$                               —OCF3
—$OCF_2H$                              —OCF2H
—$CF_3$                                —CF3
—$OCH$=CH—$CF_3$                       —OVCF3
—C≡N                                   —C

3) Bonding Group —Zₙ—                  Symbol

—$C_nH_{2n}$—                          n
—COO—                                  E
—CH=CH—                                V
—$CH_2O$—                              1O
—$OCH_2$—                              O1
—$CF_2O$—                              X
—C≡C—                                  T

4) Ring Structure —Aₙ—                 Symbol

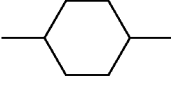                   H

                   B

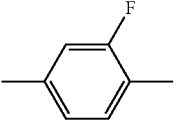                   B(F)

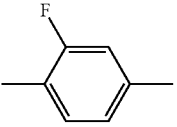                   B(2F)

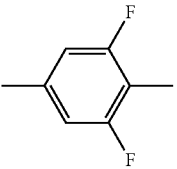                   B(F,F)

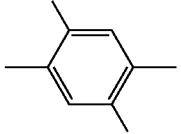                   B(2F,5F)

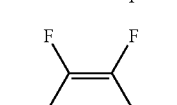                   B(2F,3F)

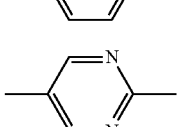                   Py

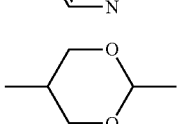                   G

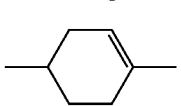                  ch

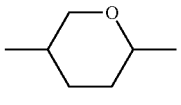                  dh

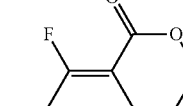                  ICma(8F)

5) Examples of Description

Example 1  4O—Icma(8F)-3

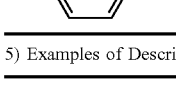

Example 2  3-BB(F,F)XB(F,F)—F

Example 3  3-HB—O2

TABLE 3-continued

Method for Description of Compounds using Symbols
R—(A$_1$)—Z$_1$ . . . —Z$_n$—(A$_n$)—R'

Example 4  3-HBB(2F,3F)—O2

Use Example 1

| | | |
|---|---|---|
| 4O-ICma(8F)-3 | (No. 39) | 5% |
| 2-HB-C | (15-1) | 5% |
| 3-HB-C | (15-1) | 12% |
| 3-HB-O2 | (2-5) | 15% |
| 2-BTB-1 | (2-10) | 3% |
| 3-HHB-F | (13-1) | 3% |
| 3-HHB-1 | (3-1) | 7% |
| 3-HHB-O1 | (3-1) | 4% |
| 3-HHB-3 | (3-1) | 13% |
| 3-HHEB-F | (13-10) | 3% |
| 5-HHEB-F | (13-10) | 4% |
| 2-HHB(F)-F | (13-2) | 7% |
| 3-HHB(F)-F | (13-2) | 7% |
| 5-HHB(F)-F | (13-2) | 7% |
| 3-HHB(F,F)-F | (13-3) | 5% |

NI = 85.8° C.; η = 20.0 mPa · s; Δn = 0.094; Δε = 4.6.

Use Example 2

| | | |
|---|---|---|
| 4O-ICma(8F)-5 | (No. 41) | 4% |
| 3-HB-CL | (12-2) | 13% |
| 3-HH-4 | (2-1) | 12% |
| 3-HB-O2 | (2-5) | 8% |
| 3-HHB(F,F)-F | (13-3) | 3% |
| 3-HBB(F,F)-F | (13-24) | 28% |
| 5-HBB(F,F)-F | (13-24) | 23% |
| 5-HBB(F)B-2 | (4-5) | 5% |
| 5-HBB(F)B-3 | (4-5) | 4% |

Use Example 3

| | | |
|---|---|---|
| 2O-ICma(8F)-5 | (No. 17) | 3% |
| 7-HB(F,F)-F | (12-4) | 3% |
| 3-HB-O2 | (2-5) | 7% |
| 2-HHB(F)-F | (13-2) | 10% |
| 3-HHB(F)-F | (13-2) | 9% |
| 5-HHB(F)-F | (13-2) | 10% |
| 2-HBB(F)-F | (13-23) | 9% |
| 3-HBB(F)-F | (13-23) | 9% |
| 5-HBB(F)-F | (13-23) | 15% |
| 2-HBB-F | (13-22) | 4% |
| 3-HBB-F | (13-22) | 3% |
| 5-HBB-F | (13-22) | 3% |
| 3-HBB(F,F)-F | (13-24) | 5% |
| 5-HBB(F,F)-F | (13-24) | 10% |

Use Example 4

| | | |
|---|---|---|
| 2O-ICma(8F)-3 | (No. 15) | 5% |
| 5-HB-CL | (12-2) | 16% |
| 3-HH-4 | (2-1) | 12% |
| 3-HH-5 | (2-1) | 4% |
| 3-HHB-F | (13-1) | 4% |
| 3-HHB-CL | (13-1) | 3% |
| 4-HHB-CL | (13-1) | 3% |
| 3-HHB(F)-F | (13-2) | 9% |
| 4-HHB(F)-F | (13-2) | 8% |
| 5-HHB(F)-F | (13-2) | 9% |
| 7-HHB(F)-F | (13-2) | 8% |
| 5-HBB(F)-F | (13-23) | 3% |
| 1O1-HBBH-5 | (4-1) | 3% |
| 3-HHBB(F,F)-F | (14-6) | 2% |
| 4-HHBB(F,F)-F | (14-6) | 2% |
| 5-HHBB(F,F)-F | (14-6) | 3% |
| 3-HH2BB(F,F)-F | (14-15) | 3% |
| 4-HH2BB(F,F)-F | (14-15) | 3% |

Use Example 5

| | | |
|---|---|---|
| 2O-ICma(8F)H-5 | Similar to (No. 347) | 4% |
| 3-HHB(F,F)-F | (13-3) | 8% |
| 3-H2HB(F,F)-F | (13-15) | 8% |
| 4-H2HB(F,F)-F | (13-15) | 8% |
| 5-H2HB(F,F)-F | (13-15) | 8% |
| 3-HBB(F,F)-F | (13-24) | 20% |
| 5-HBB(F,F)-F | (13-24) | 20% |
| 3-H2BB(F,F)-F | (13-27) | 10% |
| 5-HHBB(F,F)-F | (14-6) | 3% |
| 5-HHEBB-F | (14-17) | 2% |
| 3-HH2BB(F,F)-F | (14-15) | 3% |
| 1O1-HBBH-4 | (4-1) | 3% |
| 1O1-HBBH-5 | (4-1) | 3% |

Use Example 6

| | | |
|---|---|---|
| 2O-ICma(8F)B-5 | Similar to (No. 397) | 3% |
| 5-HB-F | (12-2) | 12% |
| 6-HB-F | (12-2) | 9% |
| 7-HB-F | (12-2) | 7% |
| 2-HHB-OCF3 | (13-1) | 7% |
| 3-HHB-OCF3 | (13-1) | 7% |
| 4-HHB-OCF3 | (13-1) | 7% |
| 5-HHB-OCF3 | (13-1) | 5% |
| 3-HH2B-OCF3 | (13-4) | 3% |
| 5-HH2B-OCF3 | (13-4) | 4% |
| 3-HHB(F,F)-OCF2H | (13-3) | 3% |
| 3-HHB(F,F)-OCF3 | (13-3) | 4% |
| 3-HH2B(F)-F | (13-5) | 3% |
| 3-HBB(F)-F | (13-23) | 10% |
| 5-HBB(F)-F | (13-23) | 10% |
| 5-HBBH-3 | (4-1) | 3% |
| 3-HB(F)BH-3 | (4-2) | 3% |

Use Example 7

| | | |
|---|---|---|
| 4O-ICma(8F)-3 | (No. 39) | 3% |
| 5-HB-CL | (12-2) | 8% |
| 3-HH-4 | (2-1) | 8% |
| 3-HHB-1 | (3-1) | 5% |

-continued

| | | |
|---|---|---|
| 3-HHB(F,F)-F | (13-3) | 8% |
| 3-HBB(F,F)-F | (13-24) | 18% |
| 5-HBB(F,F)-F | (13-24) | 17% |
| 3-HHEB(F,F)-F | (13-12) | 9% |
| 4-HHEB(F,F)-F | (13-12) | 4% |
| 5-HHEB(F,F)-F | (13-12) | 4% |
| 2-HBEB(F,F)-F | (13-39) | 3% |
| 3-HBEB(F,F)-F | (13-39) | 4% |
| 5-HBEB(F,F)-F | (13-39) | 3% |
| 3-HHBB(F,F)-F | (14-6) | 6% |

NI = 77.0° C.; η = 24.7 mPa·s; Δn = 0.100; Δε = 8.5

Use Example 8

| | | |
|---|---|---|
| 4O-ICma(8F)-5 | (No. 41) | 4% |
| 3-HB-CL | (12-2) | 5% |
| 5-HB-CL | (12-2) | 3% |
| 3-HHB-OCF3 | (13-1) | 5% |
| 3-H2HB-OCF3 | (13-13) | 5% |
| 5-H4HB-OCF3 | (13-19) | 15% |
| V-HHB(F)-F | (13-2) | 4% |
| 3-HHB(F)-F | (13-2) | 4% |
| 5-HHB(F)-F | (13-2) | 6% |
| 3-H4HB(F,F)-CF3 | (13-21) | 8% |
| 5-H4HB(F,F)-CF3 | (13-21) | 10% |
| 5-H2HB(F,F)-F | (13-15) | 4% |
| 5-H4HB(F,F)-F | (13-21) | 7% |
| 2-H2BB(F)-F | (13-27) | 5% |
| 3-H2BB(F)-F | (13-27) | 10% |
| 3-HBEB(F,F)-F | (13-39) | 5% |

Use Example 9

| | | |
|---|---|---|
| 2O-ICma(8F)-5 | (No. 17) | 5% |
| 5-HB-CL | (12-2) | 15% |
| 7-HB(F,F)-F | (12-4) | 3% |
| 3-HH-4 | (2-1) | 9% |
| 3-HH-5 | (2-1) | 5% |
| 3-HB-O2 | (2-5) | 13% |
| 3-HHB-1 | (3-1) | 7% |
| 3-HHB-O1 | (3-1) | 6% |
| 2-HHB(F)-F | (13-2) | 7% |
| 3-HHB(F)-F | (13-2) | 8% |
| 5-HHB(F)-F | (13-2) | 7% |
| 3-HHB(F,F)-F | (13-3) | 5% |
| 3-H2HB(F,F)-F | (13-15) | 5% |
| 4-H2HB(F,F)-F | (13-15) | 5% |

Use Example 10

| | | |
|---|---|---|
| 2O-ICma(8F)-3 | (No. 15) | 3% |
| 5-HB-CL | (12-2) | 3% |
| 7-HB(F)-F | (12-3) | 5% |
| 3-HH-4 | (2-1) | 8% |
| 3-HH-5 | (2-1) | 11% |
| 3-HB-O2 | (2-5) | 12% |
| 3-HHEB-F | (13-10) | 8% |
| 5-HHEB-F | (13-10) | 9% |
| 3-HHEB(F,F)-F | (13-12) | 10% |
| 4-HHEB(F,F)-F | (13-12) | 5% |
| 3-GHB(F,F)-F | (13-109) | 4% |
| 4-GHB(F,F)-F | (13-109) | 6% |
| 5-GHB(F,F)-F | (13-109) | 7% |
| 2-HHB(F,F)-F | (13-3) | 4% |
| 3-HHB(F,F)-F | (13-3) | 5% |

Use Example 11

| | | |
|---|---|---|
| 2O-ICma(8F)B-5 | Similar to (No. 397) | 3% |
| 1V2-BEB(F,F)-C | (15-15) | 6% |
| 3-HB-C | (15-1) | 17% |
| 2-BTB-1 | (2-10) | 10% |
| 5-HH-VFF | (2-1) | 30% |
| 3-HHB-1 | (3-1) | 5% |
| VFF-HHB-1 | (3-1) | 8% |
| VFF2-HHB-1 | (3-1) | 10% |
| 3-H2BTB-2 | (3-17) | 5% |
| 3-H2BTB-3 | (3-17) | 3% |
| 3-H2BTB-4 | (3-17) | 3% |

Use Example 12

| | | |
|---|---|---|
| 2O-ICma(8F)-5 | (No. 17) | 3% |
| 4O-ICma(8F)-5 | (No. 41) | 3% |
| 5-HB(F)B(F,F)XB(F,F)-F | (14-41) | 5% |
| 3-BB(F)B(F,F)XB(F,F)-F | (14-47) | 3% |
| 4-BB(F)B(F,F)XB(F,F)-F | (14-47) | 7% |
| 5-BB(F)B(F,F)XB(F,F)-F | (14-47) | 3% |
| 3-HH-V | (2-1) | 38% |
| 3-HH-V1 | (2-1) | 5% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (12-1) | 3% |
| 3-BB(F,F)XB(F,F)-F | (13-97) | 10% |
| 3-HHBB(F,F)-F | (14-6) | 3% |

Use Example 13

| | | |
|---|---|---|
| 2O-ICma(8F)-3 | (No. 15) | 3% |
| 3-GB(F)B(F,F)XB(F,F)-F | (14-57) | 5% |
| 3-BB(F)B(F,F)XB(F,F)-F | (14-47) | 5% |
| 4-BB(F)B(F,F)XB(F,F)-F | (14-47) | 6% |
| 5-BB(F)B(F,F)XB(F,F)-F | (14-47) | 3% |
| 3-HH-V | (2-1) | 38% |
| 3-HH-V1 | (2-1) | 6% |
| 3-HHEH-5 | (3-13) | 3% |
| 3-HHB-1 | (3-1) | 5% |
| V-HHB-1 | (3-1) | 4% |
| V2-BB(F)B-1 | (3-6) | 5% |
| 1V2-BB-F | (12-1) | 3% |
| 3-BB(F,F)XB(F,F)-F | (13-97) | 5% |
| 3-GB(F,F)XB(F,F)-F | (13-113) | 5% |
| 3-HHBB(F,F)-F | (14-6) | 4% |

Use Example 14

| | | |
|---|---|---|
| 2O-ICma(8F)H-5 | Similar to (No. 347) | 3% |
| 3-GB(F)B(F,F)XB(F,F)-F | (14-57) | 3% |
| 4-GB(F)B(F,F)XB(F,F)-F | (14-57) | 4% |
| 5-GB(F)B(F,F)XB(F,F)-F | (14-57) | 3% |
| 3-BB(F)B(F,F)XB(F,F)-F | (14-47) | 3% |

-continued

| | | |
|---|---|---|
| 4-BB(F)B(F,F)XB(F,F)-F | (14-47) | 5% |
| 3-HH-V | (2-1) | 39% |
| 3-HH-V1 | (2-1) | 6% |
| 3-HHEH-5 | (3-13) | 3% |
| 3-HHB-1 | (3-1) | 3% |
| V-HHB-1 | (3-1) | 6% |
| V2-BB(F)B-1 | (3-6) | 3% |
| 1V2-BB-F | (12-1) | 4% |
| 3-BB(F,F)XB(F,F)-F | (13-97) | 6% |
| 3-GB(F,F)XB(F,F)-F | (13-113) | 5% |
| 3-HHBB(F,F)-F | (14-6) | 4% |

Use Example 15

| | | |
|---|---|---|
| 4O-ICma(8F)-3 | (No. 39) | 4% |
| 2-dhBB(F,F)XB(F,F)-F | (14-50) | 5% |
| 3-dhBB(F,F)XB(F,F)-F | (14-50) | 3% |
| 5-HB(F)B(F,F)XB(F,F)-F | (14-41) | 3% |
| 4-BB(F)B(F,F)XB(F,F)-F | (14-47) | 4% |
| 3-HH-V | (2-1) | 33% |
| 3-HH-V1 | (2-1) | 15% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (12-1) | 3% |
| 3-BB(F,F)XB(F,F)-F | (13-97) | 10% |
| 3-HHBB(F,F)-F | (14-6) | 3% |

INDUSTRIAL APPLICABILITY

A liquid crystal composition containing compound (1) can be used in a liquid crystal projector, a liquid crystal television and so forth.

What is claimed is:

1. A liquid crystal composition, containing at least one compound represented by formula (1) as component (a):

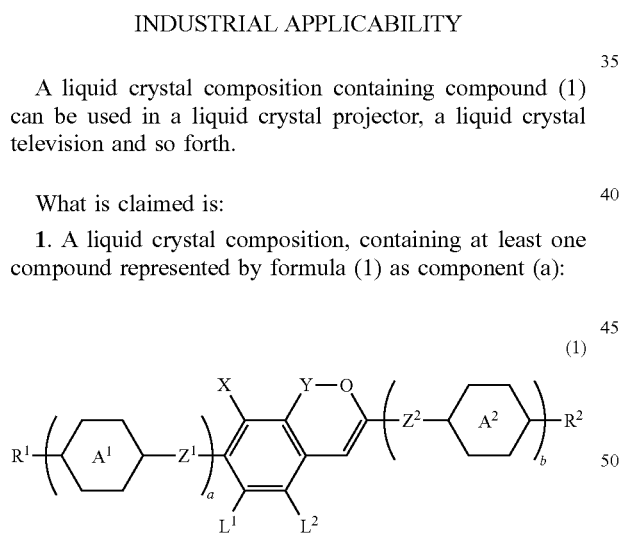

wherein, in formula (1),
$R^1$ and $R^2$ are independently hydrogen, alkyl having 1 to 16 carbons, alkenyl having 2 to 16 carbons, cyclopropyl, cyclobutyl or cyclopentyl, and in the alkyl and the alkenyl, at least one —CH$_2$—is optionally replaced by —O—, —S—, —CO—, —COO—, —OCO—, —OCOO—, —C≡C—, cyclopropane-1,2-diyl or —Si(CH$_3$)$_2$—, and in the groups, at least one hydrogen is optionally replaced by fluorine or chlorine, and in the groups, at least one —CH$_3$ is optionally replaced by any one of monovalent groups (G1) to (G4) below;

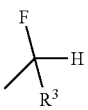

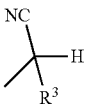

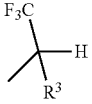

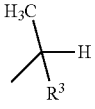

wherein, in groups (G1) to (G4),
$R^3$ is alkyl having 1 to 12 carbons or alkenyl having 2 to 12 carbons, and in the alkyl and the alkenyl, at least one —CH$_2$— is optionally replaced by —O—, and in the groups, at least one hydrogen is optionally replaced by fluorine or chlorine; and in formula (1),
ring A$^1$ and ring A$^2$ are independently 1,4-cyclohexylene, 1,4-cyclohexenylene, 1,4-phenylene, decahydronaphthalene-2,6-diyl, tetrahydronaphthalene-2,6-diyl or naphthalene-2,6-diyl, and in the groups, one or two pieces of —CH$_2$— is optionally replaced by —O—, —S—, —CO—, —CF$_2$—, —SiH$_2$— or —Si(CH$_3$)$_2$—, and one or two pieces of —CH$_2$CH$_2$— is optionally replaced by —CH=CH— or —CH=N—, and in the groups, at least one hydrogen on an aromatic ring is optionally replaced by halogen, —CF$_3$, —CHF$_2$, —CH$_2$F, —OCF$_3$, —OCHF$_2$, —OCH$_2$F, or —C≡N;

$Z^1$ and $Z^2$ are independently a single bond or alkylene having 1 to 4 carbons, and one —CH$_2$— is optionally replaced by —O— or —CO—, and at least one —CH$_2$CH$_2$— is optionally replaced by —CH=CH— or —C≡C—, and in the groups, at least one hydrogen is optionally replaced by fluorine or chlorine;

X, L$^1$ and L$^2$ are independently hydrogen or halogen;
Y is —CO— or —CF$_2$—; and
a and b are independently 0, 1 or 2.

2. The liquid crystal composition according to claim 1, further containing at least one compound selected from the group of compounds represented by formulas (2) to (4) as component (b):

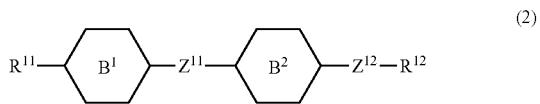

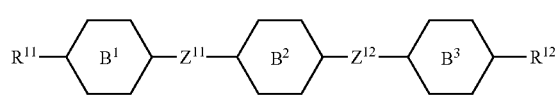

-continued

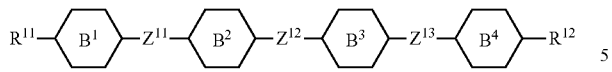
(4)

wherein, in formulas (2) to (4),

R$^{11}$ and R$^{12}$ are independently alkyl having 1 to 10 carbons or alkenyl having 2 to 10 carbons, and in the alkyl and the alkenyl, at least one —CH$_2$— is optionally replaced by —O—, and in the groups, at least one hydrogen is optionally replaced by fluorine;

ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and Z$^{11}$, Z$^{12}$ and Z$^{13}$ are independently a single bond, —COO—, —CH$_2$CH$_2$—, —CH=CH— or C≡C—.

3. The liquid crystal composition according to claim 1, wherein component (a) is at least one compound represented by formula (1-1):

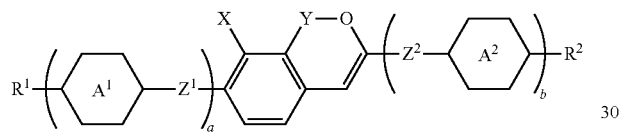
(1-1)

wherein, in formula (1-1),

R$^1$ and R$^2$ are independently hydrogen, alkyl having 1 to 14 carbons or alkenyl having 2 to 14 carbons, and in the alkyl and the alkenyl, one or two pieces of —CH$_2$— is optionally replaced by —O—, and in the groups, at least one hydrogen is optionally replaced by fluorine, and in the groups, at least one —CH$_3$ is optionally replaced by any one of monovalent groups (G1) to (G4) below;

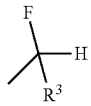
(G1)

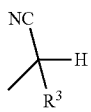
(G2)

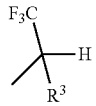
(G3)

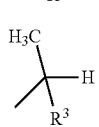
(G4)

wherein, in groups (G1) to (G4),

R$^3$ is alkyl having 1 to 10 carbons, and in the alkyl, at least one —CH$_2$— is optionally replaced by —O—; and in formula (1-1), ring A$^1$ and ring A$^2$ are independently 1,4-cyclohexylene, 1,4-cyclohexenylene, 1,4-phenylene, decahydronaphthalene-2,6-diyl, tetrahydronaphthalene-2,6-diyl or naphthalene-2,6-diyl, and in the groups, one or two pieces of —CH$_2$— is optionally replaced by —O—, and one or two pieces of —CH$_2$CH$_2$— is optionally replaced by —CH=CH—, and in the groups, at least one hydrogen on an aromatic ring is optionally replaced by fluorine;

Z$^1$ and Z$^2$ are independently a single bond, —O—, —COO—, —OCO—, —CH$_2$O—, —OCH$_2$—, —CF$_2$O—, —OCF$_2$—, —CH$_2$CH$_2$—, —CF$_2$CF$_2$—, —CH=CH—, —CF=CF—, —C≡C—, —(CH$_2$)$_4$— or —CH$_2$CH=CHCH$_2$—;

X is hydrogen, fluorine or chlorine;

Y is —CO— or —CF$_2$—; and a and b are independently 0, 1 or 2.

4. The liquid crystal composition according to claim 3, wherein, in formula (1-1), R$^1$ and R$^2$ are independently hydrogen, alkyl having 1 to 14 carbons or alkenyl having 2 to 14 carbons, and in the alkyl and the alkenyl, one or two pieces of —CH$_2$— is optionally replaced by —O—, and in the groups, at least one hydrogen is optionally replaced by fluorine;

ring A$^1$ and ring A$^2$ are independently 1,4-cyclohexylene, 1,4-cyclohexenylene, 1,3-dioxane-2,5-diyl, tetrahydropyran-2,5-diyl, 1,4-phenylene, 3-fluoro-1,4-phenylene, 3,5-difluoro-1,4-phenylene, pyridine-2,5-diyl or pyrimidine-2,5-diyl;

Z$^1$ and Z$^2$ are independently a single bond, —O—, —COO—, —OCO—, —CH$_2$O—, —OCH$_2$—, —CF$_2$O—, —OCF$_2$—, —CH$_2$CH$_2$— or —CH=CH—;

X is hydrogen or fluorine;

Y is —CO— or —CF$_2$—; and a and b are independently 0, 1 or 2, and a sum of a and b is 0, 1 or 2.

5. The liquid crystal composition according to claim 3, wherein, in formula (1-1), R$^1$ and R$^2$ are independently alkyl having 1 to 8 carbons, alkoxy having 1 to 8 carbons or alkenyl having 2 to 8 carbons;

ring A$^1$ and ring A$^2$ are independently 1,4-cyclohexylene, 1,4-phenylene or 1,4-phenylene in which at least one hydrogen is replaced by fluorine;

Z$^1$ and Z$^2$ are independently a single bond, —O—, —COO—, —OCO—, —CH$_2$O—, —OCH$_2$— or —CH$_2$CH$_2$—;

X is hydrogen or fluorine;

Y is —CO— or —CF$_2$—; and a and b are independently 0, 1 or 2, and a sum of a and b is 0, 1 or 2.

6. The liquid crystal composition according to claim 1, wherein component (a) is at least one compound selected from the group of compounds represented by formulas (1a) to (1t):

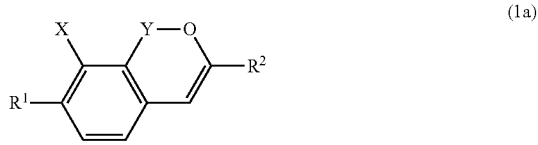
(1a)

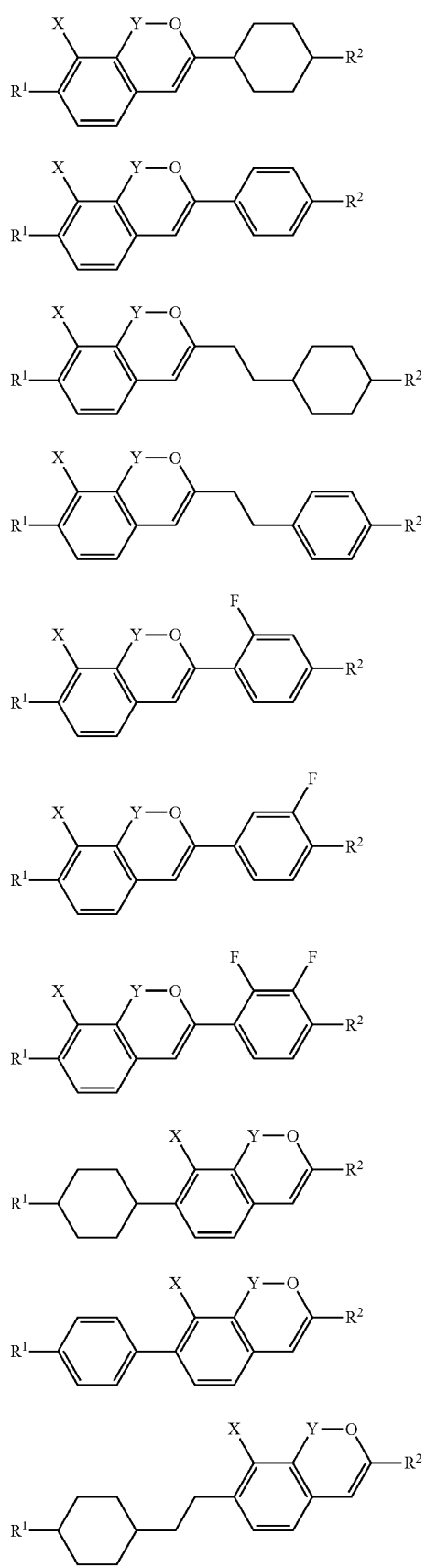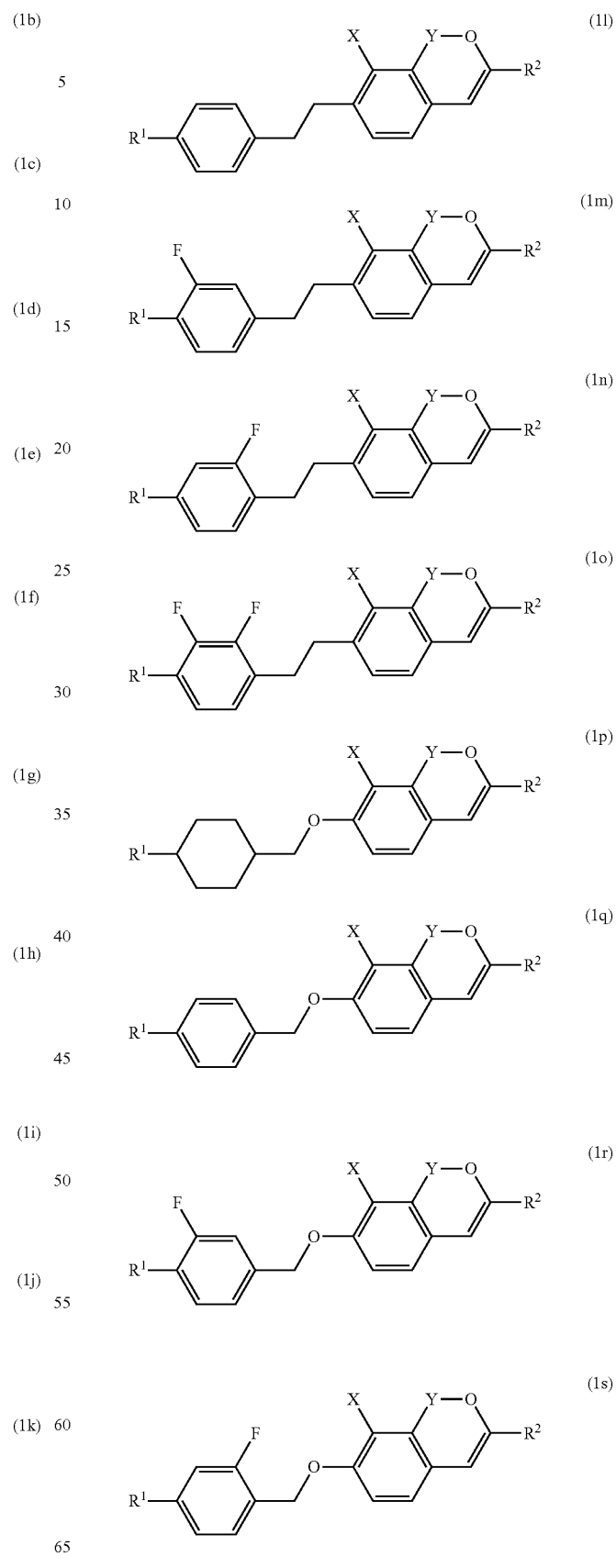

-continued

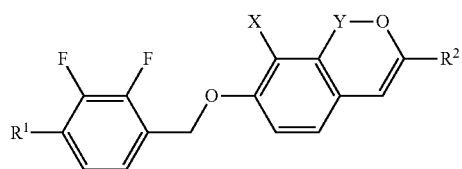
(1t)

wherein, in formulas (1a) to (1),

R¹ and R² are independently alkyl having 1 to 12 carbons, alkoxy having 1 to 12 carbons or alkenyl having 2 to 12 carbons;

X is hydrogen, fluorine or chlorine; and

Y is —CO— or —CF$_2$—.

7. The liquid crystal composition according to claim 1, wherein component (a) is at least one compound selected from the group of compounds represented by formulas (1 a-1) to (1 t-1):

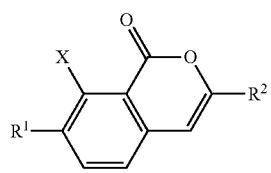
(1a-1)

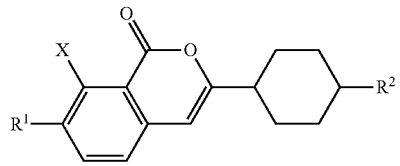
(1b-1)

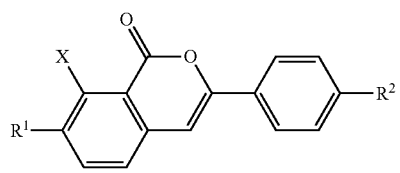
(1c-1)

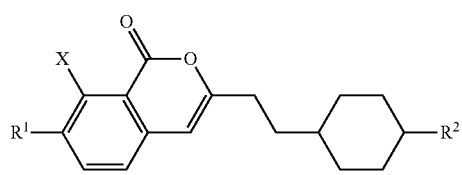
(1d-1)

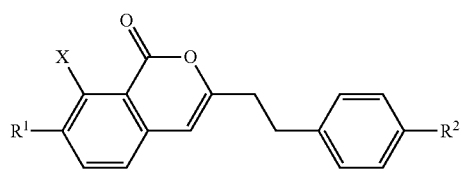
(1e-1)

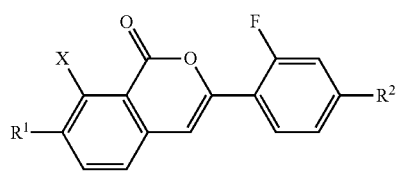
(1f-1)

-continued

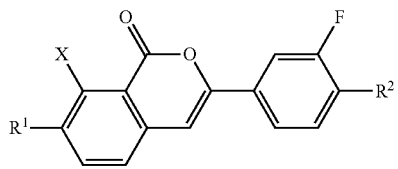
(1g-1)

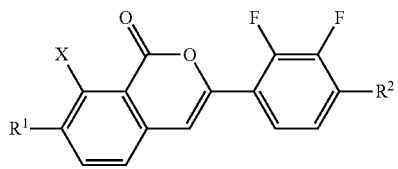
(1h-1)

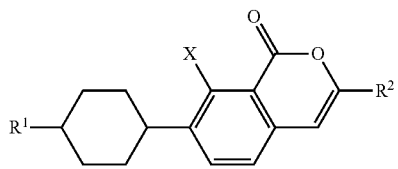
(1i-1)

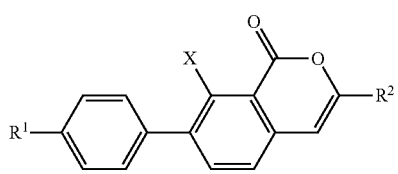
(1j-1)

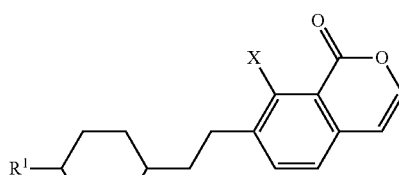
(1k-1)

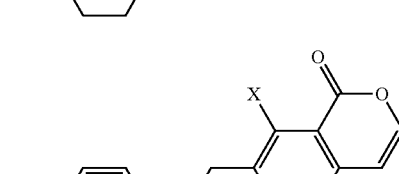
(1l-1)

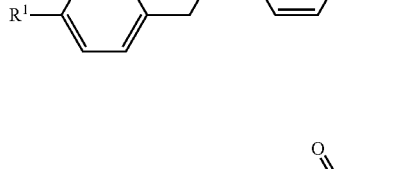
(1m-1)

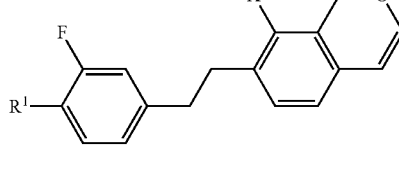
(1n-1)

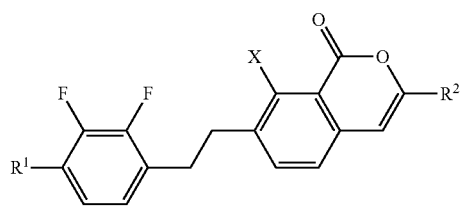
(1o-1)

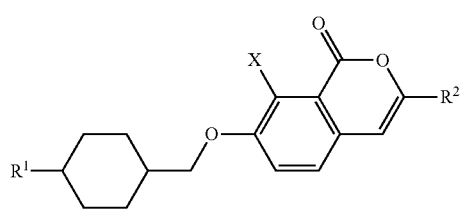
(1p-1)

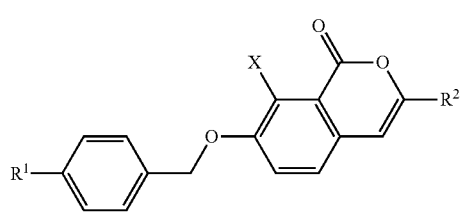
(1q-1)

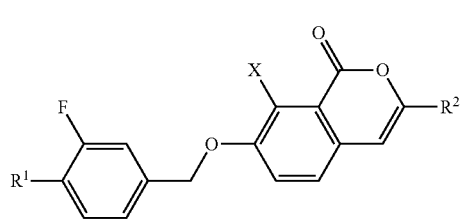
(1r-1)

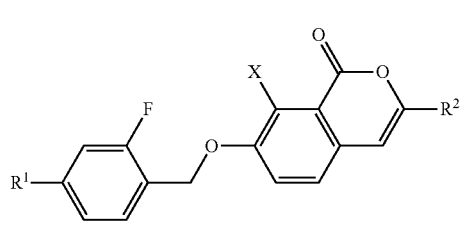
(1s-1)

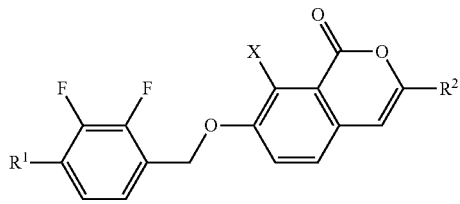
(1t-1)

wherein, in formulas (1a-1) to (1t-1),
$R^1$ and $R^2$ are independently alkyl having 1 to 12 carbons, alkoxy having 1 to 12 carbons or alkenyl having 2 to 12 carbons; and
X is hydrogen or fluorine.

8. The liquid crystal composition according to claim 1, wherein component (a) is at least one compound selected from the group of compounds represented by formulas (1a-11) and (1a-12):

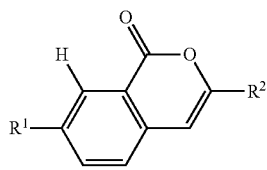
(1a-11)

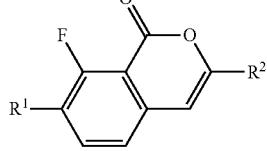
(1a-12)

wherein, in formulas (1a-11) and (1a-12), $R^1$ and $R^2$ are independently alkyl having 1 to 12 carbons, alkoxy having 1 to 12 carbons or alkenyl having 2 to 12 carbons.

9. The liquid crystal composition according to claim 1, further containing at least one compound selected from the group of compounds represented by formulas (5) to (11) as component (c):

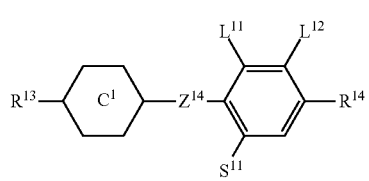
(5)

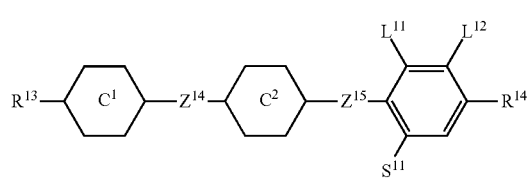
(6)

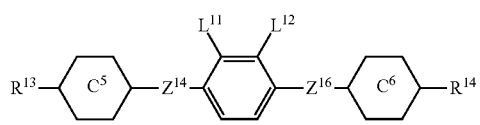
(7)

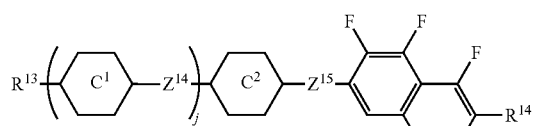
(8)

-continued

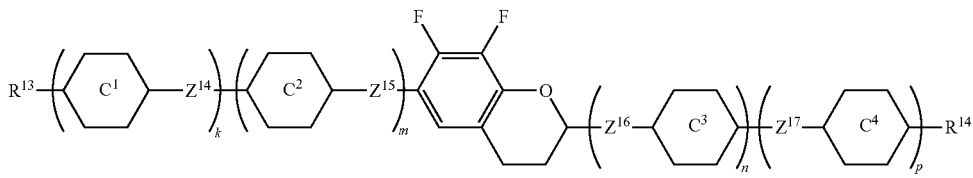

(9)

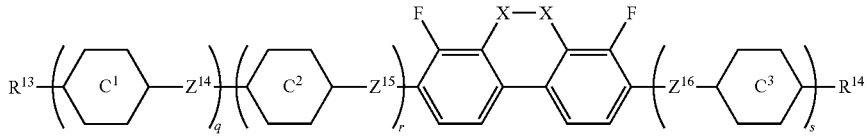

(10)

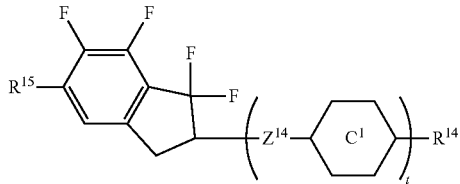

(11)

wherein, in formulas (5) to (11), $R^{13}$, $R^{14}$ and $R^{15}$ are independently alkyl having 1 to 10 carbons or alkenyl having 2 to 10 carbons, and in the alkyl and the alkenyl, at least one —$CH_2$— is optionally replaced by —O—, and in the groups, at least one hydrogen is optionally replaced by fluorine, and $R^{15}$ is hydrogen or fluorine;

ring $C^1$, ring $C^2$, ring $C^3$ and ring $C^4$ are independently 1,4-cyclohexylene, 1,4-cyclohexenylene, 1,4-phenylene in which at least one hydrogen is optionally replaced by fluorine, tetrahydropyran-2,5-diyl or decahydronaphthalene-2,6-diyl;

ring $C^5$ and ring $C^6$ are independently 1,4-cyclohexylene, 1,4-cyclohexenylene, 1,4-phenylene, tetrahydropyran-2,5-diyl or decahydronaphthalene-2,6-diyl;

$Z^{14}$, $Z^{15}$, $Z^{16}$ and $Z^{17}$ are independently a single bond, —COO—, —$CH_2O$—, —$OCF_2$—, —$CH_2CH_2$— or —$OCF_2CH_2CH_2$—;

$L^{11}$ and $L^{12}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

10. The liquid crystal composition according to claim 1, further containing at least one compound selected from the group of compounds represented by formulas (12) to (14) as component (d):

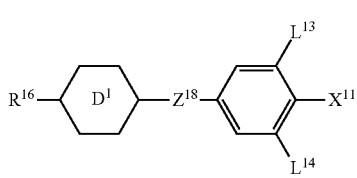 (12)

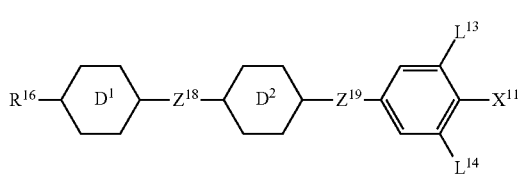 (13)

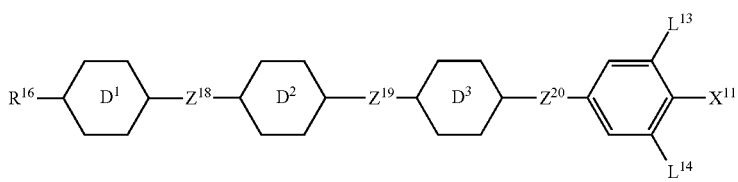 (14)

wherein, in formulas (12) to (14), $R^{16}$ is alkyl having 1 to 10 carbons or alkenyl having 2 to 10 carbons, and in the alkyl and the alkenyl, at least one —$CH_2$— is optionally replaced by —O—, and in the groups, at least one hydrogen is optionally replaced by fluorine;

$X^{11}$ is fluorine, chlorine, —$CF_3$, —$CHF_2$, —$CH_2F$, —$OCF_3$, —$OCHF_2$, —$OCF_2CHF_2$ or —$OCF_2CHFCF_3$;

ring $D^1$, ring $D^2$ and ring $D^3$ are independently 1,4-cyclohexylene, 1,4-phenylene in which at least one hydrogen is optionally replaced by fluorine, tetrahydropyran-2,5-diyl, 1,3-dioxane-2,5-diyl or pyrimidine-2,5-diyl;

$Z^{18}$, $Z^{19}$ and $Z^{20}$ are independently a single bond, —COO—, —CH$_2$O—, —CF$_2$O—, —OCF$_2$—, —CH$_2$CH$_2$—, —CH=CH—, —C≡C— or —(CH$_2$)$_4$—; and $L^{13}$ and $L^{14}$ are independently hydrogen or fluorine.

11. The liquid crystal composition according to claim 1, further containing at least one compound selected from compounds represented by formula (15) as component (e):

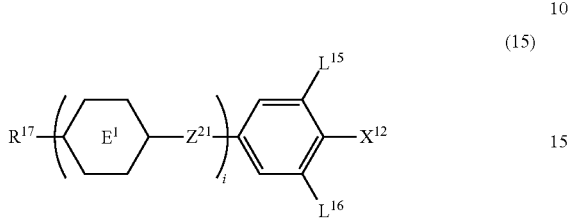

(15)

wherein, in formula (15),
$R^{17}$ is alkyl having 1 to 10 carbons or alkenyl having 2 to 10 carbons, and in the alkyl and the alkenyl, at least one —CH$_2$— is optionally replaced by —O—, and in the groups, at least one hydrogen is optionally replaced by fluorine;

$X^{12}$ is —C≡N or —C≡C—C≡N;

ring $E^1$ is 1,4-cyclohexylene, 1,4-phenylene in which at least one hydrogen is optionally replaced by fluorine, tetrahydropyran-2,5-diyl, 1,3-dioxane-2,5-diyl or pyrimidine-2,5-diyl;

$Z^{21}$ is a single bond, —COO—, —CH$_2$O—, —CF$_2$O—, —OCF$_2$—, —CH$_2$CH$_2$— or —C≡C—;

$L^{15}$ and $L^{16}$ are independently hydrogen or fluorine; and i is 1, 2, 3 or 4.

12. A compound, represented by formula (1-2):

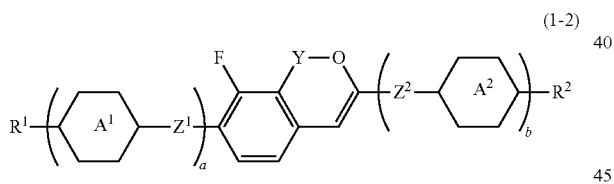

(1-2)

wherein, in formula (1-2),
$R^1$ and $R^2$ are independently hydrogen, alkyl having 1 to 14 carbons or alkenyl having 2 to 14 carbons, and in the alkyl and the alkenyl, one or two pieces of —CH$_2$— is optionally replaced by —O—, and in the groups, at least one hydrogen is optionally replaced by fluorine;

ring $A^1$ and ring $A^2$ are independently 1,4-cyclohexylene, 1,4-cyclohexenylene, 1,3-dioxane-2,5-diyl, tetrahydropyran-2,5-diyl, 1,4-phenylene, 3-fluoro-1,4-phenylene, 3,5-difluoro-1,4-phenylene, pyridine-2,5-diyl or pyrimidine-2,5-diyl;

$Z^1$ and $Z^2$ are independently a single bond, —O—, —COO—, —OCO—, —CH$_2$O—, —OCH$_2$—, —CF$_2$O—, —OCF$_2$—, —CH$_2$CH$_2$— or —CH=CH—;

Y is —CO— or —CF$_2$—; and a and b are independently 0, 1 or 2, and a sum of a and b is 0, 1 or 2.

13. The compound according to claim 12, represented by any one of formulas (1a-2) to (1t-2):

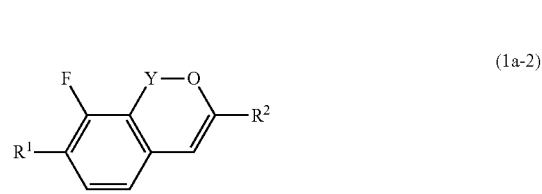
(1a-2)

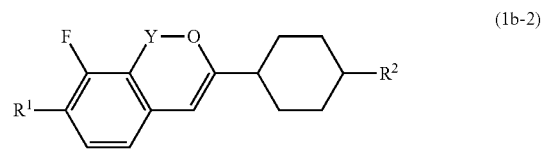
(1b-2)

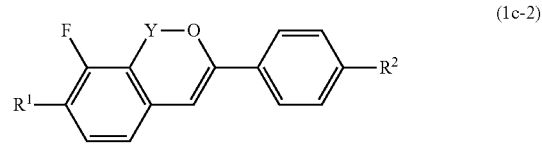
(1c-2)

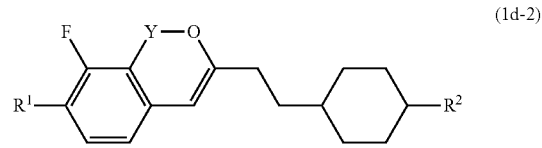
(1d-2)

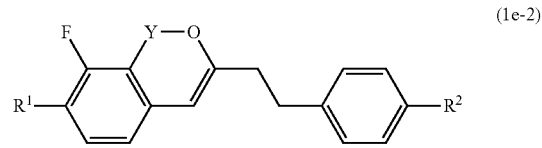
(1e-2)

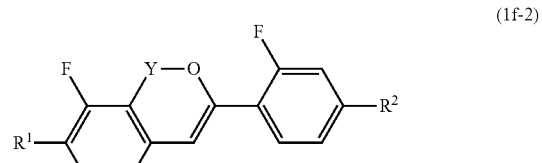
(1f-2)

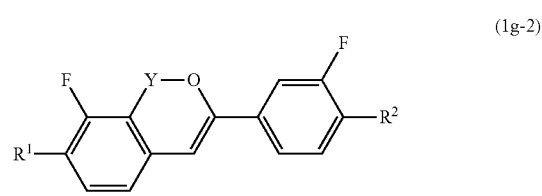
(1g-2)

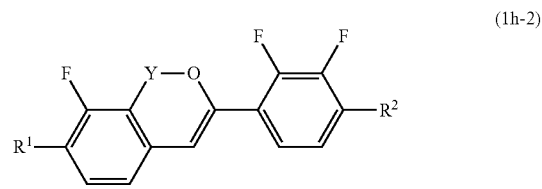
(1h-2)

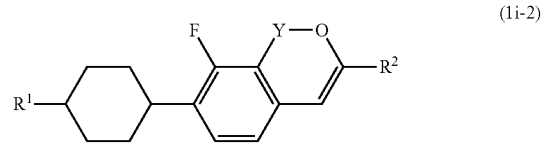
(1i-2)

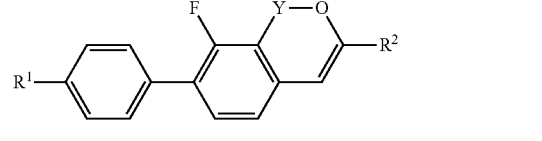
(1j-2)

-continued
(1k-2) 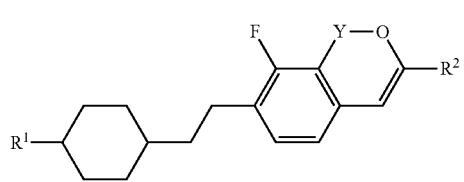
(1l-2) 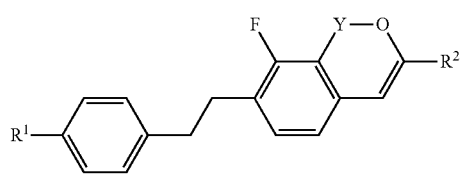
(1m-2) 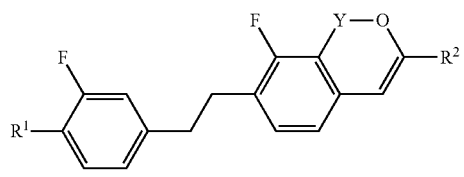
(1n-2) 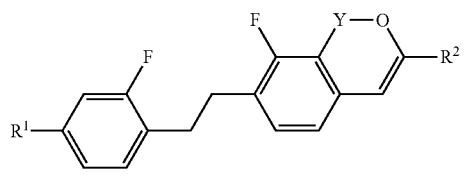
(1o-2) 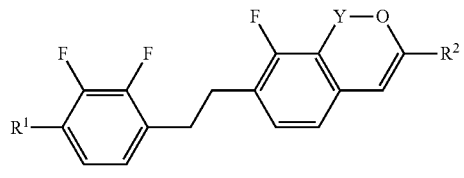
(1p-2) 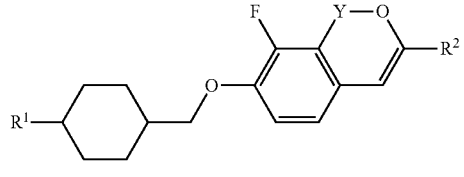
(1q-2) 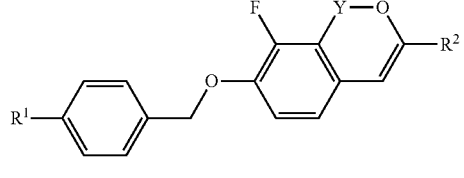
(1r-2) 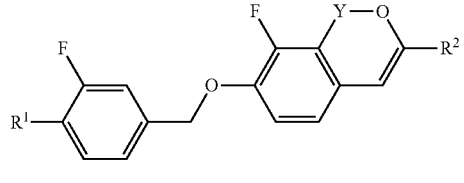
(1s-2) 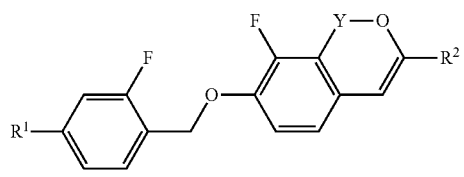
-continued
(1t-2) 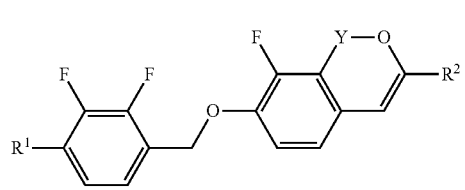
wherein, in formulas (1a-2) to (1t-2),
$R^1$ and $R^2$ are independently alkyl having 1 to 12 carbons, alkoxy having 1 to 12 carbons or alkenyl having 2 to 12 carbons; and
Y is —CO— or —CF$_2$—.
14. The compound according to claim 12, represented by any one of formulas (1a-3) to (1t-3):
(1a-3) 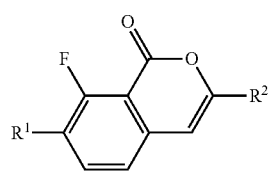
(1b-3) 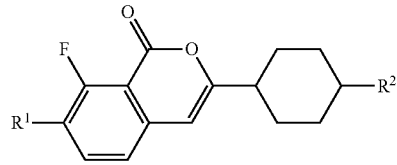
(1c-3) 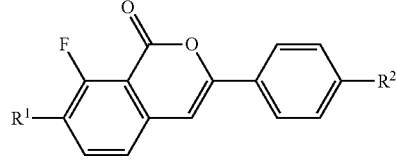
(1d-3) 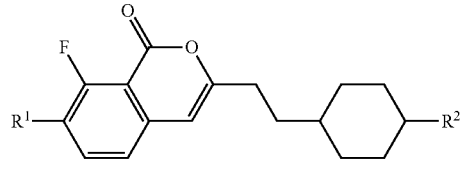
(1e-3) 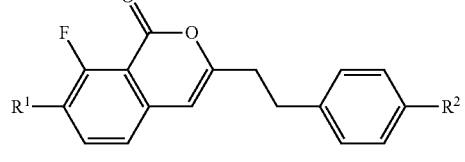
(1f-3) 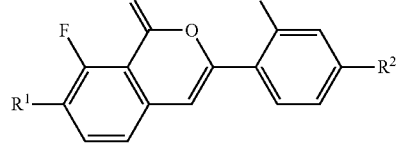

(1g-3) 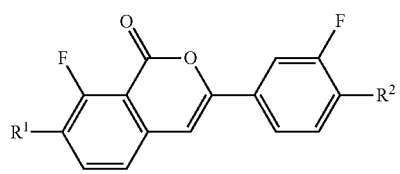
(1h-3) 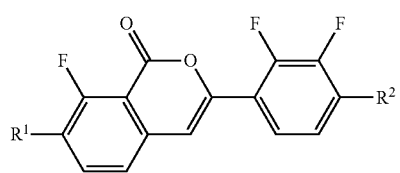
(1i-3) 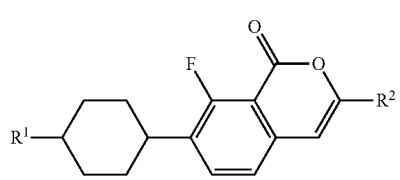
(1j-3) 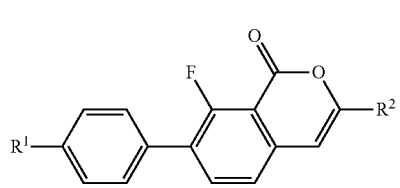
(1k-3) 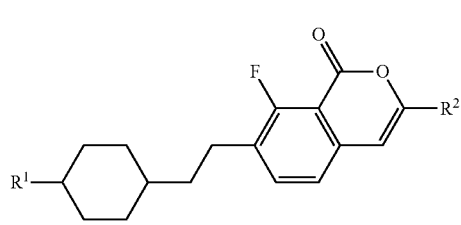
(1l-3) 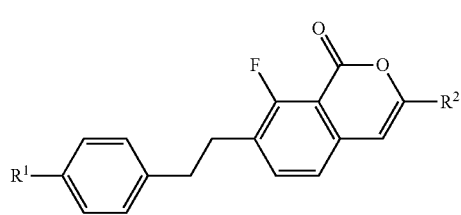
(1m-3) 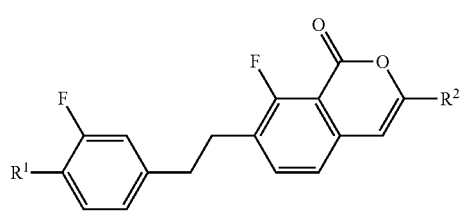
(1n-3) 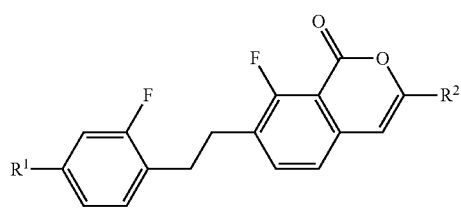
(1o-3) 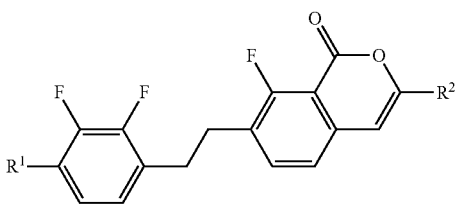
(1p-3) 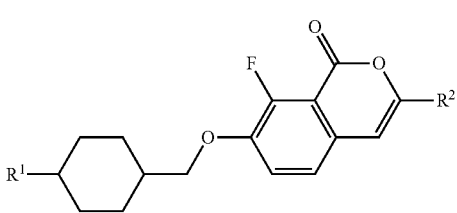
(1q-3) 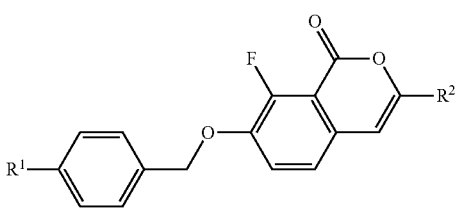
(1r-3) 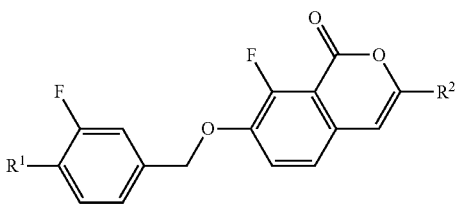
(1s-3) 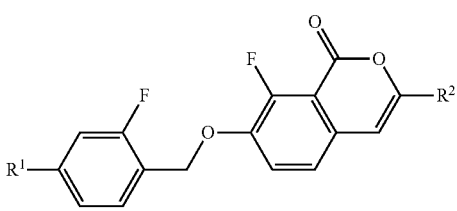
(1t-3) 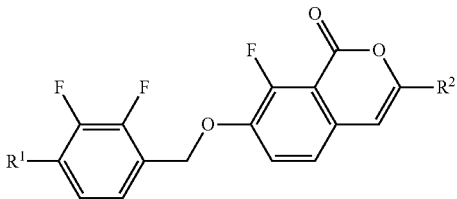
wherein, in formulas (1a-3) to (1t-3), $R^1$ and $R^2$ are independently alkyl having 1 to 12 carbons, alkoxy having 1 to 12 carbons or alkenyl having 2 to 12 carbons.
15. The compound according to claim 12, represented by formula (1a-12):

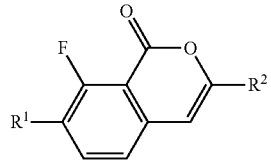
(1a-12)

wherein, in formula (1a-12), $R^1$ and $R^2$ are independently alkyl having 1 to 12 carbons, alkoxy having 1 to 12 carbons or alkenyl having 2 to 12 carbons.

16. The compound according to claim 15, wherein, in formula (1a-12), $R^1$ is alkoxy having 1 to 12 carbons, and $R^2$ is alkyl having 1 to 12 carbons, alkoxy having 1 to 12 carbons or alkenyl having 2 to 12 carbons.

17. A liquid crystal display device, including the liquid crystal composition according to claim 1.

* * * * *